(12) United States Patent
Kwon et al.

(10) Patent No.: US 8,815,935 B2
(45) Date of Patent: Aug. 26, 2014

(54) INHIBITORS OF PROTEIN PRENYLTRANSFERASES

(75) Inventors: Ohyun Kwon, Los Angeles, CA (US); Fuyuhiko Tamanoi, Los Angeles, CA (US); Hannah Fiji, Fontana, CA (US); Masaru Watanabe, Yahaba (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/614,789

(22) Filed: Sep. 13, 2012

(65) Prior Publication Data

US 2013/0102639 A1 Apr. 25, 2013

Related U.S. Application Data

(63) Continuation of application No. 13/056,077, filed as application No. PCT/US2008/009106 on Jul. 28, 2008, now abandoned.

(51) Int. Cl.
*C07D 207/48* (2006.01)
*A61K 31/40* (2006.01)
*C07D 207/20* (2006.01)
*C07D 211/96* (2006.01)

(52) U.S. Cl.
CPC ............ *C07D 211/96* (2013.01); *C07D 207/48* (2013.01); *C07D 207/20* (2013.01)
USPC .......................................... 514/424; 548/542

(58) Field of Classification Search
None
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 8,093,274 B2 | 1/2012 | Tamanoi et al. |

FOREIGN PATENT DOCUMENTS

| WO | WO-2004015130 A2 | 2/2004 |
| WO | WO-2004110996 A1 | 12/2004 |
| WO | WO-2007111948 A2 | 10/2007 |

OTHER PUBLICATIONS

Tamanoi et al. (2001) Protein farnesylation in mammalian cells: effects of farnesyltransferase inhibitors on cancer cells. Cell. Molec. Life Sciences vol. 58, pp. 1636-1649.
Carrico, D. et al, (2005) Design, synthesis, and evaluation of potent and selective benzoyleneurea-based inhibitors of protein geranylgeranyltransferase-1, Bioorg. Med Chem. vol. 13, pp. 677-688.
O'Regan, R.M. et al., (2004) Farnesyl transferase inhibitors: the next targeted therapies for breast cancer? Endocr. Relat. Cancer vol. 11, pp. 191-205.
Oualid, F.E. et al., (2005) A Combinatorial Approach toward the Generation of Ambiphilic Peptide-Based Inhibitors of Protein:Geranylgeranyl Transferase-1, J. Comb. Chem. vol. 7, pp. 703-713.
Peterson, Y.K. et al., (2006) A Novel Protein Geranylgeranyltransferase-I Inhibitor with High Potency, Selectivity and Cellular Activity, J. Biol. Chem., Published Mar. 3.
Richter, H. et al., "Polymer Bound 3-Hydroxy-2-methylidenepropionic Acids. A Template for Multiple Core Structure Libraries" J. Org. Chem. 1999, vol. 64, pp. 1362-1365.
Purandare, A. V. et al., "Solid-phase synthesis of 'diverse' heterocycles" Tetrahedron Lett. 2002, vol. 43, pp. 3903-3906.
Huang, X.et al., "Solid-Phase synthesis of 4(1H)-Quinolone and Pyrimidine Derivatives Based on a New Scaffold-Polymer-Bound Cyclic Malonic Acid Ester" J. Org.. Chem. 2002, vol. 67, pp. 6731-6737.
Couladouros E. A.et al., "Generation of Libraries of Pharmacophoric Structures with Increased Complexity and Diversity by Employing Polymorphic Scaffolds" Angew. Chem., Int. Ed. 2002, vol. 41, pp. 3677-3680.
Bertozzi, F. et al., "A Combinatorial Scaffold Approach Based upon a Multicomponent Reaction" Org. Lett. 2003, vol. 5, pp. 1551-1554.
Taylor, S. J. et al., "Synthetic Strategy toward Skeletal Diversity via Solid-Supported, Otherwise Unstable Reactive Intermediates" Angew. Chem., Int. Ed. 2004, vol. 43, pp. 1681-1685.
Tempest, P.A et al., (1997) Cyclobutenedione derivatives on solid support: Toward multiple core structure libraries. J. Am. Chem. Soc. vol. 119, pp. 7607-7608.
Ding, S. et al., "A Combinatorial Scaffold Approach toward Kinase-Directed Heterocycle Libraries" J. Am. Chem. Soc. 2002, vol. 124, pp. 1594-1596.
Kwon, O. et al., "Skeletal Diversity via a Branched Pathway: Efficient Synthesis of 29,400 Discrete, Polycyclic Compounds and Their Arraying into Stock Solutions" J. Am. Chem. Soc. 2002, vol. 124, pp. 13402-13404.
Burke, M. D. et al., "Generating Diverse Skeletons of Small Molecules Combinatorially" Science 2003, vol. 302, pp. 613-618.
Clark, E.A. et al., (2000) Genomic analysis of metastasis reveals an essential role for RhoC. Nature vol. 406, pp. 466-467.
Hakem, A. et al., (2005) RhoC is dispensable for embryogenesis and tumor initiation but essential for metastasis. Genes & Develop. vol. 19, pp. 1974-1979.
Lobell, R.B. et al., (2002) Preclinical and clinical pharmacodynamic assessment of L-778,123, a dual inhibitor of farnesyl:protein transferase and geranylgeranyl:protein transferase type-I Mol. Cancer Ther. vol. 1, pp. 747-758.
McGovern, S.L. et al., (2003) A common mechanism underlying promiscuous inhibitors from virtual and high-throughput screening. J. Med. Chem. vol. 45, pp. 1712-1722.
McGovern, S.L. et al., (2003) A specific mechanism of nonspecific inhibition. J. Med. Chem. vol. 46, pp. 4265-4272.

(Continued)

*Primary Examiner* — Michael Barker
(74) *Attorney, Agent, or Firm* — Venable LLP; Nancy J. Axelrod; Michael A. Gollin

(57) ABSTRACT

The present invention is directed to novel compounds. These compounds can be useful in inhibiting the activity of protein prenyltransferases including GGTase I and/or RabGGTase. The compounds can also be used as anti-cancer therapeutics including as part of methods for treating cancer, in assays, and in kits.

30 Claims, 78 Drawing Sheets

(56) References Cited

OTHER PUBLICATIONS

Finegold, A.A. et al., (1991) Protein geranylgeranyltransferase of *Saccharomyces cerevisiae* is specific for Cys-Xaa-Xaa-Leu motif and requires the CDC43 gene product but not the DPRI gene product. Proc. Natl. Acad. Sci. USA vol. 88, pp. 4448-4452.

Furka, A. et al., (1988), in Highlights of Modern Biochemistry, Proceedings of the 14th International Congress of Biochemistry, Prague, Czechoslovakia (VSP, Utrecht, Netherlands), vol. 13, pp. 47.

Furka, A. et al., (1991), Int. J. Pept. Protein Res. vol. 37, pp. 487.

Houghton, R. A. et al., (1991) "Generation and use of synthetic peptide combinatorial libraries for basic research and drug discovery" Nature vol. 354, pp. 84-86.

Lam, K. S. et al., (1991) "A new type of synthetic peptide library for identifying ligand-binding activity" Nature vol. 354, pp. 82-84.

Mukaiyama, T. et al., (1975), "A Convenient Method for the Synthesis of Carboxylic Esters" Chem. Lett. pp. 1045-1048.

Mukaiyama, T. et al., (1976) "Betaine as an Effective Acid Captor: A Convenient Method for the Synthesis of Carboxylic Esters" Chem. Lett. vol. 13-14.

Saigo, K. et al., (1977) "New Method for the Preparation of Carboxylix Esters" Bull. Chem. Soc. Jpn. vol. 50, pp. 1863-1866.

Miyata, O. et al., (1991) "Stereospecific Nucleophilic Addition Reactions to Olefins. Addition of Thiols to αβ-Unsaturated Carboxylic Acid Derivatives" J. Org. Chem. vol. 56, pp. 6556-6564.

Ball, C. P. et al., (1998) "Chameleon Catches in Combinatorial Chemistry: Tebbe Olefination of Polymer Supported Esters and the Synthesis of Amines, Cyclohexanones, Enones, Methyl Ketones and Thiazoles" Chem. Commun. pp. 2019-2020.

Barrett, A. G. M. et al., (2001) "Solid-Phase Synthesis of Isoxazoles Using Vinyl Ethers as Chamelon Catches" Org. Lett. vol. 3, pp. 3165-3168.

Mori, A. et al., (1985) "Resolution of Ketones via Chiral Acetals. Kinetic Approach" J. Org. Chem., vol. 50, pp. 5444-5446.

Lienhard, G. E. et al., (1969) "On the Mechanism of Acid-Catalyzed Enolization of Ketones" J. Am. Chem. Soc. vol. 91, pp. 1146-1153.

Lang, R. W. et al., (1990) "α-Allenic Esters from α-Phosphoranylidene Esters and Acid Chlorides: Ethyl 2,3-Pentadienoate" Org. Synth. Coll. vol. 7, pp. 232-235.

Scholz, D. et al., (1999) "Expedient Synthesis of α-substituted αβ-unsaturated γ-amino acids (dipeptide memetics); Wittig reaction of α-amino aldehydes with a-substituted alkoxycarbonylphosphoranes" Synth. Commun. vol. 29, pp. 1143-1155.

McKay, W. R. et al., (1981) "Removal of toluene-*p*-sulfonyl groups from sulfonamides. Part 4. Synthesis of phenylglyoxal imine monomers" J. Chem. Soc., Perkin Trans. vol. 1, pp. 2435-2442.

Jennings, W. B. et al., (1991) "The titanium tetrachloride induced synthesis of N-phosphinoylimines and N-sulfonylimines directly from aromatic aldehydes" Tetrahedron, vol. 47, pp. 5561-5568.

Love, B. E. et al., (1994) "Preparation of N-Tosylaldimines" Synlett pp. 493-494.

Bilodeau, M. T. et al., (1998) "Solid-Supported Synthesis of Irnidazoles: A strategy for Direct Resin-Attachment to the Imidazole Core," J. Org. Chem. vol. 63, pp. 2800-2801.

Chemla, F. et al., (2000) "An Easy Synthesis of Aliphatic and Aromatic N-Sulfonyl Aldimines," Synthesis, pp. 75-77.

Gerritz, S.W. et al., (2003) "High-Throughput Manual Parallel Synthesis Using SynPhase Crowns and Lanterns" J. Comb. Chem. vol. 5, pp. 110-117.

Feliu, L. et al., (2003) "Spiroimidazolidinone Library Derivatives on SynPhase Lanterns" J. Comb. Chem. vol. 5, pp. 356-361.

Lim, K.H. et al., (2006), Current Biology vol. 16, pp. 2385.

Lim, K.H. et al, (2005), Cancer Cell vol. 7, pp. 533.

Vogt, A.et al., J. Biol. Chem. vol. 272, pp. 27224. (1997).

Mira J-P et al., PNAS vol. 97, pp. 185. (2000).

Pille, J-Y et al., Molecular Therapy vol. 11, pp. 267. (2004).

Sebti and Hamilton (2001) Farnesyltransferase and geranylgeranyltransferase I inhibitors as novel agents for cancer and cardiovascular diseases. In "Farnesyltransferase inhibitors in cancer therapy" eds. Sebti and Hamilton, Humana Press, pp. 197-219.

Zhao, G.-L. et al., (2005) "Aza-Baylis-Hillman Reactions of N-Tosylated Aldimines with Activated Allenes and Alkynes in the Presence of Various Lewis Base Promoters," J. Org. Chem. vol. 70, pp. 9975-9984.

Wurz, R.P. et al., (2005) "Catalytic Asymmetric Synthesis of Piperidine Derivatives through the [4+2] Annulation of Imines with Allenes," J. Am. Chem. Soc., 2005, vol. 127, pp. 12234-12235.

Zhu, X.-F. et al., (2005) "A highly diastereoselective synthesis of 3-carbethoxy-2,5-disubstituted-3-pyrrolines by phosphine catalysis," Tetrahedron, vol. 61, pp. 6276-6282.

Zhu, X.-F. et al., (2003), An Expedient Phosphine-Catalyzed [4+2] Annulation: Synthesis of Highly Functionalized Tetrahydropyridines, J. Am. Chem. Soc., vol. 125, pp. 4716-4717.

Shi, M. et al., (2002) "Lewis Base Effects in the Baylis-Hillman Reaction of Imines with Methyl Vinyl Ketone," Eur. J. Org. Chem, pp. 696-701.

Xu, Z. et al., (1999), "Phosphine-catalyzed [3+2] cycloaddition reactions of substituted 2-alkynoates or 2,3-allenoates with electron-deficient olefins and imines," Tetrahedron Letters, vol. 40, pp. 549-552.

Vasudevan, A. et al., (1999), "Potent, Highly Selective, and Non-Thiol Inhibitors of Protein Geranylgeranyltransferase-I," J. Med. Chem., vol. 42, pp. 1333-1340.

Ma, S. et al., (2004), "An Efficient Synthesis of 4-Halo-5-hydroxyfuran-2(5H)-ones via the Sequential Halolactonization and γ-Hydroxylation of 4-Aryl-2,3-alkadienoic Acids," J. Org. Chem., vol. 69, pp. 1429-1431.

PCT Application No. US2007/07135, International Search Report dated May 30, 2008.

PCT Application No. US2008/09106, International Search Report dated Dec. 19, 2008.

Castellano, et al., (2007), J.A.C.S., vol. 129, pp. 5843-5845.

Watanabe et al. (2008), J. Biological Chem., vol. 283, No. 15, pp. 9571-9579.

Lu et al., (2009), "In vivo Antitumor Effect of a Novel Inhibitor of Protein Geranylgeranyltransferase-I", Mol Cancer Ther, vol. 8, No. 5, pp. 1218-1226.

Chan et al., (2011), Identification and Characterization of Mechanism of Action of P61-E7, a Novel Phosphine Catalysis-Based Inhibitor of Geranylgeranyltransferase-I, Plos One, vol. 6, Issue 10, pp. 1-13.

Watanabe et al., (2008), "Inhibitors of Protein Geranylgeranyltransferase I and Rab Geranylgeranyltransferase Identified from a Library of Allenoate-derived Compounds", Journal of Biological Chemistry, vol. 283, No. 15, pp. 9571-9579.

Reaction conditions. (a) allenoic acid, Mukaiyama's reagent, DIPEA or Et₃N, DCM, rt, 12 h; (b) PPh₃ or PBu₃, imine, benzene or DCM, rt or 60 °C; (c) 2.5% TFA/DCM, 12 h; (d) thiol, n-BuLi, −25 °C, THF.

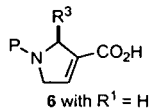 1 allenoic acid x 30 imines = 30 compounds
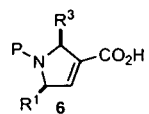 10 allenoic acids x 21 imines = 210 compounds
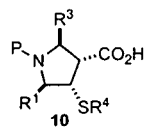 7 allenoic acids x 25 imines x 19 thiols = 3,325 compounds
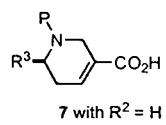 1 allenoic acid x 26 imines = 26 compounds
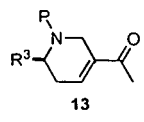 1 allenoic acid x 25 imines = 25 compounds
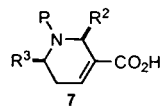 11 allenoic acids x 31 imines = 341 compounds
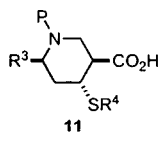 1 allenoic acid x 21 imines x 17 thiols = 357 compounds
Total 4,314 compounds
FIG. 11A

| 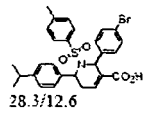 7 K-ras/RhoA | C40 R³ = 4-chlorophenyl P = 2-methylbenzene-sulfonyl | C13 R³ = 3,4-dichlorophenyl P = 4-methylbenzene-sulfonyl | C15 R³ = 3-bromophenyl P = 4-methylbenzene-sulfonyl | C12 R³ = 3-chlorophenyl P = 4-methylbenzene-sulfonyl | C27 R³ = 4-chlorophenyl P = 4-chlorobenzene-sulfonyl | C30 R³ = 4-methylphenyl P = 4-chlorobenzene-sulfonyl |
|---|---|---|---|---|---|---|
| B06 R² = 3-bromophenyl | 10.6/8.8 | 8.6/3.2 | 9.4/3.7 | 11.0/7.0 | 8.6/5.0 | 8.4/7.4 |
| B05 R² = 3-chlorophenyl | P3-E5 41.7/24.8 14.7/7.5 | 10.7/4.5 | 9.8/7.9 | (43.7/6.0) | P3-D9 33.1/26.7 | |
| B07 R² = 3-methylphenyl | 15.6/12.4 | 12.6/10.3 | 16.1/14.3 | | | |
| B04 R² = 3-fluorophenyl | 5.4/3.0 | | 17.0/15.0 | | | |
| B02 R² = phenyl | 13.4/5.8 | | 35.2/19.4 | | | |
| B10* R² = 4-bromophenyl | | 18.7/11.3 | | | | |
| B03 R² = 2-fluorophenyl | 8.4/4.1 | | | | | |
| B08 R² = 4-fluorophenyl | 15.6/12.6 | | | | | |
| B09 R² = 4-chlorophenyl | | 17.7/12.1 | | | | |
| B11 R² = 4-methylphenyl | | 12.4/15.6 | | | | |

| Compound (MW) | Structure | Enzyme inhibitoin (IC50, μM) K-Ras4B | RhoA |
|---|---|---|---|
| GGTI-298 | 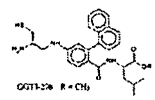 | 2.3 | 1.6 |
| GGTI-2166 | 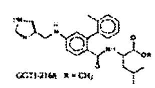 | 0.6 | 0.5 |
| P4-E5 (503.72) | 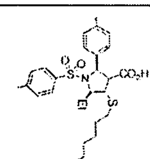 | 50.0 | 50.0 |
| P4-F1 (551.76) | 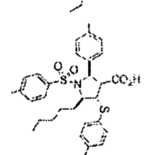 | 65.0 | 100.0 |
| P5-D9 (391.87) | 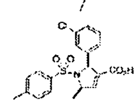 | 20.0 | 30.0 |
| P5-D10 (426.31) | 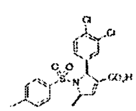 | 38.0 | 45.0 |

FIG. 17A

| Compound (MW) | Structure | Enzyme inhibitoin (IC$_{50}$, mM) | |
|---|---|---|---|
| | | K-Ras4B | RhoA |
| P5-G4 (468.39) | 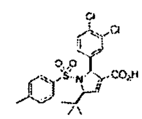 | 33.0 | 40.0 |
| P5-G7 (385.48) | 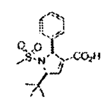 | 15.0 | 23.0 |
| P5-G11 (417.49) | 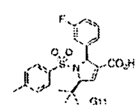 | 18.0 | 23.0 |
| P5-H3 (357.85) | 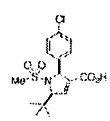 | 45.0 | > 50.0 |
| P5-H6 (433.95) | 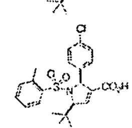 | 2.0 | 2.5 |
| P23-D5 (454.36) | 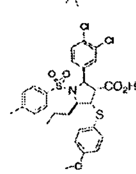 | <2.0 | <2.5 |

FIG. 17B

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B04 | 3-F-benzyl | C01 | Ph | Ts | B04C01 | yellow | - | 1 | 3.8854 | 6.2 | 451.51 | 1.373 | 10 | A11 | 63.7 |
| 2 | B04 | 3-F-benzyl | C02 | 4-MeC₆H₄ | Ts | B04C02 | yellow | - | 1 | 3.8282 | 6.5 | 465.54 | 1.396 | 10 | B2 | 77.3 |
| 3 | B04 | 3-F-benzyl | C03 | 4-EtC₆H₄ | Ts | B04C03 | yellow | - | 1 | 3.8543 | 7.3 | 479.56 | 1.522 | 10 | B3 | 55.0 |
| 4 | B04 | 3-F-benzyl | C04 | 4-MeOC₆H₄ | Ts | B04C04 | yellow | - | 1 | 3.8265 | 5.1 | 481.54 | 1.059 | 10 | B4 | 87.5 |
| 5 | B04 | 3-F-benzyl | C05 | 4-EtOC₆H₄ | Ts | B04C05 | yellow | - | 1 | 3.8758 | 4.6 | 495.56 | 0.928 | 10 | B5 | 87.5 |
| 6 | B04 | 3-F-benzyl | C06 | piperonyl | Ts | B04C06 | yellow | - | 1 | 3.831 | 6.4 | 495.52 | 1.292 | 10 | B6 | 90.9 |
| 7 | B04 | 3-F-benzyl | C09 | 4-CNC₆H₄ | Ts | B04C09 | yellow | - | 1 | 3.8642 | 6.7 | 476.52 | 1.406 | 10 | B7 | 88.3 |
| 8 | B04 | 3-F-benzyl | C10 | 2-FC₆H₄ | Ts | B04C10 | yellow | - | 1 | 3.8634 | 7.3 | 469.5 | 1.555 | 10 | B8 | 75.0 |
| 9 | B04 | 3-F-benzyl | C11 | 4-ClC₆H₄ | Ts | B04C11 | yellow | - | 1 | 3.802 | 9.2 | 485.95 | 1.893 | 10 | B9 | 78.2 |
| 10 | B04 | 3-F-benzyl | C12 | 3-ClC₆H₄ | Ts | B04C12 | yellow | - | 1 | 3.823 | 9.6 | 485.95 | 1.976 | 10 | B10 | 52.8 |
| 11 | B04 | 3-F-benzyl | C13 | 3,4-di-ClC₆H₄ | Ts | B04C13 | yellow | - | 1 | 3.8856 | 9.7 | 520.4 | 1.864 | 10 | B11 | 45.1 |
| 12 | B04 | 3-F-benzyl | C15 | 3-BrC₆H₄ | Ts | B04C15 | yellow | - | 1 | 3.8721 | 8.3 | 530.41 | 1.565 | 10 | C2 | |
| 13 | B04 | 3-F-benzyl | C19 | Ph | Ms | B04C19 | yellow | - | 1 | 3.8916 | 6.9 | 375.41 | 1.838 | 10 | C3 | 86.6 |
| 14 | B04 | 3-F-benzyl | C20 | 3,4-di-MeOC₆H₄ | Ts | B04C20 | yellow | - | 1 | 3.834 | 8.2 | 511.56 | 1.603 | 10 | C4 | 88.9 |
| 15 | B04 | 3-F-benzyl | C21 | 2-thiophene | Ts | B04C21 | yellow | - | 1 | 3.8798 | 3.2 | 457.54 | 0.699 | 10 | C5 | 81.8 |
| 16 | B04 | 3-F-benzyl | C23 | 4-FC₆H₄ | Ts | B04C23 | yellow | - | 1 | 3.8029 | 8.0 | 469.5 | 1.704 | 10 | C6 | 70.1 |
| 17 | B04 | 3-F-benzyl | C24 | 4-i-PrC₆H₄ | Ts | B04C24 | yellow | - | 1 | 3.8345 | 8.4 | 493.59 | 1.702 | 10 | C7 | 72.8 |
| 18 | B04 | 3-F-benzyl | C26 | 3-FC₆H₄ | Ts | B04C26 | yellow | - | 1 | 3.7987 | 8.6 | 469.5 | 1.832 | 10 | C8 | 69.9 |
| 19 | B04 | 3-F-benzyl | C27 | 4-ClC₆H₄ | 4-ClBs | B04C27 | yellow | - | 1 | 3.8927 | 9.0 | 506.37 | 1.777 | 10 | C9 | 44.8 |
| 20 | B04 | 3-F-benzyl | C28 | 4-ClC₆H₄ | Ms | B04C28 | yellow | - | 1 | 3.8436 | 6.0 | 409.86 | 1.464 | 10 | C10 | 69.9 |
| 21 | B04 | 3-F-benzyl | C30 | 4-MeC₆H₄ | 4-ClBs | B04C30 | yellow | - | 1 | 3.7806 | 7.3 | 485.95 | 1.502 | 10 | C11 | 54.5 |
| 22 | B04 | 3-F-benzyl | C33 | 3-MeC₆H₄ | Ts | B04C33 | yellow | - | 1 | 3.8956 | 7.1 | 465.54 | 1.525 | 10 | D2 | 75.6 |
| 23 | B04 | 3-F-benzyl | C35 | 4-MeOC₆H₄ | Bs | B04C35 | yellow | - | 1 | 3.789 | 6.0 | 467.51 | 1.283 | 10 | D3 | 91.8 |
| 24 | B04 | 3-F-benzyl | C37 | 4-MeOC₆H₄ | 4-ClBs | B04C37 | yellow | - | 1 | 3.8798 | 7.3 | 501.95 | 1.454 | 10 | D4 | 69.3 |
| 25 | B04 | 3-F-benzyl | C38 | 4-MeOC₆H₄ | 2-Ts | B04C38 | yellow | - | 1 | 3.8063 | 5.1 | 481.54 | 1.059 | 10 | D5 | 66.6 |
| 26 | B04 | 3-F-benzyl | C39 | 3-MeOC₆H₄ | Ts | B04C39 | yellow | - | 1 | 3.8694 | 5.8 | 481.54 | 1.204 | 10 | D6 | 82.9 |
| 27 | B04 | 3-F-benzyl | C40 | 4-ClC₆H₄ | 2-Ts | B04C40 | yellow | - | 1 | 3.8131 | 7.4 | 485.95 | 1.523 | 10 | D7 | |
| 28 | B04 | 3-F-benzyl | C41 | 4-MeC₆H₄ | 2-Ts | B04C41 | yellow | - | 1 | 3.812 | 7.8 | 465.54 | 1.675 | 10 | D8 | 63.4 |
| 29 | B04 | 3-F-benzyl | C42 | 4-MeC₆H₄ | 2-MCBs | B04C42 | yellow | - | 1 | 3.8314 | 9.0 | 509.55 | 1.766 | 10 | D9 | 64.5 |
| 30 | B04 | 3-F-benzyl | C43 | 4-MeC₆H₄ | Bs | B04C43 | yellow | - | 1 | 3.8651 | 7.6 | 451.51 | 1.683 | 10 | D10 | 64.9 |
| 31 | B04 | 3-F-benzyl | C46 | 4-MeC₆H₄ | Ms | B04C46 | yellow | - | 1 | 3.8144 | 4.8 | 389.44 | 1.233 | 10 | D11 | 75.0 |

FIG. 19-1

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B05 | 3-Cl-benzyl | C01 | Ph | Ts | B05C01 | red | - | 1 | 3.8587 | 7 | 467.96 | 1.49585 | 10 | E2 | 71.3 |
| 2 | B05 | 3-Cl-benzyl | C02 | 4-MeC₆H₄ | Ts | B05C02 | red | - | 1 | 3.808 | 7.5 | 481.99 | 1.55605 | 10 | E3 | 69.4 |
| 3 | B05 | 3-Cl-benzyl | C03 | 4-EtC₆H₄ | Ts | B05C03 | red | - | 1 | 3.8006 | 7.5 | 496.02 | 1.51204 | 10 | E4 | 73.6 |
| 4 | B05 | 3-Cl-benzyl | C04 | 4-MeOC₆H₄ | Ts | B05C04 | red | - | 1 | 3.9238 | 5.5 | 497.99 | 1.10444 | 10 | E5 | 89.3 |
| 5 | B05 | 3-Cl-benzyl | C05 | 4-EtOC₆H₄ | Ts | B05C05 | red | - | 1 | 3.9246 | 7 | 512.02 | 1.36713 | 10 | E6 | 78.9 |
| 6 | B05 | 3-Cl-benzyl | C06 | piperonyl | Ts | B05C06 | red | - | 1 | 3.8919 | 8.5 | 511.97 | 1.66025 | 10 | E7 | 73.9 |
| 7 | B05 | 3-Cl-benzyl | C09 | 4-CNC₆H₄ | Ts | B05C09 | red | - | 1 | 3.8746 | 9.2 | 492.97 | 1.36624 | 10 | E8 | 70.9 |
| 8 | B05 | 3-Cl-benzyl | C10 | 2-FC₆H₄ | Ts | B05C10 | red | - | 1 | 3.8986 | 7.7 | 485.95 | 1.58453 | 10 | E9 | 70.1 |
| 9 | B05 | 3-Cl-benzyl | C11 | 4-ClC₆H₄ | Ts | B05C11 | red | - | 1 | 3.9032 | 8.4 | 502.41 | 1.67194 | 10 | E10 | 59.2 |
| 10 | B05 | 3-Cl-benzyl | C12 | 3-ClC₆H₄ | Ts | B05C12 | red | - | 1 | 3.8962 | 8 | 502.41 | 1.59232 | 10 | E11 | 43.8 |
| 11 | B05 | 3-Cl-benzyl | C13 | 3,4-di-ClC₆H₄ | Ts | B05C13 | red | - | 1 | 3.846 | 8.8 | 536.85 | 1.63919 | 10 | F2 | 26 |
| 12 | B05 | 3-Cl-benzyl | C15 | 3-BrC₆H₄ | Ts | B05C15 | red | - | 1 | 3.8828 | 6.9 | 546.86 | 1.26175 | 10 | F3 | |
| 13 | B05 | 3-Cl-benzyl | C19 | Ph | Ms | B05C19 | red | - | 1 | 3.8471 | 6.5 | 391.87 | 1.65871 | 10 | F4 | 72.4 |
| 14 | B05 | 3-Cl-benzyl | C20 | 3,4-di-MeOC₆H₄ | Ts | B05C20 | red | - | 1 | 3.9123 | 6.7 | 528.02 | 1.26889 | 10 | F5 | 87.8 |
| 15 | B05 | 3-Cl-benzyl | C21 | 2-thiophene | Ts | B05C21 | red | - | 1 | 3.8257 | 5.9 | 473.99 | 1.24475 | 10 | F6 | 79.5 |
| 16 | B05 | 3-Cl-benzyl | C23 | 4-FC₆H₄ | Ts | B05C23 | red | - | 1 | 3.843 | 7.2 | 485.95 | 1.48163 | 10 | F7 | 66.7 |
| 17 | B05 | 3-Cl-benzyl | C24 | 4-i-PrC₆H₄ | Ts | B05C24 | red | - | 1 | 3.862 | 6.7 | 510.04 | 1.31362 | 10 | F8 | 63.1 |
| 18 | B05 | 3-Cl-benzyl | C26 | 3-FC₆H₄ | Ts | B05C26 | red | - | 1 | 3.8907 | 7.2 | 485.95 | 1.48163 | 10 | F9 | 62.3 |
| 19 | B05 | 3-Cl-benzyl | C27 | 4-ClC₆H₄ | 4-ClBs | B05C27 | red | - | 1 | 3.8903 | - | 522.83 | - | - | - | - |
| 20 | B05 | 3-Cl-benzyl | C28 | 4-ClC₆H₄ | Ms | B05C28 | red | - | 1 | 3.9032 | 6.7 | 426.31 | 1.57163 | 10 | F10 | 60.3 |
| 21 | B05 | 3-Cl-benzyl | C30 | 4-MeC₆H₄ | 4-ClBs | B05C30 | red | - | 1 | 3.819 | 5.9 | 502.41 | 1.17434 | 10 | F11 | 60 |
| 22 | B05 | 3-Cl-benzyl | C33 | 3-MeC₆H₄ | Ts | B05C33 | red | - | 1 | 3.8978 | 8.3 | 481.99 | 1.72203 | 10 | G2 | 57.6 |
| 23 | B05 | 3-Cl-benzyl | C35 | 4-MeOC₆H₄ | Bs | B05C35 | red | - | 1 | 3.8401 | 6.3 | 483.96 | 1.30176 | 10 | G3 | 56.1 |
| 24 | B05 | 3-Cl-benzyl | C37 | 4-MeOC₆H₄ | 4-ClBs | B05C37 | red | - | 1 | 3.8846 | 6.1 | 518.41 | 1.17667 | 10 | G4 | 53.2 |
| 25 | B05 | 3-Cl-benzyl | C38 | 4-MeOC₆H₄ | 2-Ts | B05C38 | red | - | 1 | 3.7664 | 5.3 | 497.99 | 1.06428 | 10 | G5 | 66.1 |
| 26 | B05 | 3-Cl-benzyl | C39 | 3-MeOC₆H₄ | Ts | B05C39 | red | - | 1 | 3.7817 | 5.5 | 497.99 | 1.10444 | 10 | G6 | 67.1 |
| 27 | B05 | 3-Cl-benzyl | C40 | 4-ClC₆H₄ | 2-Ts | B05C40 | red | - | 1 | 3.8856 | - | 502.41 | - | - | - | - |
| 28 | B05 | 3-Cl-benzyl | C41 | 4-MeC₆H₄ | 2-Ts | B05C41 | red | - | 1 | 3.9098 | 7.5 | 481.99 | 1.55605 | 10 | G7 | 62.3 |
| 29 | B05 | 3-Cl-benzyl | C42 | 4-MeC₆H₄ | 2-MCBs | B05C42 | red | - | 1 | 3.9037 | 8.8 | 526 | 1.673 | 10 | G8 | 56.2 |
| 30 | B05 | 3-Cl-benzyl | C43 | 4-MeC₆H₄ | Bs | B05C43 | red | - | 1 | 3.9564 | 7 | 467.96 | 1.49585 | 10 | G9 | 56.7 |
| 31 | B05 | 3-Cl-benzyl | C46 | 4-MeC₆H₄ | Ms | B05C46 | red | - | 1 | 3.8694 | 6.7 | 405.9 | 1.65065 | 10 | G10 | 64.4 |

FIG. 19-2

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B06 | 3-Br-benzyl | C01 | Ph | Ts | B06C01 | blue | - | 1 | 3.8753 | 9.3 | 512.42 | 1.815 | 10 | G11 | 65.9 |
| 2 | B06 | 3-Br-benzyl | C02 | 4-MeC₆H₄ | Ts | B06C02 | blue | - | 1 | 3.902 | 8.9 | 526.44 | 1.691 | 10 | H2 | 75.6 |
| 3 | B06 | 3-Br-benzyl | C03 | 4-EtC₆H₄ | Ts | B06C03 | blue | - | 1 | 3.8581 | 9.8 | 540.47 | 1.813 | 10 | H3 | 75.4 |
| 4 | B06 | 3-Br-benzyl | C04 | 4-MeOC₆H₄ | Ts | B06C04 | blue | - | 1 | 3.8407 | 8.4 | 542.44 | 1.549 | 10 | H4 | 84.5 |
| 5 | B06 | 3-Br-benzyl | C05 | 4-EtOC₆H₄ | Ts | B06C05 | blue | - | 1 | 3.8549 | 3.9 | 556.47 | 0.701 | 10 | H5 | 78.4 |
| 6 | B06 | 3-Br-benzyl | C06 | piperonyl | Ts | B06C06 | blue | - | 1 | 3.8207 | 8.3 | 556.42 | 1.492 | 10 | H6 | 75.1 |
| 7 | B06 | 3-Br-benzyl | C09 | 4-CNC₆H₄ | Ts | B06C09 | blue | - | 1 | 3.8963 | 8.8 | 537.42 | 1.637 | 10 | H7 | 93.5 |
| 8 | B06 | 3-Br-benzyl | C10 | 2-FC₆H₄ | Ts | B06C10 | blue | - | 1 | 3.7938 | 8.6 | 530.41 | 1.621 | 10 | H8 | 71.2 |
| 9 | B06 | 3-Br-benzyl | C11 | 4-ClC₆H₄ | Ts | B06C11 | blue | - | 1 | 3.9816 | 10.2 | 546.86 | 1.865 | 10 | H9 | 56.6 |
| 10 | B06 | 3-Br-benzyl | C12 | 3-ClC₆H₄ | Ts | B06C12 | blue | - | 1 | 3.9598 | 9.1 | 546.86 | 1.664 | 10 | H10 | 23.1 |
| 11 | B06 | 3-Br-benzyl | C13 | 3,4-di-ClC₆H₄ | Ts | B06C13 | blue | - | 1 | 3.8919 | 8.5 | 581.31 | 1.462 | 10 | H11 | 24.9 |
| 12 | B06 | 3-Br-benzyl | C15 | 3-BrC₆H₄ | Ts | B06C15 | blue | - | 1 | 3.9431 | 8.7 | 591.31 | 1.471 | 11 | A2 | 15.2 |
| 13 | B06 | 3-Br-benzyl | C19 | Ph | Ms | B06C19 | blue | - | 1 | 3.9571 | 7.2 | 436.32 | 1.650 | 11 | A3 | 63.5 |
| 14 | B06 | 3-Br-benzyl | C20 | 3,4-di-MeOC₆H₄ | Ts | B06C20 | blue | - | 1 | 3.9459 | 7.7 | 572.47 | 1.345 | 11 | A4 | 59.0 |
| 15 | B06 | 3-Br-benzyl | C21 | 2-thiophene | Ts | B06C21 | blue | - | 1 | 3.8734 | 6.1 | 518.44 | 1.177 | 11 | A5 | 55.0 |
| 16 | B06 | 3-Br-benzyl | C23 | 4-FC₆H₄ | Ts | B06C23 | blue | - | 1 | 3.9404 | 8.4 | 530.41 | 1.584 | 11 | A6 | 57.2 |
| 17 | B06 | 3-Br-benzyl | C24 | 4-i-PrC₆H₄ | Ts | B06C24 | blue | - | 1 | 3.9 | 7.8 | 554.5 | 1.407 | 11 | A7 | 41.1 |
| 18 | B06 | 3-Br-benzyl | C26 | 3-FC₆H₄ | Ts | B06C26 | blue | - | 1 | 3.8511 | 9.8 | 530.41 | 1.848 | 11 | A8 | 67.1 |
| 19 | B06 | 3-Br-benzyl | C27 | 4-ClC₆H₄ | 4-ClBs | B06C27 | blue | - | 1 | 3.8225 | 10.1 | 567.28 | 1.780 | 11 | A9 | 17.3 |
| 20 | B06 | 3-Br-benzyl | C28 | 4-ClC₆H₄ | Ms | B06C28 | blue | - | 1 | 3.8772 | 4.4 | 470.76 | 0.935 | 11 | A10 | 50.4 |
| 21 | B06 | 3-Br-benzyl | C30 | 4-MeC₆H₄ | 4-ClBs | B06C30 | blue | - | 1 | 3.827 | 10.5 | 546.86 | 1.920 | 11 | A11 | 19.9 |
| 22 | B06 | 3-Br-benzyl | C33 | 3-MeC₆H₄ | Ts | B06C33 | blue | - | 1 | 3.7765 | 9.8 | 526.44 | 1.862 | 11 | B2 | 39.5 |
| 23 | B06 | 3-Br-benzyl | C35 | 4-MeOC₆H₄ | Bs | B06C35 | blue | - | 1 | 3.8363 | 7.2 | 528.41 | 1.363 | 11 | B3 | 58.2 |
| 24 | B06 | 3-Br-benzyl | C37 | 4-MeOC₆H₄ | 4-ClBs | B06C37 | blue | - | 1 | 3.8648 | 9.2 | 562.86 | 1.635 | 11 | B4 | 60.7 |
| 25 | B06 | 3-Br-benzyl | C38 | 4-MeOC₆H₄ | 2-Ts | B06C38 | blue | - | 1 | 3.9049 | 8.5 | 542.44 | 1.567 | 11 | B5 | 51.9 |
| 26 | B06 | 3-Br-benzyl | C39 | 3-MeOC₆H₄ | Ts | B06C39 | blue | - | 1 | 3.9614 | 7.3 | 542.44 | 1.346 | 11 | B6 | 55.3 |
| 27 | B06 | 3-Br-benzyl | C40 | 4-ClC₆H₄ | 2-Ts | B06C40 | blue | - | 1 | 3.9839 | 9.6 | 546.86 | 1.755 | 11 | B7 | 19.2 |
| 28 | B06 | 3-Br-benzyl | C41 | 4-MeC₆H₄ | 2-Ts | B06C41 | blue | - | 1 | 3.8955 | 8.3 | 526.44 | 1.577 | 11 | B8 | 50.0 |
| 29 | B06 | 3-Br-benzyl | C42 | 4-MeC₆H₄ | 2-MCBs | B06C42 | blue | - | 1 | 3.844 | 9.4 | 570.45 | 1.648 | 11 | B9 | 64.9 |
| 30 | B06 | 3-Br-benzyl | C43 | 4-MeC₆H₄ | Bs | B06C43 | blue | - | 1 | 3.9604 | 8.2 | 512.42 | 1.600 | 11 | B10 | 67.2 |
| 31 | B06 | 3-Br-benzyl | C46 | 4-MeC₆H₄ | Ms | B06C46 | blue | - | 1 | 4.0024 | 6.8 | 450.35 | 1.510 | 11 | B11 | 66.6 |

FIG. 19-3

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B07 | 3-Me-benzyl | C01 | Ph | Ts | B07C01 | green | - | 1 | 3.8955 | 4.6 | 447.55 | 1.028 | 11 | C2 | 64.9 |
| 2 | B07 | 3-Me-benzyl | C02 | 4-MeC₆H₄ | Ts | B07C02 | green | - | 1 | 3.9315 | 6.4 | 461.57 | 1.387 | 11 | C3 | 66.3 |
| 3 | B07 | 3-Me-benzyl | C03 | 4-EtC₆H₄ | Ts | B07C03 | green | - | 1 | 3.8319 | 7.1 | 475.6 | 1.493 | 11 | C4 | 60.5 |
| 4 | B07 | 3-Me-benzyl | C04 | 4-MeOC₆H₄ | Ts | B07C04 | green | - | 1 | 3.8146 | 6.5 | 477.57 | 1.361 | 11 | C5 | 67.3 |
| 5 | B07 | 3-Me-benzyl | C05 | 4-EtOC₆H₄ | Ts | B07C05 | green | - | 1 | 3.8454 | 5.2 | 491.6 | 1.058 | 11 | C6 | 65.3 |
| 6 | B07 | 3-Me-benzyl | C06 | piperonyl | Ts | B07C06 | green | - | 1 | 3.8279 | 7.5 | 491.56 | 1.526 | 11 | C7 | 70.6 |
| 7 | B07 | 3-Me-benzyl | C09 | 4-CNC₆H₄ | Ts | B07C09 | green | - | 1 | 3.8375 | 8.5 | 472.56 | 1.799 | 11 | C8 | 66.7 |
| 8 | B07 | 3-Me-benzyl | C10 | 2-FC₆H₄ | Ts | B07C10 | green | - | 1 | 3.9119 | 8 | 465.54 | 1.718 | 11 | C9 | 62.8 |
| 9 | B07 | 3-Me-benzyl | C11 | 4-ClC₆H₄ | Ts | B07C11 | green | - | 1 | 3.9136 | 8.7 | 481.99 | 1.805 | 11 | C10 | 66.0 |
| 10 | B07 | 3-Me-benzyl | C12 | 3-ClC₆H₄ | Ts | B07C12 | green | - | 1 | 3.8582 | 9.1 | 481.99 | 1.888 | 11 | C11 | 46.9 |
| 11 | B07 | 3-Me-benzyl | C13 | 3,4-di-ClC₆H₄ | Ts | B07C13 | green | - | 1 | 3.9343 | 7.7 | 516.44 | 1.491 | 11 | D2 | 20.2 |
| 12 | B07 | 3-Me-benzyl | C15 | 3-BrC₆H₄ | Ts | B07C15 | green | - | 1 | 3.8538 | 8.7 | 526.44 | 1.653 | 11 | D3 | 31.9 |
| 13 | B07 | 3-Me-benzyl | C19 | Ph | Ms | B07C19 | green | - | 1 | 3.884 | 6.8 | 371.45 | 1.831 | 11 | D4 | 68.1 |
| 14 | B07 | 3-Me-benzyl | C20 | 3,4-di-MeOC₆H₄ | Ts | B07C20 | green | - | 1 | 3.9643 | 7.4 | 507.6 | 1.458 | 11 | D5 | 76.0 |
| 15 | B07 | 3-Me-benzyl | C21 | 2-thiophene | Ts | B07C21 | green | - | 1 | 3.9299 | 5.2 | 453.57 | 1.146 | 11 | D6 | 68.9 |
| 16 | B07 | 3-Me-benzyl | C23 | 4-FC₆H₄ | Ts | B07C23 | green | - | 1 | 3.9591 | 7 | 465.54 | 1.504 | 11 | D7 | 78.1 |
| 17 | B07 | 3-Me-benzyl | C24 | 4-i-PrC₆H₄ | Ts | B07C24 | green | - | 1 | 3.7804 | 7.1 | 489.63 | 1.450 | 11 | D8 | 57.1 |
| 18 | B07 | 3-Me-benzyl | C26 | 3-FC₆H₄ | Ts | B07C26 | green | - | 1 | 3.7883 | 7.2 | 465.54 | 1.547 | 11 | D9 | 60.5 |
| 19 | B07 | 3-Me-benzyl | C27 | 4-ClC₆H₄ | 4-ClBs | B07C27 | green | - | 1 | 3.9212 | 7.7 | 502.41 | 1.533 | 11 | D10 | 39.5 |
| 20 | B07 | 3-Me-benzyl | C28 | 4-ClC₆H₄ | Ms | B07C28 | green | - | 1 | 3.8653 | 5.5 | 405.9 | 1.355 | 11 | D11 | 45.5 |
| 21 | B07 | 3-Me-benzyl | C30 | 4-MeC₆H₄ | 4-ClBs | B07C30 | green | - | 1 | 3.8135 | 7.1 | 481.99 | 1.473 | 11 | E2 | 59.5 |
| 22 | B07 | 3-Me-benzyl | C33 | 3-MeC₆H₄ | Ts | B07C33 | green | - | 1 | 3.7967 | 6 | 461.57 | 1.300 | 11 | E3 | 58.0 |
| 23 | B07 | 3-Me-benzyl | C35 | 4-MeOC₆H₄ | Bs | B07C35 | green | - | 1 | 3.9539 | 4.7 | 463.55 | 1.014 | 11 | E4 | 72.6 |
| 24 | B07 | 3-Me-benzyl | C37 | 4-MeOC₆H₄ | 4-ClBs | B07C37 | green | - | 1 | 3.8789 | 6.8 | 497.99 | 1.365 | 11 | E5 | 85.8 |
| 25 | B07 | 3-Me-benzyl | C38 | 4-MeOC₆H₄ | 2-Ts | B07C38 | green | - | 1 | 3.9593 | 6.1 | 477.57 | 1.277 | 11 | E6 | 61.3 |
| 26 | B07 | 3-Me-benzyl | C39 | 3-MeOC₆H₄ | Ts | B07C39 | green | - | 1 | 3.9299 | 5.8 | 477.57 | 1.214 | 11 | E7 | 98.6 |
| 27 | B07 | 3-Me-benzyl | C40 | 4-ClC₆H₄ | 2-Ts | B07C40 | green | - | 1 | 3.966 | 7.4 | 481.99 | 1.535 | 11 | E8 | 91.1 |
| 28 | B07 | 3-Me-benzyl | C41 | 4-MeC₆H₄ | 2-Ts | B07C41 | green | - | 1 | 3.8769 | 7.8 | 461.57 | 1.690 | 11 | E9 | 53.4 |
| 29 | B07 | 3-Me-benzyl | C42 | 4-MeC₆H₄ | 2-MCBs | B07C42 | green | - | 1 | 3.8449 | 7.9 | 505.58 | 1.563 | 11 | E10 | 54.2 |
| 30 | B07 | 3-Me-benzyl | C43 | 4-MeC₆H₄ | Bs | B07C43 | green | - | 1 | 3.9102 | 6.5 | 447.55 | 1.452 | 11 | E11 | 69.8 |
| 31 | B07 | 3-Me-benzyl | C46 | 4-MeC₆H₄ | Ms | B07C46 | green | - | 1 | 3.9858 | 5.8 | 385.48 | 1.505 | 11 | F2 | 56.0 |

FIG. 19-4

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B08 | 4-F-benzyl | C01 | Ph | Ts | B08C01 | brown | - | 1 | 3.9214 | 7 | 451.51 | 1.550 | 11 | F3 | 68.1 |
| 2 | B08 | 4-F-benzyl | C02 | 4-MeC₆H₄ | Ts | B08C02 | brown | - | 1 | 3.7781 | 7 | 465.54 | 1.504 | 11 | F4 | 67.7 |
| 3 | B08 | 4-F-benzyl | C03 | 4-EtC₆H₄ | Ts | B08C03 | brown | - | 1 | 3.8887 | 4.9 | 479.56 | 1.022 | 11 | F5 | 55.2 |
| 4 | B08 | 4-F-benzyl | C04 | 4-MeOC₆H₄ | Ts | B08C04 | brown | - | 1 | 3.8164 | 7 | 481.54 | 1.454 | 11 | F6 | 72.9 |
| 5 | B08 | 4-F-benzyl | C05 | 4-EtOC₆H₄ | Ts | B08C05 | brown | - | 1 | 3.8507 | 7.2 | 495.56 | 1.453 | 11 | F7 | 66.2 |
| 6 | B08 | 4-F-benzyl | C06 | piperonyl | Ts | B08C06 | brown | - | 1 | 3.8741 | 6.9 | 495.52 | 1.392 | 11 | F8 | 68.2 |
| 7 | B08 | 4-F-benzyl | C09 | 4-CNC₆H₄ | Ts | B08C09 | brown | - | 1 | 3.8586 | 7.3 | 476.52 | 1.532 | 11 | F9 | 65.1 |
| 8 | B08 | 4-F-benzyl | C10 | 2-FC₆H₄ | Ts | B08C10 | brown | - | 1 | 3.8925 | 9.3 | 469.5 | 1.981 | 11 | F10 | 56.0 |
| 9 | B08 | 4-F-benzyl | C11 | 4-ClC₆H₄ | Ts | B08C11 | brown | - | 1 | 3.8882 | 9.1 | 485.95 | 1.873 | 11 | F11 | 62.0 |
| 10 | B08 | 4-F-benzyl | C12 | 3-ClC₆H₄ | Ts | B08C12 | brown | - | 1 | 3.9663 | 9.8 | 485.95 | 2.017 | 11 | G2 | 60.6 |
| 11 | B08 | 4-F-benzyl | C13 | 3,4-di-ClC₆H₄ | Ts | B08C13 | brown | - | 1 | 3.8939 | 9.8 | 520.4 | 1.883 | 11 | G3 | 38.2 |
| 12 | B08 | 4-F-benzyl | C15 | 3-BrC₆H₄ | Ts | B08C15 | brown | - | 1 | 3.8558 | 9.6 | 530.41 | 1.810 | 11 | G4 | 62.7 |
| 13 | B08 | 4-F-benzyl | C19 | Ph | Ms | B08C19 | brown | - | 1 | 3.9448 | 6.7 | 375.41 | 1.785 | 11 | G5 | 67.2 |
| 14 | B08 | 4-F-benzyl | C20 | 3,4-di-MeOC₆H₄ | Ts | B08C20 | brown | - | 1 | 3.86 | 5.8 | 511.56 | 1.134 | 11 | G6 | 69.8 |
| 15 | B08 | 4-F-benzyl | C21 | 2-thiophene | Ts | B08C21 | brown | - | 1 | 3.8989 | 6.5 | 457.54 | 1.421 | 11 | G7 | 62.3 |
| 16 | B08 | 4-F-benzyl | C23 | 4-FC₆H₄ | Ts | B08C23 | brown | - | 1 | 3.8504 | 9.1 | 469.5 | 1.938 | 11 | G8 | 66.8 |
| 17 | B08 | 4-F-benzyl | C24 | 4-i-PrC₆H₄ | Ts | B08C24 | brown | - | 1 | 3.869 | 9.1 | 493.59 | 1.844 | 11 | G9 | 50.9 |
| 18 | B08 | 4-F-benzyl | C26 | 3-FC₆H₄ | Ts | B08C26 | brown | - | 1 | 3.8266 | 5.4 | 469.5 | 1.150 | 11 | G10 | 63.4 |
| 19 | B08 | 4-F-benzyl | C27 | 4-ClC₆H₄ | 4-ClBs | B08C27 | brown | - | 1 | 3.8285 | 7.6 | 506.37 | 1.501 | 11 | G11 | 43.5 |
| 20 | B08 | 4-F-benzyl | C28 | 4-ClC₆H₄ | Ms | B08C28 | brown | - | 1 | 3.8761 | 7.8 | 409.86 | 1.903 | 11 | H2 | 50.2 |
| 21 | B08 | 4-F-benzyl | C30 | 4-MeC₆H₄ | 4-ClBs | B08C30 | brown | - | 1 | 3.8284 | 8.7 | 485.95 | 1.790 | 11 | H3 | 60.0 |
| 22 | B08 | 4-F-benzyl | C33 | 3-MeC₆H₄ | Ts | B08C33 | brown | - | 1 | 3.9162 | 8.3 | 465.54 | 1.783 | 11 | H4 | 71.2 |
| 23 | B08 | 4-F-benzyl | C35 | 4-MeOC₆H₄ | Bs | B08C35 | brown | - | 1 | 3.9894 | 7.4 | 467.51 | 1.583 | 11 | H5 | 67.7 |
| 24 | B08 | 4-F-benzyl | C37 | 4-MeOC₆H₄ | 4-ClBs | B08C37 | brown | - | 1 | 3.8671 | 7.2 | 501.95 | 1.434 | 11 | H6 | 67.2 |
| 25 | B08 | 4-F-benzyl | C38 | 4-MeOC₆H₄ | 2-Ts | B08C38 | brown | - | 1 | 3.8833 | 7.1 | 481.54 | 1.474 | 11 | H7 | 66.1 |
| 26 | B08 | 4-F-benzyl | C39 | 3-MeOC₆H₄ | Ts | B08C39 | brown | - | 1 | 3.9112 | 6.5 | 481.54 | 1.350 | 11 | H8 | 65.0 |
| 27 | B08 | 4-F-benzyl | C40 | 4-ClC₆H₄ | 2-Ts | B08C40 | brown | - | 1 | 3.8755 | 9.5 | 485.95 | 1.955 | 11 | H9 | 28.8 |
| 28 | B08 | 4-F-benzyl | C41 | 4-MeC₆H₄ | 2-Ts | B08C41 | brown | - | 1 | 3.9781 | 6.5 | 465.54 | 1.396 | 11 | H10 | 50.9 |
| 29 | B08 | 4-F-benzyl | C42 | 4-MeC₆H₄ | 2-MCBs | B08C42 | brown | - | 1 | 3.8797 | 7.9 | 509.55 | 1.550 | 11 | H11 | 76.9 |
| 30 | B08 | 4-F-benzyl | C43 | 4-MeC₆H₄ | Bs | B08C43 | brown | - | 1 | 3.9832 | 7.6 | 451.51 | 1.683 | 12 | A2 | 68.1 |
| 31 | B08 | 4-F-benzyl | C46 | 4-MeC₆H₄ | Ms | B08C46 | brown | - | 1 | 3.9014 | 6.2 | 389.44 | 1.592 | 12 | A3 | 84.4 |

FIG. 19-5

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B09 | 4-Cl-benzyl | C01 | Ph | Ts | B09C01 | black | - | 1 | 3.8622 | 7.1 | 467.96 | 1.517 | 12 | A4 | 69.7 |
| 2 | B09 | 4-Cl-benzyl | C02 | 4-MeC₆H₄ | Ts | B09C02 | black | - | 1 | 3.934 | 8.1 | 481.99 | 1.631 | 12 | A5 | 67.4 |
| 3 | B09 | 4-Cl-benzyl | C03 | 4-EtC₆H₄ | Ts | B09C03 | black | - | 1 | 3.8639 | 8.2 | 496.02 | 1.653 | 12 | A6 | 89.8 |
| 4 | B09 | 4-Cl-benzyl | C04 | 4-MeOC₆H₄ | Ts | B09C04 | black | - | 1 | 3.7926 | 6.4 | 497.99 | 1.285 | 12 | A7 | 91.4 |
| 5 | B09 | 4-Cl-benzyl | C05 | 4-EtOC₆H₄ | Ts | B09C05 | black | - | 1 | 3.9027 | 6.1 | 512.02 | 1.191 | 12 | A8 | 71.6 |
| 6 | B09 | 4-Cl-benzyl | C06 | piperonyl | Ts | B09C06 | black | - | 1 | 3.8131 | 8.1 | 511.97 | 1.582 | 12 | A9 | 73.4 |
| 7 | B09 | 4-Cl-benzyl | C09 | 4-CNC₆H₄ | Ts | B09C09 | black | - | 1 | 3.8429 | 7 | 492.97 | 1.420 | 12 | A10 | 73.1 |
| 8 | B09 | 4-Cl-benzyl | C10 | 2-FC₆H₄ | Ts | B09C10 | black | - | 1 | 3.9037 | 6.1 | 485.95 | 1.255 | 12 | A11 | 58.2 |
| 9 | B09 | 4-Cl-benzyl | C11 | 4-ClC₆H₄ | Ts | B09C11 | black | - | 1 | 3.9635 | 7.9 | 502.41 | 1.572 | 12 | B2 | 52.8 |
| 10 | B09 | 4-Cl-benzyl | C12 | 3-ClC₆H₄ | Ts | B09C12 | black | - | 1 | 3.8343 | 7.5 | 502.41 | 1.493 | 12 | B3 | 60.4 |
| 11 | B09 | 4-Cl-benzyl | C13 | 3,4-di-ClC₆H₄ | Ts | B09C13 | black | - | 1 | 3.9104 | 7.9 | 536.85 | 1.472 | 12 | B4 | 21.3 |
| 12 | B09 | 4-Cl-benzyl | C15 | 3-BrC₆H₄ | Ts | B09C15 | black | - | 1 | 3.9064 | 8.2 | 546.86 | 1.499 | 12 | B5 | 68.1 |
| 13 | B09 | 4-Cl-benzyl | C19 | Ph | Ms | B09C19 | black | - | 1 | 3.9387 | 7.1 | 391.87 | 1.812 | 12 | B6 | 82.1 |
| 14 | B09 | 4-Cl-benzyl | C20 | 3,4-di-MeOC₆H₄ | Ts | B09C20 | black | - | 1 | 3.9088 | 7.7 | 528.02 | 1.458 | 12 | B7 | 83.2 |
| 15 | B09 | 4-Cl-benzyl | C21 | 2-thiophene | Ts | B09C21 | black | - | 1 | 3.8131 | 9.1 | 473.99 | 1.920 | 12 | B8 | 75.6 |
| 16 | B09 | 4-Cl-benzyl | C23 | 4-FC₆H₄ | Ts | B09C23 | black | - | 1 | 3.8636 | 7.2 | 485.95 | 1.482 | 12 | B9 | 64.8 |
| 17 | B09 | 4-Cl-benzyl | C24 | 4-i-PrC₆H₄ | Ts | B09C24 | black | - | 1 | 3.8089 | 8.3 | 510.04 | 1.627 | 12 | B10 | 57.6 |
| 18 | B09 | 4-Cl-benzyl | C26 | 3-FC₆H₄ | Ts | B09C26 | black | - | 1 | 3.9232 | 6.7 | 485.95 | 1.379 | 12 | B11 | 63.5 |
| 19 | B09 | 4-Cl-benzyl | C27 | 4-ClC₆H₄ | 4-ClBs | B09C27 | black | - | 1 | 3.8887 | 9 | 522.83 | 1.721 | 12 | C2 | 57.7 |
| 20 | B09 | 4-Cl-benzyl | C28 | 4-ClC₆H₄ | Ms | B09C28 | black | - | 1 | 3.8798 | 7.8 | 426.31 | 1.830 | 12 | C3 | 55.0 |
| 21 | B09 | 4-Cl-benzyl | C30 | 4-MeC₆H₄ | 4-ClBs | B09C30 | black | - | 1 | 3.9376 | 7.9 | 502.41 | 1.572 | 12 | C4 | 63.8 |
| 22 | B09 | 4-Cl-benzyl | C33 | 3-MeC₆H₄ | Ts | B09C33 | black | - | 1 | 3.8755 | 8.7 | 481.99 | 1.805 | 12 | C5 | 74.7 |
| 23 | B09 | 4-Cl-benzyl | C35 | 4-MeOC₆H₄ | Bs | B09C35 | black | - | 1 | 3.9022 | 6.7 | 483.96 | 1.384 | 12 | C6 | 86.8 |
| 24 | B09 | 4-Cl-benzyl | C37 | 4-MeOC₆H₄ | 4-ClBs | B09C37 | black | - | 1 | 3.8891 | 8.1 | 518.41 | 1.562 | 12 | C7 | 72.6 |
| 25 | B09 | 4-Cl-benzyl | C38 | 4-MeOC₆H₄ | 2-Ts | B09C38 | black | - | 1 | 3.9023 | 7.5 | 497.99 | 1.506 | 12 | C8 | 80.0 |
| 26 | B09 | 4-Cl-benzyl | C39 | 3-MeOC₆H₄ | Ts | B09C39 | black | - | 1 | 3.9709 | 6.9 | 497.99 | 1.386 | 12 | C9 | 54.1 |
| 27 | B09 | 4-Cl-benzyl | C40 | 4-ClC₆H₄ | 2-Ts | B09C40 | black | - | 1 | 3.9324 | 8.9 | 502.41 | 1.771 | 12 | C10 | 54.4 |
| 28 | B09 | 4-Cl-benzyl | C41 | 4-MeC₆H₄ | 2-Ts | B09C41 | black | - | 1 | 3.8729 | 8.2 | 481.99 | 1.701 | 12 | C11 | 86.8 |
| 29 | B09 | 4-Cl-benzyl | C42 | 4-MeC₆H₄ | 2-MCBs | B09C42 | black | - | 1 | 3.8961 | 8.1 | 526 | 1.540 | 12 | D2 | 81.4 |
| 30 | B09 | 4-Cl-benzyl | C43 | 4-MeC₆H₄ | Bs | B09C43 | black | - | 1 | 3.7927 | 7.1 | 467.96 | 1.517 | 12 | D3 | 79.9 |
| 31 | B09 | 4-Cl-benzyl | C46 | 4-MeC₆H₄ | Ms | B09C46 | black | - | 1 | 3.8474 | 7 | 405.9 | 1.725 | 12 | D4 | 79.1 |

FIG. 19-6

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B10 | 4-Br-benzyl | C01 | Ph | Ts | B10C01 | natural | - | 1 | 3.8618 | 7.6 | 512.42 | 1.433 | 12 | D5 | 74.6 |
| 2 | B10 | 4-Br-benzyl | C02 | 4-MeC₆H₄ | Ts | B10C02 | natural | - | 1 | 3.8264 | 8.7 | 526.44 | 1.653 | 12 | D6 | 68.1 |
| 3 | B10 | 4-Br-benzyl | C03 | 4-EtC₆H₄ | Ts | B10C03 | natural | - | 1 | 3.8567 | 7.8 | 540.47 | 1.443 | 12 | D7 | 69.2 |
| 4 | B10 | 4-Br-benzyl | C04 | 4-MeOC₆H₄ | Ts | B10C04 | natural | - | 1 | 3.9759 | 6.9 | 542.44 | 1.272 | 12 | D8 | 72.1 |
| 5 | B10 | 4-Br-benzyl | C05 | 4-EtOC₆H₄ | Ts | B10C05 | natural | - | 1 | 3.9174 | 6.9 | 556.47 | 1.240 | 12 | D9 | 79.4 |
| 6 | B10 | 4-Br-benzyl | C06 | piperonyl | Ts | B10C06 | natural | - | 1 | 3.9141 | 8.6 | 556.42 | 1.546 | 12 | D10 | 74.4 |
| 7 | B10 | 4-Br-benzyl | C09 | 4-CNC₆H₄ | Ts | B10C09 | natural | - | 1 | 3.9202 | 7.9 | 537.42 | 1.470 | 12 | D11 | 70.6 |
| 8 | B10 | 4-Br-benzyl | C10 | 2-FC₆H₄ | Ts | B10C10 | natural | - | 1 | 3.9717 | 8.2 | 530.41 | 1.546 | 12 | E2 | 72.8 |
| 9 | B10 | 4-Br-benzyl | C11 | 4-ClC₆H₄ | Ts | B10C11 | natural | - | 1 | 3.9209 | 10.1 | 546.86 | 1.847 | 12 | E3 | 57.5 |
| 10 | B10 | 4-Br-benzyl | C12 | 3-ClC₆H₄ | Ts | B10C12 | natural | - | 1 | 3.9545 | 9 | 546.86 | 1.646 | 12 | E4 | 69.2 |
| 11 | B10 | 4-Br-benzyl | C13 | 3,4-di-ClC₆H₄ | Ts | B10C13 | natural | - | 1 | 4.0275 | 10.2 | 581.31 | 1.755 | 12 | E5 | 22.8 |
| 12 | B10 | 4-Br-benzyl | C15 | 3-BrC₆H₄ | Ts | B10C15 | natural | - | 1 | 3.9462 | 8.5 | 591.31 | 1.437 | 12 | E6 | 57.9 |
| 13 | B10 | 4-Br-benzyl | C19 | Ph | Ms | B10C19 | natural | - | 1 | 3.938 | 6.6 | 436.32 | 1.513 | 12 | E7 | 83.6 |
| 14 | B10 | 4-Br-benzyl | C20 | 3,4-di-MeOC₆H₄ | Ts | B10C20 | natural | - | 1 | 3.8685 | 6.6 | 572.47 | 1.153 | 12 | E8 | 74.0 |
| 15 | B10 | 4-Br-benzyl | C21 | 2-thiophene | Ts | B10C21 | natural | - | 1 | 3.9122 | 6 | 518.44 | 1.157 | 12 | E9 | 71.2 |
| 16 | B10 | 4-Br-benzyl | C23 | 4-FC₆H₄ | Ts | B10C23 | natural | - | 1 | 3.9159 | 8.4 | 530.41 | 1.584 | 12 | E10 | 62.6 |
| 17 | B10 | 4-Br-benzyl | C24 | 4-i-PrC₆H₄ | Ts | B10C24 | natural | - | 1 | 3.8778 | 7.8 | 554.5 | 1.407 | 12 | E11 | 89.7 |
| 18 | B10 | 4-Br-benzyl | C26 | 3-FC₆H₄ | Ts | B10C26 | natural | - | 1 | 3.911 | 6.8 | 530.41 | 1.282 | 12 | F2 | 60.8 |
| 19 | B10 | 4-Br-benzyl | C27 | 4-ClC₆H₄ | 4-ClBs | B10C27 | natural | - | 1 | 3.8591 | 7.7 | 567.28 | 1.357 | 12 | F3 | 32.6 |
| 20 | B10 | 4-Br-benzyl | C28 | 4-ClC₆H₄ | Ms | B10C28 | natural | - | 1 | 3.938 | 9.3 | 470.76 | 1.976 | 12 | F4 | 53.6 |
| 21 | B10 | 4-Br-benzyl | C30 | 4-MeC₆H₄ | 4-ClBs | B10C30 | natural | - | 1 | 3.8572 | 8.3 | 546.86 | 1.518 | 12 | F5 | 69.5 |
| 22 | B10 | 4-Br-benzyl | C33 | 3-MeC₆H₄ | Ts | B10C33 | natural | - | 1 | 3.9298 | 7.4 | 526.44 | 1.406 | 12 | F6 | 73.5 |
| 23 | B10 | 4-Br-benzyl | C35 | 4-MeOC₆H₄ | Bs | B10C35 | natural | - | 1 | 3.8919 | 6.5 | 528.41 | 1.230 | 12 | F7 | 82.3 |
| 24 | B10 | 4-Br-benzyl | C37 | 4-MeOC₆H₄ | 4-ClBs | B10C37 | natural | - | 1 | 3.9217 | 7.2 | 562.86 | 1.279 | 12 | F8 | 76.2 |
| 25 | B10 | 4-Br-benzyl | C38 | 4-MeOC₆H₄ | 2-Ts | B10C38 | natural | - | 1 | 3.9291 | 5.7 | 542.44 | 1.051 | 12 | F9 | 63.7 |
| 26 | B10 | 4-Br-benzyl | C39 | 3-MeOC₆H₄ | Ts | B10C39 | natural | - | 1 | 3.9653 | 6 | 542.44 | 1.106 | 12 | F10 | 65.8 |
| 27 | B10 | 4-Br-benzyl | C40 | 4-ClC₆H₄ | 2-Ts | B10C40 | natural | - | 1 | 3.9146 | 8.6 | 546.86 | 1.573 | 12 | F11 | 36.6 |
| 28 | B10 | 4-Br-benzyl | C41 | 4-MeC₆H₄ | 2-Ts | B10C41 | natural | - | 1 | 3.8854 | 9.3 | 526.44 | 1.767 | 12 | G2 | 82.0 |
| 29 | B10 | 4-Br-benzyl | C42 | 4-MeC₆H₄ | 2-MCBs | B10C42 | natural | - | 1 | 3.9981 | 9.3 | 570.45 | 1.630 | 12 | G3 | 77.4 |
| 30 | B10 | 4-Br-benzyl | C43 | 4-MeC₆H₄ | Bs | B10C43 | natural | - | 1 | 3.8968 | 7.7 | 512.42 | 1.503 | 12 | G4 | 78.4 |
| 31 | B10 | 4-Br-benzyl | C46 | 4-MeC₆H₄ | Ms | B10C46 | natural | - | 1 | 3.8785 | 7.5 | 450.35 | 1.665 | 12 | G5 | 84.5 |

FIG. 19-7

| entry | acid | R¹ | imine | Ar | SO₂R² | label | spindle | cogs | # | tare | weight | MW | acetone | plate | well | Kras |
|---|---|---|---|---|---|---|---|---|---|---|---|---|---|---|---|---|
| 1 | B11 | 4-Me-benzyl | C01 | Ph | Ts | B11C01 | white | red | 1 | 3.8774 | 7.3 | 447.55 | 1.631 | 12 | G6 | 87.5 |
| 2 | B11 | 4-Me-benzyl | C02 | 4-MeC₆H₄ | Ts | B11C02 | white | red | 1 | 3.8779 | 7.7 | 461.57 | 1.568 | 12 | G7 | 73.6 |
| 3 | B11 | 4-Me-benzyl | C03 | 4-EtC₆H₄ | Ts | B11C03 | white | red | 1 | 3.9099 | 9 | 475.6 | 1.892 | 12 | G8 | 87.0 |
| 4 | B11 | 4-Me-benzyl | C04 | 4-MeOC₆H₄ | Ts | B11C04 | white | red | 1 | 3.9782 | 5.8 | 477.57 | 1.214 | 12 | G9 | 73.8 |
| 5 | B11 | 4-Me-benzyl | C05 | 4-EtOC₆H₄ | Ts | B11C05 | white | red | 1 | 3.927 | 4.7 | 491.6 | 0.956 | 12 | G10 | 63.2 |
| 6 | B11 | 4-Me-benzyl | C06 | piperonyl | Ts | B11C06 | white | red | 1 | 3.8986 | 7 | 491.56 | 1.424 | 12 | G11 | 75.7 |
| 7 | B11 | 4-Me-benzyl | C09 | 4-CNC₆H₄ | Ts | B11C09 | white | red | 1 | 4.0069 | 5.4 | 472.56 | 1.143 | 12 | H2 | 90.9 |
| 8 | B11 | 4-Me-benzyl | C10 | 2-FC₆H₄ | Ts | B11C10 | white | red | 1 | 3.9939 | 6.9 | 465.54 | 1.482 | 12 | H3 | 92.9 |
| 9 | B11 | 4-Me-benzyl | C11 | 4-ClC₆H₄ | Ts | B11C11 | white | red | 1 | 3.9314 | 7.5 | 481.99 | 1.556 | 12 | H4 | 60.7 |
| 10 | B11 | 4-Me-benzyl | C12 | 3-ClC₆H₄ | Ts | B11C12 | white | red | 1 | 3.9142 | 8.6 | 481.99 | 1.784 | 12 | H5 | 66.1 |
| 11 | B11 | 4-Me-benzyl | C13 | 3,4-di-ClC₆H₄ | Ts | B11C13 | white | red | 1 | 4.013 | 9.3 | 516.44 | 1.801 | 12 | H6 | 17.4 |
| 12 | B11 | 4-Me-benzyl | C15 | 3-BrC₆H₄ | Ts | B11C15 | white | red | 1 | 3.9324 | 8 | 526.44 | 1.520 | 12 | H7 | 67.4 |
| 13 | B11 | 4-Me-benzyl | C19 | Ph | Ms | B11C19 | white | red | 1 | 3.8997 | 6.1 | 371.45 | 1.642 | 12 | H8 | 90.4 |
| 14 | B11 | 4-Me-benzyl | C20 | 3,4-di-MeOC₆H₄ | Ts | B11C20 | white | red | 1 | 3.855 | 5.8 | 507.6 | 1.143 | 12 | H9 | 89.3 |
| 15 | B11 | 4-Me-benzyl | C21 | 2-thiophene | Ts | B11C21 | white | red | 1 | 3.8659 | 5.2 | 453.57 | 1.146 | 12 | H10 | 73.4 |
| 16 | B11 | 4-Me-benzyl | C23 | 4-FC₆H₄ | Ts | B11C23 | white | red | 1 | 3.8806 | 6.8 | 465.54 | 1.461 | 12 | H11 | 54.8 |
| 17 | B11 | 4-Me-benzyl | C24 | 4-i-PrC₆H₄ | Ts | B11C24 | white | red | 1 | 3.9042 | 7.9 | 489.63 | 1.613 | 13 | A2 | 63.7 |
| 18 | B11 | 4-Me-benzyl | C26 | 3-FC₆H₄ | Ts | B11C26 | white | red | 1 | 3.9227 | 7.9 | 465.54 | 1.697 | 13 | A3 | 81.3 |
| 19 | B11 | 4-Me-benzyl | C27 | 4-ClC₆H₄ | 4-ClBs | B11C27 | white | red | 1 | 3.948 | 8.1 | 502.41 | 1.612 | 13 | A4 | 53.9 |
| 20 | B11 | 4-Me-benzyl | C28 | 4-ClC₆H₄ | Ms | B11C28 | white | red | 1 | 3.9648 | 7.6 | 405.9 | 1.872 | 13 | A5 | 90.6 |
| 21 | B11 | 4-Me-benzyl | C30 | 4-MeC₆H₄ | 4-ClBs | B11C30 | white | red | 1 | 3.9023 | 7.2 | 481.99 | 1.494 | 13 | A6 | 53.0 |
| 22 | B11 | 4-Me-benzyl | C33 | 3-MeC₆H₄ | Ts | B11C33 | white | red | 1 | 3.9327 | 6.8 | 461.57 | 1.473 | 13 | A7 | 82.4 |
| 23 | B11 | 4-Me-benzyl | C35 | 4-MeOC₆H₄ | Bs | B11C35 | white | red | 1 | 3.9769 | 5.1 | 463.55 | 1.100 | 13 | A8 | 88.2 |
| 24 | B11 | 4-Me-benzyl | C37 | 4-MeOC₆H₄ | 4-ClBs | B11C37 | white | red | 1 | 3.9445 | 5.6 | 497.99 | 1.125 | 13 | A9 | 72.5 |
| 25 | B11 | 4-Me-benzyl | C38 | 4-MeOC₆H₄ | 2-Ts | B11C38 | white | red | 1 | 3.9482 | 6 | 477.57 | 1.256 | 13 | A10 | 86.0 |
| 26 | B11 | 4-Me-benzyl | C39 | 3-MeOC₆H₄ | Ts | B11C39 | white | red | 1 | 3.9644 | 5.3 | 477.57 | 1.110 | 13 | A11 | 63.1 |
| 27 | B11 | 4-Me-benzyl | C40 | 4-ClC₆H₄ | 2-Ts | B11C40 | white | red | 1 | 3.893 | 7.3 | 481.99 | 1.515 | 13 | B2 | 61.6 |
| 28 | B11 | 4-Me-benzyl | C41 | 4-MeC₆H₄ | 2-Ts | B11C41 | white | red | 1 | 3.9436 | 8.1 | 461.57 | 1.755 | 13 | B3 | 88.3 |
| 29 | B11 | 4-Me-benzyl | C42 | 4-MeC₆H₄ | 2-MCBs | B11C42 | white | red | 1 | 3.9048 | 6.6 | 505.58 | 1.305 | 13 | B4 | 89.4 |
| 30 | B11 | 4-Me-benzyl | C43 | 4-MeC₆H₄ | Bs | B11C43 | white | red | 1 | 3.8639 | 8 | 447.55 | 1.788 | 13 | B5 | 99.8 |
| 31 | B11 | 4-Me-benzyl | C46 | 4-MeC₆H₄ | Ms | B11C46 | white | red | 1 | 3.9685 | 6.2 | 385.48 | 1.608 | 13 | B6 | 78.0 |

FIG. 19-8

| entry | acid | R¹ | imine | Ar | SO₂R² | label | spindle | cogs | # | tare | weight | MW | acetone | plate | well | kRas |
|---|---|---|---|---|---|---|---|---|---|---|---|---|---|---|---|---|
| 1 | B12 | 4-t-Bu-benzyl | C01 | Ph | Ts | B12C01 | white | blue | 1 | 3.9389 | 6.5 | 489.63 | 1.328 | 13 | B7 | 75.2 |
| 2 | B12 | 4-t-Bu-benzyl | C02 | 4-MeC₆H₄ | Ts | B12C02 | white | blue | 1 | 3.9859 | 7.4 | 503.65 | 1.469 | 13 | B8 | 85.5 |
| 3 | B12 | 4-t-Bu-benzyl | C03 | 4-EtC₆H₄ | Ts | B12C03 | white | blue | 1 | 4.0035 | 8.2 | 517.68 | 1.584 | 13 | B9 | 79.7 |
| 4 | B12 | 4-t-Bu-benzyl | C04 | 4-MeOC₆H₄ | Ts | B12C04 | white | blue | 1 | 3.9366 | 6.5 | 519.65 | 1.251 | 13 | B10 | 91.1 |
| 5 | B12 | 4-t-Bu-benzyl | C05 | 4-EtOC₆H₄ | Ts | B12C05 | white | blue | 1 | 4.0016 | 4.7 | 533.68 | 0.881 | 13 | B11 | 58.7 |
| 6 | B12 | 4-t-Bu-benzyl | C06 | piperonyl | Ts | B12C06 | white | blue | 1 | 4.0039 | 5 | 533.64 | 0.937 | 13 | C2 | 87.2 |
| 7 | B12 | 4-t-Bu-benzyl | C09 | 4-CNC₆H₄ | Ts | B12C09 | white | blue | 1 | 3.9294 | 8.2 | 514.64 | 1.593 | 13 | C3 | 87.7 |
| 8 | B12 | 4-t-Bu-benzyl | C10 | 2-FC₆H₄ | Ts | B12C10 | white | blue | 1 | 3.9443 | 8 | 507.62 | 1.576 | 13 | C4 | 84.2 |
| 9 | B12 | 4-t-Bu-benzyl | C11 | 4-ClC₆H₄ | Ts | B12C11 | white | blue | 1 | 3.9831 | 7.8 | 524.07 | 1.488 | 13 | C5 | 102.5 |
| 10 | B12 | 4-t-Bu-benzyl | C12 | 3-ClC₆H₄ | Ts | B12C12 | white | blue | 1 | 3.9991 | 8.4 | 524.07 | 1.603 | 13 | C6 | 78.8 |
| 11 | B12 | 4-t-Bu-benzyl | C13 | 3,4-di-ClC₆H₄ | Ts | B12C13 | white | blue | 1 | 3.9228 | 8.6 | 558.52 | 1.540 | 13 | C7 | 74.3 |
| 12 | B12 | 4-t-Bu-benzyl | C15 | 3-BrC₆H₄ | Ts | B12C15 | white | blue | 1 | 3.8799 | 6.7 | 568.52 | 1.178 | 13 | C8 | 82.8 |
| 13 | B12 | 4-t-Bu-benzyl | C19 | Ph | Ms | B12C19 | white | blue | 1 | 3.9363 | 6.5 | 413.53 | 1.572 | 13 | C9 | 73.3 |
| 14 | B12 | 4-t-Bu-benzyl | C20 | 3,4-di-MeOC₆H₄ | Ts | B12C20 | white | blue | 1 | 3.8905 | 5.4 | 549.68 | 0.982 | 13 | C10 | 90.4 |
| 15 | B12 | 4-t-Bu-benzyl | C21 | 2-thiophene | Ts | B12C21 | white | blue | 1 | 3.8694 | 5.9 | 495.65 | 1.190 | 13 | C11 | 68.1 |
| 16 | B12 | 4-t-Bu-benzyl | C23 | 4-FC₆H₄ | Ts | B12C23 | white | blue | 1 | 3.8674 | 6.9 | 507.62 | 1.359 | 13 | D2 | 85.1 |
| 17 | B12 | 4-t-Bu-benzyl | C24 | 4-i-PrC₆H₄ | Ts | B12C24 | white | blue | 1 | 3.9922 | 5.1 | 531.71 | 0.959 | 13 | D3 | 88.3 |
| 18 | B12 | 4-t-Bu-benzyl | C26 | 3-FC₆H₄ | Ts | B12C26 | white | blue | 1 | 3.97 | 7.2 | 507.62 | 1.418 | 13 | D4 | 77.2 |
| 19 | B12 | 4-t-Bu-benzyl | C27 | 4-ClC₆H₄ | 4-ClBs | B12C27 | white | blue | 1 | 3.9913 | 8.1 | 544.49 | 1.488 | 13 | D5 | 110.0 |
| 20 | B12 | 4-t-Bu-benzyl | C28 | 4-ClC₆H₄ | Ms | B12C28 | white | blue | 1 | 3.9241 | 6.9 | 447.97 | 1.540 | 13 | D6 | 60.4 |
| 21 | B12 | 4-t-Bu-benzyl | C30 | 4-MeC₆H₄ | 4-ClBs | B12C30 | white | blue | 1 | 3.9865 | 7.1 | 524.07 | 1.355 | 13 | D7 | 74.4 |
| 22 | B12 | 4-t-Bu-benzyl | C33 | 3-MeC₆H₄ | Ts | B12C33 | white | blue | 1 | 3.917 | 7.4 | 503.65 | 1.469 | 13 | D8 | 56.1 |
| 23 | B12 | 4-t-Bu-benzyl | C35 | 4-MeOC₆H₄ | Bs | B12C35 | white | blue | 1 | 3.9422 | 5.6 | 505.63 | 1.108 | 13 | D9 | 82.2 |
| 24 | B12 | 4-t-Bu-benzyl | C37 | 4-MeOC₆H₄ | 4-ClBs | B12C37 | white | blue | 1 | 3.966 | 6.5 | 540.07 | 1.204 | 13 | D10 | 68.5 |
| 25 | B12 | 4-t-Bu-benzyl | C38 | 4-MeOC₆H₄ | 2-Ts | B12C38 | white | blue | 1 | 4.0067 | 6.5 | 519.65 | 1.251 | 13 | D11 | 70.7 |
| 26 | B12 | 4-t-Bu-benzyl | C39 | 3-MeOC₆H₄ | Ts | B12C39 | white | blue | 1 | 3.8941 | 6.3 | 519.65 | 1.212 | 13 | E2 | 95.8 |
| 27 | B12 | 4-t-Bu-benzyl | C40 | 4-ClC₆H₄ | 2-Ts | B12C40 | white | blue | 1 | 3.9123 | 8.8 | 524.07 | 1.679 | 13 | E3 | 97.3 |
| 28 | B12 | 4-t-Bu-benzyl | C41 | 4-MeC₆H₄ | 2-Ts | B12C41 | white | blue | 1 | 3.835 | 8.8 | 489.63 | 1.797 | 13 | E4 | 80.9 |
| 29 | B12 | 4-t-Bu-benzyl | C42 | 4-MeC₆H₄ | 2-MCBs | B12C42 | white | blue | 1 | 3.9042 | 7.9 | 547.66 | 1.443 | 13 | E5 | 110.7 |
| 30 | B12 | 4-t-Bu-benzyl | C43 | 4-MeC₆H₄ | Bs | B12C43 | white | blue | 1 | 3.9127 | 8.7 | 489.63 | 1.777 | 13 | E6 | 81.6 |
| 31 | B12 | 4-t-Bu-benzyl | C46 | 4-MeC₆H₄ | Ms | B12C46 | white | blue | 1 | 4.0169 | 6 | 427.56 | 1.403 | 13 | E7 | 78.2 |

FIG. 19-9

| entry | acid | R¹ | imine | Ar | SO₂R² | label | spindle | cogs | tare | weight | MW | acetone | plate | well | kRas |
|---|---|---|---|---|---|---|---|---|---|---|---|---|---|---|---|
| 1 | B01 | Me | C01 | Ph | Ts | Tebbe | B01C01T | natural | red | 3.9807 | 1.9 | 355.45 | 0.535 | 9 | A2 | 98.8 |
| 2 | B01 | Me | C02 | 4-MeC₆H₄ | Ts | Tebbe | B01C02T | natural | yellow | 3.9265 | 2.7 | 369.48 | 0.731 | 9 | A3 | 90.6 |
| 3 | B01 | Me | C03 | 4-EtC₆H₄ | Ts | Tebbe | B01C03T | natural | blue | 3.938 | 2.9 | 383.5 | 0.756 | 9 | A4 | 99.5 |
| 4 | B01 | Me | C04 | 4-MeOC₆H₄ | Ts | Tebbe | B01C04T | natural | red/green | 3.9139 | 1.8 | 385.48 | 0.467 | 9 | A5 | 99.7 |
| 5 | B01 | Me | C05 | 4-EtOC₆H₄ | Ts | Tebbe | B01C05T | natural | yellow/white | 3.9637 | 1.5 | 399.5 | 0.375 | 9 | A6 | 89.0 |
| 6 | B01 | Me | C06 | piperonyl | Ts | Tebbe | B01C06T | natural | green | 3.9901 | 3.2 | 399.46 | 0.801 | 9 | A7 | 104.3 |
| 7 | B01 | Me | C10 | 2-FC₆H₄ | Ts | Tebbe | B01C10T | natural | natural | 3.918 | 3.6 | 373.44 | 0.964 | 9 | A8 | 80.8 |
| 8 | B01 | Me | C11 | 4-ClC₆H₄ | Ts | Tebbe | B01C11T | natural | brown | 3.8492 | 3.6 | 389.9 | 0.923 | 9 | A9 | 80.8 |
| 9 | B01 | Me | C12 | 3-ClC₆H₄ | Ts | Tebbe | B01C12T | natural | black | 3.9816 | 4 | 389.9 | 1.026 | 9 | C5 | 86.0 |
| 10 | B01 | Me | C15 | 3-BrC₆H₄ | Ts | Tebbe | B01C15T | natural | blue/natural | 3.8968 | 2.6 | 434.35 | 0.599 | 9 | C6 | 104.9 |
| 11 | B01 | Me | C16 | 1-naphthyl | Ts | Tebbe | B01C16T | natural | blue/green | 3.9189 | 3.1 | 405.51 | 0.764 | 9 | A10 | 95.6 |
| 12 | B01 | Me | C20 | 3,4-di-MeOC₆H₄ | Ts | Tebbe | B01C20T | natural | white/natural | 3.989 | 2.5 | 415.5 | 0.602 | 9 | A11 | 83.8 |
| 13 | B01 | Me | C21 | 2-thiophene | Ts | Tebbe | B01C21T | natural | green/brown | 3.9351 | 2.5 | 361.48 | 0.692 | 9 | B2 | 90.3 |
| 14 | B01 | Me | C24 | 4-i-PrC₆H₄ | Ts | Tebbe | B01C24T | natural | brown/black | 3.926 | 2.9 | 397.53 | 0.730 | 9 | B3 | 105.4 |
| 15 | B01 | Me | C25 | 3,4,5-tri-MeOC₆H₄ | Ts | Tebbe | B01C25T | natural | white/black | 3.9282 | 2 | 445.53 | 0.449 | 9 | B4 | 92.3 |
| 16 | B01 | Me | C30 | 4-MeC₆H₄ | 4-ClBs | Tebbe | B01C30T | natural | blue/white | 3.9323 | 3.3 | 389.9 | 0.846 | 9 | B5 | 112.3 |
| 17 | B01 | Me | C33 | 3-MeC₆H₄ | Ts | Tebbe | B01C33T | natural | green/natural | 3.9545 | 2.3 | 369.48 | 0.622 | 9 | B6 | 101.5 |
| 18 | B01 | Me | C34 | 4-MeOC₆H₄ | 2-MCBs | Tebbe | B01C34T | natural | black/blue | 3.9149 | 1.8 | 429.49 | - | - | - | |
| 19 | B01 | Me | C35 | 4-MeOC₆H₄ | Bs | Tebbe | B01C35T | natural | red/white | 3.9877 | 2.6 | 371.45 | 0.700 | 9 | B7 | 110.4 |
| 20 | B01 | Me | C36 | 4-MeC₆H₄ | 2-Ns | Tebbe | B01C36T | natural | yellow/natural | 4.0217 | 0 | 400.45 | - | - | - | 110.5 |
| 21 | B01 | Me | C37 | 4-MeOC₆H₄ | 4-ClBs | Tebbe | B01C37T | natural | blue/brown | 3.986 | 2.5 | 405.8951 | 0.616 | 9 | B8 | |
| 22 | B01 | Me | C38 | 4-MeOC₆H₄ | 2-Ts | Tebbe | B01C38T | natural | green/black | 3.9966 | 3.5 | 385.48 | 0.908 | 9 | B9 | 77.3 |
| 23 | B01 | Me | C39 | 3-MeOC₆H₄ | Ts | Tebbe | B01C39T | natural | white/red | 3.9712 | 2 | 385.48 | 0.519 | 9 | B10 | 85.0 |
| 24 | B01 | Me | C40 | 4-ClC₆H₄ | 2-Ts | Tebbe | B01C40T | natural | white/brown | 3.9809 | 2 | 389.9 | 0.513 | 9 | B11 | 91.9 |
| 25 | B01 | Me | C41 | 4-MeC₆H₄ | 2-Ts | Tebbe | B01C41T | natural | natural/black | 3.967 | 3 | 369.48 | 0.812 | 9 | C2 | 85.3 |
| 26 | B01 | Me | C42 | 4-MeC₆H₄ | 2-MCBs | Tebbe | B01C42T | natural | natural/yellow | 3.9135 | 2.6 | 413.49 | - | - | - | |
| 27 | B01 | Me | C43 | 4-MeC₆H₄ | Bs | Tebbe | B01C43T | natural | brown/red | 3.9603 | 2 | 369.48 | 0.541 | 9 | C3 | 99.0 |
| 28 | B01 | Me | C46 | 4-MeC₆H₄ | Ms | Tebbe | B01C46T | natural | black/yellow | 3.9687 | 0.6 | 293.38 | 0.205 | 9 | C4 | 108.1 |

FIG. 19-10

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E01 | Ph | B01C01E01 | natural | red | 1 | 3.8732 | 2.9 | 467.60 | 0.620 | 13 | H4 | 49.3 |
| 2 | B01 | Me | C02 | 4-MeC₆H₄ | Ts | E01 | Ph | B01C02E01 | natural | yellow | 1 | 3.9642 | 4.2 | 481.63 | 0.872 | 13 | H5 | 63.2 |
| 3 | B01 | Me | C03 | 4-EtC₆H₄ | Ts | E01 | Ph | B01C03E01 | natural | blue | 1 | 3.8766 | 4.8 | 495.65 | 0.968 | 13 | H6 | 45.7 |
| 4 | B01 | Me | C04 | 4-MeOC₆H₄ | Ts | E01 | Ph | B01C04E01 | natural | red/green | 1 | 3.8694 | 4.6 | 497.63 | 0.924 | 13 | H7 | 79.6 |
| 5 | B01 | Me | C05 | 4-EtOC₆H₄ | Ts | E01 | Ph | B01C05E01 | natural | yellow/white | 1 | 3.977 | 4.0 | 511.65 | 0.782 | 13 | H8 | 61.1 |
| 6 | B01 | Me | C06 | piperonyl | Ts | E01 | Ph | B01C06E01 | natural | green | 1 | 3.9131 | 4.2 | 511.61 | 0.821 | 13 | H9 | 57.4 |
| 7 | B01 | Me | C10 | 2-FC₆H₄ | Ts | E01 | Ph | B01C10E01 | natural | natural | 1 | 3.9068 | 5.1 | 485.59 | 1.050 | 13 | H10 | 51.0 |
| 8 | B01 | Me | C11 | 4-ClC₆H₄ | Ts | E01 | Ph | B01C11E01 | natural | brown | 1 | 3.8946 | 4.7 | 502.05 | 0.936 | 13 | H11 | 40.0 |
| 9 | B01 | Me | C12 | 3-ClC₆H₄ | Ts | E01 | Ph | B01C12E01 | natural | black | 1 | 3.9593 | 4.2 | 502.05 | 0.837 | 14 | A02 | 87.5 |
| 10 | B01 | Me | C15 | 3-BrC₆H₄ | Ts | E01 | Ph | B01C15E01 | natural | blue/natural | 1 | 3.9062 | -- | 546.50 | -- | -- | -- | |
| 11 | B01 | Me | C20 | 3,4-di-MeOC₆H₄ | Ts | E01 | Ph | B01C20E01 | natural | white/natural | 1 | 3.8013 | 7.3 | 527.65 | 1.383 | 14 | A03 | 111.8 |
| 12 | B01 | Me | C25 | 3,4,5-tri-MeOC₆H₄ | Ts | E01 | Ph | B01C25E01 | natural | white/black | 1 | 3.8618 | 3.3 | 557.68 | 0.592 | 14 | A04 | 83.7 |
| 13 | B01 | Me | C30 | 4-MeC₆H₄ | 4-ClBs | E01 | Ph | B01C30E01 | natural | blue/white | 1 | 3.9321 | 4.2 | 502.05 | 0.837 | 14 | A05 | 87.1 |
| 14 | B01 | Me | C35 | 4-MeOC₆H₄ | Bs | E01 | Ph | B01C35E01 | natural | red/white | 1 | 3.9188 | 4.2 | 483.60 | 0.868 | 14 | A06 | 103.1 |
| 15 | B01 | Me | C37 | 4-MeOC₆H₄ | 4-ClBs | E01 | Ph | B01C37E01 | natural | blue/brown | 1 | 3.9052 | 4.7 | 518.04 | 0.907 | 14 | A07 | 97.2 |
| 16 | B01 | Me | C38 | 4-MeOC₆H₄ | 2-Ts | E01 | Ph | B01C38E01 | natural | green/black | 1 | 3.9938 | 5.1 | 497.63 | 1.025 | 14 | A08 | 84.8 |
| 17 | B01 | Me | C39 | 3-MeOC₆H₄ | Ts | E01 | Ph | B01C39E01 | natural | white/red | 1 | 3.8506 | 4.0 | 497.63 | 0.804 | 14 | A09 | 86.1 |
| 18 | B01 | Me | C40 | 4-ClC₆H₄ | 2-Ts | E01 | Ph | B01C40E01 | natural | white/brown | 1 | 3.8362 | 4.7 | 502.05 | 0.936 | 14 | A10 | 75.5 |
| 19 | B01 | Me | C41 | 4-MeC₆H₄ | 2-Ts | E01 | Ph | B01C41E01 | natural | natural/black | 1 | 3.8914 | 5.6 | 481.63 | 1.163 | 14 | A11 | 69.5 |
| 20 | B01 | Me | C43 | 4-MeC₆H₄ | Bs | E01 | Ph | B01C43E01 | natural | brown/red | 1 | 3.9219 | 4.6 | 467.60 | 0.984 | 14 | B02 | 92.0 |
| 21 | B01 | Me | C46 | 4-MeC₆H₄ | Ms | E01 | Ph | B01C46E01 | natural | black/yellow | 1 | 3.9448 | 2.6 | 405.53 | 0.641 | 14 | B03 | 99.6 |

FIG. 19-11

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E02 | p-tolyl | B01C01E02 | natural | red | 1 | 3.9863 | 3.0 | 481.63 | 0.6229 | 14 | B04 | 98.0 |
| 2 | B01 | Me | C02 | 4-MeC₆H₄ | Ts | E02 | p-tolyl | B01C02E02 | natural | yellow | 1 | 3.8286 | 4.7 | 495.65 | 0.9482 | 14 | B05 | 62.4 |
| 3 | B01 | Me | C03 | 4-EtC₆H₄ | Ts | E02 | p-tolyl | B01C03E02 | natural | blue | 1 | 3.9404 | 4.2 | 509.68 | 0.8240 | 14 | B06 | 85.0 |
| 4 | B01 | Me | C04 | 4-MeOC₆H₄ | Ts | E02 | p-tolyl | B01C04E02 | natural | red/green | 1 | 3.8774 | 4.2 | 511.65 | 0.8209 | 14 | B07 | 91.8 |
| 5 | B01 | Me | C05 | 4-EtOC₆H₄ | Ts | E02 | p-tolyl | B01C05E02 | natural | yellow/white | 1 | 3.9237 | 4.4 | 525.68 | 0.8370 | 14 | B08 | 65.4 |
| 6 | B01 | Me | C06 | piperonyl | Ts | E02 | p-tolyl | B01C06E02 | natural | green | 1 | 3.8646 | 5.5 | 525.64 | 1.0463 | 14 | B09 | 77.8 |
| 7 | B01 | Me | C10 | 2-FC₆H₄ | Ts | E02 | p-tolyl | B01C10E02 | natural | natural | 1 | 3.8964 | 4.2 | 499.62 | 0.8406 | 14 | B10 | 80.4 |
| 8 | B01 | Me | C11 | 4-ClC₆H₄ | Ts | E02 | p-tolyl | B01C11E02 | natural | brown | 1 | 3.8456 | 3.5 | 516.07 | 0.6782 | 14 | B11 | 76.1 |
| 9 | B01 | Me | C12 | 3-ClC₆H₄ | Ts | E02 | p-tolyl | B01C12E02 | natural | black | 1 | 3.9178 | 4.7 | 516.07 | 0.9107 | 14 | C02 | 88.8 |
| 10 | B01 | Me | C15 | 3-BrC₆H₄ | Ts | E02 | p-tolyl | B01C15E02 | natural | blue/natural | 1 | 3.9333 | 5.1 | 560.52 | 0.9099 | 14 | C03 | 94.0 |
| 12 | B01 | Me | C20 | 3,4-di-MeOC₆H₄ | Ts | E02 | p-tolyl | B01C20E02 | natural | white/natural | 1 | 3.9426 | 5.0 | 541.68 | 0.9231 | 14 | C04 | 105.3 |
| 15 | B01 | Me | C25 | 3,4,5-tri-MeOC₆H₄ | Ts | E02 | p-tolyl | B01C25E02 | natural | white/black | 1 | 3.9321 | 4.2 | 571.7 | 0.7347 | 14 | C05 | 95.6 |
| 16 | B01 | Me | C30 | 4-MeC₆H₄ | 4-ClBs | E02 | p-tolyl | B01C30E02 | natural | blue/white | 1 | 3.8999 | 3.5 | 516.07 | 0.6782 | 14 | C06 | 92.4 |
| 19 | B01 | Me | C35 | 4-MeOC₆H₄ | Bs | E02 | p-tolyl | B01C35E02 | natural | red/white | 1 | 3.8494 | 5.0 | 497.63 | 1.0048 | 14 | C07 | 84.8 |
| 21 | B01 | Me | C37 | 4-MeOC₆H₄ | 4-ClBs | E02 | p-tolyl | B01C37E02 | natural | blue/brown | 1 | 3.8587 | 4.9 | 532.07 | 0.9209 | 14 | C08 | 83.2 |
| 22 | B01 | Me | C38 | 4-MeOC₆H₄ | 2-Ts | E02 | p-tolyl | B01C38E02 | natural | green/black | 1 | 3.8726 | 6.2 | 511.65 | 1.2118 | 14 | C09 | 78.5 |
| 23 | B01 | Me | C39 | 3-MeOC₆H₄ | Ts | E02 | p-tolyl | B01C39E02 | natural | white/red | 1 | 3.8561 | 4.7 | 511.65 | 0.9186 | 14 | C10 | 77.0 |
| 24 | B01 | Me | C40 | 4-ClC₆H₄ | 2-Ts | E02 | p-tolyl | B01C40E02 | natural | white/brown | 1 | 3.9408 | 3.5 | 516.07 | 0.6782 | 14 | C11 | 74.8 |
| 25 | B01 | Me | C41 | 4-MeC₆H₄ | 2-Ts | E02 | p-tolyl | B01C41E02 | natural | natural/black | 1 | 3.9387 | 5.5 | 495.65 | 1.1097 | 14 | D02 | 92.4 |
| 27 | B01 | Me | C43 | 4-MeC₆H₄ | Bs | E02 | p-tolyl | B01C43E02 | natural | brown/red | 1 | 3.9434 | 3.5 | 481.63 | 0.7267 | 14 | D03 | 91.3 |
| 28 | B01 | Me | C46 | 4-MeC₆H₄ | Ms | E02 | p-tolyl | B01C46E02 | natural | black/yellow | 1 | 3.9046 | 2.1 | 419.56 | 0.5005 | 14 | D04 | 108.2 |

FIG. 19-12

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E04 | 4-MeOC₆H₄ | B01C01E04 | natural | red | 1 | 3.8506 | 2.7 | 497.63 | 0.543 | 14 | D05 | 99.1 |
| 2 | B01 | Me | C02 | 4-MeC₆H₄ | Ts | E04 | 4-MeOC₆H₄ | B01C02E04 | natural | yellow | 1 | 3.9265 | 3.3 | 511.65 | 0.645 | 14 | D06 | 78.4 |
| 3 | B01 | Me | C03 | 4-EtC₆H₄ | Ts | E04 | 4-MeOC₆H₄ | B01C03E04 | natural | blue | 1 | 3.9224 | 5.4 | 525.68 | 1.027 | 14 | D07 | 90.8 |
| 4 | B01 | Me | C04 | 4-MeOC₆H₄ | Ts | E04 | 4-MeOC₆H₄ | B01C04E04 | natural | red/green | 1 | 3.9047 | 4.4 | 527.65 | 0.834 | 14 | D08 | 97.0 |
| 5 | B01 | Me | C05 | 4-EtOC₆H₄ | Ts | E04 | 4-MeOC₆H₄ | B01C05E04 | natural | yellow/white | 1 | 3.8678 | 3.3 | 541.68 | 0.609 | 14 | D09 | 79.1 |
| 6 | B01 | Me | C06 | piperonyl | Ts | E04 | 4-MeOC₆H₄ | B01C06E04 | natural | green | 1 | 3.8998 | 4.6 | 541.64 | 0.849 | 14 | D10 | 100.2 |
| 7 | B01 | Me | C10 | 2-FC₆H₄ | Ts | E04 | 4-MeOC₆H₄ | B01C10E04 | natural | natural | 1 | 3.9335 | 4.4 | 515.62 | 0.853 | 14 | D11 | 100.4 |
| 8 | B01 | Me | C11 | 4-ClC₆H₄ | Ts | E04 | 4-MeOC₆H₄ | B01C11E04 | natural | brown | 1 | 3.9087 | 3.7 | 532.07 | 0.695 | 14 | E02 | 85.5 |
| 9 | B01 | Me | C12 | 3-ClC₆H₄ | Ts | E04 | 4-MeOC₆H₄ | B01C12E04 | natural | black | 1 | 3.8569 | 2.9 | 532.07 | 0.545 | 14 | E03 | 93.3 |
| 10 | B01 | Me | C15 | 3-BrC₆H₄ | Ts | E04 | 4-MeOC₆H₄ | B01C15E04 | natural | blue/natural | 1 | 3.8472 | 3.1 | 576.52 | 0.538 | 14 | E04 | 81.4 |
| 12 | B01 | Me | C20 | 3,4-di-MeOC₆H₄ | Ts | E04 | 4-MeOC₆H₄ | B01C20E04 | natural | white/natural | 1 | 3.8563 | 4.6 | 557.68 | 0.825 | 14 | E05 | 101.1 |
| 15 | B01 | Me | C25 | 3,4,5-tri-MeOC₆H₄ | Ts | E04 | 4-MeOC₆H₄ | B01C25E04 | natural | white/black | 1 | 3.8551 | 4.4 | 587.7 | 0.749 | 14 | E06 | 110.1 |
| 18 | B01 | Me | C30 | 4-MeC₆H₄ | 4-ClBs | E04 | 4-MeOC₆H₄ | B01C30E04 | natural | blue/white | 1 | 3.9156 | 4.7 | 532.07 | 0.883 | 14 | E07 | 82.7 |
| 19 | B01 | Me | C35 | 4-MeOC₆H₄ | Bs | E04 | 4-MeOC₆H₄ | B01C35E04 | natural | red/white | 1 | 3.8763 | 4.4 | 513.63 | 0.857 | 14 | E08 | 90.5 |
| 21 | B01 | Me | C37 | 4-MeOC₆H₄ | 4-ClBs | E04 | 4-MeOC₆H₄ | B01C37E04 | natural | blue/brown | 1 | 3.9268 | 4.5 | 548.07 | 0.821 | 14 | E09 | 80.8 |
| 22 | B01 | Me | C38 | 4-MeOC₆H₄ | 2-Ts | E04 | 4-MeOC₆H₄ | B01C38E04 | natural | green/black | 1 | 3.8617 | 5.3 | 527.65 | 1.004 | 14 | E10 | 82.2 |
| 23 | B01 | Me | C39 | 3-MeOC₆H₄ | Ts | E04 | 4-MeOC₆H₄ | B01C39E04 | natural | white/red | 1 | 3.9261 | 3.9 | 527.65 | 0.739 | 14 | E11 | 101.1 |
| 24 | B01 | Me | C40 | 4-ClC₆H₄ | 2-Ts | E04 | 4-MeOC₆H₄ | B01C40E04 | natural | white/brown | 1 | 3.9051 | 4.4 | 532.07 | 0.827 | 14 | F02 | 85.6 |
| 25 | B01 | Me | C41 | 4-MeC₆H₄ | 2-Ts | E04 | 4-MeOC₆H₄ | B01C41E04 | natural | natural/black | 1 | 3.8401 | 4.8 | 511.65 | 0.938 | 14 | F03 | 97.5 |
| 27 | B01 | Me | C43 | 4-MeC₆H₄ | Bs | E04 | 4-MeOC₆H₄ | B01C43E04 | natural | brown/red | 1 | 3.9369 | 4.4 | 497.63 | 0.884 | 14 | F04 | 100.3 |
| 28 | B01 | Me | C46 | 4-MeC₆H₄ | Ms | E04 | 4-MeOC₆H₄ | B01C46E04 | natural | black/yellow | 1 | 3.8727 | 2.4 | 435.56 | 0.551 | 14 | F05 | 99.0 |

FIG. 19-13

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E05 | 4-ClC₆H₄ | B01C01E05 | natural | red | 1 | 3.8894 | 3.4 | 502.05 | 0.677 | 14 | F06 | 64.1 |
| 2 | B01 | Me | C02 | 4-MeC₆H₄ | Ts | E05 | 4-ClC₆H₄ | B01C02E05 | natural | yellow | 1 | 3.8852 | 4.5 | 516.07 | 0.872 | 14 | F07 | 57.0 |
| 3 | B01 | Me | C03 | 4-EtC₆H₄ | Ts | E05 | 4-ClC₆H₄ | B01C03E05 | natural | blue | 1 | 3.861 | 5.5 | 530.10 | 1.038 | 14 | F08 | 72.0 |
| 4 | B01 | Me | C04 | 4-MeOC₆H₄ | Ts | E05 | 4-ClC₆H₄ | B01C04E05 | natural | red/green | 1 | 3.9823 | 4.1 | 532.07 | 0.771 | 14 | F09 | 55.3 |
| 5 | B01 | Me | C05 | 4-EtOC₆H₄ | Ts | E05 | 4-ClC₆H₄ | B01C05E05 | natural | yellow/white | 1 | 3.8432 | 3.2 | 546.10 | 0.586 | 14 | F10 | 72.4 |
| 6 | B01 | Me | C06 | piperonyl | Ts | E05 | 4-ClC₆H₄ | B01C06E05 | natural | green | 1 | 3.8678 | 4.4 | 546.05 | 0.806 | 14 | F11 | 90.9 |
| 7 | B01 | Me | C10 | 2-FC₆H₄ | Ts | E05 | 4-ClC₆H₄ | B01C10E05 | natural | natural | 1 | 3.9699 | 3.8 | 520.04 | 0.731 | 14 | G02 | 88.8 |
| 8 | B01 | Me | C11 | 4-ClC₆H₄ | Ts | E05 | 4-ClC₆H₄ | B01C11E05 | natural | brown | 1 | 3.9399 | 3.9 | 536.49 | 0.727 | 14 | G03 | 52.1 |
| 9 | B01 | Me | C12 | 3-ClC₆H₄ | Ts | E05 | 4-ClC₆H₄ | B01C12E05 | natural | black | 1 | 3.8433 | 4.3 | 536.49 | 0.802 | 14 | G04 | 110.9 |
| 10 | B01 | Me | C15 | 3-BrC₆H₄ | Ts | E05 | 4-ClC₆H₄ | B01C15E05 | natural | blue/natural | 1 | 3.9949 | 3.0 | 580.94 | 0.516 | 14 | G05 | 120.4 |
| 12 | B01 | Me | C20 | 3,4-di-MeOC₆H₄ | Ts | E05 | 4-ClC₆H₄ | B01C20E05 | natural | white/natural | 1 | 3.8867 | 4.0 | 562.10 | 0.712 | 14 | G06 | 106.8 |
| 15 | B01 | Me | C25 | 3,4,5-tri-MeOC₆H₄ | Ts | E05 | 4-ClC₆H₄ | B01C25E05 | natural | white/black | 1 | 3.9411 | 3.4 | 592.12 | 0.574 | 14 | H5 | 102.5 |
| 18 | B01 | Me | C30 | 4-MeC₆H₄ | 4-ClBs | E05 | 4-ClC₆H₄ | B01C30E05 | natural | blue/white | 1 | 3.9281 | 3.6 | 536.49 | 0.857 | 14 | G07 | 42.3 |
| 19 | B01 | Me | C35 | 4-MeOC₆H₄ | Bs | E05 | 4-ClC₆H₄ | B01C35E05 | natural | red/white | 1 | 3.8418 | 3.8 | 518.04 | 0.734 | 14 | G08 | 88.8 |
| 21 | B01 | Me | C37 | 4-MeOC₆H₄ | 4-ClBs | E05 | 4-ClC₆H₄ | B01C37E05 | natural | blue/brown | 1 | 3.8116 | 2.0 | 552.49 | 0.362 | 14 | G09 | 73.2 |
| 22 | B01 | Me | C38 | 4-MeOC₆H₄ | 2-Ts | E05 | 4-ClC₆H₄ | B01C38E05 | natural | green/black | 1 | 3.9441 | 6.0 | 532.07 | 1.128 | 14 | G10 | 72.2 |
| 23 | B01 | Me | C39 | 3-MeOC₆H₄ | Ts | E05 | 4-ClC₆H₄ | B01C39E05 | natural | white/red | 1 | 3.9557 | 4.4 | 532.07 | 0.827 | 14 | G11 | 60.3 |
| 24 | B01 | Me | C40 | 4-ClC₆H₄ | 2-Ts | E05 | 4-ClC₆H₄ | B01C40E05 | natural | white/brown | 1 | 3.9516 | 4.9 | 536.49 | 0.913 | 14 | H02 | 83.5 |
| 25 | B01 | Me | C41 | 4-MeC₆H₄ | 2-Ts | E05 | 4-ClC₆H₄ | B01C41E05 | natural | natural/black | 1 | 3.9135 | 5.2 | 516.07 | 1.008 | 14 | H03 | 6.0 |
| 27 | B01 | Me | C43 | 4-MeC₆H₄ | Bs | E05 | 4-ClC₆H₄ | B01C43E05 | natural | brown/red | 1 | 3.8689 | 4.4 | 502.05 | 0.876 | 14 | H04 | 78.3 |
| 28 | B01 | Me | C46 | 4-MeC₆H₄ | Ms | E05 | 4-ClC₆H₄ | B01C46E05 | natural | black/yellow | 1 | 3.8796 | 3.5 | 439.98 | 0.795 | 14 | H05 | 105.4 |

FIG. 19-14

| entry | acid | R¹ | imine | Ar | SO₂R² | thiol | R⁴ | label | spindle | cogs | # | tare | weight | MW | acetone | plate | well | kRas |
|---|---|---|---|---|---|---|---|---|---|---|---|---|---|---|---|---|---|---|
| 1 | B01 | Me | C01 | Ph | Ts | E06 | Bn | B01C01E06 | natural | red | 1 | 3.9616 | 4.6 | 481.63 | 0.955 | 14 | H07 | 92.1 |
| 2 | B01 | Me | C02 | 4-MeC₆H₄ | Ts | E06 | Bn | B01C02E06 | natural | yellow | 1 | 3.8659 | 6.0 | 495.65 | 1.332 | 14 | H08 | 93.1 |
| 3 | B01 | Me | C03 | 4-EtC₆H₄ | Ts | E06 | Bn | B01C03E06 | natural | blue | 1 | 3.8649 | 5.7 | 509.68 | 1.118 | 14 | H09 | 63.1 |
| 4 | B01 | Me | C04 | 4-MeOC₆H₄ | Ts | E06 | Bn | B01C04E06 | natural | red/green | 1 | 3.9465 | 5.0 | 511.65 | 0.977 | 14 | H10 | 104.7 |
| 5 | B01 | Me | C05 | 4-EtOC₆H₄ | Ts | E06 | Bn | B01C05E06 | natural | yellow/white | 1 | 3.8547 | 5.1 | 525.68 | 0.970 | 15 | H11 | 50.9 |
| 6 | B01 | Me | C06 | piperonyl | Ts | E06 | Bn | B01C06E06 | natural | green | 1 | 3.8915 | 6.5 | 525.64 | 1.237 | 15 | A02 | 63.1 |
| 7 | B01 | Me | C10 | 2-FC₆H₄ | Ts | E06 | Bn | B01C10E06 | natural | natural | 1 | 3.8897 | 5.3 | 499.62 | 1.061 | 15 | A03 | 12.8 |
| 8 | B01 | Me | C11 | 4-ClC₆H₄ | Ts | E06 | Bn | B01C11E06 | natural | brown | 1 | 3.8707 | 5.3 | 516.07 | 1.027 | 15 | A04 | 11.5 |
| 9 | B01 | Me | C12 | 3-ClC₆H₄ | Ts | E06 | Bn | B01C12E06 | natural | black | 1 | 3.8287 | 5.3 | 516.07 | 1.027 | 15 | A05 | 11.5 |
| 10 | B01 | Me | C15 | 3-BrC₆H₄ | Ts | E06 | Bn | B01C15E06 | natural | blue/natural | 1 | 3.9097 | 5.3 | 560.52 | 0.946 | 15 | A06 | 5.5 |
| 12 | B01 | Me | C20 | 3,4-di-MeOC₆H₃ | Ts | E06 | Bn | B01C20E06 | natural | white/natural | 1 | 3.8934 | 5.7 | 541.68 | 1.052 | 15 | A07 | 54.5 |
| 15 | B01 | Me | C25 | 3,4,5-tri-MeOC₆H₂ | Ts | E06 | Bn | B01C25E06 | natural | white/black | 1 | 3.8767 | 4.6 | 571.7 | 0.805 | 15 | A08 | 63.7 |
| 16 | B01 | Me | C30 | 4-MeC₆H₄ | 4-ClBs | E06 | Bn | B01C30E06 | natural | blue/white | 1 | 3.9451 | 5.9 | 516.07 | 1.143 | 15 | A09 | 40.3 |
| 19 | B01 | Me | C35 | 4-MeOC₆H₄ | Bs | E06 | Bn | B01C35E06 | natural | red/white | 1 | 3.855 | 6.5 | 497.63 | 1.306 | 15 | A10 | 57.3 |
| 21 | B01 | Me | C37 | 4-MeOC₆H₄ | 4-ClBs | E06 | Bn | B01C37E06 | natural | blue/brown | 1 | 3.8879 | 5.2 | 532.07 | 0.977 | 15 | A11 | 28.7 |
| 22 | B01 | Me | C38 | 4-MeOC₆H₄ | 2-Ts | E06 | Bn | B01C38E06 | natural | green/black | 1 | 3.9986 | 5.8 | 511.65 | 1.134 | 15 | B02 | 33.9 |
| 23 | B01 | Me | C39 | 3-MeOC₆H₄ | Ts | E06 | Bn | B01C39E06 | natural | white/red | 1 | 3.897 | 5.2 | 511.65 | 1.016 | 15 | B03 | 85.0 |
| 24 | B01 | Me | C40 | 4-ClC₆H₄ | 2-Ts | E06 | Bn | B01C40E06 | natural | white/brown | 1 | 3.9815 | 6.7 | 516.07 | 1.298 | 15 | B04 | 8.7 |
| 25 | B01 | Me | C41 | 4-MeC₆H₄ | 2-Ts | E06 | Bn | B01C41E06 | natural | natural/black | 1 | 3.9729 | 5.7 | 495.65 | 1.150 | 15 | B05 | 32.0 |
| 27 | B01 | Me | C43 | 4-MeC₆H₄ | Bs | E06 | Bn | B01C43E06 | natural | brown/red | 1 | 3.855 | 5.6 | 481.63 | 1.163 | 15 | B06 | 47.4 |
| 28 | B01 | Me | C46 | 4-MeC₆H₄ | Ms | E06 | Bn | B01C46E06 | natural | black/yellow | 1 | 3.8994 | 2.7 | 419.56 | 0.644 | 15 | B07 | 81.8 |

FIG. 19-15

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E07 | t-butyl-Bn | B01C01E07 | natural | red | 1 | 3.896 | 3.2 | 537.73 | 0.595 | 15 | B08 | 55.9 |
| 2 | B01 | Me | C02 | 4-MeC₆H₄ | Ts | E07 | t-butyl-Bn | B01C02E07 | natural | yellow | 1 | 3.891 | 5.3 | 551.76 | 0.961 | 15 | B09 | 69.6 |
| 3 | B01 | Me | C03 | 4-EtC₆H₄ | Ts | E07 | t-butyl-Bn | B01C03E07 | natural | blue | 1 | 3.7687 | 3.4 | 565.79 | 0.601 | 15 | B10 | 64.4 |
| 4 | B01 | Me | C04 | 4-MeOC₆H₄ | Ts | E07 | t-butyl-Bn | B01C04E07 | natural | red/green | 1 | 3.8702 | 4.7 | 567.76 | 0.828 | 15 | B11 | 44.1 |
| 5 | B01 | Me | C05 | 4-EtOC₆H₄ | Ts | E07 | t-butyl-Bn | B01C05E07 | natural | yellow/white | 1 | 3.8308 | 3.4 | 581.79 | 0.584 | 15 | C02 | 46.0 |
| 6 | B01 | Me | C06 | piperonyl | Ts | E07 | t-butyl-Bn | B01C06E07 | natural | green | 1 | 3.8332 | 3.7 | 581.74 | 0.636 | 15 | C03 | 59.3 |
| 7 | B01 | Me | C10 | 2-FC₆H₄ | Ts | E07 | t-butyl-Bn | B01C10E07 | natural | natural | 1 | 3.9286 | 3.5 | 555.72 | 0.630 | 15 | C04 | 71.9 |
| 8 | B01 | Me | C11 | 4-ClC₆H₄ | Ts | E07 | t-butyl-Bn | B01C11E07 | natural | brown | 1 | 3.8349 | -- | 572.18 | -- | -- | -- | -- |
| 9 | B01 | Me | C12 | 3-ClC₆H₄ | Ts | E07 | t-butyl-Bn | B01C12E07 | natural | black | 1 | 3.8751 | 3.5 | 572.18 | 0.612 | 15 | C05 | 89.6 |
| 10 | B01 | Me | C15 | 3-BrC₆H₄ | Ts | E07 | t-butyl-Bn | B01C15E07 | natural | blue/natural | 1 | 3.6783 | -- | 616.63 | -- | -- | -- | -- |
| 12 | B01 | Me | C20 | 3,4-di-MeOC₆H₃ | Ts | E07 | t-butyl-Bn | B01C20E07 | natural | white/natural | 1 | 3.8476 | 3.9 | 597.79 | 0.652 | 15 | C06 | 78.9 |
| 15 | B01 | Me | C25 | 3,4,5-tri-MeOC₆H₂ | Ts | E07 | t-butyl-Bn | B01C25E07 | natural | white/black | 1 | 3.8807 | 3.9 | 627.81 | 0.621 | 15 | C07 | 71.3 |
| 16 | B01 | Me | C30 | 4-MeC₆H₄ | 4-ClBs | E07 | t-butyl-Bn | B01C30E07 | natural | blue/white | 1 | 3.8425 | 4.6 | 572.18 | 0.804 | 15 | C08 | 62.0 |
| 19 | B01 | Me | C35 | 4-MeOC₆H₄ | Bs | E07 | t-butyl-Bn | B01C35E07 | natural | red/white | 1 | 3.9073 | 4.0 | 553.73 | 0.722 | 15 | C09 | 53.0 |
| 21 | B01 | Me | C37 | 4-MeOC₆H₄ | 4-ClBs | E07 | t-butyl-Bn | B01C37E07 | natural | blue/brown | 1 | 3.8754 | 5.1 | 588.18 | 0.867 | 15 | C10 | 66.0 |
| 22 | B01 | Me | C38 | 4-MeOC₆H₄ | 2-Ts | E07 | t-butyl-Bn | B01C38E07 | natural | green/black | 1 | 3.8498 | 4.7 | 567.76 | 0.828 | 15 | C11 | 67.2 |
| 23 | B01 | Me | C39 | 3-MeOC₆H₄ | Ts | E07 | t-butyl-Bn | B01C39E07 | natural | white/red | 1 | 3.847 | 2.7 | 567.76 | 0.476 | 15 | D02 | 69.5 |
| 24 | B01 | Me | C40 | 4-ClC₆H₄ | 2-Ts | E07 | t-butyl-Bn | B01C40E07 | natural | white/brown | 1 | 3.8246 | 5.4 | 572.18 | 0.944 | 15 | D03 | 43.1 |
| 25 | B01 | Me | C41 | 4-MeC₆H₄ | 2-Ts | E07 | t-butyl-Bn | B01C41E07 | natural | natural/black | 1 | 3.7918 | 5.0 | 551.76 | 0.906 | 15 | D04 | 69.5 |
| 27 | B01 | Me | C43 | 4-MeC₆H₄ | Bs | E07 | t-butyl-Bn | B01C43E07 | natural | brown/red | 1 | 3.8519 | 3.0 | 537.73 | 0.558 | 15 | D05 | 68.1 |
| 28 | B01 | Me | C46 | 4-MeC₆H₄ | Ms | E07 | t-butyl-Bn | B01C46E07 | natural | black/yellow | 1 | 3.8051 | -- | 475.66 | -- | -- | -- | -- |

FIG. 19-16

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E09 | 4-Cl-Bn | B01C01E09 | natural | red | 1 | 3.889 | 3.3 | 516.07 | 0.639 | 15 | D06 | 23.7 |
| 2 | B01 | Me | C02 | 4-MeC₆H₄ | Ts | E09 | 4-Cl-Bn | B01C02E09 | natural | yellow | 1 | 3.8385 | 6.2 | 530.10 | 1.170 | 15 | D07 | 50.9 |
| 3 | B01 | Me | C03 | 4-EtC₆H₄ | Ts | E09 | 4-Cl-Bn | B01C03E09 | natural | blue | 1 | 3.7836 | 6.6 | 544.13 | 1.213 | 15 | D08 | 43.7 |
| 4 | B01 | Me | C04 | 4-MeOC₆H₄ | Ts | E09 | 4-Cl-Bn | B01C04E09 | natural | red/green | 1 | 3.8243 | 5.7 | 546.10 | 1.044 | 15 | D09 | 40.7 |
| 5 | B01 | Me | C05 | 4-EtOC₆H₄ | Ts | E09 | 4-Cl-Bn | B01C05E09 | natural | yellow/white | 1 | 3.8294 | 4.3 | 560.12 | 0.768 | 15 | D10 | 3.1 |
| 6 | B01 | Me | C06 | piperonyl | Ts | E09 | 4-Cl-Bn | B01C06E09 | natural | green | 1 | 3.8105 | 5.5 | 560.08 | 0.982 | 15 | D11 | 37.4 |
| 7 | B01 | Me | C10 | 2-FC₆H₄ | Ts | E09 | 4-Cl-Bn | B01C10E09 | natural | natural | 1 | 3.8252 | 5.6 | 534.06 | 1.049 | 15 | E02 | 61.4 |
| 8 | B01 | Me | C11 | 4-ClC₆H₄ | Ts | E09 | 4-Cl-Bn | B01C11E09 | natural | brown | 1 | 3.8216 | 5.0 | 550.52 | 0.908 | 15 | E03 | 15.5 |
| 9 | B01 | Me | C12 | 3-ClC₆H₄ | Ts | E09 | 4-Cl-Bn | B01C12E09 | natural | black | 1 | 3.9109 | 5.3 | 550.52 | 0.963 | 15 | E04 | 13.5 |
| 10 | B01 | Me | C15 | 3-BrC₆H₄ | Ts | E09 | 4-Cl-Bn | B01C15E09 | natural | blue/natural | 1 | 3.8292 | 4.7 | 594.97 | 0.790 | 15 | E05 | 8.0 |
| 12 | B01 | Me | C20 | 3,4-di-MeOC₆H₄ | Ts | E09 | 4-Cl-Bn | B01C20E09 | natural | white/natural | 1 | 3.89 | 5.2 | 576.12 | 0.903 | 15 | E06 | 69.1 |
| 15 | B01 | Me | C25 | 3,4,5-tri-MeOC₆H₄ | Ts | E09 | 4-Cl-Bn | B01C25E09 | natural | white/black | 1 | 3.8448 | 4.2 | 606.15 | 0.693 | 15 | E07 | 44.9 |
| 16 | B01 | Me | C30 | 4-MeC₆H₄ | 4-ClBs | E09 | 4-Cl-Bn | B01C30E09 | natural | blue/white | 1 | 3.8422 | 5.4 | 550.52 | 0.981 | 15 | E08 | 30.8 |
| 19 | B01 | Me | C35 | 4-MeOC₆H₄ | Bs | E09 | 4-Cl-Bn | B01C35E09 | natural | red/white | 1 | 3.8601 | 5.7 | 532.07 | 1.071 | 15 | E09 | 31.9 |
| 21 | B01 | Me | C37 | 4-MeOC₆H₄ | 4-ClBs | E09 | 4-Cl-Bn | B01C37E09 | natural | blue/brown | 1 | 3.8813 | 6.1 | 566.52 | 1.077 | 15 | E10 | 27.1 |
| 22 | B01 | Me | C38 | 4-MeOC₆H₄ | 2-Ts | E09 | 4-Cl-Bn | B01C38E09 | natural | green/black | 1 | 3.8913 | 6.8 | 546.10 | 1.245 | 15 | E11 | 23.9 |
| 23 | B01 | Me | C39 | 3-MeOC₆H₄ | Ts | E09 | 4-Cl-Bn | B01C39E09 | natural | white/red | 1 | 3.8978 | 4.7 | 546.10 | 0.861 | 15 | F02 | 64.3 |
| 24 | B01 | Me | C40 | 4-ClC₆H₄ | 2-Ts | E09 | 4-Cl-Bn | B01C40E09 | natural | white/brown | 1 | 3.8191 | 6.8 | 550.52 | 1.235 | 15 | F03 | 21.5 |
| 25 | B01 | Me | C41 | 4-MeC₆H₄ | 2-Ts | E09 | 4-Cl-Bn | B01C41E09 | natural | natural/black | 1 | 3.8507 | 6.6 | 530.10 | 1.245 | 15 | F04 | 20.4 |
| 27 | B01 | Me | C43 | 4-MeC₆H₄ | Bs | E09 | 4-Cl-Bn | B01C43E09 | natural | brown/red | 1 | 3.7896 | 4.8 | 516.07 | 0.930 | 15 | F05 | 22.0 |
| 28 | B01 | Me | C46 | 4-MeC₆H₄ | Ms | E09 | 4-Cl-Bn | B01C46E09 | natural | black/yellow | 1 | 3.8314 | 2.4 | 454.00 | 0.529 | 15 | F06 | 51.1 |

FIG. 19-17

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E15 | phenethyl | B01C01E15 | natural | red | 1 | 3.8461 | 4.5 | 495.65 | 0.908 | 15 | F07 | 16.5 |
| 2 | B01 | Me | C02 | 4-MeC₆H₄ | Ts | E15 | phenethyl | B01C02E15 | natural | yellow | 1 | 3.875 | 5.9 | 509.68 | 1.158 | 15 | F08 | 22.6 |
| 3 | B01 | Me | C03 | 4-EtC₆H₄ | Ts | E15 | phenethyl | B01C03E15 | natural | blue | 1 | 3.8484 | 6.2 | 523.71 | 1.184 | 15 | F09 | 2.3 |
| 4 | B01 | Me | C04 | 4-MeOC₆H₄ | Ts | E15 | phenethyl | B01C04E15 | natural | red/green | 1 | 3.8852 | 5.9 | 525.68 | 1.122 | 15 | F10 | 28.8 |
| 5 | B01 | Me | C05 | 4-EtOC₆H₄ | Ts | E15 | phenethyl | B01C05E15 | natural | yellow/white | 1 | 3.8121 | 5.7 | 539.71 | 1.056 | 15 | F11 | 24.6 |
| 6 | B01 | Me | C06 | piperonyl | Ts | E15 | phenethyl | B01C06E15 | natural | green | 1 | 3.827 | 6.7 | 539.66 | 1.242 | 15 | G02 | 6.5 |
| 7 | B01 | Me | C10 | 2-FC₆H₄ | Ts | E15 | phenethyl | B01C10E15 | natural | natural | 1 | 3.9042 | 4.4 | 513.64 | 0.857 | 15 | G03 | 3.4 |
| 8 | B01 | Me | C11 | 4-ClC₆H₄ | Ts | E15 | phenethyl | B01C11E15 | natural | brown | 1 | 3.8294 | 6.1 | 530.1 | 1.151 | 15 | G04 | 15.1 |
| 9 | B01 | Me | C12 | 3-ClC₆H₄ | Ts | E15 | phenethyl | B01C12E15 | natural | black | 1 | 3.8474 | 4.5 | 530.1 | 0.849 | 15 | G05 | 4.8 |
| 10 | B01 | Me | C15 | 3-BrC₆H₄ | Ts | E15 | phenethyl | B01C15E15 | natural | blue/natural | 1 | 3.8581 | 5.4 | 574.55 | 0.940 | 15 | G06 | 4.7 |
| 12 | B01 | Me | C20 | 3,4-di-MeOC₆H₄ | Ts | E15 | phenethyl | B01C20E15 | natural | white/natural | 1 | 3.8956 | 5.2 | 555.71 | 0.936 | 15 | G07 | 44.1 |
| 15 | B01 | Me | C25 | 3,4,5-tri-MeOC₆H₄ | Ts | E15 | phenethyl | B01C25E15 | natural | white/black | 1 | 3.9577 | 5.4 | 585.73 | 0.922 | 15 | G08 | 43.5 |
| 16 | B01 | Me | C30 | 4-MeC₆H₄ | 4-ClBs | E15 | phenethyl | B01C30E15 | natural | blue/white | 1 | 3.8662 | 6.3 | 530.1 | 1.188 | 15 | G09 | 22.7 |
| 19 | B01 | Me | C35 | 4-MeOC₆H₄ | Bs | E15 | phenethyl | B01C35E15 | natural | red/white | 1 | 3.8656 | 6.2 | 511.65 | 1.212 | 15 | G10 | 28.3 |
| 21 | B01 | Me | C37 | 4-MeOC₆H₄ | 4-ClBs | E15 | phenethyl | B01C37E15 | natural | blue/brown | 1 | 3.8388 | 7.1 | 546.1 | 1.300 | 15 | G11 | 75.3 |
| 22 | B01 | Me | C38 | 4-MeOC₆H₄ | 2-Ts | E15 | phenethyl | B01C38E15 | natural | green/black | 1 | 3.8252 | 5.9 | 525.68 | 1.122 | 15 | H02 | 19.6 |
| 23 | B01 | Me | C39 | 3-MeOC₆H₄ | Ts | E15 | phenethyl | B01C39E15 | natural | white/red | 1 | 3.8815 | 4.4 | 525.68 | 0.837 | 15 | H03 | 20.8 |
| 24 | B01 | Me | C40 | 4-ClC₆H₄ | 2-Ts | E15 | phenethyl | B01C40E15 | natural | white/brown | 1 | 3.8926 | 6.0 | 530.1 | 1.132 | 15 | H04 | 12.6 |
| 25 | B01 | Me | C41 | 4-MeC₆H₄ | 2-Ts | E15 | phenethyl | B01C41E15 | natural | natural/black | 1 | 3.9346 | 8.0 | 509.68 | 1.570 | 15 | H05 | 10.2 |
| 27 | B01 | Me | C43 | 4-MeC₆H₄ | Bs | E15 | phenethyl | B01C43E15 | natural | brown/red | 1 | 3.9186 | 5.6 | 495.65 | 1.130 | 15 | H06 | 55.5 |
| 28 | B01 | Me | C46 | 4-MeC₆H₄ | Ms | E15 | phenethyl | B01C46E15 | natural | black/yellow | 1 | 3.8611 | 4.3 | 433.58 | 0.992 | 15 | H07 | 76.9 |

FIG. 19-18

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E16 | ethyl | B01C01E16 | natural | red | 1 | 3.865 | 2.9 | 419.56 | 0.691 | 15 | H08 | 94.8 |
| 2 | B01 | Me | C02 | 4-MeC₆H₄ | Ts | E16 | ethyl | B01C02E16 | natural | yellow | 1 | 3.9705 | 4.5 | 433.58 | 1.038 | 15 | H09 | 90.1 |
| 3 | B01 | Me | C03 | 4-EtC₆H₄ | Ts | E16 | ethyl | B01C03E16 | natural | blue | 1 | 3.9011 | 4.4 | 447.61 | 0.983 | 15 | H10 | 84.6 |
| 4 | B01 | Me | C04 | 4-MeOC₆H₄ | Ts | E16 | ethyl | B01C04E16 | natural | red/green | 1 | 3.8476 | 4.5 | 449.58 | 1.001 | 15 | H11 | 96.3 |
| 5 | B01 | Me | C05 | 4-EtOC₆H₄ | Ts | E16 | ethyl | B01C05E16 | natural | yellow/white | 1 | 3.8122 | 4.0 | 463.61 | 0.863 | 16 | A02 | 87.1 |
| 6 | B01 | Me | C06 | piperonyl | Ts | E16 | ethyl | B01C06E16 | natural | green | 1 | 3.8865 | 5.8 | 463.57 | 1.251 | 16 | A03 | 91.5 |
| 7 | B01 | Me | C10 | 2-FC₆H₄ | Ts | E16 | ethyl | B01C10E16 | natural | natural | 1 | 3.9316 | 3.0 | 437.55 | 0.686 | 16 | A04 | 89.4 |
| 8 | B01 | Me | C11 | 4-ClC₆H₄ | Ts | E16 | ethyl | B01C11E16 | natural | brown | 1 | 3.9173 | 4.8 | 454.00 | 1.057 | 16 | A05 | 87.8 |
| 9 | B01 | Me | C12 | 3-ClC₆H₄ | Ts | E16 | ethyl | B01C12E16 | natural | black | 1 | 3.8136 | 2.8 | 454.00 | 0.617 | 16 | A06 | 75.7 |
| 10 | B01 | Me | C15 | 3-BrC₆H₄ | Ts | E16 | ethyl | B01C15E16 | natural | blue/natural | 1 | 3.816 | 4.0 | 498.45 | 0.802 | 16 | A07 | 82.7 |
| 12 | B01 | Me | C20 | 3,4-di-MeOC₆H₄ | Ts | E16 | ethyl | B01C20E16 | natural | white/natural | 1 | 3.8718 | 5.9 | 479.61 | 1.230 | 16 | A08 | 74.4 |
| 15 | B01 | Me | C25 | 3,4,5-tri-MeOC₆H₄ | Ts | E16 | ethyl | B01C25E16 | natural | white/black | 1 | 3.8229 | 3.8 | 509.64 | 0.746 | 16 | A09 | 90.4 |
| 16 | B01 | Me | C30 | 4-MeC₆H₄ | 4-ClBs | E16 | ethyl | B01C30E16 | natural | blue/white | 1 | 3.8114 | 3.4 | 454.00 | 0.749 | 16 | A10 | 58.3 |
| 19 | B01 | Me | C35 | 4-MeOC₆H₄ | Bs | E16 | ethyl | B01C35E16 | natural | red/white | 1 | 3.8337 | 3.2 | 435.56 | 0.735 | 16 | A11 | 89.9 |
| 21 | B01 | Me | C37 | 4-MeOC₆H₄ | 4-ClBs | E16 | ethyl | B01C37E16 | natural | blue/brown | 1 | 3.8623 | 3.7 | 470.00 | 0.787 | 16 | B02 | 72.9 |
| 22 | B01 | Me | C38 | 4-MeOC₆H₄ | 2-Ts | E16 | ethyl | B01C38E16 | natural | green/black | 1 | 3.8007 | 5.4 | 449.58 | 1.201 | 16 | B03 | 71.1 |
| 23 | B01 | Me | C39 | 3-MeOC₆H₄ | Ts | E16 | ethyl | B01C39E16 | natural | white/red | 1 | 3.931 | 3.0 | 449.58 | 0.667 | 16 | B04 | 84.8 |
| 24 | B01 | Me | C40 | 4-ClC₆H₄ | 2-Ts | E16 | ethyl | B01C40E16 | natural | white/brown | 1 | 3.8443 | 4.3 | 454.00 | 0.947 | 16 | B05 | 63.2 |
| 25 | B01 | Me | C41 | 4-MeC₆H₄ | 2-Ts | E16 | ethyl | B01C41E16 | natural | natural/black | 1 | 3.8599 | 4.5 | 433.58 | 1.038 | 16 | B06 | 83.6 |
| 27 | B01 | Me | C43 | 4-MeC₆H₄ | Bs | E16 | ethyl | B01C43E16 | natural | brown/red | 1 | 3.8731 | 2.7 | 419.56 | 0.644 | 16 | B07 | 95.0 |
| 28 | B01 | Me | C46 | 4-MpC₆H₄ | Ms | E16 | ethyl | B01C46E16 | natural | black/yellow | 1 | 3.8102 | 2.2 | 357.49 | 0.615 | 16 | B08 | 94.8 |

FIG. 19-19

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E18 | n-propyl | B01C01E18 | natural | red | 1 | 3.8177 | 3.5 | 433.58 | 0.807 | 16 | B09 | 75.7 |
| 2 | B01 | Me | C02 | 4-MeC₆H₄ | Ts | E18 | n-propyl | B01C02E18 | natural | yellow | 1 | 3.7956 | 3.6 | 447.61 | 0.804 | 16 | B10 | 69.8 |
| 3 | B01 | Me | C03 | 4-EtC₆H₄ | Ts | E18 | n-propyl | B01C03E18 | natural | blue | 1 | 3.7926 | 4.5 | 461.64 | 0.975 | 16 | B11 | 69.0 |
| 4 | B01 | Me | C04 | 4-MeOC₆H₄ | Ts | E18 | n-propyl | B01C04E18 | natural | red/green | 1 | 3.9556 | 5.5 | 463.61 | 1.273 | 16 | C02 | 88.9 |
| 5 | B01 | Me | C05 | 4-EtOC₆H₄ | Ts | E18 | n-propyl | B01C05E18 | natural | yellow/white | 1 | 3.9316 | 4.8 | 477.64 | 1.005 | 16 | C03 | 84.9 |
| 6 | B01 | Me | C06 | piperonyl | Ts | E18 | n-propyl | B01C06E18 | natural | green | 1 | 3.8653 | 4.0 | 477.59 | 0.838 | 16 | C04 | 83.6 |
| 7 | B01 | Me | C10 | 2-FC₆H₄ | Ts | E18 | n-propyl | B01C10E18 | natural | natural | 1 | 3.8491 | 4.4 | 451.57 | 0.974 | 16 | C05 | 91.1 |
| 8 | B01 | Me | C11 | 4-ClC₆H₄ | Ts | E18 | n-propyl | B01C11E18 | natural | brown | 1 | 3.907 | 4.1 | 468.03 | 0.876 | 16 | C06 | 71.0 |
| 9 | B01 | Me | C12 | 3-ClC₆H₄ | Ts | E18 | n-propyl | B01C12E18 | natural | black | 1 | 3.8735 | 4.0 | 468.03 | 0.855 | 16 | C07 | 78.8 |
| 10 | B01 | Me | C15 | 3-BrC₆H₄ | Ts | E18 | n-propyl | B01C15E18 | natural | blue/natural | 1 | 3.913 | 3.0 | 512.48 | 0.585 | 16 | C08 | 88.5 |
| 12 | B01 | Me | C20 | 3,4-di-MeOC₆H₄ | Ts | E18 | n-propyl | B01C20E18 | natural | white/natural | 1 | 3.9107 | 5.5 | 493.64 | 1.114 | 16 | C09 | 91.4 |
| 15 | B01 | Me | C25 | 3,4,5-tri-MeOC₆H₄ | Ts | E18 | n-propyl | B01C25E18 | natural | white/black | 1 | 3.8825 | 5.1 | 523.66 | 0.974 | 16 | C10 | 75.0 |
| 16 | B01 | Me | C30 | 4-MeC₆H₄ | 4-ClBs | E18 | n-propyl | B01C30E18 | natural | blue/white | 1 | 3.8971 | 5.6 | 468.03 | 1.197 | 16 | C11 | 83.2 |
| 19 | B01 | Me | C35 | 4-MeOC₆H₄ | Bs | E18 | n-propyl | B01C35E18 | natural | red/white | 1 | 3.8437 | 4.9 | 449.58 | 1.090 | 16 | D02 | 89.5 |
| 21 | B01 | Me | C37 | 4-MeOC₆H₄ | 4-ClBs | E18 | n-propyl | B01C37E18 | natural | blue/brown | 1 | 3.8386 | 5.7 | 484.03 | 1.178 | 16 | D03 | 72.8 |
| 22 | B01 | Me | C38 | 4-MeOC₆H₄ | 2-Ts | E18 | n-propyl | B01C38E18 | natural | green/black | 1 | 3.9102 | 4.6 | 463.61 | 0.992 | 16 | D04 | 88.4 |
| 23 | B01 | Me | C39 | 3-MeOC₆H₄ | Ts | E18 | n-propyl | B01C39E18 | natural | white/red | 1 | 3.8693 | 2.2 | 463.61 | 0.475 | 16 | D05 | 73.9 |
| 24 | B01 | Me | C40 | 4-ClC₆H₄ | 2-Ts | E18 | n-propyl | B01C40E18 | natural | white/brown | 1 | 3.8098 | 4.3 | 468.03 | 0.919 | 16 | D06 | 53.3 |
| 25 | B01 | Me | C41 | 4-MeC₆H₄ | 2-Ts | E18 | n-propyl | B01C41E18 | natural | natural/black | 1 | 3.8928 | 5.3 | 447.61 | 1.184 | 16 | D07 | 59.4 |
| 27 | B01 | Me | C43 | 4-MeC₆H₄ | Bs | E18 | n-propyl | B01C43E18 | natural | brown/red | 1 | 3.8736 | 3.8 | 433.58 | 0.876 | 16 | D08 | 100.2 |
| 28 | B01 | Me | C46 | 4-MeC₆H₄ | Ms | E18 | n-propyl | B01C46E18 | natural | black/yellow | 1 | 3.8808 | 1.7 | 371.51 | 0.458 | 16 | D09 | 96.8 |

FIG. 19-20

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E21 | isobutyl | B01C01E21 | natural | red | 1 | 3.9056 | 2.7 | 447.61 | 0.603 | 16 | D10 | 85.18 |
| 2 | B01 | Me | C02 | 4-MeC₆H₄ | Ts | E21 | isobutyl | B01C02E21 | natural | yellow | 1 | 3.8244 | 4.2 | 461.64 | 0.910 | 16 | D11 | 83.5 |
| 3 | B01 | Me | C03 | 4-EtC₆H₄ | Ts | E21 | isobutyl | B01C03E21 | natural | blue | 1 | 3.8117 | 4.3 | 475.66 | 0.904 | 16 | E02 | 68.5 |
| 4 | B01 | Me | C04 | 4-MeOC₆H₄ | Ts | E21 | isobutyl | B01C04E21 | natural | red/green | 1 | 3.8978 | 5.3 | 477.64 | 1.110 | 16 | E03 | 79.3 |
| 5 | B01 | Me | C05 | 4-EtOC₆H₄ | Ts | E21 | isobutyl | B01C05E21 | natural | yellow/white | 1 | 3.8669 | 4.0 | 491.66 | 0.814 | 16 | E04 | 83.1 |
| 6 | B01 | Me | C06 | piperonyl | Ts | E21 | isobutyl | B01C06E21 | natural | green | 1 | 3.89 | 4.4 | 491.62 | 0.895 | 16 | E05 | 81.7 |
| 7 | B01 | Me | C10 | 2-FC₆H₄ | Ts | E21 | isobutyl | B01C10E21 | natural | natural | 1 | 3.8233 | 3.3 | 465.6 | 0.709 | 16 | E06 | 56.8 |
| 8 | B01 | Me | C11 | 4-ClC₆H₄ | Ts | E21 | isobutyl | B01C11E21 | natural | brown | 1 | 3.886 | 4.4 | 482.06 | 0.913 | 16 | E07 | 86.8 |
| 9 | B01 | Me | C12 | 3-ClC₆H₄ | Ts | E21 | isobutyl | B01C12E21 | natural | black | 1 | 3.844 | 2.0 | 482.06 | 0.415 | 16 | E08 | 79.7 |
| 10 | B01 | Me | C15 | 3-BrC₆H₄ | Ts | E21 | isobutyl | B01C15E21 | natural | blue/natural | 1 | 3.9015 | 3.7 | 526.51 | 0.703 | 16 | E09 | 18.8 |
| 12 | B01 | Me | C20 | 3,4-di-MeOC₆H₄ | Ts | E21 | isobutyl | B01C20E21 | natural | white/natural | 1 | 3.8282 | 5.0 | 507.66 | 0.985 | 16 | E10 | 91.6 |
| 15 | B01 | Me | C25 | 3,4,5-tri-MeOC₆H₄ | Ts | E21 | isobutyl | B01C25E21 | natural | white/black | 1 | 3.8494 | 3.4 | 537.69 | 0.632 | 16 | E11 | 98.3 |
| 16 | B01 | Me | C30 | 4-MeC₆H₄ | 4-ClBs | E21 | isobutyl | B01C30E21 | natural | blue/white | 1 | 3.9195 | 2.7 | 482.06 | 0.560 | 16 | F02 | 66.3 |
| 19 | B01 | Me | C35 | 4-MeOC₆H₄ | Bs | E21 | isobutyl | B01C35E21 | natural | red/white | 1 | 3.8147 | 4.3 | 463.61 | 0.928 | 16 | F03 | 70.2 |
| 21 | B01 | Me | C37 | 4-MeOC₆H₄ | 4-ClBs | E21 | isobutyl | B01C37E21 | natural | blue/brown | 1 | 3.9109 | 5.2 | 498.06 | 1.044 | 16 | F04 | 75.6 |
| 22 | B01 | Me | C38 | 4-MeOC₆H₄ | 2-Ts | E21 | isobutyl | B01C38E21 | natural | green/black | 1 | 3.9356 | 4.6 | 477.64 | 0.963 | 16 | F05 | 79.7 |
| 23 | B01 | Me | C39 | 3-MeOC₆H₄ | Ts | E21 | isobutyl | B01C39E21 | natural | white/red | 1 | 3.7871 | 2.9 | 477.64 | 0.607 | 16 | F06 | 64.5 |
| 24 | B01 | Me | C40 | 4-ClC₆H₄ | 2-Ts | E21 | isobutyl | B01C40E21 | natural | white/brown | 1 | 3.9283 | 5.0 | 482.06 | 1.037 | 16 | F07 | 76.1 |
| 25 | B01 | Me | C41 | 4-MeC₆H₄ | 2-Ts | E21 | isobutyl | B01C41E21 | natural | natural/black | 1 | 3.8467 | 4.4 | 461.64 | 0.953 | 16 | F08 | 78.3 |
| 27 | B01 | Me | C43 | 4-MeC₆H₄ | Bs | E21 | isobutyl | B01C43E21 | natural | brown/red | 1 | 3.8999 | 3.7 | 447.61 | 0.827 | 16 | F09 | 51.0 |
| 28 | B01 | Me | C46 | 4-MeC₆H₄ | Ms | E21 | isobutyl | B01C46E21 | natural | black/yellow | 1 | 3.8727 | 1.7 | 385.54 | 0.441 | 16 | F10 | 73.1 |

FIG. 19-21

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E22 | n-butyl | B01C01E22 | natural | red | 1 | 3.8861 | 1.9 | 447.61 | 0.424 | 16 | F11 | 93.4 |
| 2 | B01 | Me | C02 | 4-MeC₆H₄ | Ts | E22 | n-butyl | B01C02E22 | natural | yellow | 1 | 3.8289 | 2.9 | 461.64 | 0.628 | 16 | G02 | 82.6 |
| 3 | B01 | Me | C03 | 4-EtC₆H₄ | Ts | E22 | n-butyl | B01C03E22 | natural | blue | 1 | 3.8376 | 4.7 | 475.66 | 0.988 | 16 | G03 | 58.3 |
| 4 | B01 | Me | C04 | 4-MeOC₆H₄ | Ts | E22 | n-butyl | B01C04E22 | natural | red/green | 1 | 3.9387 | 4.7 | 477.64 | 0.984 | 16 | G04 | 74.5 |
| 5 | B01 | Me | C05 | 4-EtOC₆H₄ | Ts | E22 | n-butyl | B01C05E22 | natural | yellow/white | 1 | 3.8325 | 4.0 | 491.66 | 0.814 | 16 | G05 | 66.0 |
| 6 | B01 | Me | C06 | piperonyl | Ts | E22 | n-butyl | B01C06E22 | natural | green | 1 | 3.9076 | 3.9 | 491.62 | 0.793 | 16 | G06 | 80.4 |
| 7 | B01 | Me | C10 | 2-FC₆H₄ | Ts | E22 | n-butyl | B01C10E22 | natural | natural | 1 | 3.887 | 4.6 | 465.6 | 0.945 | 16 | G07 | 86.3 |
| 8 | B01 | Me | C11 | 4-ClC₆H₄ | Ts | E22 | n-butyl | B01C11E22 | natural | brown | 1 | 3.917 | 4.2 | 482.06 | 0.871 | 16 | G08 | 81.5 |
| 9 | B01 | Me | C12 | 3-ClC₆H₄ | Ts | E22 | n-butyl | B01C12E22 | natural | black | 1 | 3.8667 | 4.5 | 482.06 | 0.933 | 16 | G09 | 16.7 |
| 10 | B01 | Me | C15 | 3-BrC₆H₄ | Ts | E22 | n-butyl | B01C15E22 | natural | blue/natural | 1 | 3.9098 | 3.1 | 526.51 | 0.589 | 16 | G10 | 9.0 |
| 12 | B01 | Me | C20 | 3,4-di-MeOC₆H₄ | Ts | E22 | n-butyl | B01C20E22 | natural | white/natural | 1 | 3.8239 | 3.9 | 507.66 | 0.768 | 16 | G11 | 114.5 |
| 15 | B01 | Me | C25 | 3,4,5-tri-MeOC₆H₄ | Ts | E22 | n-butyl | B01C25E22 | natural | white/black | 1 | 3.938 | 3.2 | 537.69 | 0.595 | 16 | H02 | 73.5 |
| 16 | B01 | Me | C30 | 4-MeC₆H₄ | 4-ClBs | E22 | n-butyl | B01C30E22 | natural | blue/white | 1 | 3.8655 | 3.9 | 482.06 | 0.809 | 16 | H03 | 49.2 |
| 19 | B01 | Me | C35 | 4-MeOC₆H₄ | Bs | E22 | n-butyl | B01C35E22 | natural | red/white | 1 | 3.8766 | 4.5 | 463.61 | 0.971 | 16 | H04 | 83.1 |
| 21 | B01 | Me | C37 | 4-MeOC₆H₄ | 4-ClBs | E22 | n-butyl | B01C37E22 | natural | blue/brown | 1 | 3.9568 | 5.0 | 498.06 | 1.004 | 16 | H05 | 72.9 |
| 22 | B01 | Me | C38 | 4-MeOC₆H₄ | 2-Ts | E22 | n-butyl | B01C38E22 | natural | green/black | 1 | 3.8575 | 5.3 | 477.64 | 1.110 | 16 | H06 | 88.8 |
| 23 | B01 | Me | C39 | 3-MeOC₆H₄ | Ts | E22 | n-butyl | B01C39E22 | natural | white/red | 1 | 3.8906 | 3.9 | 477.64 | 0.817 | 16 | H07 | 83.9 |
| 24 | B01 | Me | C40 | 4-ClC₆H₄ | 2-Ts | E22 | n-butyl | B01C40E22 | natural | white/brown | 1 | 3.8555 | 4.1 | 482.06 | 0.851 | 16 | H08 | 87.5 |
| 25 | B01 | Me | C41 | 4-MeC₆H₄ | 2-Ts | E22 | n-butyl | B01C41E22 | natural | natural/black | 1 | 3.8768 | 3.6 | 461.64 | 0.780 | 16 | H09 | 43.5 |
| 27 | B01 | Me | C43 | 4-MeC₆H₄ | Bs | E22 | n-butyl | B01C43E22 | natural | brown/red | 1 | 3.9442 | 3.7 | 447.61 | 0.827 | 16 | H10 | 72.6 |
| 28 | B01 | Me | C46 | 4-MeC₆H₄ | Ms | E22 | n-butyl | B01C46E22 | natural | black/yellow | 1 | 3.8509 | 2.2 | 385.54 | 0.571 | 16 | H11 | 104.1 |

FIG. 19-22

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E23 | isoamyl | B01C01E23 | natural | red | 1 | 3.9617 | 2.9 | 461.64 | 0.628 | 17 | A02 | 90.0 |
| 2 | B01 | Me | C02 | 4-MeC₆H₄ | Ts | E23 | isoamyl | B01C02E23 | natural | yellow | 1 | 3.8637 | 4.2 | 475.66 | 0.883 | 17 | A03 | 92.9 |
| 3 | B01 | Me | C03 | 4-EtC₆H₄ | Ts | E23 | isoamyl | B01C03E23 | natural | blue | 1 | 3.8597 | 4.0 | 489.69 | 0.817 | 17 | A04 | 71.9 |
| 4 | B01 | Me | C04 | 4-MeOC₆H₄ | Ts | E23 | isoamyl | B01C04E23 | natural | red/green | 1 | 3.9133 | 4.0 | 491.66 | 0.814 | 17 | A05 | 90.0 |
| 5 | B01 | Me | C05 | 4-EtOC₆H₄ | Ts | E23 | isoamyl | B01C05E23 | natural | yellow/white | 1 | 3.8992 | 4.3 | 505.69 | 0.850 | 17 | A06 | 95.9 |
| 6 | B01 | Me | C06 | piperonyl | Ts | E23 | isoamyl | B01C06E23 | natural | green | 1 | 3.9166 | 4.6 | 505.65 | 0.910 | 17 | A07 | 77.4 |
| 7 | B01 | Me | C10 | 2-FC₆H₄ | Ts | E23 | isoamyl | B01C10E23 | natural | natural | 1 | 3.8181 | 3.3 | 479.63 | 0.688 | 17 | A08 | 58.4 |
| 8 | B01 | Me | C11 | 4-ClC₆H₄ | Ts | E23 | isoamyl | B01C11E23 | natural | brown | 1 | 3.9759 | 3.5 | 496.08 | 0.706 | 17 | A09 | 39.4 |
| 9 | B01 | Me | C12 | 3-ClC₆H₄ | Ts | E23 | isoamyl | B01C12E23 | natural | black | 1 | 3.8141 | 4.3 | 496.08 | 0.867 | 17 | A10 | 26.0 |
| 10 | B01 | Me | C15 | 3-BrC₆H₄ | Ts | E23 | isoamyl | B01C15E23 | natural | blue/natural | 1 | 3.9058 | 3.9 | 540.53 | 0.722 | 17 | A11 | 19.2 |
| 12 | B01 | Me | C20 | 3,4-di-MeOC₆H₄ | Ts | E23 | isoamyl | B01C20E23 | natural | white/natural | 1 | 3.8407 | 4.5 | 521.69 | 0.863 | 17 | B02 | 91.1 |
| 15 | B01 | Me | C25 | 3,4,5-tri-MeOC₆H₄ | Ts | E23 | isoamyl | B01C25E23 | natural | white/black | 1 | 3.8982 | 4.8 | 551.72 | 0.870 | 17 | B03 | 105.7 |
| 16 | B01 | Me | C30 | 4-MeC₆H₄ | 4-ClBs | E23 | isoamyl | B01C30E23 | natural | blue/white | 1 | 3.92 | 4.6 | 456.08 | 0.927 | 17 | B04 | 77.6 |
| 19 | B01 | Me | C35 | 4-MeOC₆H₄ | Bs | E23 | isoamyl | B01C35E23 | natural | red/white | 1 | 3.9276 | 3.7 | 477.64 | 0.775 | 17 | B05 | 96.7 |
| 21 | B01 | Me | C37 | 4-MeOC₆H₄ | 4-ClBs | E23 | isoamyl | B01C37E23 | natural | blue/brown | 1 | 3.8036 | 4.2 | 512.08 | 0.820 | 17 | B06 | 81.4 |
| 22 | B01 | Me | C38 | 4-MeOC₆H₄ | 2-Ts | E23 | isoamyl | B01C38E23 | natural | green/black | 1 | 3.8899 | 4.4 | 491.66 | 0.895 | 17 | B07 | 65.9 |
| 23 | B01 | Me | C39 | 3-MeOC₆H₄ | Ts | E23 | isoamyl | B01C39E23 | natural | white/red | 1 | 3.9311 | 3.0 | 491.66 | 0.610 | 17 | B08 | 62.0 |
| 24 | B01 | Me | C40 | 4-ClC₆H₄ | 2-Ts | E23 | isoamyl | B01C40E23 | natural | white/brown | 1 | 3.9606 | 4.1 | 496.08 | 0.826 | 17 | B09 | 53.2 |
| 25 | B01 | Me | C41 | 4-MeC₆H₄ | 2-Ts | E23 | isoamyl | B01C41E23 | natural | natural/black | 1 | 3.8845 | 4.1 | 475.66 | 0.862 | 17 | B10 | 75.2 |
| 27 | B01 | Me | C43 | 4-MeC₆H₄ | Bs | E23 | isoamyl | B01C43E23 | natural | brown/red | 1 | 3.8936 | 4.0 | 461.64 | 0.866 | 17 | B11 | 79.3 |
| 28 | B01 | Me | C46 | 4-MeC₆H₄ | Ms | E23 | isoamyl | B01C46E23 | natural | black/yellow | 1 | 3.9037 | 2.4 | 399.57 | 0.601 | 17 | C02 | 93.4 |

FIG. 19-23

| entry | acid | R¹ | imine | Ar | SO₂R² | thiol | R⁴ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E24 | n-pentyl | B01C01E24 | natural | red | 1 | 3.8453 | 3.0 | 461.64 | 0.650 | 17 | C03 | 77.2 |
| 2 | B01 | Me | C02 | 4-MeC₆H₄ | Ts | E24 | n-pentyl | B01C02E24 | natural | yellow | 1 | 3.8596 | 4.7 | 475.66 | 0.988 | 17 | C04 | 74.3 |
| 3 | B01 | Me | C03 | 4-EtC₆H₄ | Ts | E24 | n-pentyl | B01C03E24 | natural | blue | 1 | 3.9294 | 5.1 | 489.69 | 1.041 | 17 | C05 | 65.8 |
| 4 | B01 | Me | C04 | 4-MeOC₆H₄ | Ts | E24 | n-pentyl | B01C04E24 | natural | red/green | 1 | 3.9026 | 5.4 | 491.66 | 1.098 | 17 | C06 | 86.7 |
| 5 | B01 | Me | C05 | 4-EtOC₆H₄ | Ts | E24 | n-pentyl | B01C05E24 | natural | yellow/white | 1 | 3.8271 | 4.1 | 505.69 | 0.811 | 17 | C07 | 89.1 |
| 6 | B01 | Me | C06 | piperonyl | Ts | E24 | n-pentyl | B01C06E24 | natural | green | 1 | 3.848 | 5.2 | 505.65 | 1.028 | 17 | C08 | 66.0 |
| 7 | B01 | Me | C10 | 2-FC₆H₄ | Ts | E24 | n-pentyl | B01C10E24 | natural | natural | 1 | 3.8417 | 3.5 | 479.63 | 0.730 | 17 | C09 | 61.4 |
| 8 | B01 | Me | C11 | 4-ClC₆H₄ | Ts | E24 | n-pentyl | B01C11E24 | natural | brown | 1 | 3.8505 | 3.7 | 496.08 | 0.746 | 17 | C10 | 59.8 |
| 9 | B01 | Me | C12 | 3-ClC₆H₄ | Ts | E24 | n-pentyl | B01C12E24 | natural | black | 1 | 3.8658 | 4.0 | 496.08 | 0.806 | 17 | C11 | 84.6 |
| 10 | B01 | Me | C15 | 3-BrC₆H₄ | Ts | E24 | n-pentyl | B01C15E24 | natural | blue/natural | 1 | 3.9243 | 4.1 | 540.53 | 0.759 | 17 | D02 | 95.1 |
| 12 | B01 | Me | C20 | 3,4-di-MeOC₆H₄ | Ts | E24 | n-pentyl | B01C20E24 | natural | white/natural | 1 | 3.848 | 5.5 | 521.69 | 1.054 | 17 | D03 | 109.2 |
| 15 | B01 | Me | C25 | 3,4,5-tri-MeOC₆H₄ | Ts | E24 | n-pentyl | B01C25E24 | natural | white/black | 1 | 3.8201 | 4.3 | 551.72 | 0.779 | 17 | D04 | 81.8 |
| 16 | B01 | Me | C30 | 4-MeC₆H₄ | 4-ClBs | E24 | n-pentyl | B01C30E24 | natural | blue/white | 1 | 3.8368 | 2.9 | 496.08 | 0.585 | 17 | D05 | 75.8 |
| 19 | B01 | Me | C35 | 4-MeOC₆H₄ | Bs | E24 | n-pentyl | B01C35E24 | natural | red/white | 1 | 3.8754 | 5.0 | 477.64 | 1.047 | 17 | D06 | 94.8 |
| 21 | B01 | Me | C37 | 4-MeOC₆H₄ | 4-ClBs | E24 | n-pentyl | B01C37E24 | natural | blue/brown | 1 | 3.9359 | 7.0 | 512.08 | 1.367 | 17 | D07 | 70.9 |
| 22 | B01 | Me | C38 | 4-MeOC₆H₄ | 2-Ts | E24 | n-pentyl | B01C38E24 | natural | green/black | 1 | 3.9208 | 7.2 | 491.66 | 1.464 | 17 | D08 | 67.1 |
| 23 | B01 | Me | C39 | 3-MeOC₆H₄ | Ts | E24 | n-pentyl | B01C39E24 | natural | white/red | 1 | 3.8955 | 5.5 | 491.66 | 1.119 | 17 | D09 | 105.4 |
| 24 | B01 | Me | C40 | 4-ClC₆H₄ | 2-Ts | E24 | n-pentyl | B01C40E24 | natural | white/brown | 1 | 3.8327 | 4.7 | 496.08 | 0.947 | 17 | D10 | 57.9 |
| 25 | B01 | Me | C41 | 4-MeC₆H₄ | 2-Ts | E24 | n-pentyl | B01C41E24 | natural | natural/black | 1 | 3.8105 | 5.5 | 475.66 | 1.156 | 17 | D11 | 62.9 |
| 27 | B01 | Me | C43 | 4-MeC₆H₄ | Bs | E24 | n-pentyl | B01C43E24 | natural | brown/red | 1 | 3.8217 | 4.5 | 461.64 | 0.975 | 17 | E02 | 81.0 |
| 28 | B01 | Me | C46 | 4-MeC₆H₄ | Ms | E24 | n-pentyl | B01C46E24 | natural | black/yellow | 1 | 3.9264 | 2.4 | 399.57 | 0.601 | 17 | E03 | 106.6 |

FIG. 19-24

| entry | acid | R$^1$ | imine | Ar | SO$_2$R$^2$ | thiol | R$^4$ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E25 | n-hexyl | B01C01E25 | natural | red | 1 | 3.8685 | 3.3 | 475.66 | 0.694 | 17 | E04 | 77.5 |
| 2 | B01 | Me | C02 | 4-MeC$_6$H$_4$ | Ts | E25 | n-hexyl | B01C02E25 | natural | yellow | 1 | 3.9384 | 3.9 | 489.69 | 0.796 | 17 | E05 | 70.9 |
| 3 | B01 | Me | C03 | 4-EtC$_6$H$_4$ | Ts | E25 | n-hexyl | B01C03E25 | natural | blue | 1 | 3.8478 | 4.2 | 503.72 | 0.834 | 17 | E06 | 70.0 |
| 4 | B01 | Me | C04 | 4-MeOC$_6$H$_4$ | Ts | E25 | n-hexyl | B01C04E25 | natural | red/green | 1 | 3.7846 | 4.0 | 505.69 | 0.791 | 17 | E07 | 83.6 |
| 5 | B01 | Me | C05 | 4-EtOC$_6$H$_4$ | Ts | E25 | n-hexyl | B01C05E25 | natural | yellow/white | 1 | 3.9272 | 3.9 | 519.72 | 0.750 | 17 | E08 | 67.5 |
| 6 | B01 | Me | C06 | piperonyl | Ts | E25 | n-hexyl | B01C06E25 | natural | green | 1 | 3.8523 | 4.3 | 519.67 | 0.827 | 17 | E09 | 62.7 |
| 7 | B01 | Me | C10 | 2-FC$_6$H$_4$ | Ts | E25 | n-hexyl | B01C10E25 | natural | natural | 1 | 3.866 | 4.3 | 493.65 | 0.871 | 17 | E10 | 75.3 |
| 8 | B01 | Me | C11 | 4-ClC$_6$H$_4$ | Ts | E25 | n-hexyl | B01C11E25 | natural | brown | 1 | 3.8503 | 4.7 | 510.11 | 0.921 | 17 | E11 | 72.2 |
| 9 | B01 | Me | C12 | 3-ClC$_6$H$_4$ | Ts | E25 | n-hexyl | B01C12E25 | natural | black | 1 | 3.908 | 4.7 | 510.11 | 0.921 | 17 | F02 | 77.3 |
| 10 | B01 | Me | C15 | 3-BrC$_6$H$_4$ | Ts | E25 | n-hexyl | B01C15E25 | natural | blue/natural | 1 | 3.8563 | 4.0 | 554.56 | 0.721 | 17 | F03 | 68.9 |
| 12 | B01 | Me | C20 | 3,4-di-MeOC$_6$H$_4$ | Ts | E25 | n-hexyl | B01C20E25 | natural | white/natural | 1 | 3.8729 | 5.5 | 535.72 | 1.027 | 17 | F04 | 97.2 |
| 15 | B01 | Me | C25 | 3,4,5-tri-MeOC$_6$H$_4$ | Ts | E25 | n-hexyl | B01C25E25 | natural | white/black | 1 | 3.817 | 4.3 | 565.74 | 0.760 | 17 | F05 | 93.6 |
| 16 | B01 | Me | C30 | 4-MeC$_6$H$_4$ | 4-ClBs | E25 | n-hexyl | B01C30E25 | natural | blue/white | 1 | 3.8706 | 4.8 | 510.11 | 0.941 | 17 | F06 | 71.8 |
| 19 | B01 | Me | C35 | 4-MeOC$_6$H$_4$ | Bs | E25 | n-hexyl | B01C35E25 | natural | red/white | 1 | 3.8156 | 5.0 | 491.66 | 1.017 | 17 | F07 | 96.2 |
| 21 | B01 | Me | C37 | 4-MeOC$_6$H$_4$ | 4-ClBs | E25 | n-hexyl | B01C37E25 | natural | blue/brown | 1 | 3.8119 | 6.0 | 526.11 | 1.140 | 17 | F08 | 68.3 |
| 22 | B01 | Me | C38 | 4-MeOC$_6$H$_4$ | 2-Ts | E25 | n-hexyl | B01C38E25 | natural | green/black | 1 | 3.9192 | 6.0 | 505.69 | 1.186 | 17 | F09 | 72.9 |
| 23 | B01 | Me | C39 | 3-MeOC$_6$H$_4$ | Ts | E25 | n-hexyl | B01C39E25 | natural | white/red | 1 | 3.8826 | 4.8 | 505.69 | 0.949 | 17 | F10 | 80.5 |
| 24 | B01 | Me | C40 | 4-ClC$_6$H$_4$ | 2-Ts | E25 | n-hexyl | B01C40E25 | natural | white/brown | 1 | 3.8903 | 4.6 | 510.11 | 0.902 | 17 | F11 | 66.3 |
| 25 | B01 | Me | C41 | 4-MeC$_6$H$_4$ | 2-Ts | E25 | n-hexyl | B01C41E25 | natural | natural/black | 1 | 3.8264 | 5.0 | 489.69 | 1.021 | 17 | G02 | 69.9 |
| 27 | B01 | Me | C43 | 4-MeC$_6$H$_4$ | Bs | E25 | n-hexyl | B01C43E25 | natural | brown/red | 1 | 3.8344 | 3.7 | 475.66 | 0.778 | 17 | G03 | 81.2 |
| 28 | B01 | Me | C46 | 4-MeC$_6$H$_4$ | Ms | E25 | n-hexyl | B01C46E25 | natural | black/yellow | 1 | 3.8879 | 2.1 | 413.59 | 0.508 | 17 | G04 | 83.1 |

FIG. 19-25

| entry | acid | R$^1$ | imine | Ar | SO$_2$R$^2$ | thiol | R$^4$ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E28 | c-pentyl | B01C01E28 | natural | red | 1 | 3.9092 | 2.6 | 459.62 | 0.566 | 17 | G05 | 93.6 |
| 2 | B01 | Me | C02 | 4-MeC$_6$H$_4$ | Ts | E28 | c-pentyl | B01C02E28 | natural | yellow | 1 | 3.9111 | 3.9 | 473.65 | 0.823 | 17 | G06 | 87.8 |
| 3 | B01 | Me | C03 | 4-EtC$_6$H$_4$ | Ts | E28 | c-pentyl | B01C03E28 | natural | blue | 1 | 3.8604 | 3.8 | 487.67 | 0.779 | 17 | G07 | 87.0 |
| 4 | B01 | Me | C04 | 4-MeOC$_6$H$_4$ | Ts | E28 | c-pentyl | B01C04E28 | natural | red/green | 1 | 3.9276 | 4.8 | 489.65 | 0.980 | 17 | G08 | 91.5 |
| 5 | B01 | Me | C05 | 4-EtOC$_6$H$_4$ | Ts | E28 | c-pentyl | B01C05E28 | natural | yellow/white | 1 | 3.8046 | 4.6 | 503.67 | 0.913 | 17 | G09 | 84.5 |
| 6 | B01 | Me | C06 | piperonyl | Ts | E28 | c-pentyl | B01C06E28 | natural | green | 1 | 3.8791 | 4.4 | 503.63 | 0.874 | 17 | G10 | 98.1 |
| 7 | B01 | Me | C10 | 2-FC$_6$H$_4$ | Ts | E28 | c-pentyl | B01C10E28 | natural | natural | 1 | 3.9175 | 3.3 | 477.61 | 0.691 | 17 | G11 | 93.4 |
| 8 | B01 | Me | C11 | 4-ClC$_6$H$_4$ | Ts | E28 | c-pentyl | B01C11E28 | natural | brown | 1 | 3.9106 | 4.4 | 494.07 | 0.891 | 17 | H02 | 94.7 |
| 9 | B01 | Me | C12 | 3-ClC$_6$H$_4$ | Ts | E28 | c-pentyl | B01C12E28 | natural | black | 1 | 3.8349 | 2.8 | 494.07 | 0.567 | 17 | H03 | 88.7 |
| 10 | B01 | Me | C15 | 3-BrC$_6$H$_4$ | Ts | E28 | c-pentyl | B01C15E28 | natural | blue/natural | 1 | 3.7849 | 3.9 | 538.52 | 0.724 | 17 | H04 | 72.1 |
| 12 | B01 | Me | C20 | 3,4-di-MeOC$_6$H$_4$ | Ts | E28 | c-pentyl | B01C20E28 | natural | white/natural | 1 | 3.8839 | 5.0 | 519.67 | 0.962 | 17 | H05 | 112.3 |
| 15 | B01 | Me | C25 | 3,4,5-tri-MeOC$_6$H$_4$ | Ts | E28 | c-pentyl | B01C25E28 | natural | white/black | 1 | 3.809 | 3.1 | 549.7 | 0.564 | 17 | H06 | 104.6 |
| 16 | B01 | Me | C30 | 4-MeC$_6$H$_4$ | 4-ClBs | E28 | c-pentyl | B01C30E28 | natural | blue/white | 1 | 3.8644 | 5.3 | 494.07 | 1.073 | 17 | H07 | 93.2 |
| 19 | B01 | Me | C35 | 4-MeOC$_6$H$_4$ | Bs | E28 | c-pentyl | B01C35E28 | natural | red/white | 1 | 3.8363 | 4.2 | 475.62 | 0.883 | 17 | H08 | 94.5 |
| 21 | B01 | Me | C37 | 4-MeOC$_6$H$_4$ | 4-ClBs | E28 | c-pentyl | B01C37E28 | natural | blue/brown | 1 | 3.8219 | 5.1 | 510.07 | 1.000 | 17 | H09 | 83.1 |
| 22 | B01 | Me | C38 | 4-MeOC$_6$H$_4$ | 2-Ts | E28 | c-pentyl | B01C38E28 | natural | green/black | 1 | 3.9439 | 6.0 | 489.65 | 1.225 | 17 | H10 | 98.2 |
| 23 | B01 | Me | C39 | 3-MeOC$_6$H$_4$ | Ts | E28 | c-pentyl | B01C39E28 | natural | white/red | 1 | 3.8106 | 4.1 | 489.65 | 0.837 | 17 | H11 | 112.6 |
| 24 | B01 | Me | C40 | 4-ClC$_6$H$_4$ | 2-Ts | E28 | c-pentyl | B01C40E28 | natural | white/brown | 1 | 3.769 | 5.3 | 494.07 | 1.073 | 18 | A02 | 92.1 |
| 25 | B01 | Me | C41 | 4-MeC$_6$H$_4$ | 2-Ts | E28 | c-pentyl | B01C41E28 | natural | natural/black | 1 | 3.8774 | 4.1 | 473.65 | 0.866 | 18 | A03 | 93.5 |
| 27 | B01 | Me | C43 | 4-MeC$_6$H$_4$ | Bs | E28 | c-pentyl | B01C43E28 | natural | brown/red | 1 | 3.8327 | 3.0 | 459.62 | 0.653 | 18 | A04 | 100.3 |
| 28 | B01 | Me | C46 | 4-MeC$_6$H$_4$ | Ms | E28 | c-pentyl | B01C46E28 | natural | black/yellow | 1 | 3.8521 | 1.0 | 397.55 | 0.252 | 18 | A05 | 110.2 |

FIG. 19-26

| entry | acid | R$^1$ | imine | Ar | SO$_2$R$^2$ | thiol | R$^4$ | label | spindle | cogs | # | tare | weight | MW | acetone | plate | well | Kras |
|---|---|---|---|---|---|---|---|---|---|---|---|---|---|---|---|---|---|---|
| 1 | B01 | Me | C01 | Ph | Ts | E30 | allyl | B01C01E30 | natural | red | 1 | 3.846 | 3.1 | 431.57 | 0.718 | 18 | A06 | 98.9 |
| 2 | B01 | Me | C02 | 4-MeC$_6$H$_4$ | Ts | E30 | allyl | B01C02E30 | natural | yellow | 1 | 3.8478 | 4.2 | 445.59 | 0.943 | 18 | A07 | 94.1 |
| 3 | B01 | Me | C03 | 4-EtC$_6$H$_4$ | Ts | E30 | allyl | B01C03E30 | natural | blue | 1 | 3.8417 | 5.1 | 459.62 | 1.110 | 18 | A08 | 89.6 |
| 4 | B01 | Me | C04 | 4-MeOC$_6$H$_4$ | Ts | E30 | natural | B01C04E30 | natural | red/green | 1 | 3.92 | 4.0 | 461.59 | 0.867 | 18 | A09 | 108.5 |
| 5 | B01 | Me | C05 | 4-EtOC$_6$H$_4$ | Ts | E30 | allyl | B01C05E30 | natural | yellow/white | 1 | 3.8986 | 3.8 | 475.62 | 0.799 | 18 | A10 | 96.7 |
| 6 | B01 | Me | C06 | piperonyl | Ts | E30 | allyl | B01C06E30 | natural | green | 1 | 3.8682 | 4.4 | 475.58 | 0.925 | 18 | A11 | 76.4 |
| 7 | B01 | Me | C10 | 2-FC$_6$H$_4$ | Ts | E30 | allyl | B01C10E30 | natural | natural | 1 | 3.8891 | 2.6 | 449.56 | 0.578 | 18 | B02 | 53.1 |
| 8 | B01 | Me | C11 | 4-ClC$_6$H$_4$ | Ts | E30 | allyl | B01C11E30 | natural | brown | 1 | 3.8789 | 4.4 | 466.01 | 0.944 | 18 | B03 | 49.1 |
| 9 | B01 | Me | C12 | 3-ClC$_6$H$_4$ | Ts | E30 | allyl | B01C12E30 | natural | black | 1 | 3.9046 | 4.1 | 466.01 | 0.880 | 18 | B04 | 46.3 |
| 10 | B01 | Me | C15 | 3-BrC$_6$H$_4$ | Ts | E30 | allyl | B01C15E30 | natural | blue/natural | 1 | 3.8649 | 3.3 | 510.46 | 0.646 | 18 | B05 | 133.6 |
| 12 | B01 | Me | C20 | 3,4-di-MeOC$_6$H$_4$ | Ts | E30 | allyl | B01C20E30 | natural | white/natural | 1 | 3.8845 | 5.1 | 491.62 | 1.037 | 18 | B06 | 108.6 |
| 15 | B01 | Me | C25 | 3,4,5-tri-MeOC$_6$H$_4$ | Ts | E30 | allyl | B01C25E30 | natural | white/black | 1 | 3.8636 | 5.2 | 521.65 | 0.997 | 18 | B07 | 109.4 |
| 16 | B01 | Me | C30 | 4-MeC$_6$H$_4$ | 4-ClBs | E30 | allyl | B01C30E30 | natural | blue/white | 1 | 3.8454 | 4.9 | 466.01 | 1.051 | 18 | B08 | 74.3 |
| 19 | B01 | Me | C35 | 4-MeOC$_6$H$_4$ | Bs | E30 | allyl | B01C35E30 | natural | red/white | 1 | 3.8078 | 4.5 | 447.57 | 1.005 | 18 | B09 | 106.5 |
| 21 | B01 | Me | C37 | 4-MeOC$_6$H$_4$ | 4-ClBs | E30 | allyl | B01C37E30 | natural | blue/brown | 1 | 3.8588 | 4.6 | 482.01 | 0.954 | 18 | B10 | 95.4 |
| 22 | B01 | Me | C38 | 4-MeOC$_6$H$_4$ | 2-Ts | E30 | allyl | B01C38E30 | natural | green/black | 1 | 3.7738 | 4.9 | 461.59 | 1.062 | 18 | B11 | 65.1 |
| 23 | B01 | Me | C39 | 3-MeOC$_6$H$_4$ | Ts | E30 | allyl | B01C39E30 | natural | white/red | 1 | 3.8399 | 2.6 | 461.59 | 0.563 | 18 | C02 | 75.1 |
| 24 | B01 | Me | C40 | 4-ClC$_6$H$_4$ | 2-Ts | E30 | allyl | B01C40E30 | natural | white/brown | 1 | 3.8981 | 4.0 | 466.01 | 0.858 | 18 | C03 | 17.8 |
| 25 | B01 | Me | C41 | 4-MeC$_6$H$_4$ | 2-Ts | E30 | allyl | B01C41E30 | natural | natural/black | 1 | 3.8599 | 5.5 | 445.59 | 1.234 | 18 | C04 | |
| 27 | B01 | Me | C43 | 4-MeC$_6$H$_4$ | Bs | E30 | allyl | B01C43E30 | natural | brown/red | 1 | 3.8399 | 4.1 | 431.57 | 0.950 | 18 | C05 | 50.7 |
| 28 | B01 | Me | C46 | 4-MeC$_6$H$_4$ | Ms | E30 | allyl | B01C46E30 | natural | black/yellow | 1 | 3.8943 | 2.1 | 369.5 | 0.568 | 18 | C06 | 91.4 |

FIG. 19-27

| ![structure] K-ras/RhoA | C40<br>R³ = 4-chlorophenyl<br>P = 2-methylbenzene-sulfonyl | C26<br>R³ = 3-fluorophenyl<br>P = 4-methylbenzenesulfonyl | C20<br>R³ = 3,4-dimethoxyphenyl<br>P = 4-methylbenzenesulfonyl |
|---|---|---|---|
| A03<br>R¹ = tert-butyl | 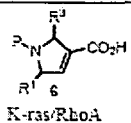<br>P5-H6<br>13.3/5.3 | 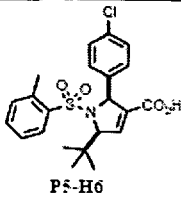<br>23.7/9.1 | 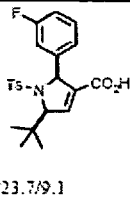<br>23.4/6.1 |
| A11<br>R¹ = cyclopentylmethyl | 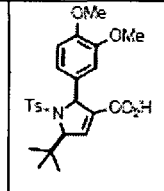<br>23.7/9.1 | | |
FIG. 28

| | | | | | |
|---|---|---|---|---|---|
| C14<br>R³ = 4-bromophenyl<br>P = 4-methylbenzene-sulfonyl | 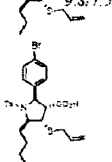<br>9.8/7.5<br><br>15.5/5.5 | | | | |
| C12<br>R³ = 2-chlorophenyl<br>P = 4-methylbenzene-sulfonyl | | 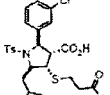<br>20.6/5.6 | 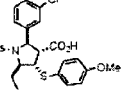<br>25.5/6.5 | | |
| C20<br>R³ = 3,4-dimethoxyphenyl<br>P = 4-methylbenzene-sulfonyl | 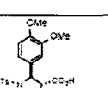<br>22.3/8.1 | | | | |
| C11<br>R³ = 4-chlorophenyl<br>P = 4-methylbenzene-sulfonyl | 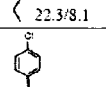<br>25.2/7.7 | | | | |
| C24<br>R³ = 4-isopropylphenyl<br>P = 4-methylbenzene-sulfonyl | 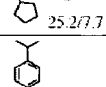<br>31.7/6.1 | | | | |
FIG. 29C

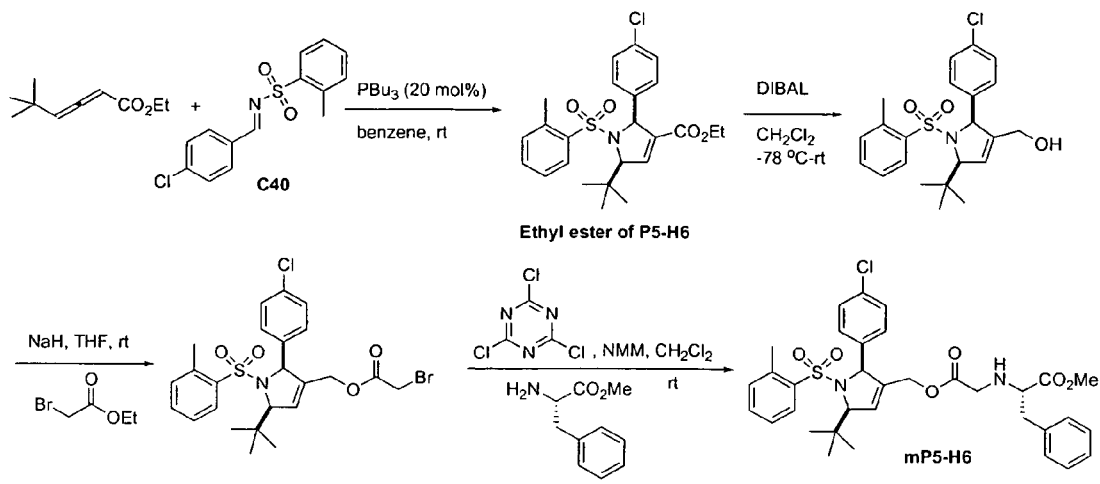
FIG. 31
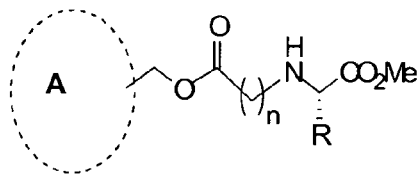
General structure of the third generation GGTIs
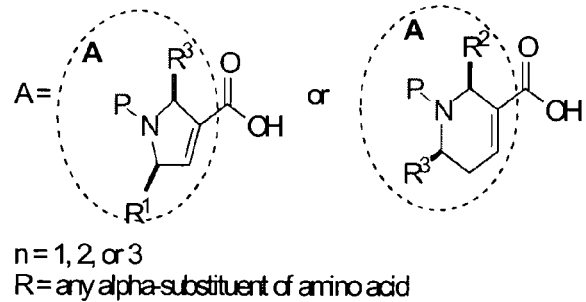
n = 1, 2, or 3
R = any alpha-substituent of amino acid
FIG. 32

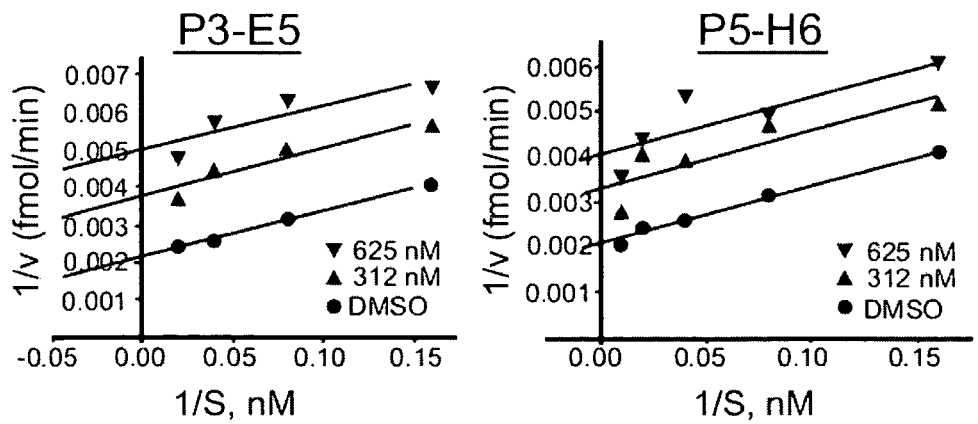
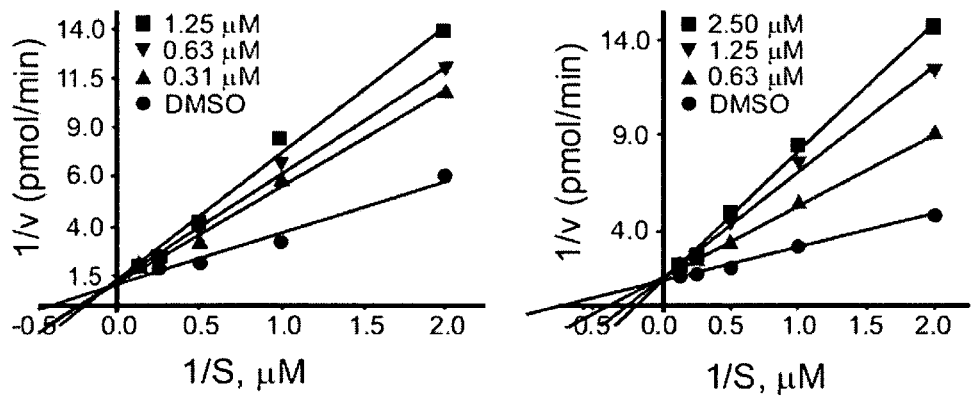
FIG. 35

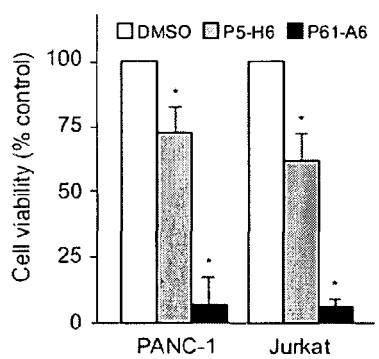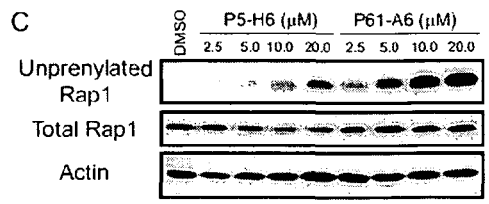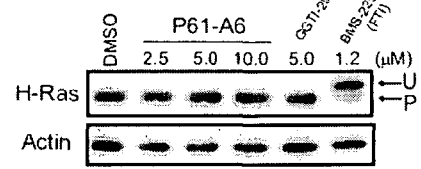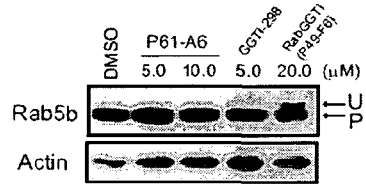
FIG. 36

A
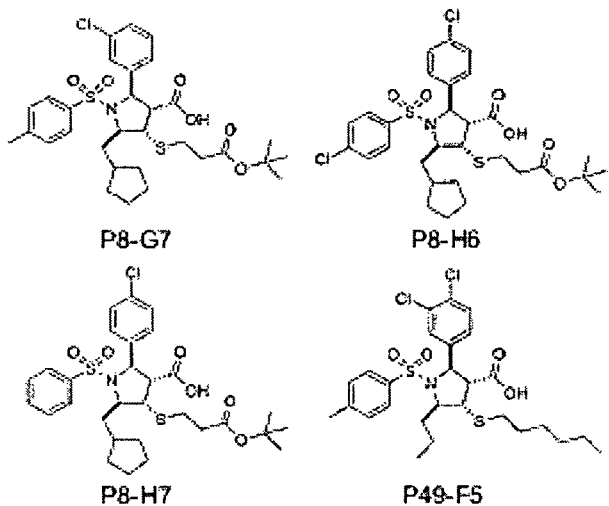
B
| | IC$_{50}$ values of dual specificity inhibitors (μM) | | |
|---|---|---|---|
| | GGTase-I | RabGGTase | FTase |
| P8-G7 | 8.7 | 4.7 | > 100 |
| P8-H6 | 8.9 | 3.1 | > 100 |
| P8-H7 | 2.4 | 7.0 | > 100 |
| P49-F5 | 5.1 | 7.0 | > 100 |
C
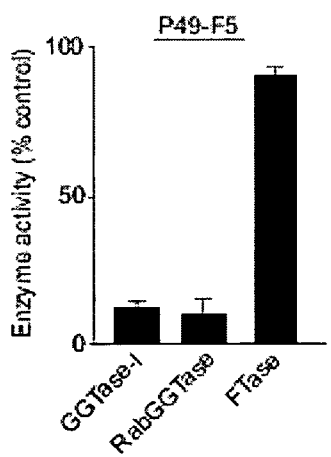
FIG. 38

A
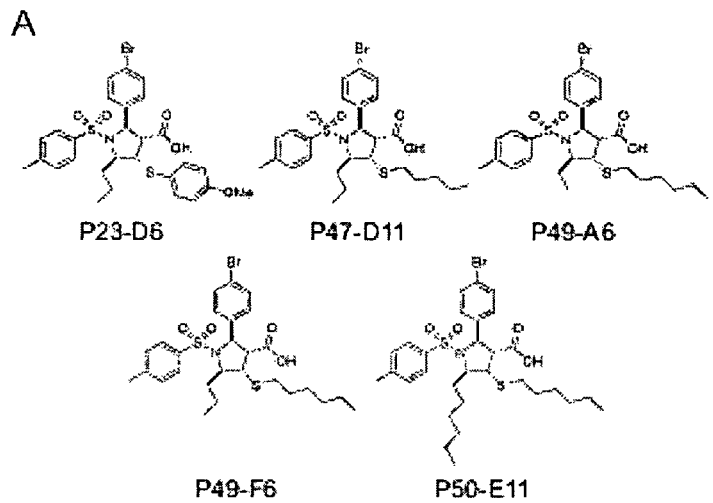
P23-D6     P47-D11     P49-A6
P49-F6     P50-E11
B
| | IC$_{50}$ values of preferential inhibitors (µM) | | |
|---|---|---|---|
| | GGTase-I | RabGGTase | FTase |
| P23-D6 | > 50 | 4.5 | > 100 |
| P47-D11 | > 50 | 3.6 | > 100 |
| P49-A6 | > 50 | 4.8 | > 100 |
| P49-F6 | > 50 | 2.1 | > 100 |
| P50-E11 | > 50 | 2.2 | > 100 |
C
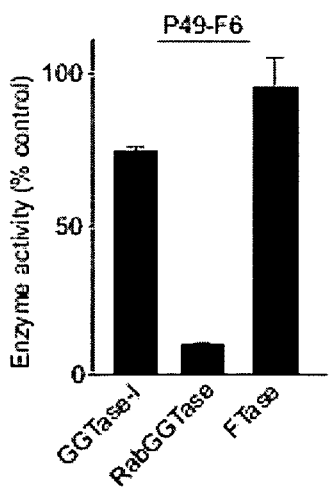
FIG. 39

DMSO
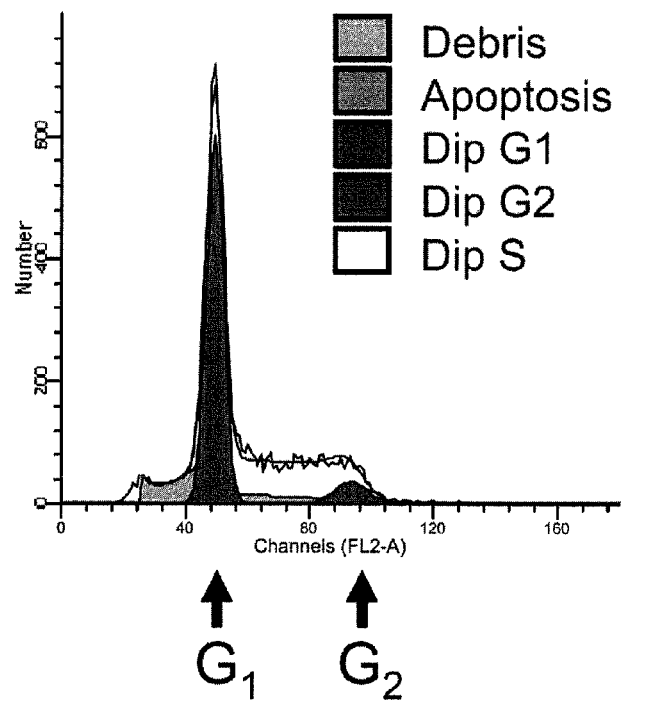
P61-A6
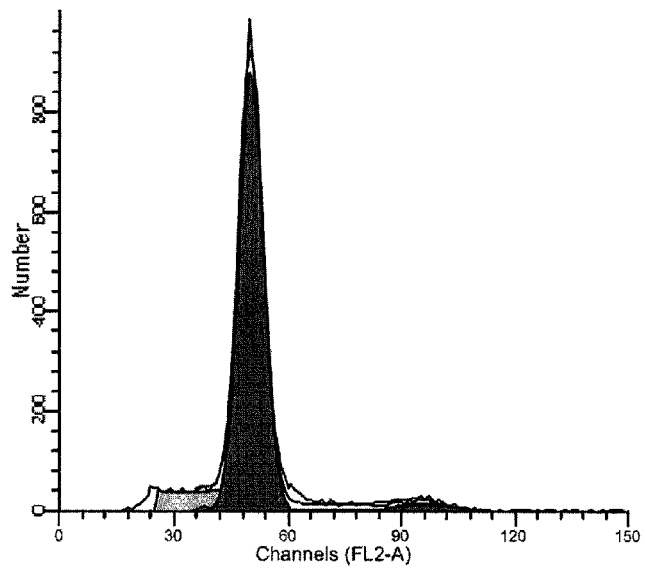
FIG. 41

P61-B6

A 03

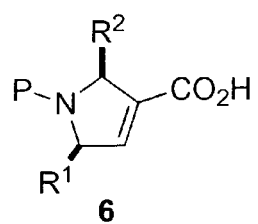
1 allenoic acid x 68 imines = 68 compounds
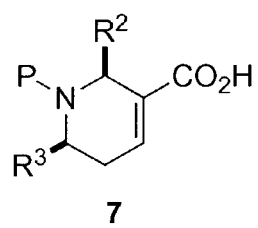
4 allenoic acid x 68 imines = 272 compounds
Total: 340 compounds
FIG. 56

| RhoA IC50s (nM) | B04 R² = 3-fluorophenyl | B05 R² = 3-chlorophenyl | B06 R² = 3-bromophenyl | B07 R² = 3-methylphenyl |
|---|---|---|---|---|
| C73 R³ = 3-chlorophenyl P = 4-bromobenzene-sulfonyl | nd | 87.1 | 169.3 | nd |
| C69 R³ = 3-bromophenyl P = 4-chlorobenzene-sulfonyl | 840.6 | 124.9 | nd | 255.7 |
| C79 R³ = 3-bromophenyl P = 4-fluorobenzene-sulfonyl | nd | 211.8 | nd | nd |
| C68 R³ = 3-chlorophenyl P = 4-chlorobenzene-sulfonyl | nd | 241.4 | nd | nd |
| C67 R³ = 3,4-dichlorophenyl P = 4-chlorobenzene-sulfonyl | nd | 310.2 | nd | nd |
| C76 R³ = 3-methylphenyl P = 4-bromobenzene-sulfonyl | nd | nd | 329.6 | nd |
| C104 R³ = 4-bromophenyl P = 4-bromobenzene-sulfonyl | nd | 397.9 | nd | nd |
| C74 R³ = 3-bromophenyl P = 4-bromobenzene-sulfonyl | nd | 529.0 | 524.9 | nd |

FIG. 59

| 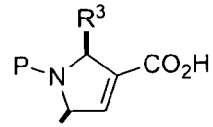<br>RhoA IC50s (nM) | C57<br>$R^3$ = 3,4-dichlorophenyl<br>P = 2-bromobenzene-sulfonyl | C90<br>$R^3$ = 4-bromophenyl<br>P = 2-chlorobenzene-sulfonyl | C47<br>$R^3$ = 3,4-dichlorophenyl<br>P = 2-bromobenzene-sulfonyl |
|---|---|---|---|
| A03<br>$R^1$ = *t*-butyl | 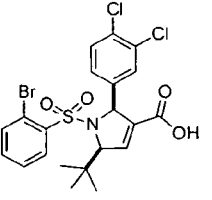<br>348.0 | 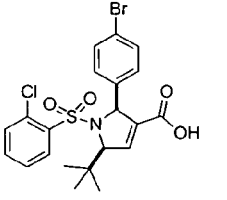<br>349.6 | 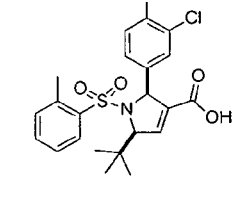<br>363.5 |
FIG. 60

INHIBITORS OF PROTEIN PRENYLTRANSFERASES

This application is a continuation application of U.S. application Ser. No. 13/056,077, filed Jan. 26, 2011, which is a national stage application of PCT/US2008/009106, which was filed on Jul. 28, 2008.

This invention was made with Government support under Grant Numbers CA032737, GM071779, and GM081282, awarded by the National Institutes of Health (NIH). The Government has certain rights in the invention.

BACKGROUND

Protein prenyltransferases, such as protein geranylgeranyl-transferase type I (GGTase-I) and Rab geranylgeranytransferase (RabGGTase), catalyze posttranslational modification of proteins, often involving the addition of isoprenoids (1-5). For example, protein farnesylation involves the addition of a C15 farnesyl group to proteins ending with the C-terminal CAAX motif (C is cysteine, A is an aliphatic amino acid and X is usually serine, methionine, glutamine, cysteine or alanine). Farnesylated proteins include Ras proteins, Rheb proteins, nuclear lamins and Hdj2.

Protein geranylgeranylation involves the addition of a longer isoprenoid, C20 geranylgeranyl group. Protein geranylgeranylation is critical for the function of a number of proteins such as RhoA, Rac and Rab.

Two different types of geranylgeranylation have been reported. Rho family proteins such as RhoA, Cdc42 and Rac as well as the γ-subunit of heterotrimeric G-proteins are geranylgeranylated at a cysteine within the CAAL motif (similar to the CAAX motif but the C-terminal amino acid is leucine or phenylalanine) at their C-termini. Rab proteins involved in protein transport across the secretory pathway and endocytosis pathway are also geranylgeranylated. These proteins usually end with CC (two cysteines) or CXC at the C-termini and both cysteines are geranylgeranylated.

Geranylgeranyl transferase type I (GGTase-I) catalyzes mono geranylgeranylation of proteins such as Rho, Rac and Cdc42. This enzyme is a heterodimer consisting of alpha and beta subunits (15). RabGGTase (or GGTase-II) catalyzes digeranylgeranylation of Rab proteins (16,17). This enzyme also contains alpha and beta subunits, but contains an additional subunit Rab Escort Protein (REP) (16,18). The REP subunit binds to the substrate Rab protein (19). The alpha and beta subunits share homology with corresponding subunits of GGTase-I.

Two prenyltransferases, protein farnesyltransferase (FTase) and protein geranylgeranyltransferase type I (GGTase I) are regarded as structurally similar enzymes. See Protein Lipidation (2001) *The Enzymes* vol. 21. (eds. Tamanoi, F. and Sigman D. S.) Academic Press. FTase consists of two subunits, alpha and beta. Its structure consists exclusively of alpha helices and the alpha subunit wraps around the beta subunit that forms a beta-beta barrel structure. GGTase I is also a heterodimer containing an alpha-subunit that is shared with FTase. Furthermore, the beta-subunit of GGTase I shares a significant similarity with the beta-subunit of FTase.

FTase catalyzes the transfer of a C15 farnesyl group from farnesyl pyrophosphate, an intermediate in cholesterol biosynthesis, to proteins such as Ras, Rheb, nuclear lamins, CENP-E, F and protein tyrosine phosphatases pRL1-3. See Tamanoi, F., Gau, C. L., Edamatsu, H., Jiang, C. and Kato-Stankiewicz, J. (2001) Protein farnesylation in mammalian cells, *Cell Mol. Life Sci.* 58, 1-14. These proteins end with the CaaX motif that is recognized by FTase. GGTase I catalyzes the transfer of a C20 geranylgeranyl group from geranylgeranyl pyrophosphate to proteins ending with the CaaL motif. Geranylgeranylated proteins include Rho, Rac, Cdc42 as well as gamma-subunit of heterotrimeric G-proteins.

Certain protein prenyltransferases have been implicated in cancer processes, including GGTase I, RabGGTase, and FTase. See Tamanoi, F., Gau, C. L., Edamatsu, H., Jiang, C. and Kato-Stankiewicz, J. (2001) Protein farnesylation in mammalian cells, *Cell Mol. Life Sci.* 58, 1-14; Carrico, D., Blaskovich, M. A., Bucher, C. J., Sebti, S. M., Hamilton, A. D. (2005) Design, synthesis, and evaluation of potent and selective benzoyleneurea-based inhibitors of protein geranylgeranyltransferase-I, *Bioorg. Med. Chem.* 13, 677-688; Peterson, Y. K., Kelly, P., Weinbaum, C. A., Casey, P. J. (2006) A Novel Protein Geranylgeranyltransferase-I Inhibitor with High Potency, Selectivity and Cellular Activity, *J. Biol. Chem.*

Further studies also demonstrate the physiological significance of protein geranylgeranylation, for example, in cancer. Knockout mice specific for the beta-subunit of GGTase-I have been established (6). Characterization of GGTase-1-deficient cells showed proliferation inhibition and accumulation of $p21^{CIP1/WAF1}$, pointing to the significance of GGTase-I in cell proliferation and cell cycle progression (6). GGTase-I deficiency reduced oncogenic K-ras-induced lung tumor formation in mice, pointing to the significance of inhibiting GGTase-I to block tumor formation (6). Recent studies also showed that a number of geranylgeranylated proteins play important roles in tumorigenesis and metastasis. In addition to RhoA and Cdc42 proteins, RalA protein was recently found to be activated downstream of Ras in most pancreatic cancer cells harboring oncogenic K-ras mutation (7). RalB plays critical roles in the survival pathway (8). RhoC is overexpressed in metastatic cancer and RhoC knockout mice exhibit defect in metastasis (9,10). Overexpression of Rab25 in breast and ovarian cancer cells has been reported, and this mutation is a determinant for aggressiveness of these cancers (11,12). Rab25 is also upregulated in prostate cancer and transitional-cell bladder cancer (11). Overexpression of other Rab proteins such as Rab5a and Rab7 in cancer has been reported (13,14).

A number of small molecule inhibitors of FTase have been developed and some of these are currently in clinical trials as anti-cancer therapeutics. See O'Regan, R. M., Khuri, F. R. (2004) Farnesyl transferase inhibitors: the next targeted therapies for breast cancer? *Endocr. Relat. Cancer* 11, 191-205; ClinicalTrials.gov: www.clinicaltrials.gov. Farnesyltransferase inhibitors (FTIs) exhibit clinical activities with leukemia, multiple myeloma, glioblastoma and advanced breast cancer. Ras proteins are farnesylated and that farnesylation and membrane association of the Ras proteins is critical for their ability to transform cells. Preclinical studies using mouse model systems driven by activated H-ras revealed dramatic ability of FTIs to inhibit tumor growth. However, subsequent studies demonstrated that FTIs are incapable of inhibiting prenylation of K-ras4B and N-ras, as these proteins are alternatively modified by geranylgeranyltransferase type I in the presence of FTIs. Thus, the effects of FTIs are speculated to be due to the inhibition of other farnesylated proteins such as Rheb, CENP-E, F, RhoB.

Compared with FTIs, development of geranylgeranyltransferase type I inhibitors (GGTIs) has lagged behind. Only a handful of compounds has been identified and most of these are derived from the CaaL peptide. See (a) Farnesyltransferase inhibitors in cancer therapy (eds. Sebti, S. M. and Hamilton, A. D.) Humana Press. (b) Oualid, F. E., van den Elst, H., Leroy, I. M., Pieterman, E., Cohen, L. H., Burm, B.

E. A., Overkleeft, H. S., van der Marel, G. A., Overhand, M. (2005) A Combinatorial Approach toward the Generation of Ambiphilic Peptide-Based Inhibitors of Protein:Geranylgeranyl Transferase-I, *J. Comb. Chem.* 7, 703-713. (c) Carrico, D., Blaskovich, M. A., Bucher, C. J., Sebti, S. M., Hamilton, A. D. (2005) Design, synthesis, and evaluation of potent and selective benzoyleneurea-based inhibitors of protein geranylgeranyltransferase-I, *Bioorg. Med. Chem.* 13, 677-688. (d) Peterson, Y. K., Kelly, P., Weinbaum, C. A., Casey, P. J. (2006) A Novel Protein Geranylgeranyltransferase-I Inhibitor with High Potency, Selectivity and Cellular Activity, *J. Biol. Chem.*

Chemical genomics intends to identify small molecule inhibitors of medically relevant targets in a systematic manner. While there are more than 100,000 proteins in the human body and approximately 10% of these are involved in human disease, only 500 have been exploited as drug targets. Thus, a vast amount of novel targets are present and identification of small molecule inhibitors of these unknown targets is of paramount importance. To maximize the chance of identifying small molecule compounds against these targets, a variety of libraries that have diverse structural motifs are needed. This is the goal of diversity-oriented synthesis (DOS). In contrast to combinatorial chemistry that aims to create a library of compounds derived from one scaffold, DOS aims to generate an array of compounds with different three-dimensional structures. See (a) Richter, H.; Walk, T.; Höltzel, A.; Jung, G. "Polymer Bound 3-Hydroxy-2-methylidenepropionic Acids. A Template for Multiple Core Structure Libraries" *J. Org. Chem.* 1999, 64, 1362-1365. (b) Purandare, A. V.; Gao, A.; Poss, M. A. "Solid-phase synthesis of 'diverse' heterocycles" *Tetrahedron Lett.* 2002, 43, 3903-3906. (c) Huang, X.; Liu, Z. "Solid-Phase synthesis of 4(1H)-Quinolone and Pyrimidine Derivatives Based on a New Scaffold—Polymer-Bound Cyclic Malonic Acid Ester" *J. Org. Chem.* 2002, 67, 6731-6737. (d) Couladouros E. A.; Strongilos, A. T. "Generation of Libraries of Pharmacophoric Structures with Increased Complexity and Diversity by Employing Polymorphic Scaffolds" *Angew. Chem., Int. Ed.* 2002, 41, 3677-3680. (e) Bertozzi, F.; Gundersen, B. V.; Gustafsson, M.; Olsson, R. "A Combinatorial Scaffold Approach Based upon a Multicomponent Reaction" *Org. Lett.* 2003, 5, 1551-1554. (f) Taylor, S. J.; Taylor, A. M.; Schreiber, S. L. "Synthetic Strategy toward Skeletal Diversity via Solid-Supported, Otherwise Unstable Reactive Intermediates" *Angew. Chem., Int. Ed.* 2004, 43, 1681-1685.

Diversity-oriented synthesis of a chemical compound library provides a powerful means to identify small molecule inhibitors against medically relevant targets. Initial screens of a pilot library followed by diversification using solid phase synthesis can yield potent inhibitors of enzymes in a relatively short period of time.

Since late 1990, a number of attempts to carry out diversity-oriented synthesis have been reported. One example is the use of squaric acid as a multireactive core molecule to generate a library consisting of different core structures. See Tempest, P. A. and Armstrong, R. W. (1997) Cyclobutenedione derivatives on solid support: Toward multiple core structure libraries. *J. Am. Chem. Soc.* 119, 7607-7608. However, very few of these examples were used in actual library synthesis. See (a) Ding, S.; Gray, N. S.; Wu, X.; Ding, Q.; Schultz, P. G. "A Combinatorial Scaffold Approach toward Kinase-Directed Heterocycle Libraries" *J. Am. Chem. Soc.* 2002, 124, 1594-1596. (b) Kwon, O.; Park, S. B.; Schreiber, S. L. "Skeletal Diversity via a Branched Pathway: Efficient Synthesis of 29,400 Discrete, Polycyclic Compounds and Their Arraying into Stock Solutions" *J. Am. Chem. Soc.* 2002, 124, 13402-13404. (c) Burke, M. D.; Berger, E. M.; Schreiber, S. L. "Generating Diverse Skeletons of Small Molecules Combinatorially" *Science* 2003, 302, 613-618. Due to drastically different reaction conditions, the yields greatly varied from one reaction to another, which discouraged adaptation of the methodology to a combinatorial library synthesis in solid-phase.

There thus exists a need for the identification of a multireactive core molecule for which more consistent reaction conditions can be used and with which more consistent yield is obtained in diversity oriented synthesis. There exists a need for novel GGTI and RabGGTase inhibiting compounds.

SUMMARY

Some exemplary embodiments of the invention are directed to compounds having the formula:

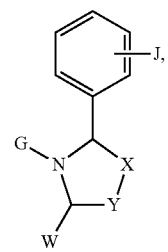

wherein J is hydrogen or is 1-2 substituents independently selected from the group consisting of halogen, $C_1$-$C_3$ alkyl, OR', SR', and NR'$_2$, where R' is alkyl.

wherein G is

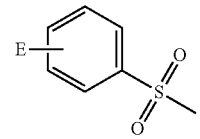

wherein E is hydrogen or is 1-2 substituents selected from the group consisting of halogen, $C_1$-$C_3$ alkyl, OR', SR', and NR'$_2$, where R' is alkyl, wherein W is selected from the group consisting of hydrogen, cyclic, linear, or branched alkyl of from 2 to 8 carbons, unsubstituted phenyl, and phenyl substituted with $C_1$-$C_3$ alkyl, halogen, OR', SR', and NR'$_2$, where R' is alkyl,

is selected from the group consisting of wherein

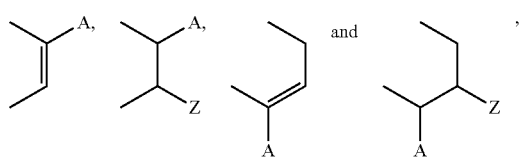

wherein A is selected from the group consisting of:

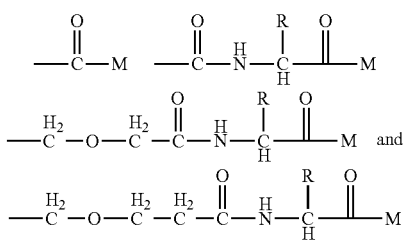

wherein M is selected from the group consisting of OH, OR", $NH_2$, NHOH, NHOR", wherein R" is methyl or ethyl, or any other group that has a polar metal binder wherein R corresponds to an alpha-substituent of natural or non-natural alpha-amino acid;

wherein Z is S—U; and wherein U is selected from the group consisting of alkyl having 10 or fewer carbons, phenyl, optionally substituted with halogen or OR", wherein R" is methyl or ethyl, and $(CH_2)_n$—$COOR^4$, wherein n=1-4 and $R^4$ is a linear or branched alkyl having four or fewer carbons.

In some embodiments of the invention the compound inhibits the activity of a protein prenyltransferase. The invention is also directed to pharmaceutical compositions comprising the compound of the invention and a pharmaceutically acceptable carrier or diluent.

Some embodiments of the invention are directed a method comprising administering the compound of the invention to a cell in an amount sufficient to inhibit the activity of GGTase I, RabGGTase, or both GGTase I and RabGGTase.

Some embodiments of the invention are directed to a method comprising administering a compound of the invention in an amount sufficient to inhibit the growth of a cancer cell. The cancer can be, but is not limited, pancreatic, leukemia, breast, lung, colon, ovarian, stomach, and prostate cancer. In some embodiments, the cancer cell comprises GGTase I modified proteins and/or RabGGTase modified proteins.

Some embodiments of the invention are directed to a method comprising administering to a subject in need of treatment for a cancer a pharmaceutical composition of the present invention in an amount sufficient to inhibit the activity of a protein prenyltransferase.

Some embodiments of the invention are directed to a method comprising measuring the GGTase I and/or RabGGTase inhibiting activity of a compound of the invention.

One of skill in the art will appreciate that the various substituent groups depicted herein can be combined with each linker or scaffold within the range of compounds that fall within the scope of the present invention. Because of the chemical characteristics of the inventive library, a person of ordinary skill can combine the "left hand" or "right hand" substitutents with the various linkers and scaffolds of the present invention. For example, the substituent groups illustrated in Tables 1-15 or elsewhere in the written description and figures including the chemical formulas described herein, may be used with any linker or scaffold disclosed herein, regardless of whether that specific substituent group is specifically depicted with that linker or on that scaffold. As will be understood, the activities of these various combinations may differ.

BRIEF DESCRIPTION OF THE DRAWINGS

FIGS. 11A-H present structures and numbers of the library compounds.

FIG. 12 presents tetrahydropyridine scaffold compounds with GGTI activity.

FIG. 13 presents piperidine scaffold compounds with GGTI activity.

FIGS. 17A and 17B present GGTI compounds with preferential inhibition of K-Ras4B-driven GGTase I activity.

FIGS. 19-1 through 19-27 present the measured Kras inhibitory activities of individual compounds.

FIGS. 20A-20C illustrate specific inhibition of GGTase I by P3-E5 and P5-H6. FIGS. 20D-F show the structure of GGTase I (D), FTase (E) and GGTase II (F).

FIGS. 21A-21D illustrate that GGTIs compete with substrate protein but do not compete with GGPP, with a scheme shown in 21E.

FIGS. 22A and 22B show inhibition of gernaylgeranylation in cells treated with P3-E5.

FIG. 23 illustrates inhibition of proliferation in K562 cells by GGTIs.

FIG. 24A illustrates that GGTIs induce G1 cell cycle arrest in K562 cells with a scheme shown in 24B.

FIGS. 25A and 25B illustrate that mP5-H6 inhibits geranylgeranylation in vivo.

FIG. 26 illustrates that mP5-H6 exhibits increased potency to inhibit proliferation of Panc-1 and Jurkat cells.

FIG. 27 illustrates exemplary GGTIs of the present invention (mP5-H6, P5-H6, and P3-E5) and some other GGTI compounds.

FIG. 28 illustrates structures of GGTIs with dihydropyrrole scaffold 6.

FIGS. 29A to 29C illustrate structures of GGTIs with pyrrolidine scaffold 10.

FIG. 31 illustrates a method of synthesizing GGTIs.

FIG. 32 illustrates a formula for exemplary compounds of the present invention.

FIG. 35 shows a kinetic analysis of GGTase-I inhibition. Double reciprocal plots were obtained from substrate velocity curves for the inhibition of GGTase-I by P3-E5 (left) and P5-H6 (right). (A) shows varying GGPP concentrations with a fixed RhoA protein concentration were used. (B) shows varying RhoA protein concentrations with a fixed GGPP concentration. The amount of GGTI used is indicated in the figure.

FIG. 36 shows the cellular activity of modified GGTI compounds. (A) shows the molecular structure of P5-H6 and modified P5-H6 compounds. K562 cells were treated with modified compounds for 72 hours and then cell number was counted. $IC_{50}$ values of cell viability relative to the DMSO were measured. (B) shows the inhibitory effect of 12.5 μM P5-H6 or P61-A6 on PANC-1 and Jurkat cell viability. Data represent the mean+/−S.D. of two measurements from two independent experiments. *, P<0.05 compared with the value for DMSO. (C-E) P5-H6 or P61-A6 treatment inhibits Rap1 geranylgeranylation in NIH3T3 cells. Whole cell lysates from cells treated with DMSO, P5-H6, P61-A6, GGTI (GGTI-298), FTI (BMS-225975) or RabGGTI (P49-F6) for 48 hours were prepared and processed for immunoblot analysis using antibody against unprenylated form of Rap1 (C: upper panel), Total-Rap1 (C: middle panel), H-Ras (D: upper panel), Rab5b (E: upper panel) or actin (C, D, and E: lower panel). The immunoblots shown represent two independent experiments for each treatment.

FIG. 38 shows the dual specificity inhibitors of GGTase-I and RabGGTase. (A) shows the molecular structure of dual specificity inhibitors. (B) shows the $IC_{50}$ values of dual specificity inhibitors against GGTase-I, RabGGTase and FTase. (C) shows the Inhibitory effect of 25 μM P49-F5 compound on in vitro activities of GGTase-I, RabGGTase and FTase.

FIG. 39 shows RabGGTase preferential inhibitors. (A) shows the molecular structure of RabGGTase inhibitors. (B) shows $IC_{50}$ values of RabGGTase preferential inhibitors against GGTase-I, RabGGTase and FTase. (C) shows the inhibitory effect of 25 μM P49-F6 compound on in vitro activities of GGTase-I, RabGGTase and FTase.

FIG. 56 shows the structures and numbers of the focused second-generation library compounds.

FIG. 59 shows tetrahydropyridine scaffold (7) with GGTI activity that exceeds the GGTI activity of P3-E5 (UC23).

FIG. 60 shows dihydropyrrole scaffold (6) with GGTI activity that exceeds the GGTI activity of P5-H6 (UC22).

DETAILED DESCRIPTION

Figure 1:
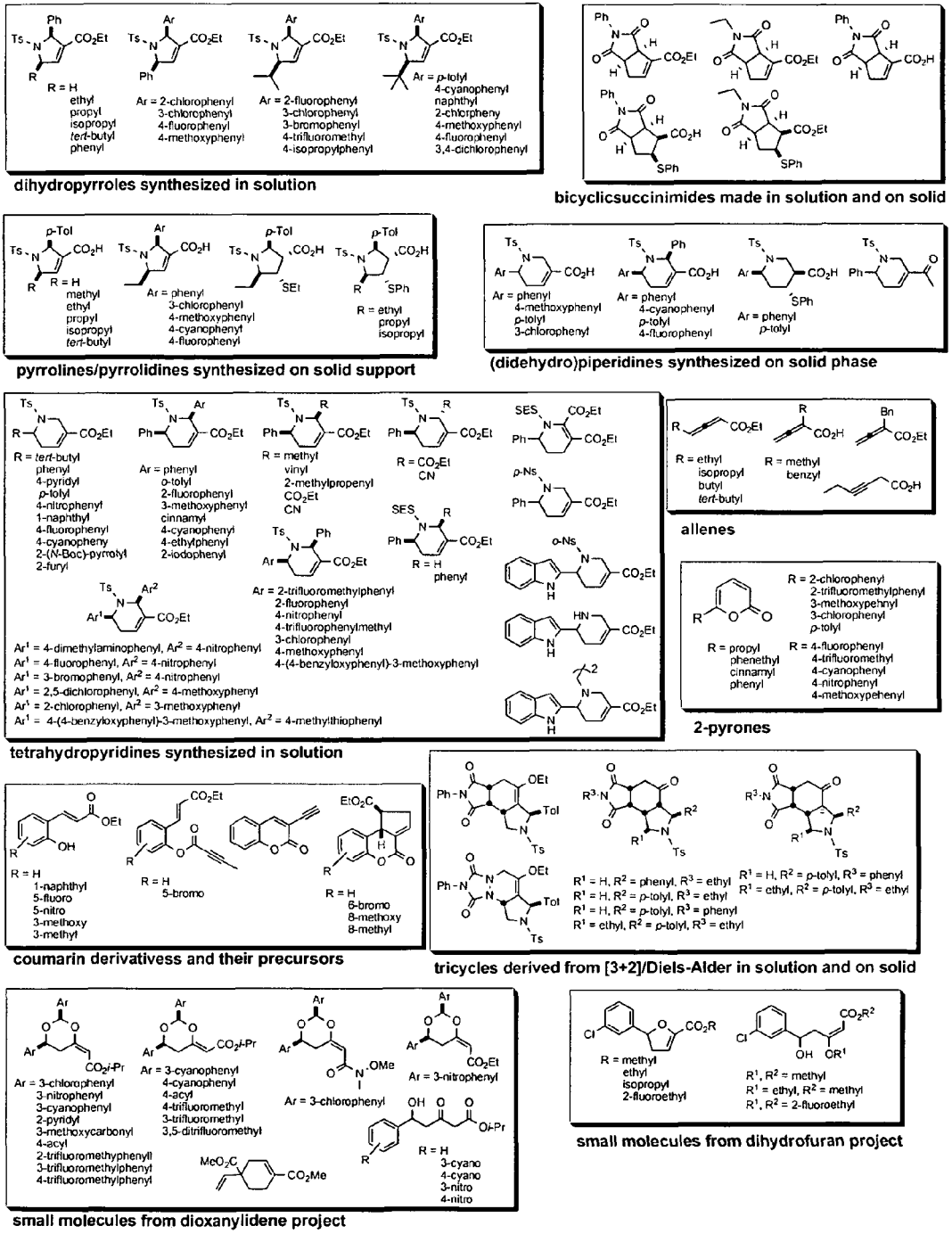
FIG. 1 presents a pilot library of compounds.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

There are several reasons that protein prenyltransferases, such as GGTase I or RabGGTase, are attractive targets for anti-cancer drug development. First, Rho proteins such as RhoA and Rac are critical in enhancing transformation. In fact, peptidomimetic inhibitors of GGTase I have shown promise in inhibiting proliferation of cancer cells. An arrest of the cell cycle at the G0/G1 phase was consistently observed with GGTase I inhibitors.

Second, one of the geranylgeranylated proteins, RhoC, has been identified as a protein involved in cancer metastasis. See (a) Clark, E. A., Golub, T. R., Lander, E. S, and Hynes, R. O. (2000) Genomic analysis of metastasis reveals an essential role for RhoC. *Nature* 406, 466-467. (b) Hakem, A., Sanchez-Sweatman, You-Ten, A., Duncan, G., Wakeham, A., Khokha, R. and Mak, T. W. (2005) RhoC is dispensable for embryogenesis and tumor initiation but essential for metastasis. *Genes & Develop.* 19, 1974-1979. Thus, blocking the function of RhoC by inhibiting its geranylgeranylation provides an effective way to inhibit metastasis. Third, GGTIs may be useful to inhibit alternative prenylation of K-Ras4B.

GGTIs that specifically inhibit K-Ras4B geranylgeranylation but do not inhibit geranylgeranylation of RhoA are of interest, as they may provide a way to overcome one of the major shortcomings of currently available FTIs. While FTIs can potently inhibit FTase, they are incapable of inhibiting K-Ras, as this protein undergoes modification by GGTase I. See Tamanoi, F., Gau, C. L., Edamatsu, H., Jiang, C. and Kato-Stankiewicz, J. (2001) Protein farnesylation in mammalian cells, *Cell Mol. Life Sci.* 58, 1-14. The combined use of FTI and GGTI as well as the use of dual specificity FTIs that could inhibit both FTase and GGTase I has been attempted. See Lobell, R. B., Liu, D., Buser, C. A., Davide, J. P., DePuy, E., Hamilton, K., Koblan, K. S., Lee, Y. Mosser, S., Motzel, S. L., Abbruzzese, J. L., Fuchs, C. S., Rowinsky, E. K., Rubin, E. H., Sharma, S., Deutsch, P. J., Mazina, K. E., Morrison, B. W., Wildonger, L., Yao, S. L. and Kohl, N. E. (2002) Preclinical and clinical pharmacodynamic assessment of L-778,123, a dual inhibitor of farnesyl:protein transferase and geranylgeranyl:protein transferase type-I. *Mol. Cancer Ther.* 1, 747-758.

As described below, embodiments of the invention are directed to the identification and characterization of small molecule inhibitors of GGTase-I with novel scaffolds from a library consisting of allenoate derived compounds. These compounds can exhibit specific inhibition of GGTase-I, often by competing with a substrate protein. It was discovered that derivatizing a carboxylic acid emanating from the core ring of one of the GGTI compounds improved their cellular activity. The improved GGTI compounds inhibit proliferation of a variety of human cancer cell lines and cause $G_1$ cell cycle arrest and induction of $p21^{CIP1/WAF1}$.

Embodiments of the invention are also directed to the identification and characterization of novel small molecule inhibitors of RabGGTase. These compounds were identified by screening the GGTI compounds described herein for compounds that also exhibited RabGGTase inhibition. This screening led to the discovery of a common structural feature for RabGGTase inhibitors; the presence of a characteristic six-atom aliphatic tail attached to the penta-substituted pyrrolidine core. Additional screening and research led to the identification of compounds with preferential inhibition of RabGGTase. It is believed that these compounds inhibit RabGGTase activity by competing with the protein substrate.

The term "inhibit" means that a compound stops or otherwise prevents at least one function of a target compound. For example, a GGTase I inhibitor can stop or otherwise prevent at least one activity a target compound, for example, an activity of the enzyme GGTase I. In some embodiments, the target compounds for the inhibitors described herein is a protein prenyltransferase. Inhibition can occur in vitro and/or in vivo using a predetermined amount of an inhibitor.

CHEMICAL DEFINITIONS

Unless specified otherwise, the following chemical definitions are used throughout the sections below.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which may be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like. "Bulky alkyl" includes cycloalkyl and branched chain alkyls with 4-8 carbons.

The term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl." For example,

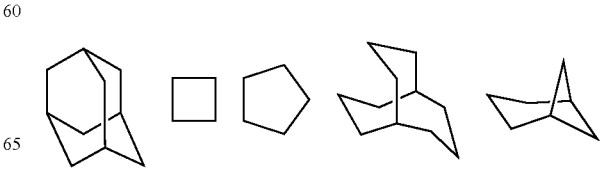

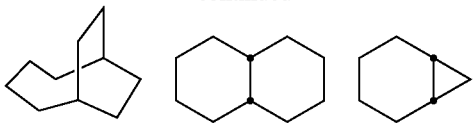

and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

The term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

Salt, crystalline, and other forms of the chemical compounds depicted in the formulas and structures shown and described herein are contemplated within the meaning of "compound" of the invention. As one of skill in the art will appreciate, the compounds described herein may be used in their salt form (e.g., a sodium, potassium, or other pharmaceutically acceptable salt) or in a crystalline form. For some compounds, e.g., mP5-H6, a salt cannot be readily prepared using conventional methods but, as one of skill in the art will appreciate, alternative methods may be used to prepare a salt. The salt or crystalline forms of the compounds described herein may be useful as part of a pharmaceutical composition.

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, fluorine, and iodine.

The term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, aryl aminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

The term "heterocyclic" or "heterocycle", as used herein, represents an unsubstituted or substituted stable 5- to 10-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

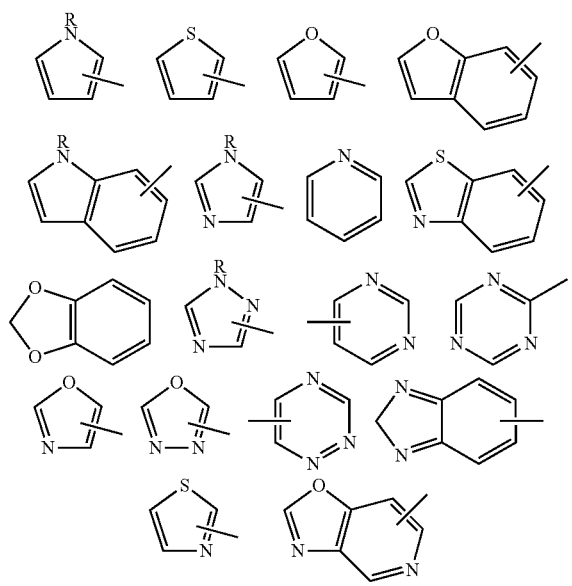

and the like.

The term "polar metal binder" means a polar group that is capable of binding, e.g., chelating, to a metal. Non-limiting examples have been disclosed in the chemical structures included in this application and its figures.

I. General Structure of Protein Prenyltransferase Inhibiting Compounds and Synthesis Methods Through library screening and other assays described to follow, numerous compounds of interest have been identified. These compounds can be useful as inhibitors of protein prenyltransferases, including GGTase I and RabGGTase.

The protein prenyltransferase inhibiting compounds described herein, in some embodiments, can be described by the following general formula referred to as Formula I:

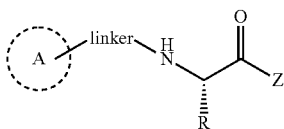

As discussed previously, one of skill in the art will appreciate that the various substituent groups depicted herein can be combined with each linker or scaffold within the range of compounds that fall within the scope of the present invention. Because of the chemical characteristics of the inventive library, a person of ordinary skill can combine the "left hand" (e.g, the A group in Formula I) or "right hand" (e.g., the groups "to the right" of the linker in Formula I) substitutents with the various linkers and scaffolds of the present invention. For example, the substituent groups illustrated in Tables 1-15 or elsewhere in the specification and figures or within any formula described herein, may be used with any linker or scaffold disclosed herein, regardless of whether that specific substituent group is specifically depicted with that linker or on that scaffold. As will be understood, the activities of these various combinations may differ.

As used in Formula I only (above), A can be any of the following (with or without the double bond within the ring):

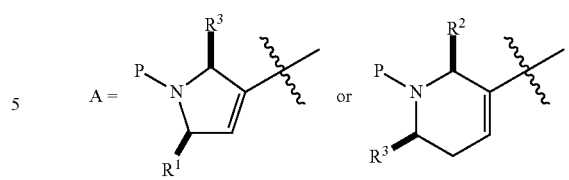

In some embodiments, the "linker" of Formula I can be any of the following:

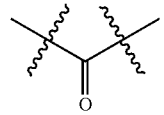
linker 1

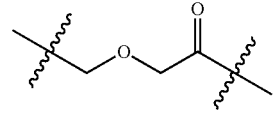
linker 2

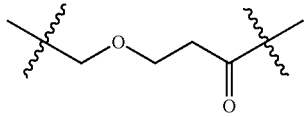
linker 3

The groups P, R1, and R2 shown in A of Formula I are described in detail to follow. Further, the group P as used in Formula I is also referred to as G in the text below.

The compounds described herein, including those described in Formula I, can be made using a variety of sythesis methods which are described herein. For example, the compounds represented by Formula 1 can be prepared using the following synthesis method:

Modification of the carboxylic acid end group:
a. For the Five-Membered Ring

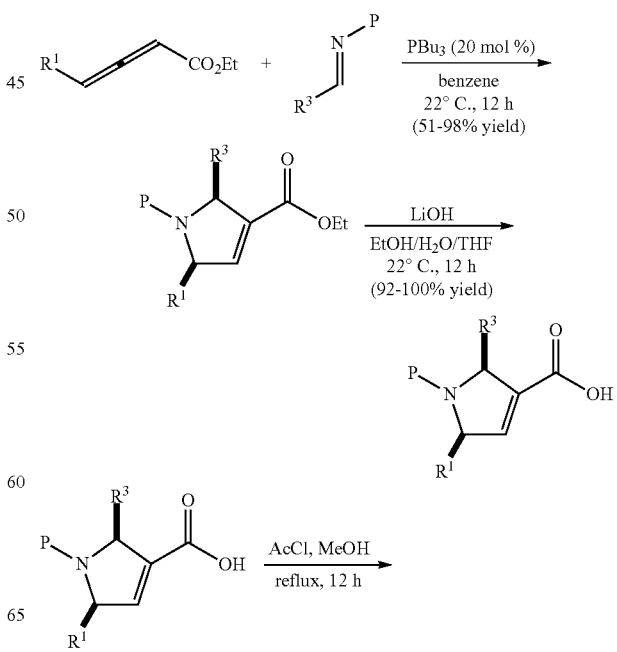

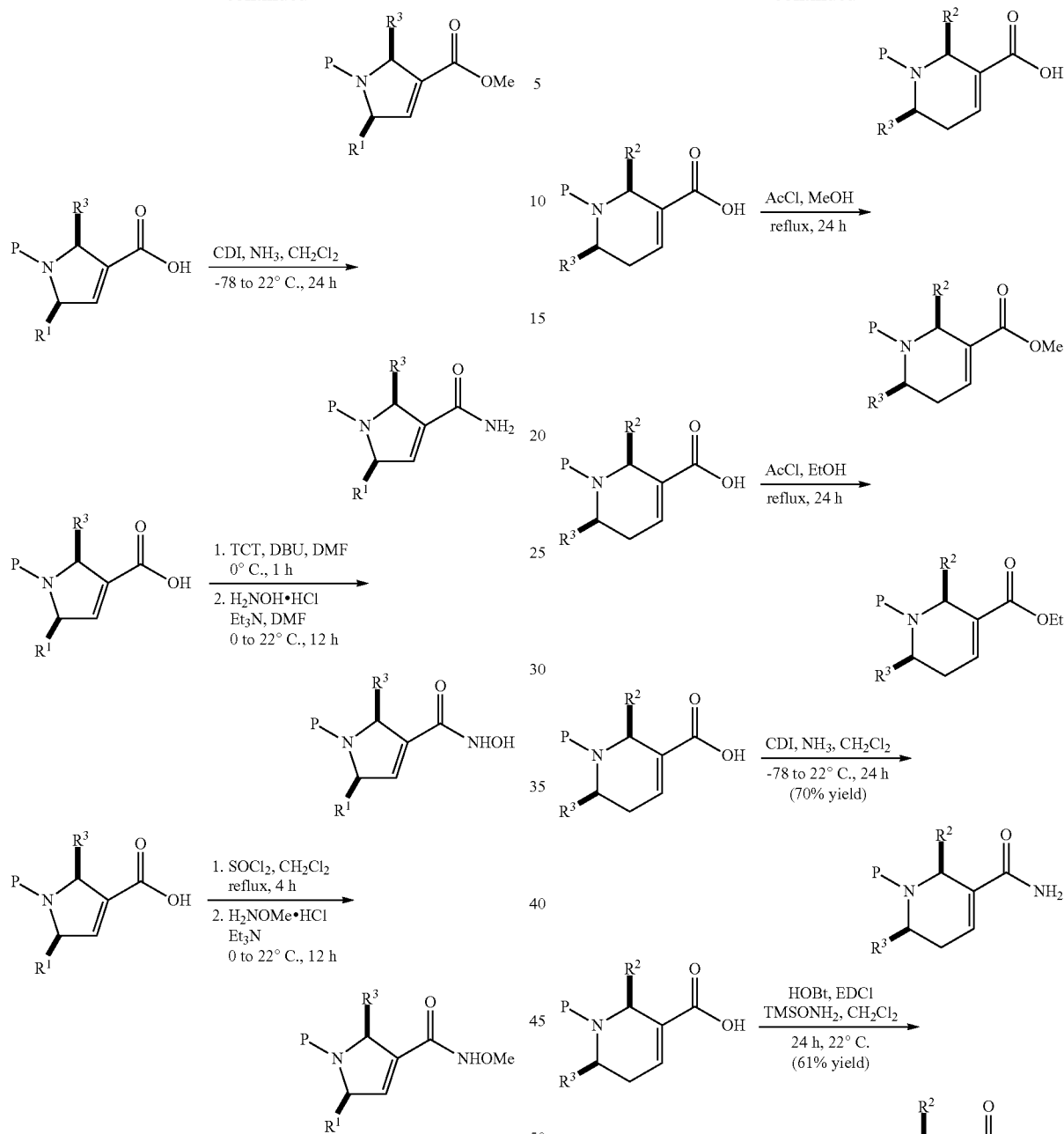
b. For the Six-Membered Ring
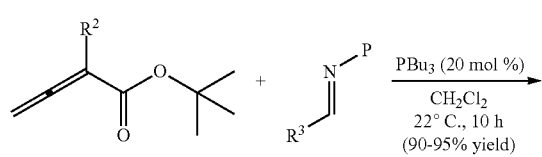
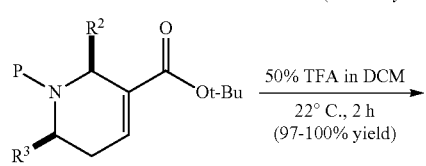
For Linker 1
a. Five-Membered Ring
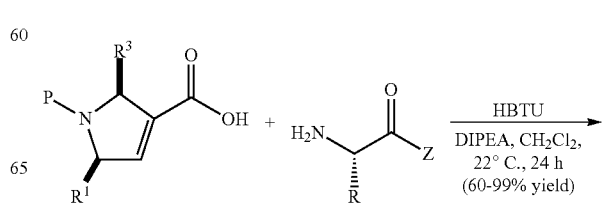

17
-continued
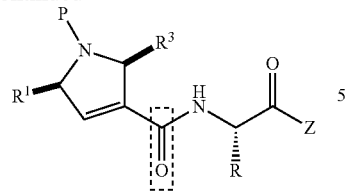
where Z=OH, OMe, NHOH, NHOMe
Note: For Z=OH, the reaction condition is: HBTU, DIPEA, L-aminoacid methyl ester, $CH_2Cl_2$, 22° C., 24 h; then LiOH, $EtOH/H_2O/THF$, 22° C., 12 h
b. Six-Membered Ring
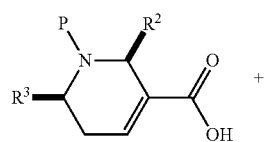
18
-continued
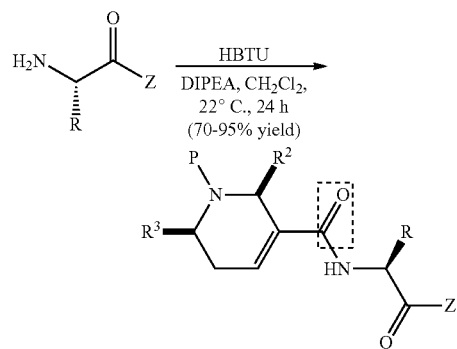
where Z=OH, OMe, NHOH, NHOMe
Note: For Z=OH, the reaction condition is: HBTU, DIPEA, L-aminoacid t-butyl ester, $CH_2Cl_2$, 22° C.; then 50% TFA in $CH_2Cl_2$, 22° C., 2 h
For Linker 2
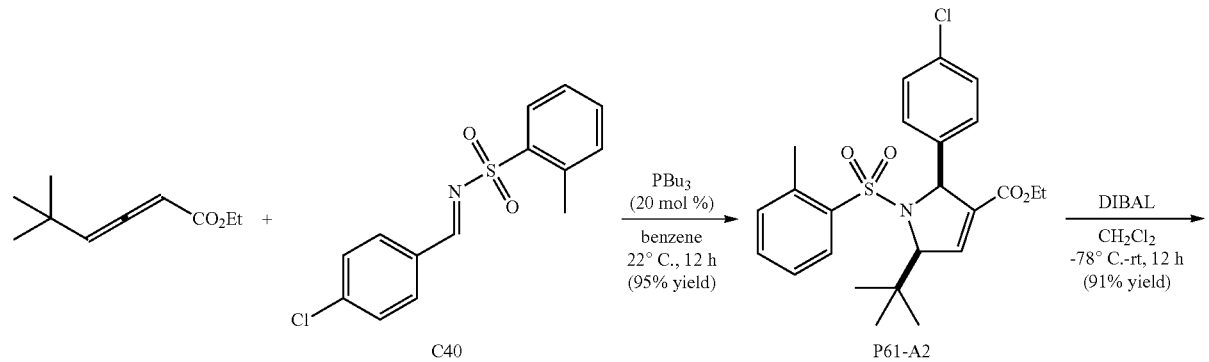
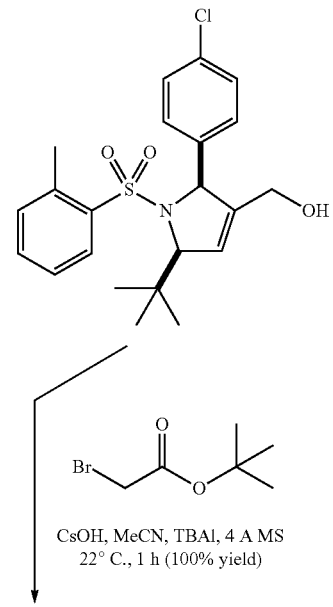

-continued
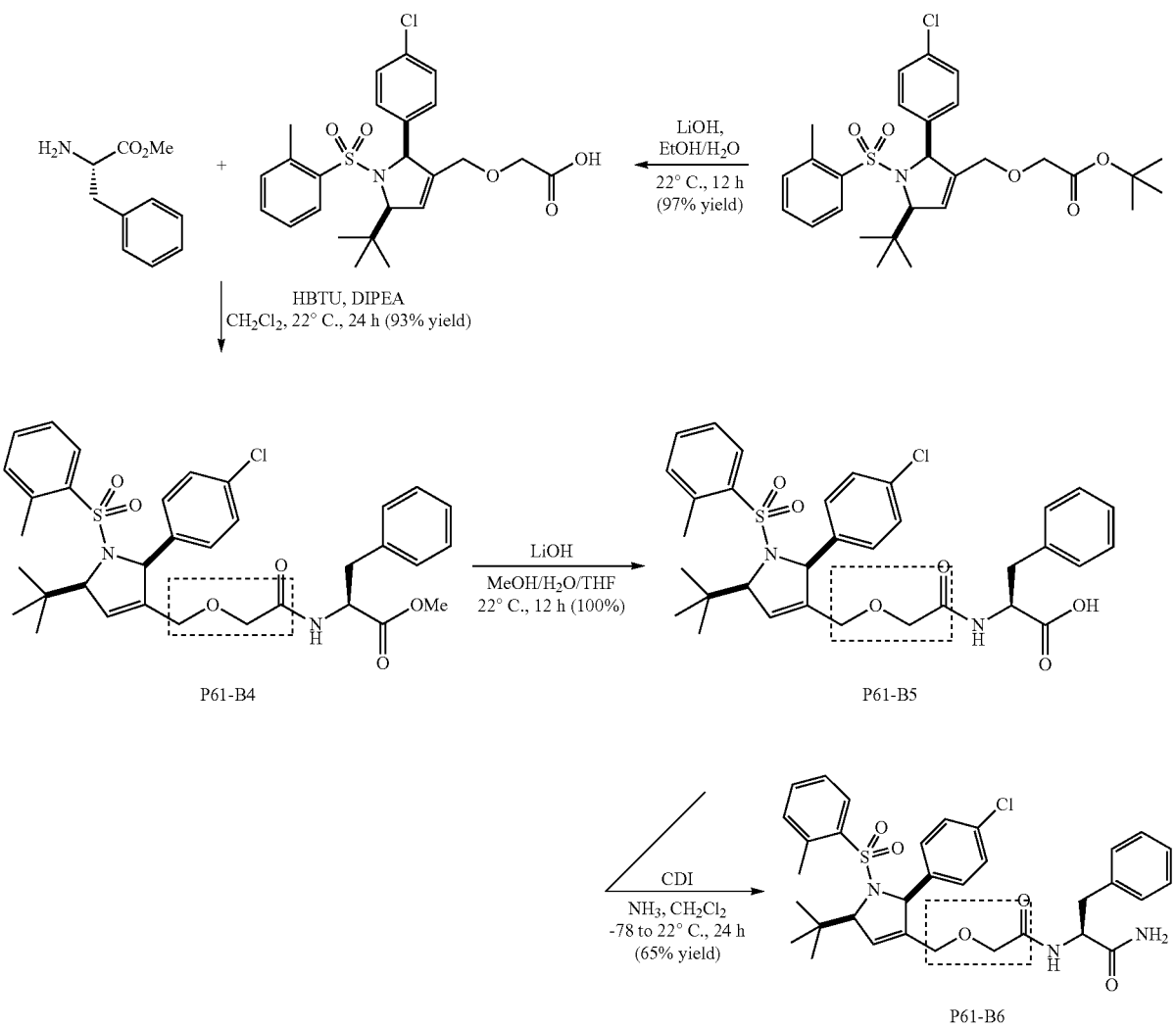
For Linker 3
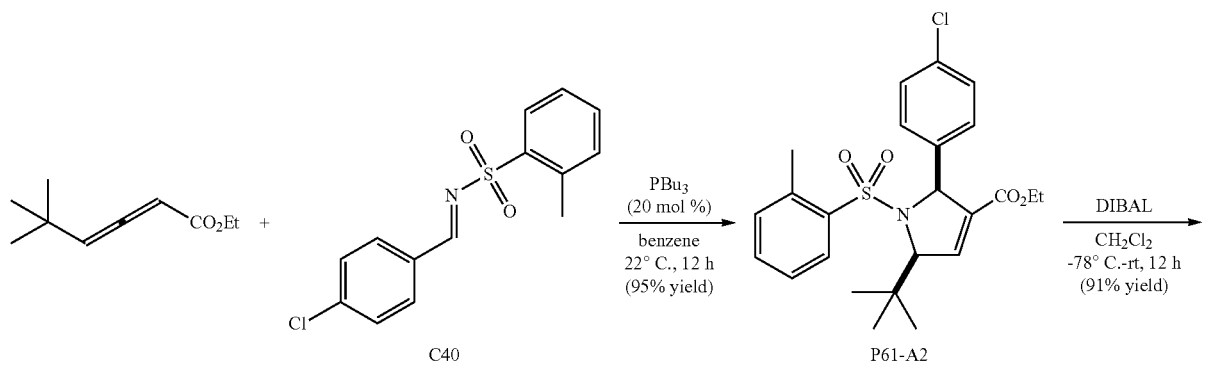

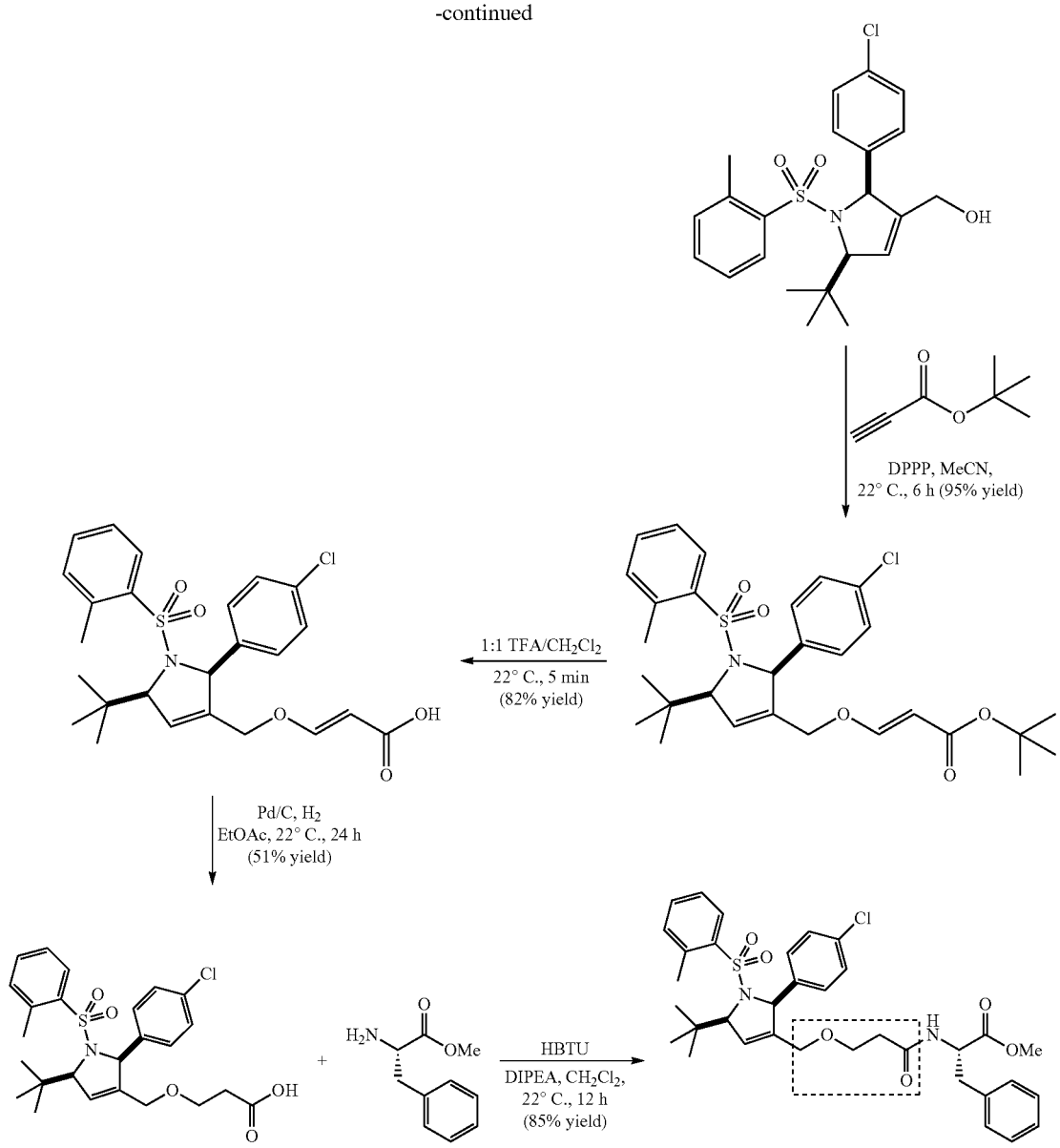

II. Pilot Library Construction and Screening

To overcome the problems associated with the diversity-oriented synthesis, an approach was developed that employs allenoates as multireactive core molecule and uses another set of building blocks (imines, aldehydes and maleimides) that react with allenoates under similar reaction conditions (phosphine catalysis). This led to the production of diverse compounds including dihydropyrroles and tetrahydropyridines.

According to the invention, inventive compounds with the novel linkers and scaffolds described herein can be produced using variations of a pilot library. A pilot library was constructed using allenoate as a multireactive core molecule. This pilot library was screened for compounds which inhibited protein farnesyltransferase (FTase), that is, farnesyltransferase inhibitors (FTIs), and for compounds which inhibited protein geranylgeranyltransferase type I (GGTase I), that is geranylgeranyltransferase type I inhibitors (GGTIs). Because these enzymes catalyze modification of signaling proteins such as Ras, Rheb and Rho, small molecule inhibitors can be anti-cancer therapeutics. 4,314 compounds were synthesized and screened for compounds with improved potency of inhibition. As discussed further below, structure activity relationship studies of these compounds pointed to the significance of certain substitution patterns on the aromatic substitutions of the scaffold ring structure of initial hits.

Construction of a Pilot Library Based on Allenoate Chemistry

The pilot library was constructed by reacting allenoates with imines, aldehydes and maleimides under phosphine catalysis conditions to produce an array of compounds including dihydropyrroles, tetrahydropyridines, bicyclic succinimides, dioxanylidenes and dihydrofurans. The 171 compounds produced for the pilot library are illustrated in FIG. 1.

Identification of Novel Inhibitors of Protein Geranylgeranyltransferase Type I

The pilot library was screened for inhibitors of protein geranylgeranyltransferase type I. Protein prenyltransferase assays were carried out by using filter binding. Two different substrates, RhoA and K-Ras4B, were used for the assay. RhoA ends with the CaaL motif and is an exclusive substrate for GGTase I, while K-Ras4B ends with the CaaX motif and is modified by both GGTase I and FTase. The presence of a polybasic domain consisting of a stretch of lysine close to the CaaX motif enables this CaaX motif to be recognized by GGTase I. Thus, RhoA and K-Ras4B are two very different substrates of this enzyme and it is of interest to identify small molecule inhibitors exhibiting preferential inhibition on reaction driven by one substrate over another.

Figure 2:
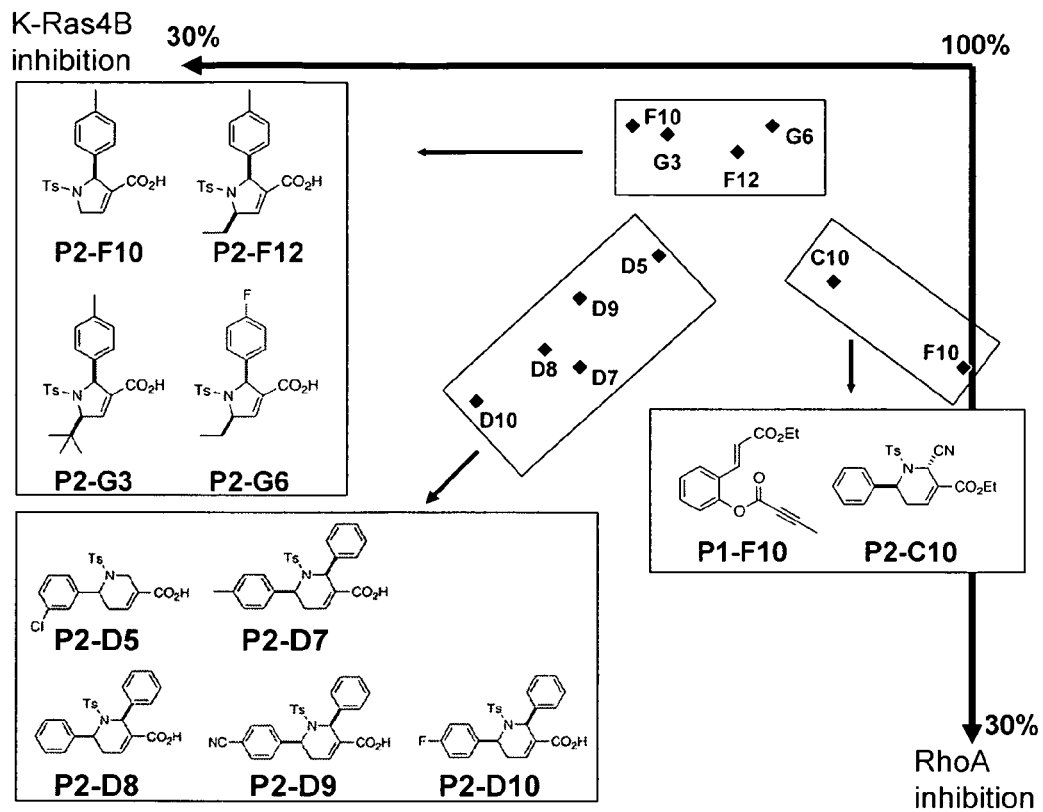
FIG. 2 presents the structure of GGTIs identified from the pilot library.

Screening of the 171-compound pilot library resulted in the identification of three groups of compounds shown in FIG. 2. In the assay, a fixed concentration of 100 µM was used and the results are plotted for the inhibition of RhoA (vertical axis) as well as for K-Ras4B (horizontal axis). A group of compounds that contain P2-D5, P2-D7, P2-D8, P2-D9 and P2-D10 inhibit GGTase I equally when using RhoA and K-Ras4B as substrates. They are 2,6-diaryl-N-tosyl-1,2,5,6-tetrahydropyridine-3-carboxylic acids, except P2-D5 that is missing an aryl substituent at C2. The second group of compounds, P2-F10, P2-F12, P2-G3 and P2-G6, exhibits somewhat stronger inhibition when using K-Ras4B as a substrate. In particular, P2-F10 demonstrates significant inhibition of GGTase I when K-Ras4B is used as a substrate, while virtually no inhibition was observed when RhoA was used as a substrate. It is worth pointing out that known GGTI compound GGTI-298 and GGTI-2166 inhibit RhoA-driven GGTase I activity slightly better than K-Ras4B-driven GGTase I activity (FIG. 17). This group of compounds possesses 5-alkyl-2-aryl-N-tosy-2,5-dihydropyrrole-3-carboxylic acid structure, which is distinct from the previously described tetrahydropyridine motif.

Another compound that is different from the above two groups was also identified. This compound, labeled P1-F10, inhibited GGTase-I when using RhoA as a substrate but virtually no inhibition was seen when K-Ras4B was used as a substrate. The GGTIs identified did not inhibit FTase at the same concentration.

Figure 3:
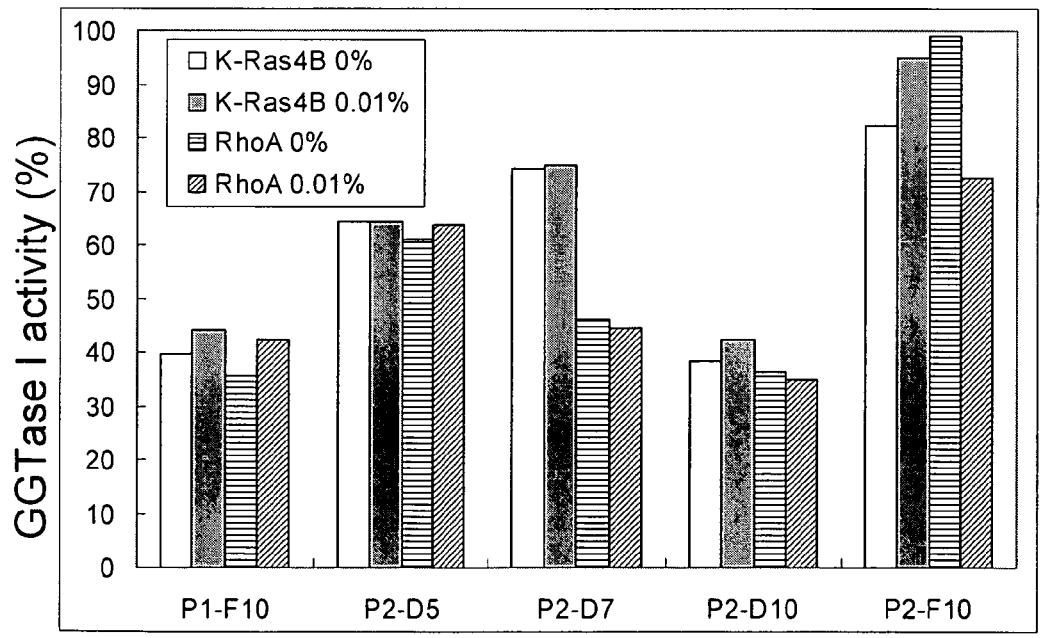
FIG. 3 illustrates that GGTI effects are not influenced by the addition of detergents.

It has been reported that some chemical compounds form aggregates at high concentrations and that these aggregates inhibit a variety of enzyme reactions. See (a) McGovern, S. L., Caselli, E., Grigorieff, N. and Shoichet, B. K. (2003) A common mechanism underlying promiscuous inhibitors from virtual and high-throughput screening. J. Med. Chem. 45, 1712-1722. (b) McGovern, S. L., Helfand, B. T., Feng, B. and Shoichet, B. K. (2003) A specific mechanism of nonspecific inhibition. J. Med. Chem. 46, 4265-4272. To exclude this possibility, one can add a detergent that can prevent formation of these aggregates. As can be seen in FIG. 3, the inhibition of GGTase I observed was unaffected by the presence of the detergent (0.01% TritonX-100). Similarly, all the inhibitions observed could be reproduced in the presence of the detergent.

Identification of Novel Inhibitors of Protein Farnesyltransferase

Figure 4:
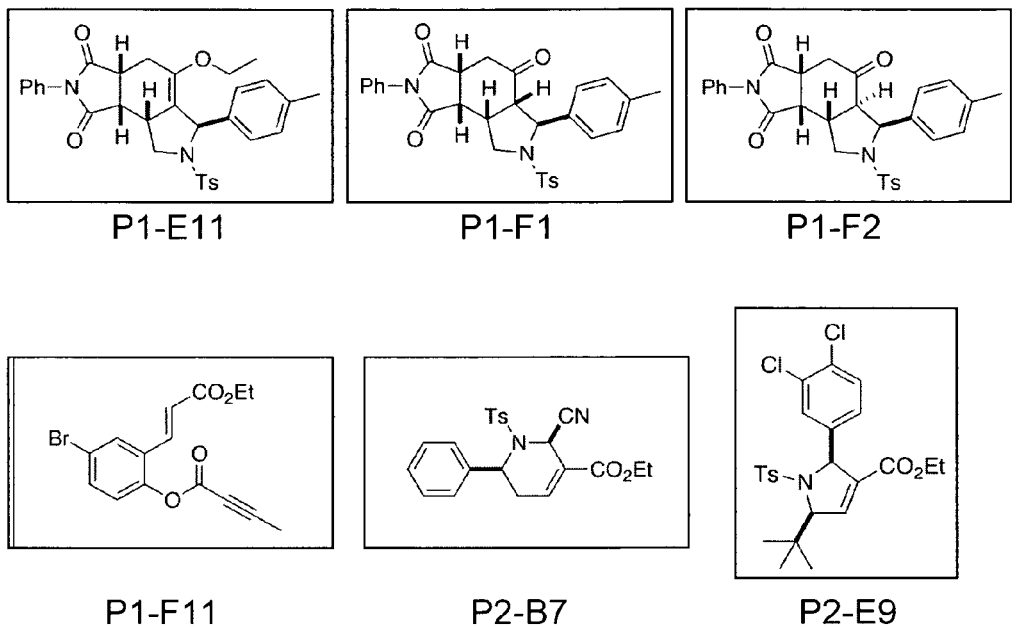
FIG. 4 presents the structure of FTIs identified from the pilot library.

To further characterize the pilot library, inhibitors of protein farnesyltransferase were identified. This was accomplished by using K-Ras4B as a substrate protein, tritiated farnesylpyrophosphate ([$^3$H]FPP) and protein farnesyltransferase. See Finegold, A. A., Johnson, D. I., Farnsworth, C. C., Gelb, M. H., Judd, S. R., Glomset, J. A. and Tamanoi, F. (1991) Protein geranylgeranyltransferase of *Saccharomyces cerevisiae* is specific for Cys-Xaa-Xaa-Leu motif and requires the CDC43 gene product but not the DPR1 gene product. *Proc. Natl. Acad. Sci. USA* 88, 4448-4452. This screen led to the identification of six hit compounds shown in FIG. 4. Interestingly, compounds P1-E 11, P1-F1 and P1-F2 contain a common structure that is distinct from those identified as GGTI compounds above. On the other hand, the structure of the compounds P1-F11, P2-B7 and P2-E9 resemble those of GGTIs. The FTI P1-F11 resembles the GGTI P1-F10, while the FTI P2-B7 resembles the GGTI P2-C10. The FTI P2-E9 is similar to the GGTI P2-G3. Similarity of some GGTI and FTI compounds may point to common structural features between the two closely related enzymes. As described before, FTase and GGTase I have similar three-dimensional structures and a shared alpha subunit. On the other hand, FTase specific inhibitors may recognize a region(s) that is different between the two enzymes. The FTIs identified here exhibit a weaker inhibition of GGTase I at the concentration that inhibits FTase.

Further Diversification of the Compound Library and Identification of Improved GGTI Compounds An advantage of using the diversity oriented library described herein is that it is possible to quickly synthesize a large number of compounds that are related to lead compounds. Split-and-pool synthesis on solid support is one of the fastest and most efficient ways of generating a large number of spatially segregated compounds. See (a) Furka, A.; Sebestyén, F.; Asgedom, M.; Dibó (1988), in *Highlights of Modern Biochemistry, Proceedings of the 14th International Congress of Biochemistry*, Prague, Czechoslovakia (VSP, Utrecht, Netherlands), 13, 47. (b) Furka, A.; Sebestyén, F.; Asgedom, M.; Dibó (1991), *Int. J. Pept. Protein Res.* 37, 487. (c) Houghton, R. A.; Pinilla, C.; Blondelle, S. E.; Appel, J. R.; Dooley, C. T.; Cuervo, J. H. (1991) "Generation and use of synthetic peptide combinatorial libraries for basic research and drug discovery" *Nature* 354, 84-86. (d) Lam, K. S.; Salmon, S. E.; Hersh, E. M.; Hruby, V. J.; Kazmierski, W. M.; Knapp, R. J. (1991) "A new type of synthetic peptide library for identifying ligand-binding activity" *Nature* 354, 82-84; (e) Obrecht, D.; Villalgordo, J. M. (1998) *Solid-Supported Combinatorial and Parallel Synthesis of Small-Molecular-Weight Compound Libraries*, Elsevier Science Ltd, Oxford. Use of the IRORI NanoKan system or SynPhase™ Lanterns alleviates the need for chemical encoding, and provides more material for a given compound than using beads. More information on these systems may be found at www.discoverypartners.com/products/irori_tech_nanokan.html or www.synphase.com/combichem/lanterns.html. It was decided to use SynPhase Lanterns but as one of skill in the art will appreciate the invention described herein is not limited to using SynPhase Lanterns (available from Mimotopes Pty Ltd., Victoria, Australia).

The SynPhase Lantern consists of a grafted mobile surface polymer (such as polystyrene) onto a rigid and unreactive base polymer that is cylindrical in appearance. The SynPhase Lantern is available in three different sizes, with loadings of 15 µmol, 35 µmol, and 75 µmol. Considering that a typical assay requires 1 nmol of a small organic molecule, 15~75 µmol of compound provides a large enough quantity of chemicals for multiple assays. The rigid polymeric support of lanterns beneath a grafted mobile phase makes weighing unnecessary and handling easier than with resins.

Figure 5:
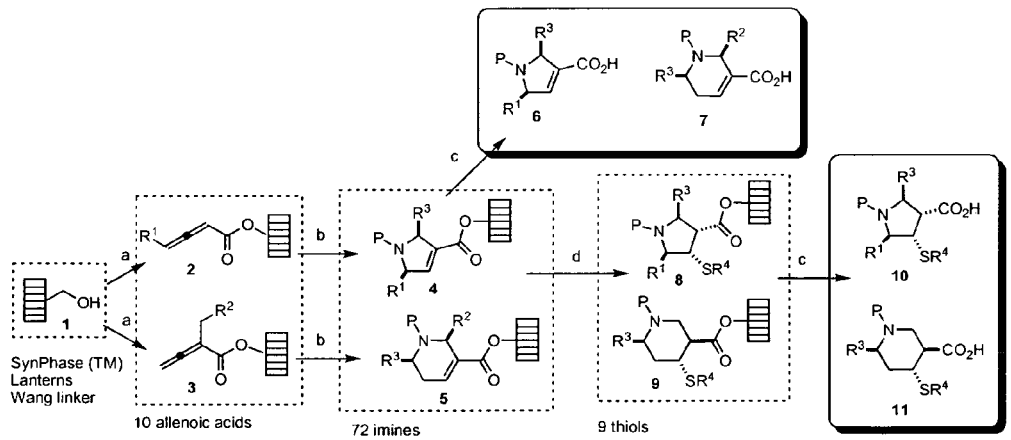
FIG. 5 presents an illustration of synthetic steps. The steps may include (a) allenoic acid, Mukaiyama's reagent, DIPEA or $Et_3N$, DCM, room temperature, for 12 hours; (b) $PPH_3$ or $PBu_3$, imine, benzene or DCM at room temperature or 60° C.; (c) 2.5% TFA/DCM for 12 hours; (d) thiol, n-BuLi, at −25° C., THF.

The overall reaction sequence for this diversification to 4,314 compounds is schematized in FIG. 5. Validation of the synthetic route on polymer support commenced with formation of resin-bound allenoates 2 and 3. In optimum loading procedures, allenoic acids were coupled with the benzyl alcohol of the SynPhase-PS Lanterns grafted with Wang resin 1 by using Mukaiyama's reagent. See (a) Mukaiyama, T.; Usui, M.; Shimada, E.; Saigo, K. (1975) "A Convenient Method for the Synthesis of Carboxylic Esters" *Chem. Lett.* 1045-1048. (b) Mukaiyama, T.; Toda, H.; Kobayashi, S. (1976) "Betaine as an Effective Acid Captor: A Convenient Method for the Synthesis of Carboxylic Esters" *Chem. Lett.* 13-14. (c) Saigo, K.; Usui, M.; Kikuchi, K.; Shimada, E.; Mukaiyama, T. (1977) "New Method for the Preparation of Carboxylix Esters" *Bull. Chem. Soc. Jpn.* 50, 1863-1866. The phosphine-catalyzed annulation between polymer-supported allenoates 2 and 3 and N-sulfonyl-arylimine proceeded smoothly to provide polymer-bound dihydropyrroles 4 and tetrahydropyridines 5. Heterocycles 4 and 5 were cleaved off the resin in order to furnish acids 6 and 7 in 91-92% yield (based on a theoretical loading of 15 μM/Lantern) after flash column chromatography (FCC). The Michael addition of thiols to 4 and 5 with n-butyl lithium as a base provided 8 and 9, which, upon trifluoroacetic acid (TFA)-mediated cleavage, provided 10 and 11. See Miyata, O.; Shinada, T.; Ninomiya, I.; Naito, T.; Date, T.; Okamura, K.; Inagaki, S. (1991) "Stereospecific Nucleophilic Addition Reactions to Olefins. Addition of Thiols to α,β-Unsaturated Carboxylic Acid Derivatives" *J. Org. Chem.* 56, 6556-6564. The relative stereochemistry of 10 and 11 was confirmed by X-ray crystallographic analysis. A Tebbe reaction on 5 furnished solid-bound enol ether 12 which could be cleaved from the polymer support under the influence of hydrochloric acid (HCl) to afford 13 in a 92% overall yield. See (a) Ball, C. P.; Barrett, A. G. M.; Commercon, A.; Compère, D.; Kuhn, C.; Roberts, R. S.; Smith, M. L.; Venier, 0. (1998) "Chameleon Catches in Combinatorial Chemistry: Tebbe Olefination of Polymer Supported Esters and the Synthesis of Amines, Cyclohexanones, Enones, Methyl Ketones and Thiazoles" *Chem. Commun.* 2019-2020. (b) Barrett, A. G. M.; Procopiou, p. A.; Voigtmann, U. (2001) "Solid-Phase Synthesis of Isoxazoles Using Vinyl Ethers as Chamelon Catches" *Org. Lett.* 3, 3165-3168.; (d) Mori, A.; Yamamoto, H. (1985) "Resolution of Ketones via Chiral Acetals. Kinetic Approach" *J. Org. Chem.,* 50, 5444-5446.; (e) Lienhard, G. E.; Wang, T. (1969) "On the Mechanism of Acid-Catalyzed Enolization of Ketones" *J. Am. Chem. Soc.* 91, 1146-1153.

After the reaction routes to synthesize analogs of the GGTI hits were validated on solid support (see 6 and 7 in FIG. 5), we purchased/made the building blocks. The chemical reactions involved in building block preparation are as follows (FIG. 6). γ-substituted allenoic acid 17 was derived from the corresponding γ-substituted allenoate 16, which in turn was made by the reaction between phosphorane 14 and acid chloride 15. See Lang, R. W.; Hansen, H.-J. (1990) "α-Allenic Esters from α-Phosphoranylidene Esters and Acid Chlorides Ethyl 2,3-Pentadienoate" *Org. Synth. Coll. Vol.* 7, 232-235. When phosphorane 14 was treated with alkyl halide 18, phosphonium halide 19 was obtained. Phosphonium halide 19 was converted to α-substituted allenoate 20 upon treatment with triethylamine (2 equiv) and acetyl chloride (1 equiv). See Scholz, D.; Weber-Roth, S.; Macoratti, E.; Francotte, E. (1999) "Expedient Synthesis of α-substituted α,β-unsaturated γ-amino acids (dipeptide memetics); Wittig reaction of α-amino aldehydes with α-substituted alkoxycarbonylphosphoranes" *Synth. Commun.* 29, 1143-1155.

α-substituted allenoic acid 21 was prepared by saponification of ester 20. N-sulfonylimine 24 was formed by the azeotropic removal of water from a refluxing toluene mixture of appropriate sulfonamide 22, aldehyde 23, and catalytic acid. See (a) McKay, W. R.; Proctor, G. R. (1981) "Removal of toluene-p-sulfonyl groups from sulfonamides. Part 4. Synthesis of phenylglyoxal imine monomers" *J. Chem. Soc., Perkin Trans.* 1, 2435-2442. (b) Jennings, W. B.; Lovely, C. J. (1991) "The titanium tetrachloride induced synthesis of N-phosphinoylimines and N-sulfonylimines directly from aromatic aldehydes" *Tetrahedron,* 47, 5561-5568. (c) Love, B. E.; Raje, P. S.; Williams II, T. C. (1994) "Preparation of N-Tosylaldimines" *Synlett* 493-494. (d) Bilodeau, M. T.; Cunningham, A. M. (1998) "Solid-Supported Synthesis of Imidazoles: A strategy for Direct Resin-Attachment to the Imidazole Core" *J. Org. Chem.* 63, 2800-2801. (e) Chemla, F.; Hebbe, V.; Normant, J.-F. (2000) "An Easy Synthesis of Aliphatic and Aromatic N-Sulfonyl Aldimines" *Synthesis,* 75-77.

Figure 6:
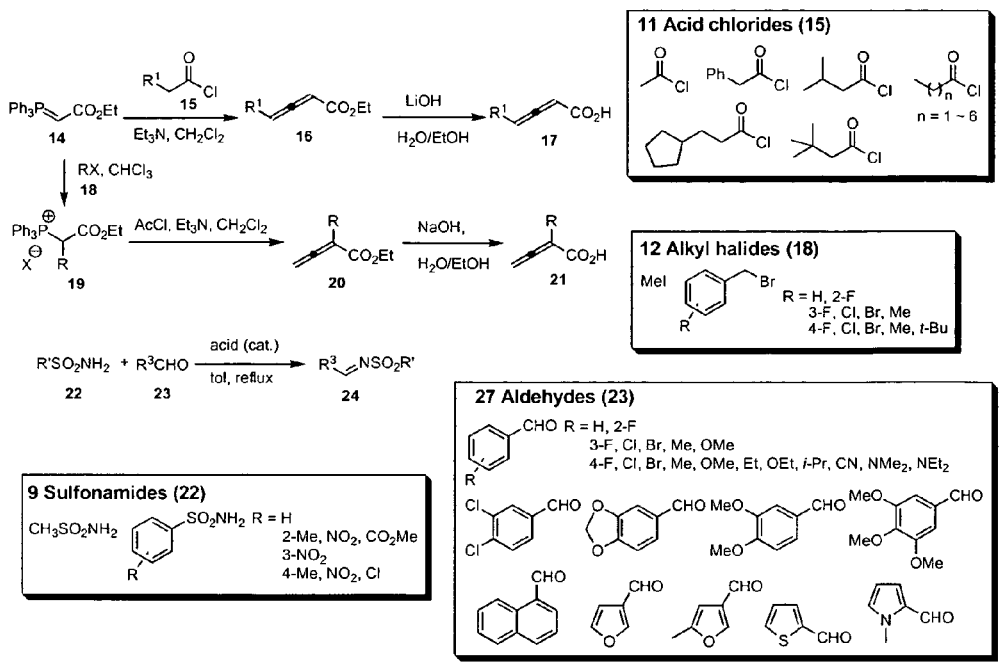
FIG. 6 presents illustrations of chemical steps in building block preparation.
Figure 7:
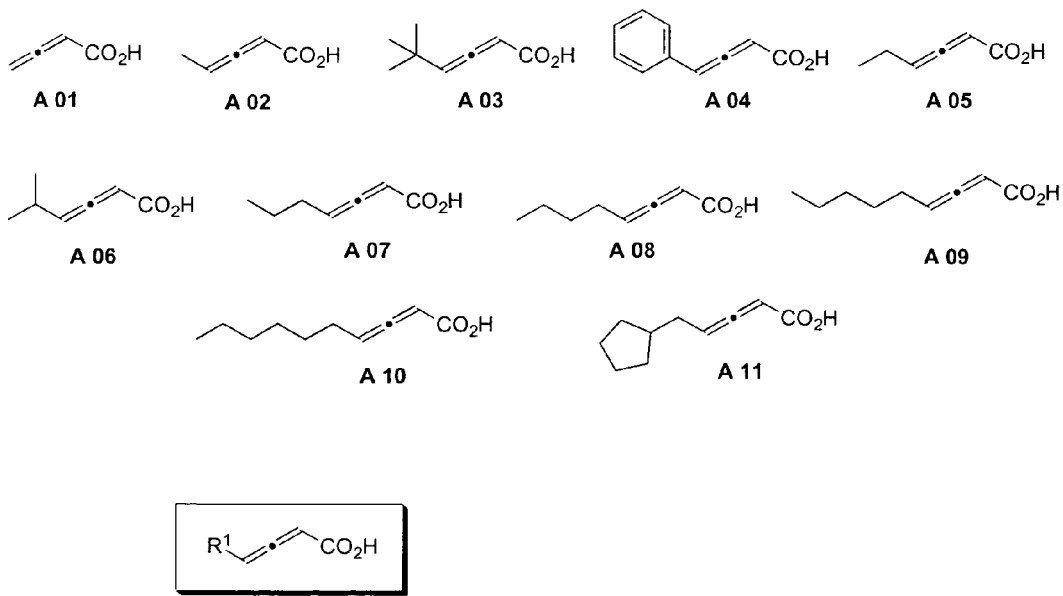
FIG. 7 presents γ-substituted allenoic acid building blocks.
Figure 8:
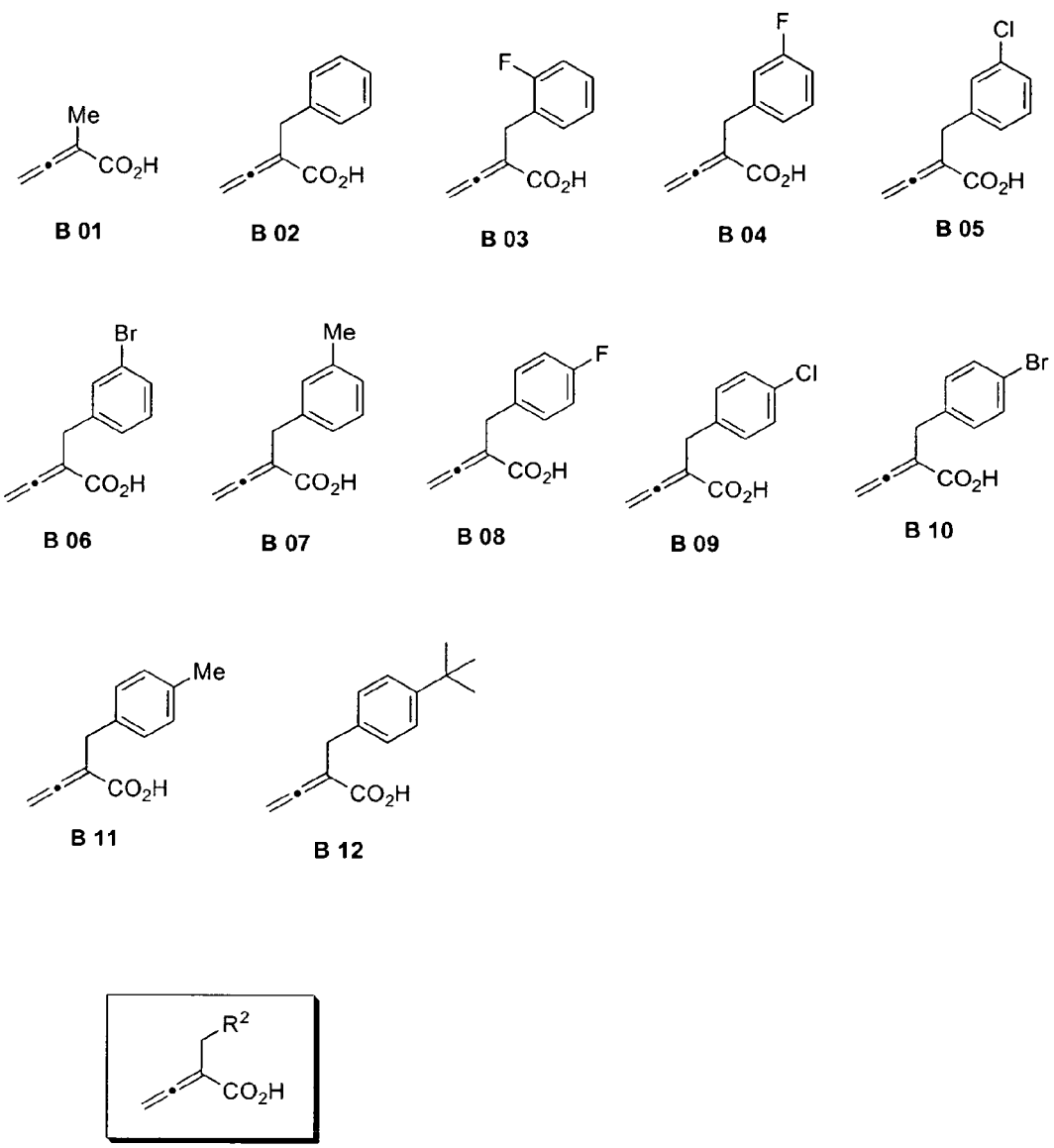
FIG. 8 presents α-substituted allenoic acid building blocks.
Figure 9:
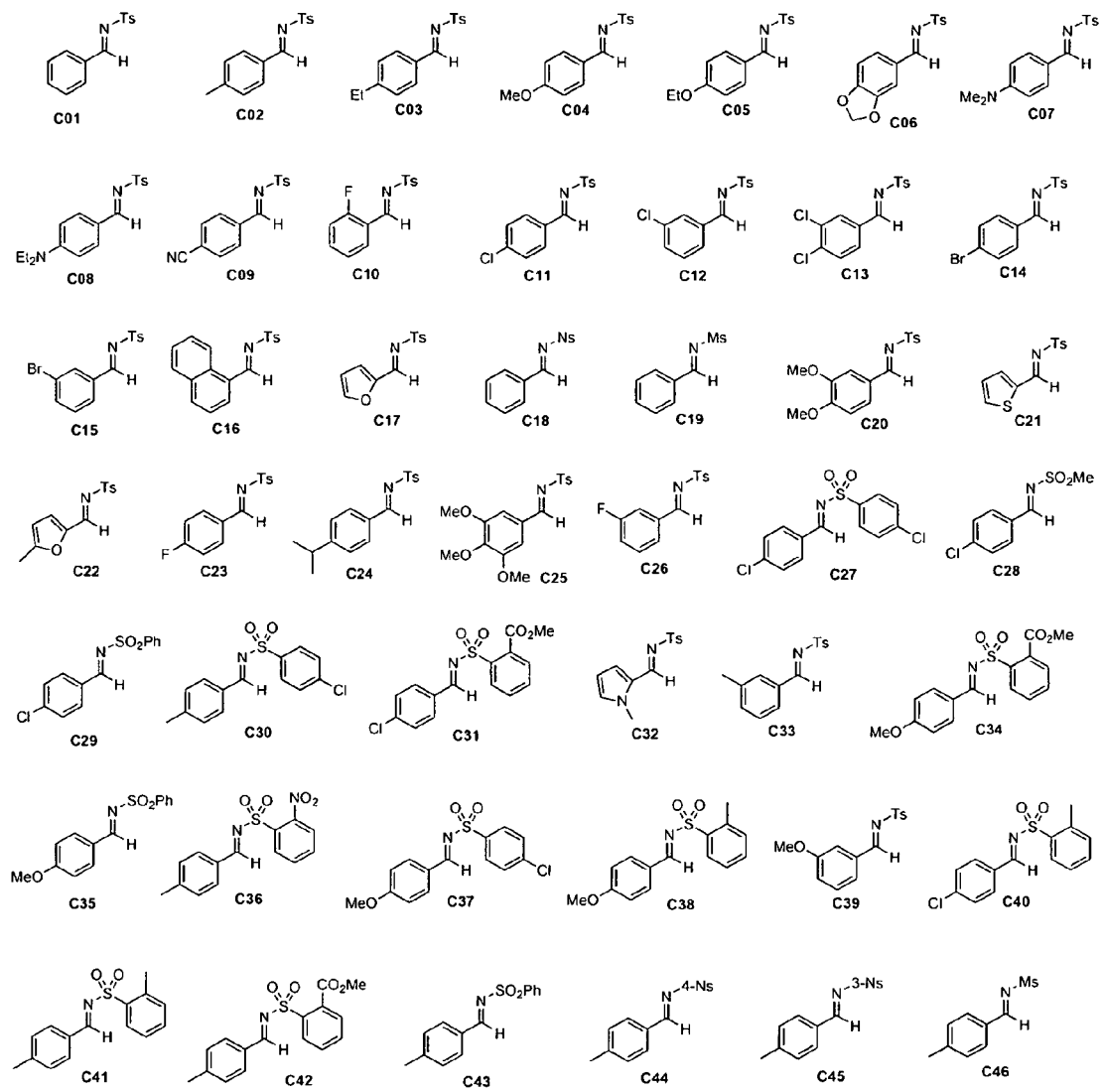
FIG. 9 presents N-sulfonylimine building blocks.
Figure 10:
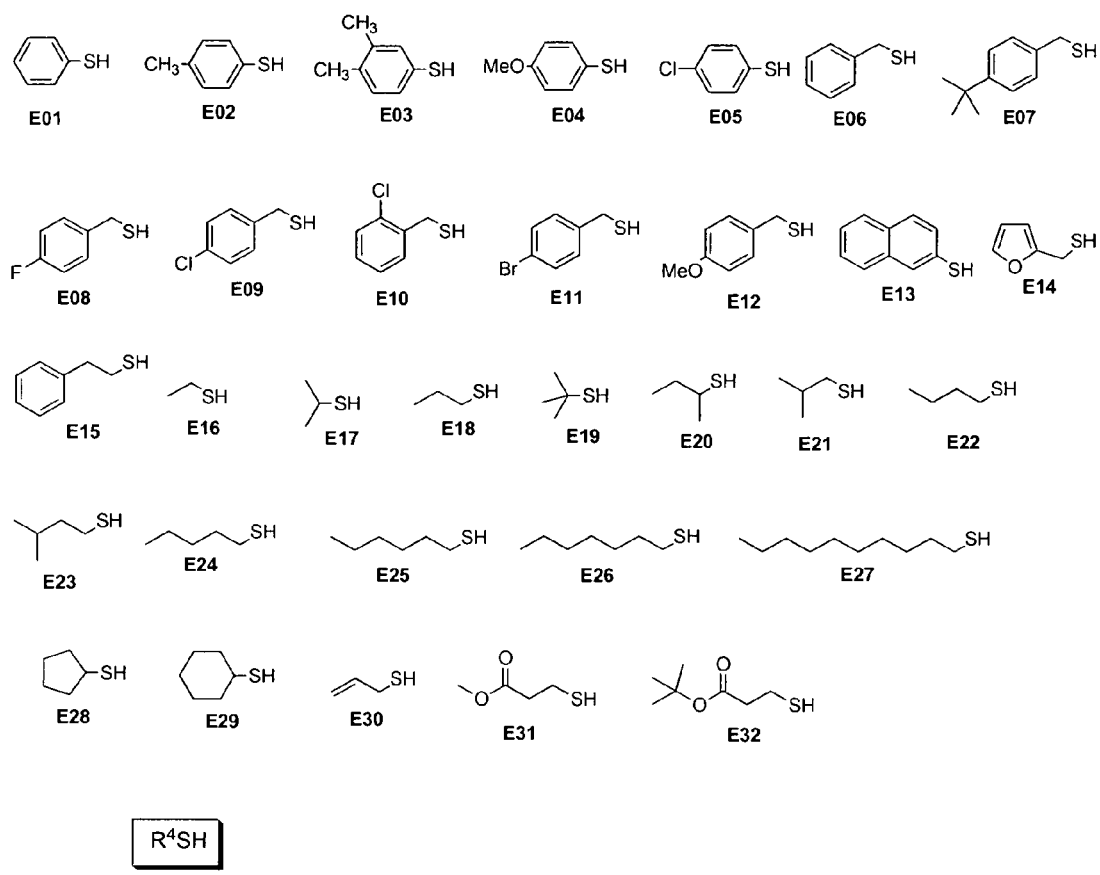
FIG. 10 presents thiol building blocks.

The building blocks synthesized as illustrated in FIG. 6 are shown in FIG. 7 (γ-substituted allenoic acid 17), FIG. 8 (α-substituted allenoic acid 21), and FIG. 9 (N-sulfonylimine 24). The other building blocks, thiols, which were purchased for the library synthesis, are shown in FIG. 10.

Once the building blocks were synthesized, they were tested to determine whether or not they would be incorporated into the synthesis of the focused library of GGTIs. Building blocks were chosen so that only the ones that provided high purity (by 1H NMR and LC/MS analysis) for the final crude products would be used in the synthesis of the library. The building blocks chosen for the synthesis of the library and the resulting number of compounds are shown in FIG. 11. Scaffolds that require distinctive set of reaction conditions are drawn separately.

For the synthesis of 2-aryl-N-sulfonyl-2,5-dihydropyrrole-3-carboxylic acid (6 with R1=H) 30 imines (C01-C03, C06, C09-C16, C18, C19, C23, C24, C26-C31, C33, C36, C40-C44, C46) provided satisfactory results to give 302-aryl-N-sulfonyl-2,5-dihydropyrrole-3-carboxylic acids (FIG. 11A).

Figure 11B:
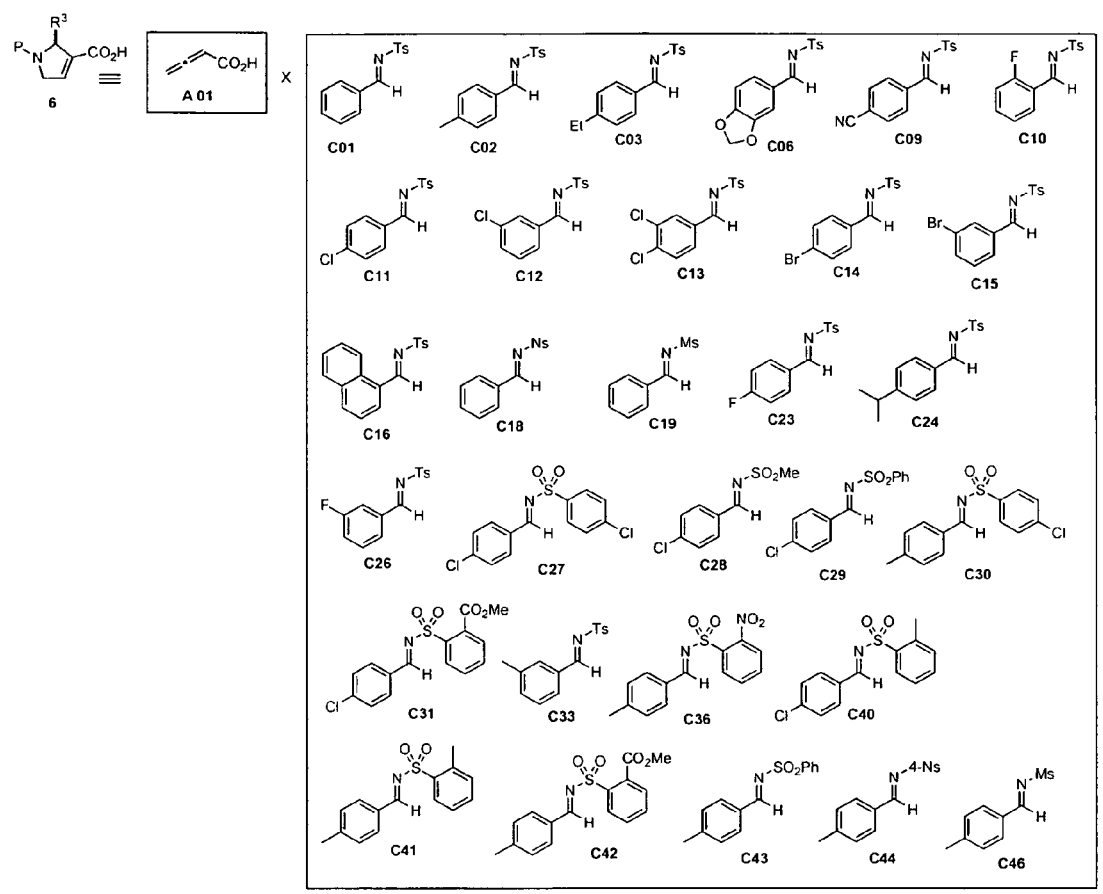

For the synthesis of 5-alkyl-2-aryl-N-sulfonyl-2,5-dihydropyrrole-3-carboxylic acid 6 10 allenoic acids (A02-A11) and 21 imines (C01-C03, C06, C09-C14, C16, C20, C23, C24, C26, C27, C29, C30, C33, C40, C41) were selected to furnish 210 (10×21) 5-alkyl-2-aryl-N-sulfonyl-2,5-dihydropyrrole-3-carboxylic acids (FIG. 11B).

Figure 11C:
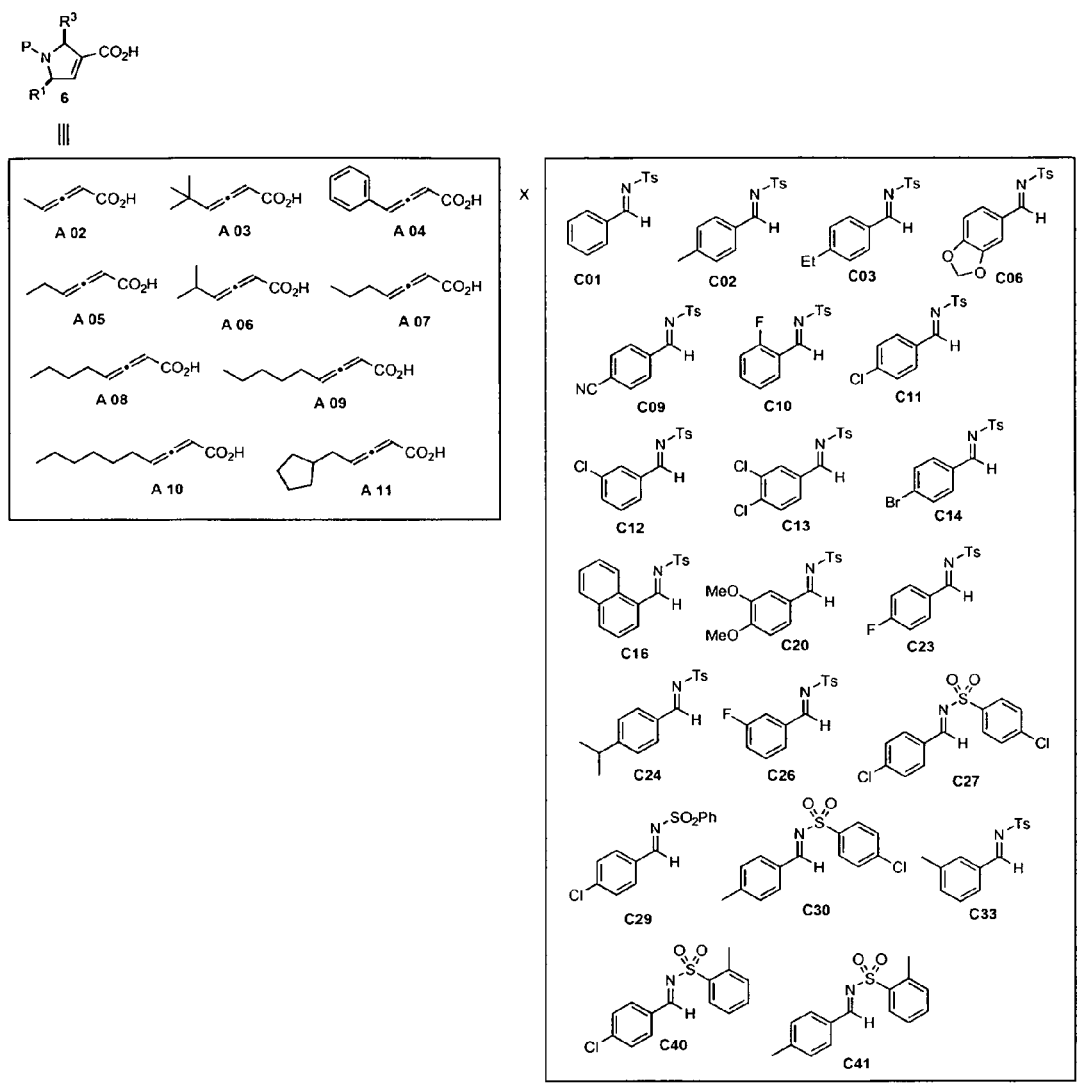

For 5-alkyl-2-aryl-4-mercapto-N-sulfonyl-2,5-dihydropyrrole-3-carboxylic acid 10 7 allenoic acids (A05-A11), 25 imines (C01-006, C09-C14, C16, C20, C21, C23, C24, C26, C27, C29, C30, C33, C35, C40, C41), and 19 thiols (E01, E02, E04, E06, E07, E16-E25, E28-E30, E32) were chosen to give 3,325 (7×25×19) 5-alkyl-2-aryl-4-mercapto-N-sulfonyl-2,5-dihydropyrrole-3-carboxylic acids (FIG. 11C).

Figure 11D:
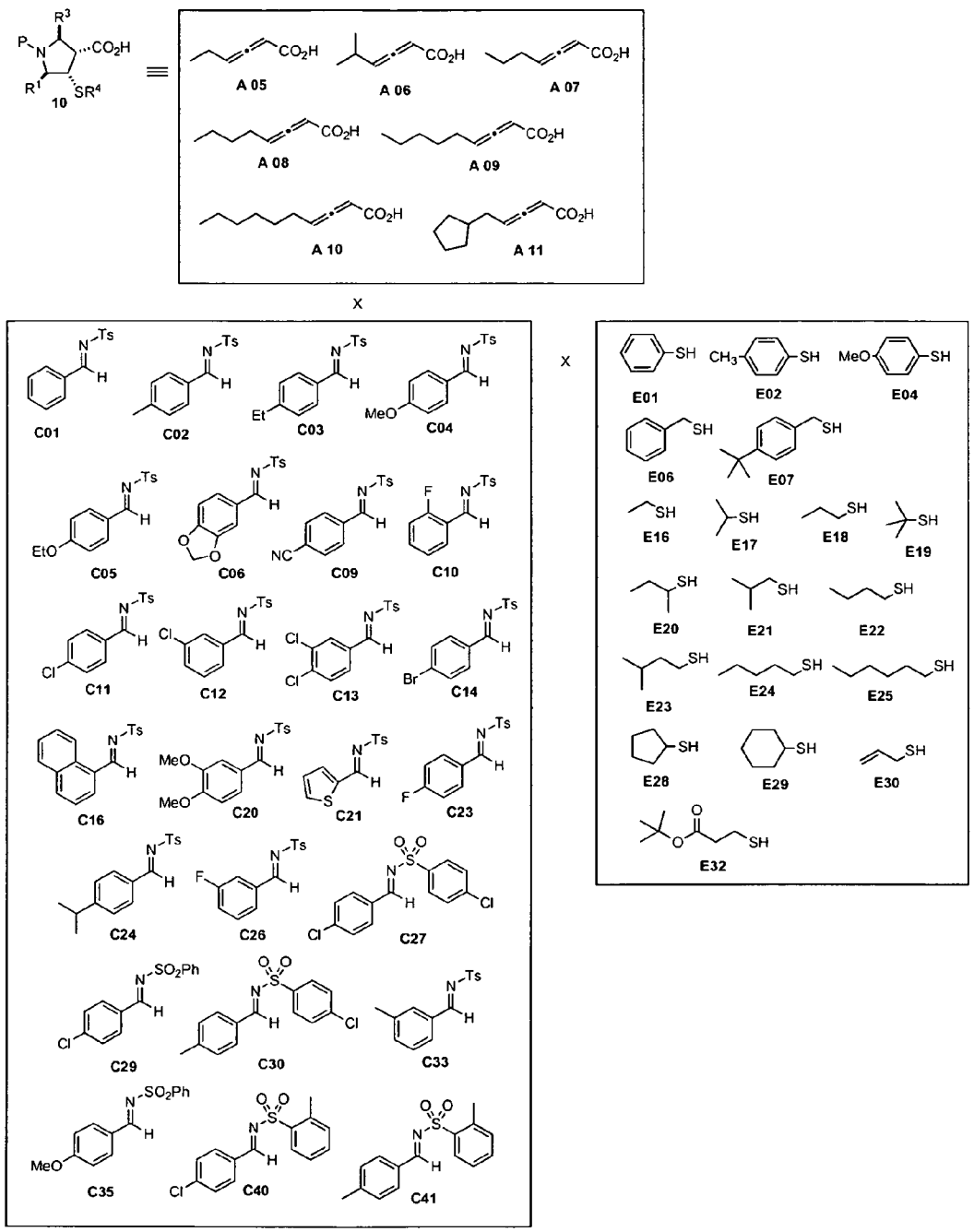

For 6-aryl-N-sulfonyl-1,2,5,6-tetrahydropyridine-3-carboxylic acid 7 (with R3=H) 26 imines (C01-006, C10, C12, C15, C16, C20, C21, C24, C25, C30, C33-C43) were selected resulting in 266-aryl-N-sulfonyl-1,2,5,6-tetrahydropyridine-3-carboxylic acids (FIG. 11D).

Figure 11E:
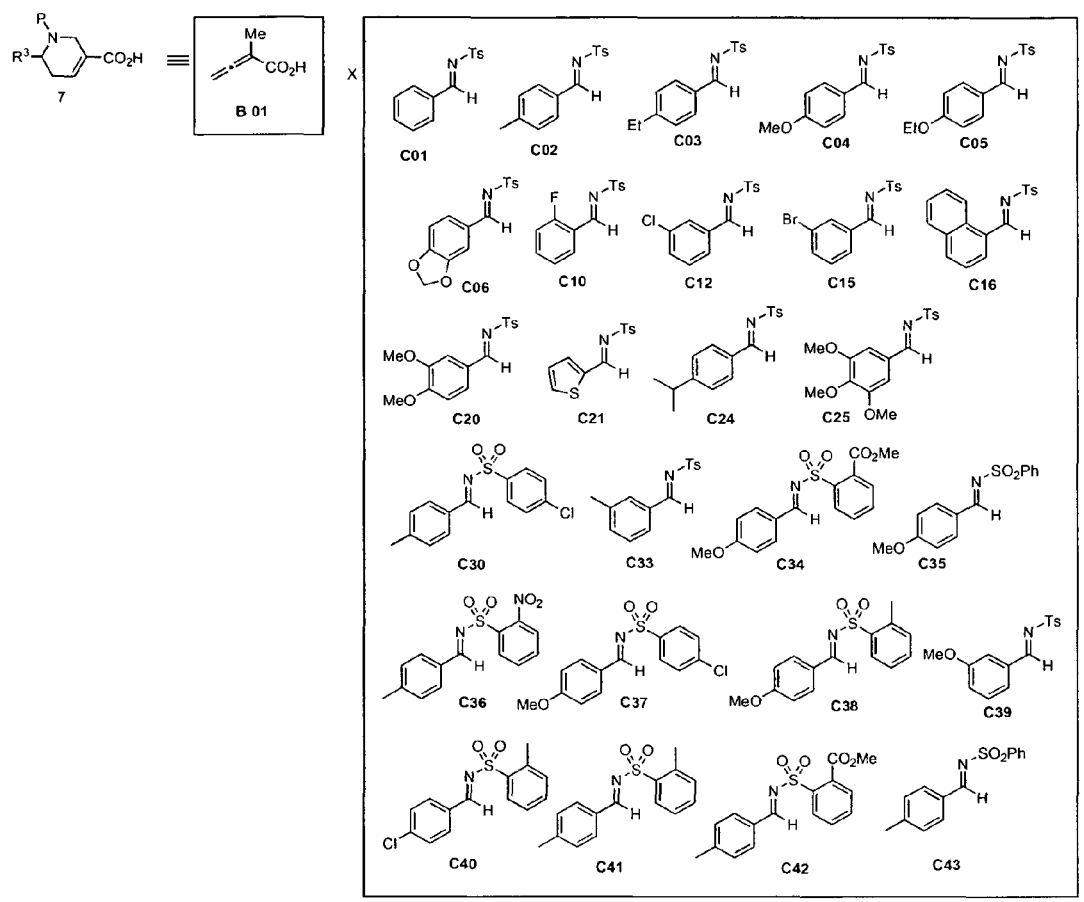

For 3-acyl-6-aryl-N-sulfonyl-1,2,5,6-tetrahydropyridine 13 25 imines (C01-C06, C10-C12, C15, C16, C20, C21, C24, C25, C30, C33-C43, C46) provided satisfactory results to give 25 3-acyl-6-aryl-N-sulfonyl-1,2,5,6-tetrahydropyridines (FIG. 11E).

Figure 11F:
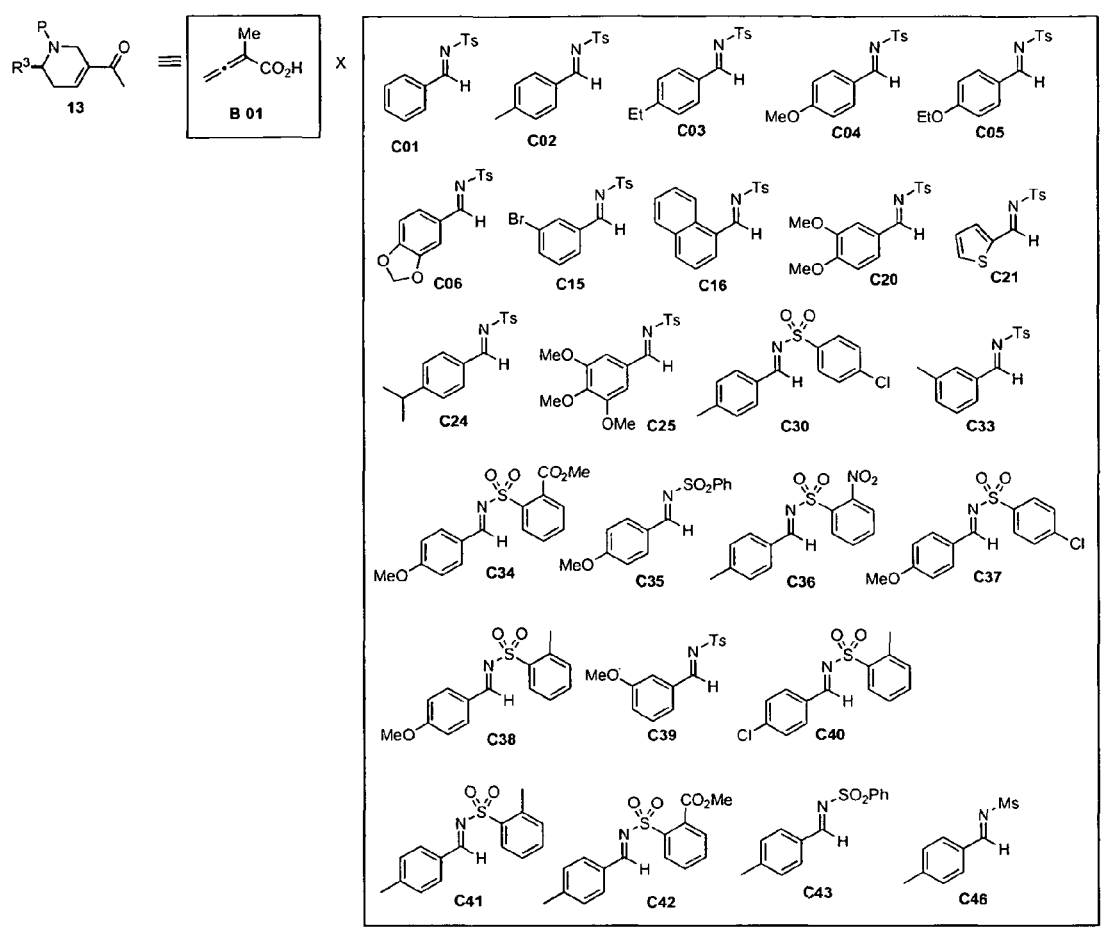

For 2,6-diaryl-N-sulfonyl-1,2,5,6-tetrahydropyridine-3-carboxylic acid 7 11 □-substituted allenoic acids (B02-B12) and 31 imines (C01-C06, C09-C13, C15, C19-C21, C23, C24, C26-C28, C30, C33, C35, C37-C43, C46) were selected resulting in 341 (11×31) 2,6-diaryl-N-sulfonyl-1,2,5,6-tetrahydropyridine-3-carboxylic acids (FIG. 11F).

Figure 11G:
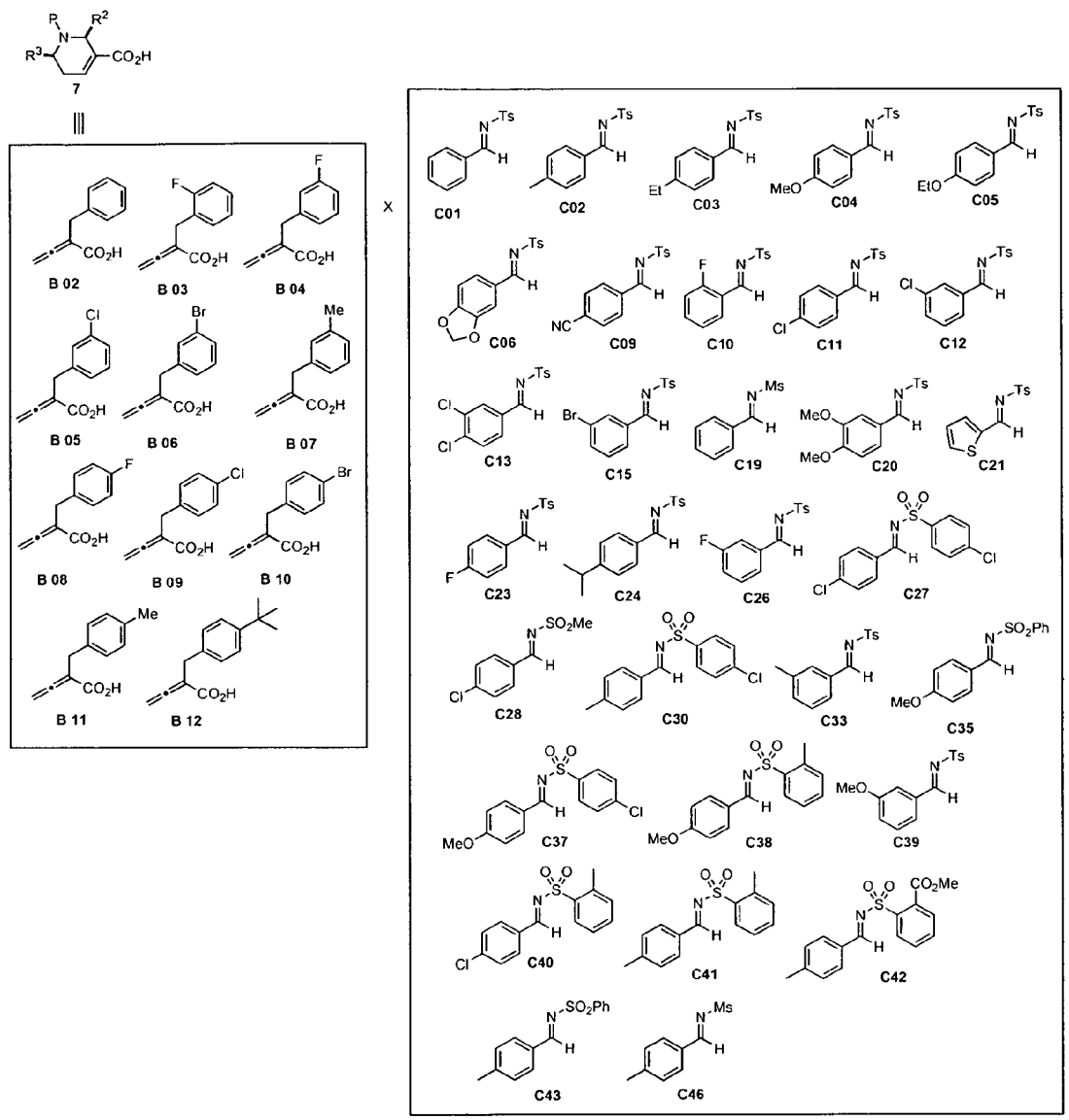
Figure 11H:
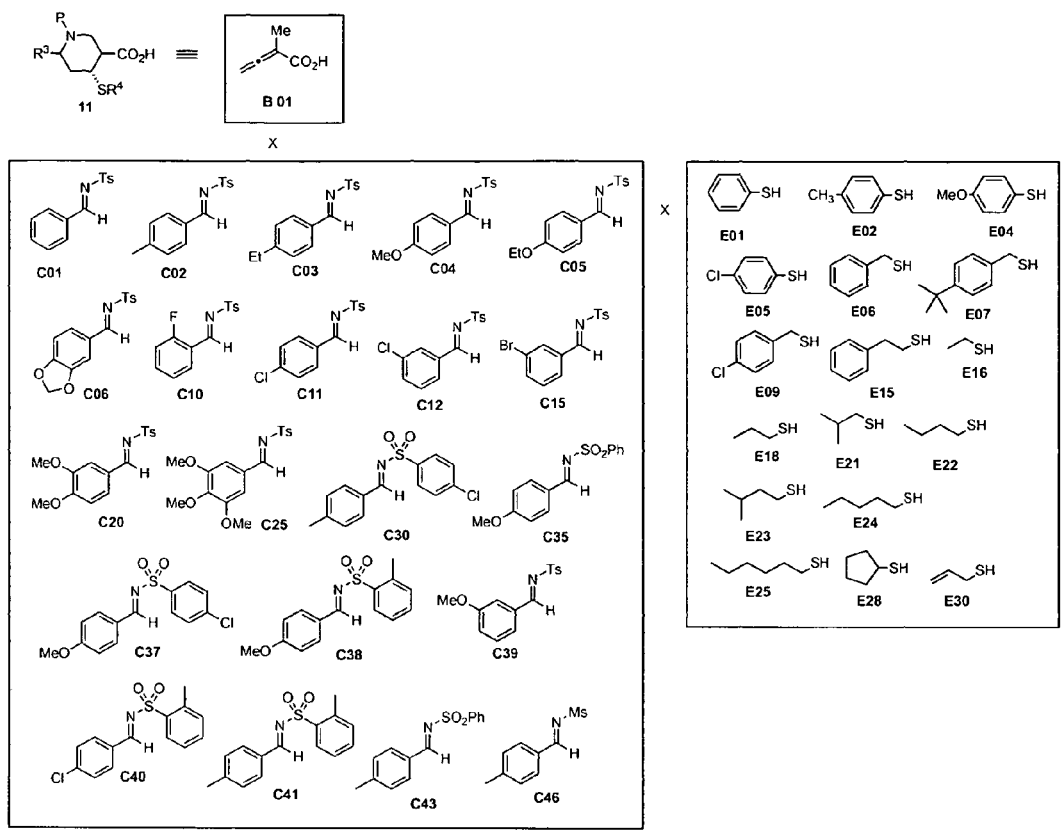

For 6-aryl-4-mercapto-N-sulfonyl-piperidine-3-carboxylic acid 11 21 imines (C01-C06, C10-C12, C15, C20, C25, C30, C35, C37-C41, C43, C46) and 17 thiols (E01, E02, E04-E07, E09, E15, E16, E18, E21-E25, E28, E30) were chosen to provide 357 (21×17) 6-aryl-4-mercapto-N-sulfonyl-piperidine-3-carboxylic acids (FIG. 11G). The total number of compounds for the library is, therefore, 4,314 compounds.

The next step was the split-and-pool synthesis of a library of heterocycles (shown in FIG. 5). The first split step of the proposed library synthesis is the coupling of 23 different allenoic acids to the benzyl alcohol of the Wang resin. In the second split step, resin-bound allenoates (MCMs) react with imines under nucleophilic phosphine catalysis conditions to generate two distinctive heterocycles 4 and 5. The last split step involves use of the α,β-unsaturated ester moiety (MCF) in stereoselective Michael addition using thiols to further increase structural diversity, resulting in two additional scaffolds 8 and 9. 240 Lanterns with resin-bound heterocycle 4, 357 with 5, 3,325 with 8, and 357 with 9 were inserted in individual vials and cleaved with 2.5% TFA in methylene chloride to provide the corresponding carboxylic acids. 25 Lanterns with polymer-bound heterocycle 5 were treated with Tebbe reagent to afford enol ether 12, which was cleaved with 0.1 N HCl in acetone to give 25 enones 13. Use of resin-bound allenoates facilitated solid-phase combinatorial synthesis of heterocyclic compounds in a split-and-pool fashion. Use of SynPhase™ Lanterns alleviated the need for chemical encoding and provide more material for a given compound. See (a) Gerritz, S. W.; Norman, M. H.; Barger, L. A.; Berman, J.; Bigham, E. C.; Bishop, M. J.; Drewry, D. H.; Garrison, D. T.; Heyer, D.; Hodson, S. J.; Kakel, J. A.; Linn, J. A.; Marron, B. E.; Nanthakumar, S. S.; Navas, F. J., III. (2003) "High-Throughput Manual Parallel Synthesis Using SynPhase Crowns and Lanterns" *J. Comb. Chem.* 5, 110-117. (b) Feliu, L.; Subra, G.; Martinez, J.; Amblard, M. (2003) "Spiroimidazolidinone Library Derivatives on SynPhase Lanterns" *J. Comb. Chem.* 5, 356-361. L-series lanterns of 15 μmol loading were used for our library synthesis. The identity of the building blocks used in the synthesis of the individual members of the library was encoded by colored spindles and cogs.

Figure 13:
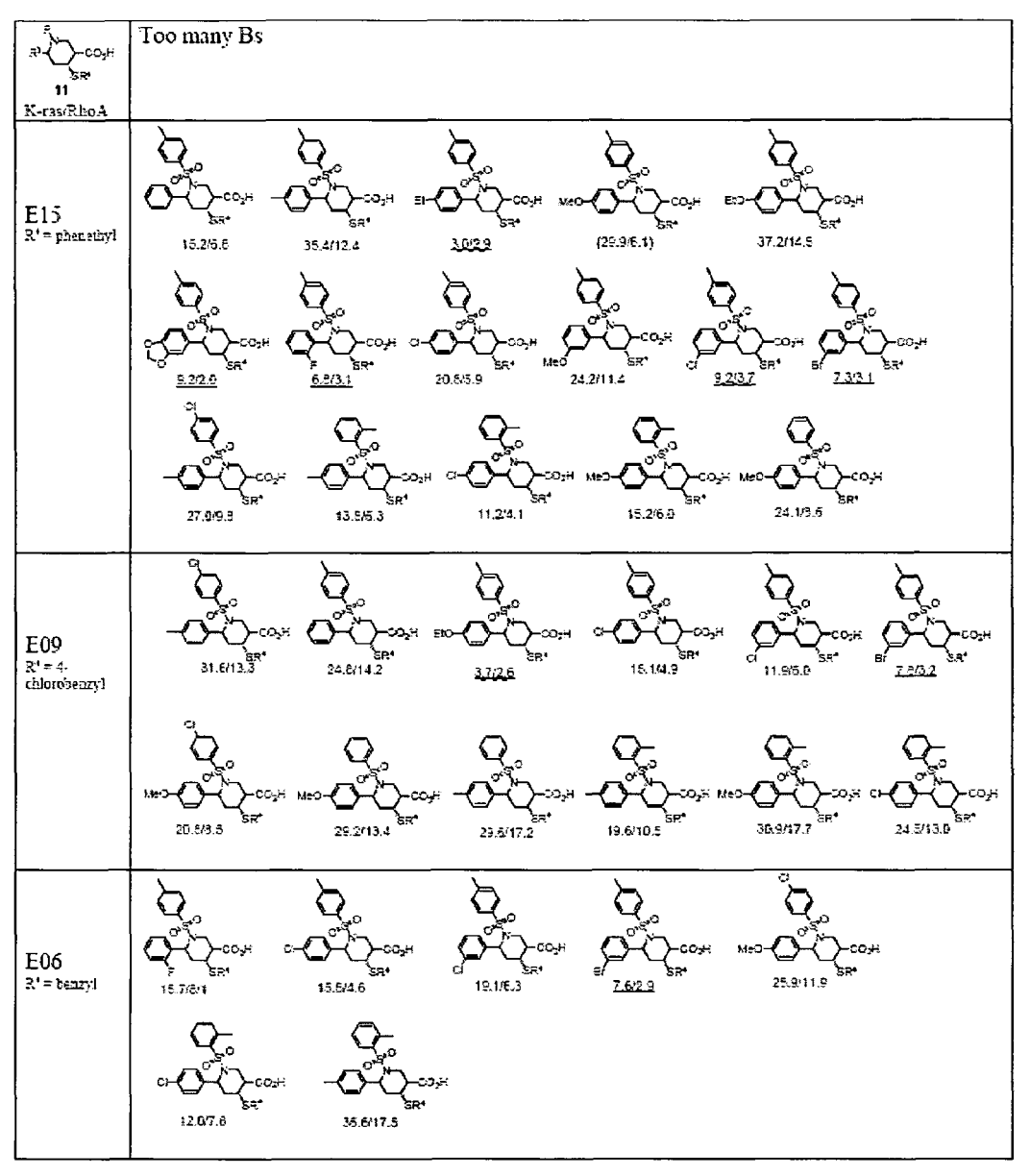
Figure 14:
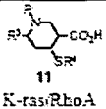
FIG. 14 presents piperidine scaffold compounds with GGTI activity.

With 4,314 small molecules in hand, their inhibitory activity against GGTase I for K-Ras4B and RhoA was examined. All members of the library that contain tetrahydropyridine and piperidine scaffolds were screened. These members correspond to 749 compounds of 7, 11, and 13. The GGTI compounds exhibiting over 80% inhibition of GGTase I activity at 50 μM concentration are shown in FIGS. 12, 13 and 14. The first compartment of each table contains the structure of a representative scaffold. The first row and the first column of each table list building blocks used to make GGTI compounds shown in the table. A pair of numbers below the structure of a GGTI is % activities of GGTase I for proteins K-Ras4B/RhoA in the presence of the GGTI compound. Smaller numbers indicate better inhibition. Activities below 10% (over 90% inhibition) for both proteins are underlined. Significantly better inhibition for RhoA over K-Ras4B is in parenthesis.

2,6-Diaryl-N-sulfonyl-1,2,5,6-tetrahydropyridine-3-carboxylic acids 7 that contain 10 α-substituted allenoic acids (in the order of frequency of appearance: B06>B05>B07>B04=B02>B10>B03=B08=B09=B11) and 7 imines (C40>C13>C15>C12=C27>C30=C24) showed prominent inhibitory activities (FIG. 12).

For the measured inhibitory activities of individual compounds, see FIGS. 19-1 through 19-27. The "label" column provides annotation (e.g., B01C01T means a compound made of B01 and C01 and the Tebbe reaction, and B01C01E21 means a compound made of building blocks B01, C01, and E21) of each compound for each entry. The "Kras" column provides % activity of GGTase I for protein K-Ras4B in the presence of the compound of that entry.

The % activity of GGTase I was determined as follows: a working solution that contained each compound in DMSO at the concentration of 1 mM was prepared. The working solution was added to GGTase I reaction mixture so that the final concentration of the compound is 50 μM. GGTase I activity was assayed by incubating [³H]GGPP with K-Ras4B or RhoA protein in the presence of GGTase I and examining radioactivity incorporated into the substrate protein by spotting onto a filter paper. After washing with TCA, ethanol and acetone, the radioactivity retained on the filter was determined by the use of a scintillation counter. GGTase I activity in the presence of DMSO was taken as a 100% value and the activity in the presence of the compound was shown as percent activity compared with the 100% value. The table in FIG. 12 shows 24 2,6-diaryl-N-sulfonyl-1,2,5,6-tetrahydropyridine-3-carboxylic acids 7 that were selected out of 367 compounds. None of the enones 13 were active indicating that the carboxylic acid moiety is crucial for the GGTI activity. For 6-aryl-4-mercapto-N-sulfonyl-piperidine-3-carboxylic acid 11 the 4-mercapto substituent appeared critical to endowing GGTase inhibitory activity. 16 compounds out of 21 possessing 4-phenethylthio moiety (E15) were active (FIG. 13). 4-Chlorobenzylthio substituent was the next best; 12 compounds out of 21 containing the 4-chlorobenzylthio moiety were active. 4-Benzylthio substituent was also good; 7 piperidines out of 21 bearing 4-benzylthio group were active. Less frequently appearing 4-mercapto substituents are summarized in FIG. 14. Nine thiols (E15>E09>E06>>E22>E05=E23=E21=E30>E24) out of 17 thiols showed up in the GGTIs. 19 imines (C15>C12=C41>C40>C01=C11>C05=C10=C30=C35= C37=C38>C02, C03, C04, C06, C39=C43) out of 21 appeared in the GGTIs. 4 Imines, C15, C12, C41 and C40, are particularly interesting since they showed up in more than three GGTI compounds. This corresponds to 47 6-aryl-4-mercapto-N-sulfonyl-piperidine-3-carboxylic acids out of 357 compounds. These 71 GGTIs exhibited better inhibition for RhoA over K-Ras4B; some with 100 fold stronger inhibitory activity for RhoA over K-Ras4B (e.g., compound P4-G5=B01C15E05).

Figure 15:
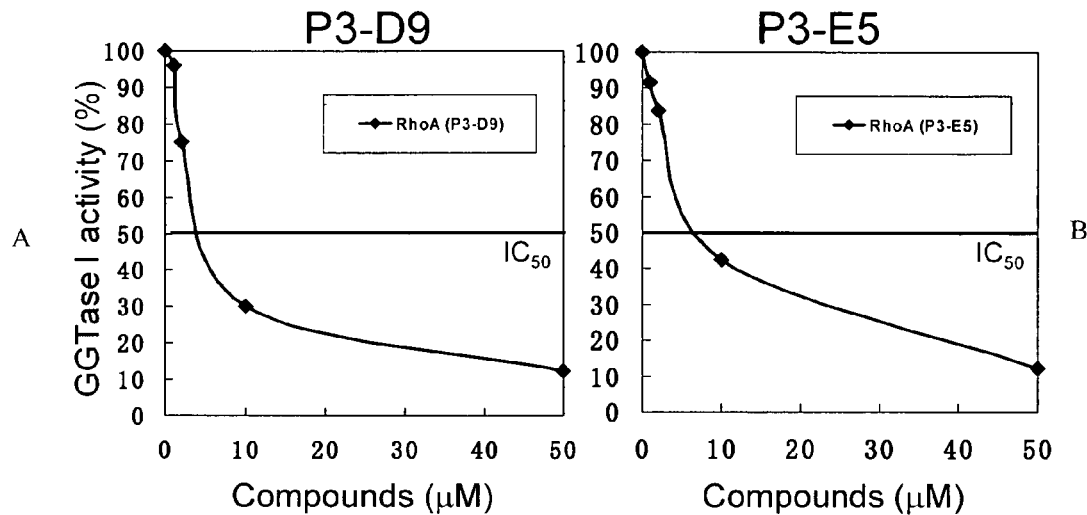
FIGS. 15A and 15B present dose dependency of GGTase I inhibition by two GGTI compounds.
Figure 16:
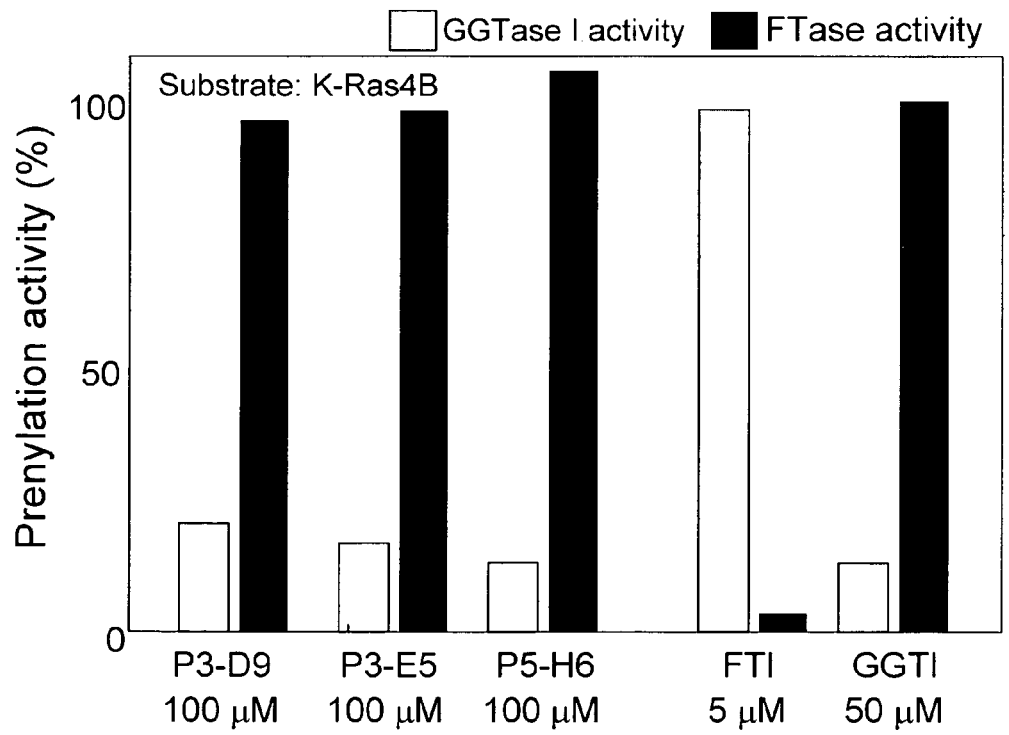
FIG. 16 presents a comparison of GGTase inhibition and FTase inhibition by three compounds.

Dose dependency of the inhibition of two compounds is shown in FIG. 15. IC50 values for the inhibition of GGTase I using RhoA as a substrate were 5 and 7 μM for P3-D9 and P3-E5, respectively (see FIG. 12 for the structures of P3-D9 and P3-E5). Under the same reaction condition, IC50 values of 1.6 and 0.5 μM were determined for the known GGTIs, GGTI-298 and GGTI-2166, respectively. Specificity of GGTase I inhibition by P3-D9 and P3-E5 was examined. As can be seen in FIG. 16, no inhibition of FTase activity was observed by these compounds even when the concentration was increased to 100 FTI compound (BMS225975) used as a control inhibits FTase but does not inhibit GGTase I. GGTI-298 inhibits GGTase I while little inhibition was observed with FTase (see FIG. 17 for the structures of P5-H6 and GGTI-298).

Identification of Substrate Specific GGTI Compounds

Our screening also led to the identification of compounds that exhibit preferential inhibition of GGTase using a particular substrate. FIG. 17 lists GGTI compounds with reproducibly stronger inhibition of K-Ras4B driven GGTase I over RhoA driven activity. For example, the novel compound P4-F1 inhibits K-Ras4B driven GGTase I activity, but does not inhibit RhoA-driven GGTase I activity. Accordingly, some embodiments of the present invention are directed to compounds that inhibit K-Ras4B.

Figure 18:
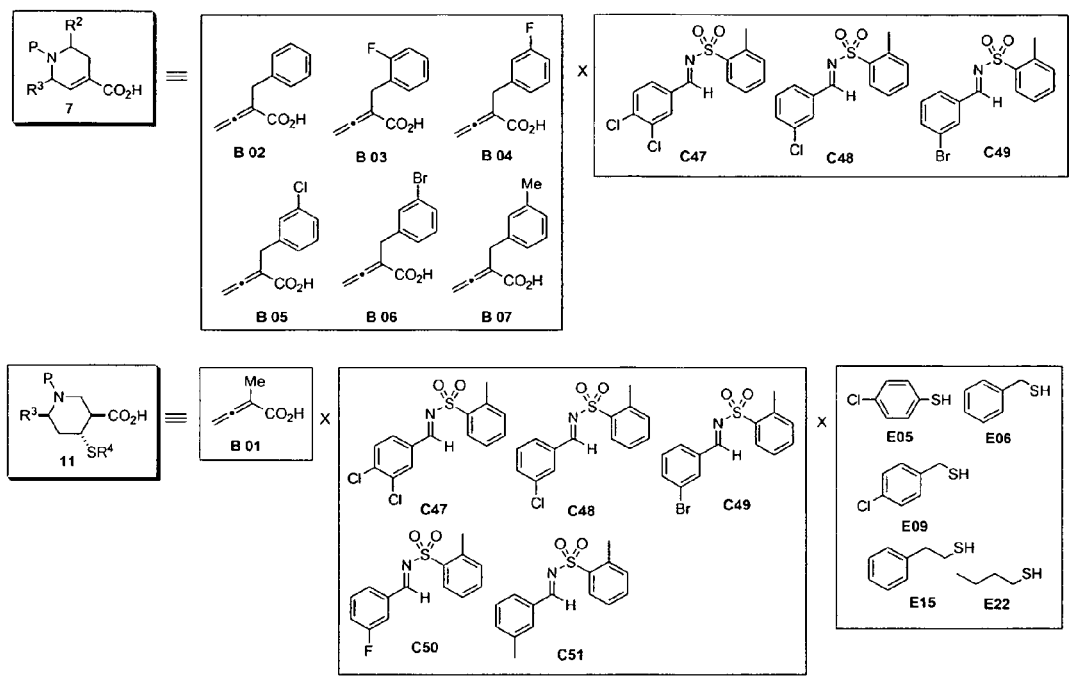
FIG. 18 presents focused future libraries based on SAR analysis.
Figure 20:
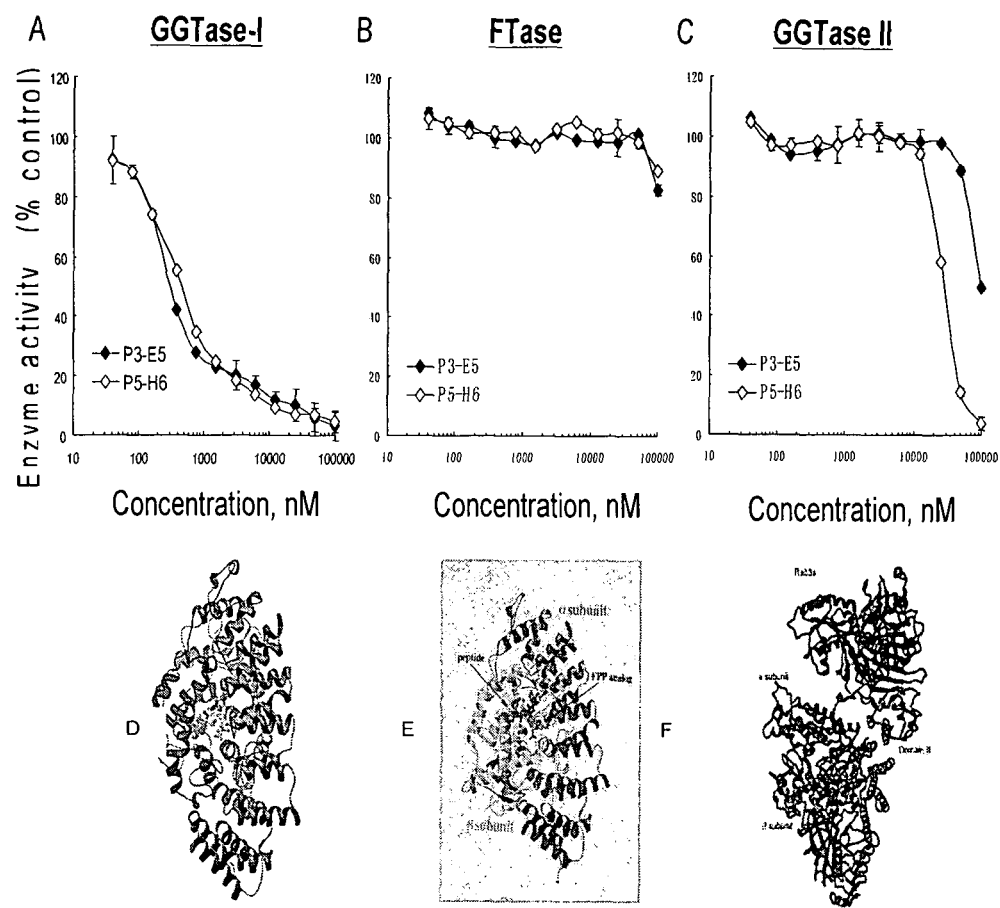
Figure 21:
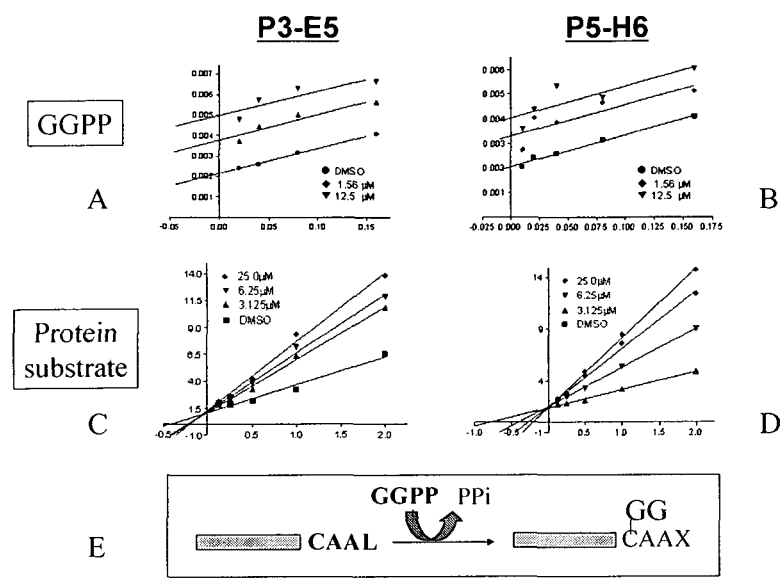

Analysis of the structures in FIG. 12 suggest construction of a library of 2,6-diaryl-N-sulfonyl-1,2,5,6-tetrahydropyridine-3-carboxylic acids 7 consisting of B02 through B07 and new imines C47 through C49 for further improvement of GGTI activity (FIG. 18). Perusal of the GGTI compounds in FIGS. 13 and 14 indicated a library of 6-aryl-4-mercapto-N-sulfonyl-piperidine-3-carboxylic acid 11 built with B01, new imines C47 through C51, and thiols (E15>E09>E06>>E22>E05) may also further improve GGTI activity

III. GGTI Compounds

The various substituents used in the pilot library described in the prior section can be combined with different linkers and scaffolds, as described below. Through the library screening and other assays described herein, numerous compounds have been identified that can inhibit GGTase I. These compounds can have the formula:

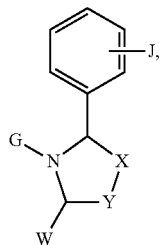

wherein J is hydrogen or is 1-2 substituents independently selected from the group consisting of halogen, $C_1$-$C_3$ alkyl, OR', SR', and NR'$_2$, where R' is alkyl,
wherein G is

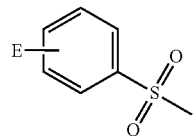

wherein E is hydrogen or is 1-2 substituents selected from the group consisting of halogen, $C_1$-$C_3$ alkyl, OR', SR', and NR'$_2$, where R' is alkyl,
wherein W is selected from the group consisting of hydrogen, cyclic, linear, or branched alkyl of from 2 to 8 carbons, unsubstituted phenyl, and phenyl substituted with $C_1$-$C_3$ alkyl, halogen, OR', SW, and NR'$_2$, where R' is alkyl,

is selected from the group consisting of wherein

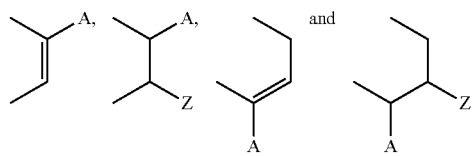

wherein A is selected from the group consisting of:

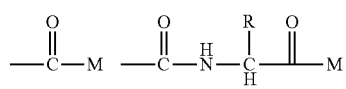

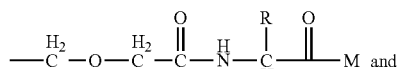

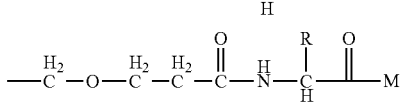

wherein M is selected from the group consisting of OH, OR", NH$_2$, NHOH, NHOR", wherein R" is methyl or ethyl, or any other group that has a polar metal binder wherein R corresponds to an alpha-substituent of natural or non-natural alpha-amino acid;

wherein Z is S—U; and wherein U is selected from the group consisting of alkyl having 10 or fewer carbons, phenyl, optionally substituted with halogen or OR", wherein R" is methyl or ethyl, and (CH$_2$), —COOR$^4$, wherein n=1-4 and R$^4$ is a linear or branched alkyl having four or fewer carbons.

In some embodiments, X-Y is any one of the following:

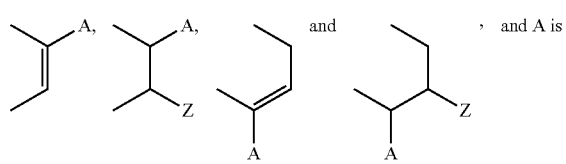

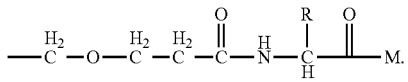

The remaining substituents can be selected from those described herein. In some embodiments, linker 3 of Formula I is used and the remaining substituents can be selected from those described herein.

In some embodiments, these compounds may be based on scaffolds 6, 7, 10, or 11. These scaffolds have the following structures:

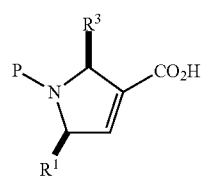

6

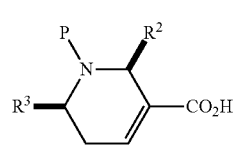

7

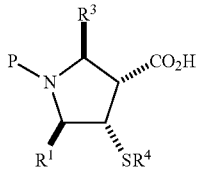

10

-continued

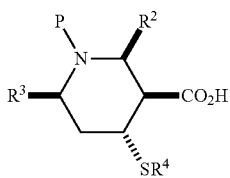
11

The compounds constructed on scaffold 6 may include substituents at R1, P and R3. R1 may be selected from the groups described in relation to W herein.

In some embodiments, P is a protecting group. While many protecting groups may be used at P, the following protecting group is preferred:

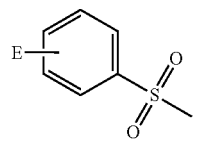

As mentioned previously, P is also represented as G herein in alternate compound formulas. In some embodiments, E is selected from the groups previously described herein for E.

R3 can be, for example, an unsubstituted phenyl or a substituted phenyl ring. The substitution (also represented as J) can be at any position on the phenyl ring.

One embodiment of the compounds that may be built from scaffold 6 is compound UC-22 (also referred to as P5-H6). This compound has the following chemical structure:

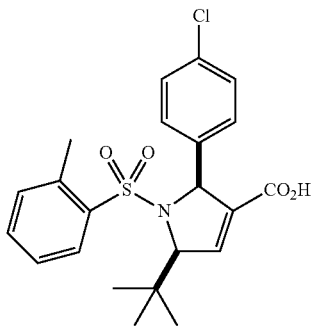 [SMILES: Cc1ccccc1S(=O)(=O)N1[C@@H](c2ccc(Cl)cc2)C(C(=O)O)=C[C@H]1C(C)(C)C]

Some exemplary compounds that inhibit GGTase I activity based on scaffold 6 include those listed in Table 1:

TABLE 1

Exemplary Compounds Based on Scaffold 6

| | C40 | C26 | C20 |
|---|---|---|---|
| (scaffold 6) | R³ = 4-chlorophenyl<br>P = 2-methylbenzene-sulfonyl | R³ = 3-fluorophenyl<br>P = 4-methylbenzenesulfonyl | R³ = 3,4-dimethoxyphenyl<br>P = 4-methylbenzenesulfonyl |

6
K-ras/RhoA

A03
R¹ = tert-butyl

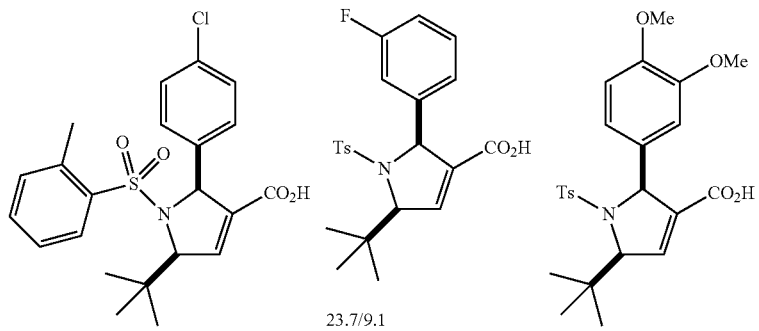

P5-H6
13.3/5.3

23.7/9.1

23.4/6.1

TABLE 1-continued

Exemplary Compounds Based on Scaffold 6

A11
R¹ = cyclopentylmethyl

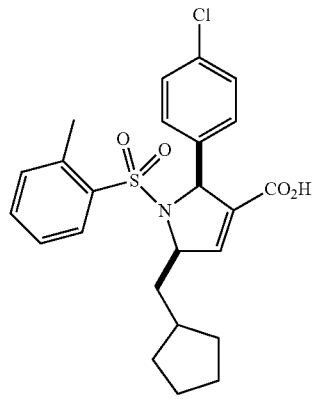 [SMILES: Cc1ccccc1S(=O)(=O)N1[C@@H](c2ccc(Cl)cc2)C(C(=O)O)=C[C@H]1CC1CCCC1]

23.7/9.1

Further compounds of interest that can be based on scaffold 6 are listed in FIG. 2. These compounds include P2-F10, P2-F12, P2-G3 and P2-G6.

In some embodiments, GGTase I inhibiting compounds can be based on scaffold 7. The compounds based on scaffold 7 may include substituents at R3, P and R2. R3 is represented herein as W and any of the groups described in relation to W may be used at position R3.

In some embodiments, P is a protecting group as described above.

R2 can be, for example, an unsubstituted phenyl or a substituted phenyl ring. The substitution (also represented as J) can be at any position on the phenyl ring.

One embodiment of the compounds that may be based on scaffold 7 is compound UC-23 (also referred to as P3-E5). This compound has the following chemical structure:

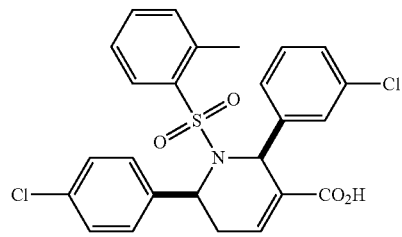 [SMILES: Cc1ccccc1S(=O)(=O)N1[C@@H](c2cccc(Cl)c2)C(C(=O)O)=CC[C@H]1c1ccc(Cl)cc1]

Some exemplary compounds that inhibit GGTase I activity based on scaffold 7 include those listed in Table 2:

TABLE 2

Exemplary Compounds Based on Scaffold 7

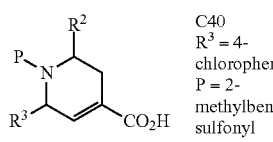

7
K-ras/RhoA

| | C40 | C13 | C15 |
|---|---|---|---|
| | R³ = 4-chlorophenyl<br>P = 2-methylbenezene-sulfonyl | R³ = 3,4-dichlorophenyl<br>P = 4-methylbenzene-sulfonyl | R³ = 3-bromophenyl<br>P = 4-methylbenzene-sulfonyl |

B06
R² = 3-bromo-phenyl

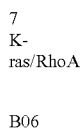

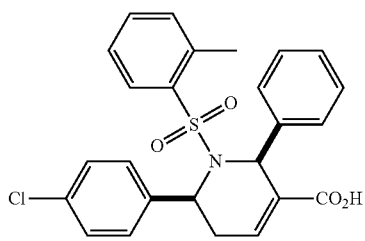

10.6/8.8

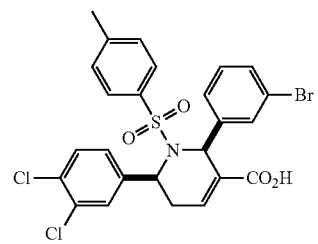

8.6/3.2

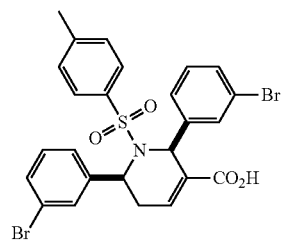

9.4/3.7

TABLE 2-continued
Exemplary Compounds Based on Scaffold 7
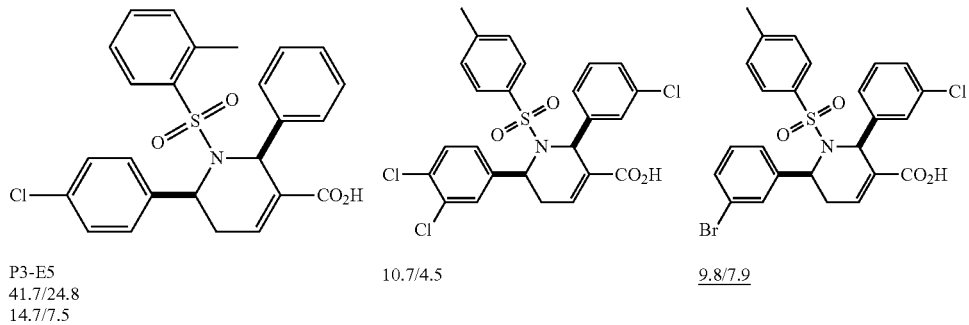
B05
R² = 3-chlorophenyl
P3-E5
41.7/24.8
14.7/7.5
10.7/4.5
9.8/7.9
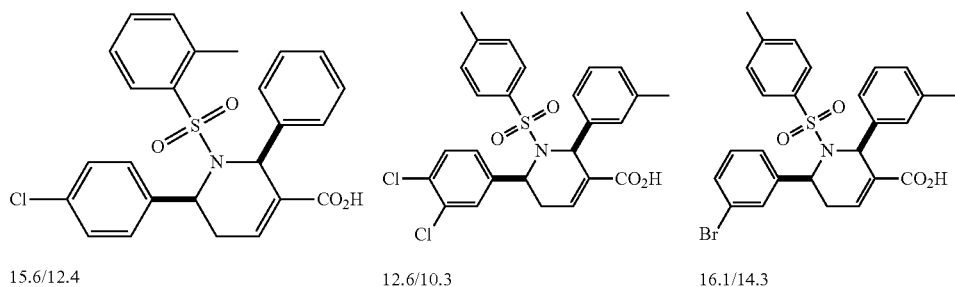
B07
R² = 3-methyl-phenyl
15.6/12.4
12.6/10.3
16.1/14.3
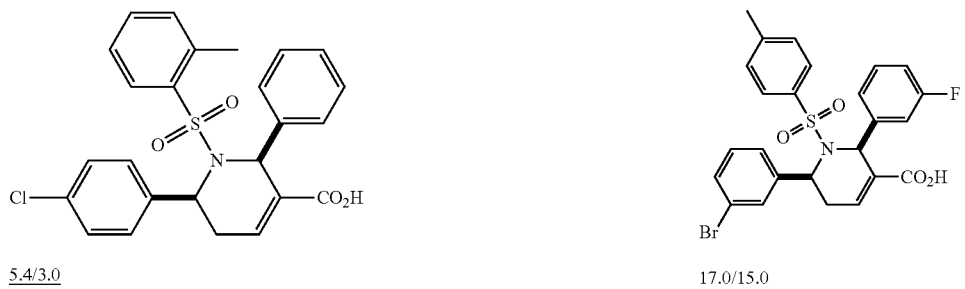
B04
R² = 3-fluorophenyl
5.4/3.0
17.0/15.0
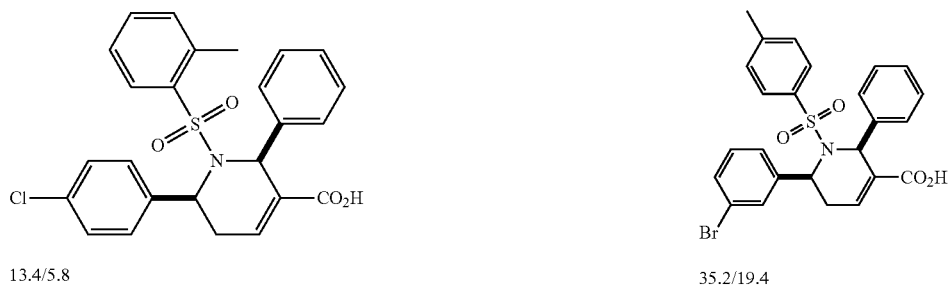
B02
R² = phenyl
13.4/5.8
35.2/19.4
B10*
R² = 4-bromo-phenyl
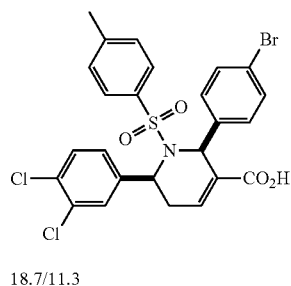
18.7/11.3

TABLE 2-continued
Exemplary Compounds Based on Scaffold 7
B03
R² = 2-fluorophenyl
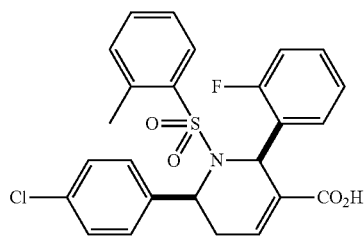
8.4/4.1
B08
R² = 4-fluorophenyl
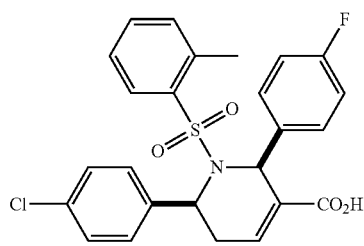
15.6/12.6
B09
R² = 4-chlorophenyl
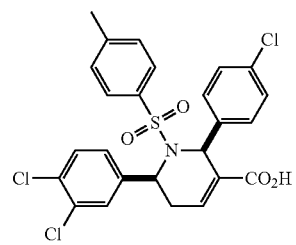
17.7/12.1
B11
R² = 4-methylphenyl
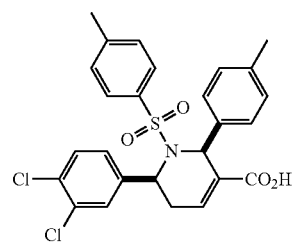
12.4/15.6
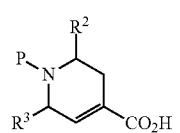
7
K-ras/RhoA
C12
R³ = 3-chlorophenyl
P = 4-methylbenzene-sulfonyl
C27
R³ = 4-chlorophenyl
P = 4-chlorobenzene-sulfonyl
C30
R³ = 4-methylphenyl
P = 4-chlorobenzene-sulfonyl

TABLE 2-continued

Exemplary Compounds Based on Scaffold 7

B06
$R^2$ = 3-bromo-phenyl 11.0/7.0

8.6/5.0

8.4/7.4

B05
$R^2$ = 3-chlorophenyl (43.7/6.0)

33.1/26.7

Further compounds of interest that can be based on scaffold 7 are listed in FIG. 2. These compounds include P2-D5, P2-D7, P2-D8, P2-D9, and P2-D10.

Other compounds may be built on scaffold 10. The compounds constructed on scaffold 10 may include substituents at R1, P, R3 and SR4 positions. R1 may be selected from the groups described as W herein.

In some embodiments, P is a protecting group as described above.

R3 can be, for example, an unsubstituted phenyl or a substituted phenyl ring. The substitution (also represented as J) can be at any position on the phenyl ring.

SR4 can be represented as thiols, with R4 being selected from the group consisting of hydrogen, alkyl of from 2 to 10 carbons.

Some exemplary compounds that inhibit GGTase I activity have been built using scaffold 10 include those listed in Table 3:

TABLE 3

Exemplary Compounds Based on Scaffold 10

10
K-ras/RhoA

C26
$R^4$ = 3-fluorophenyl
P = 4-methylbenzenesulfonyl

E30
$R^4$ = allyl 30.4/9.7

E32
$R^4$ = 2-(tert-buthoxy-carbonyl)ethyl 20.2/7.8

TABLE 3-continued
Exemplary Compounds Based on Scaffold 10
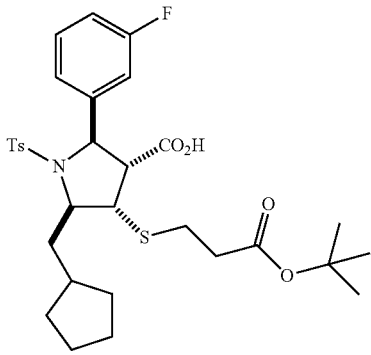
31.9/8.2
C13
R³ = 3,4-dichlorophenyl
P = 4-methylbenzene-sulfonyl
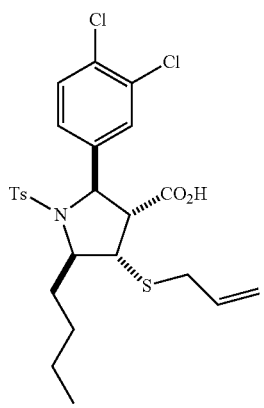
21.4/9.6
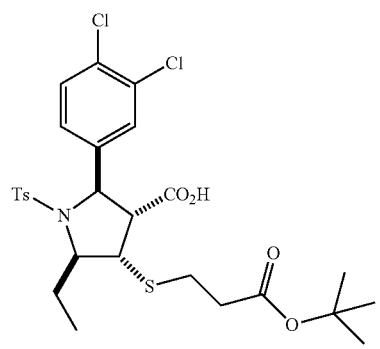
27.2/7.6
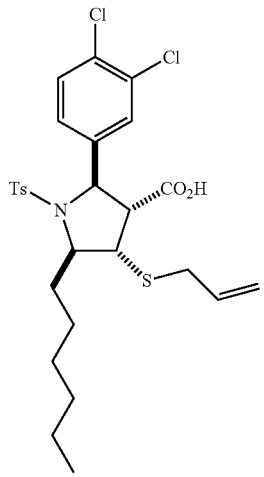
15.1/6.8
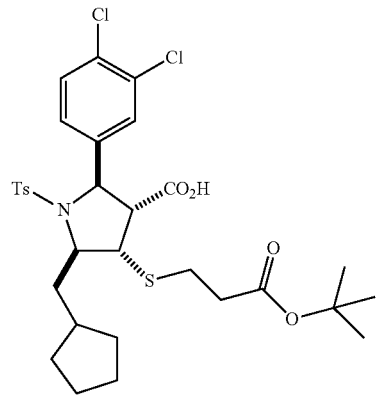
16.1/7.3

TABLE 3-continued
Exemplary Compounds Based on Scaffold 10
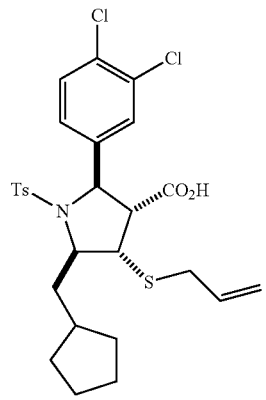
12.1/8.6
C40
R³ = 4-chlorophenyl
P = 2-methylbenzene-sulfonyl
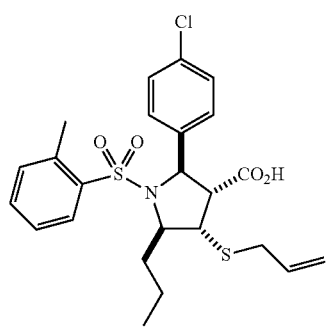
28.4/8.9
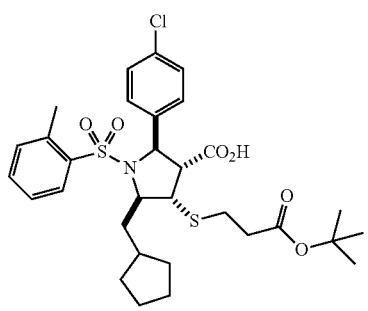
10.0/7.8
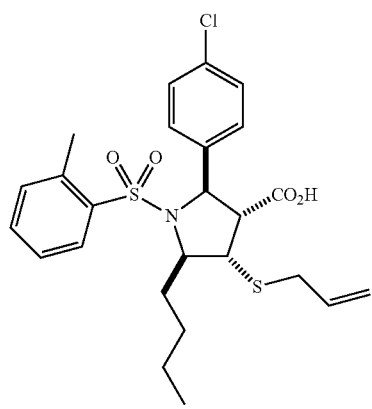 [SMILES: C=CCS[C@H]1[C@@H](C(=O)O)[C@H](c2ccc(Cl)cc2)N(S(=O)(=O)c2ccccc2C)[C@@H]1CCC]
23.1/8.4

TABLE 3-continued
Exemplary Compounds Based on Scaffold 10
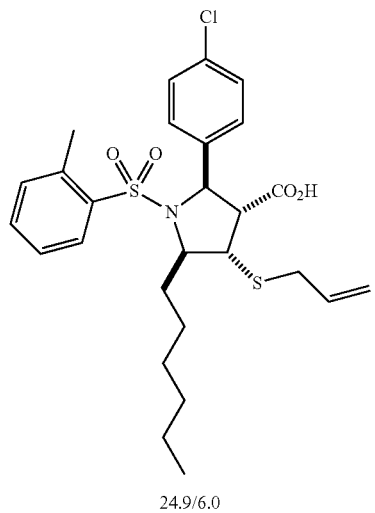 [SMILES: C=CCS[C@H]1[C@@H](C(=O)O)[C@H](c2ccc(Cl)cc2)N(S(=O)(=O)c2ccccc2C)[C@@H]1CCCCCC]
24.9/6.0
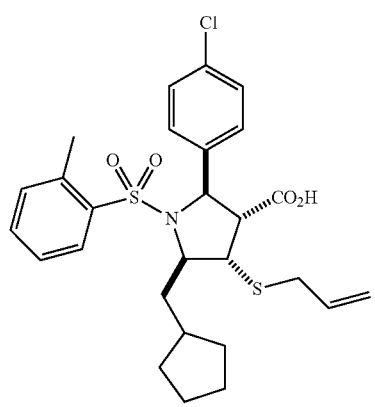
22.4/4.9
C27
R3 = 4-chlorophenyl
P = 4-chlorobenzene-sulfonyl
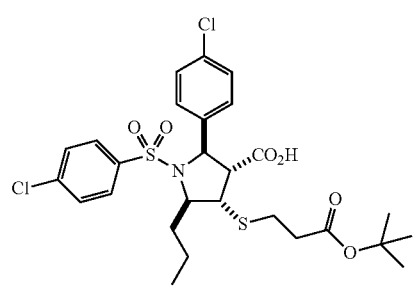
21.7/9.2
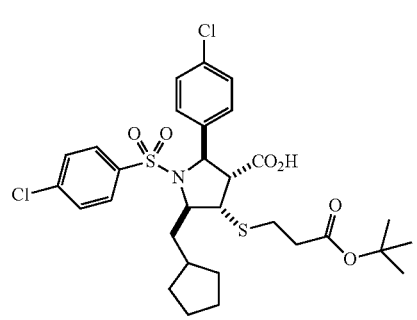
22.5/9.8

TABLE 3-continued
Exemplary Compounds Based on Scaffold 10
C29
R³ = 4-chlorophenyl
P = benzene-sulfonyl
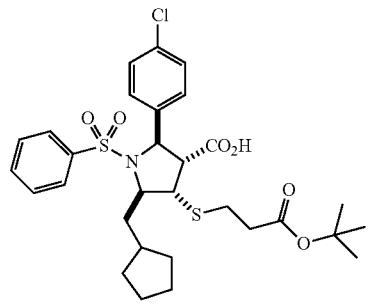
30.4/9.7
C09
R³ = 4-cyanophenyl
P = 4-methylbenzene-sulfonyl
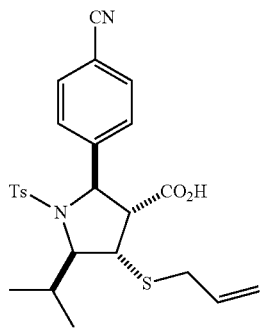
23.1/9.3
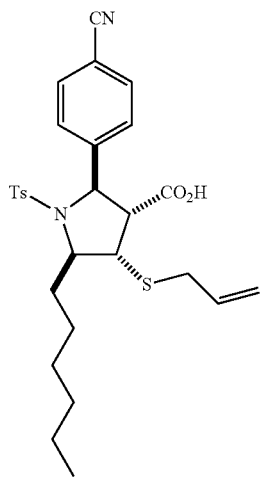
21.5/6.0

TABLE 3-continued
Exemplary Compounds Based on Scaffold 10
C14
$R^3$ = 4-bromophenyl
P = 4-methylbenzene-sulfonyl
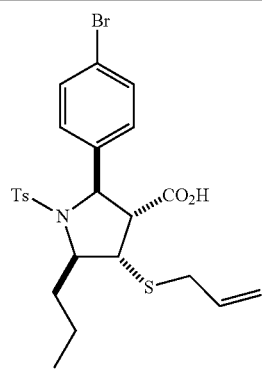
9.8/7.5
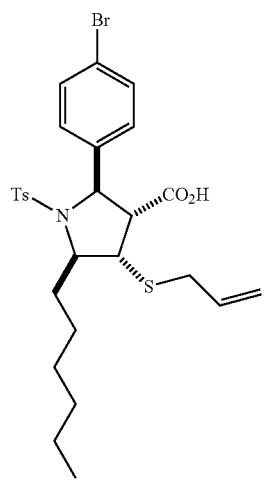
15.5/5.5
C12
$R^3$ = 2-chlorophenyl
P = 4-methylbenzene-sulfonyl
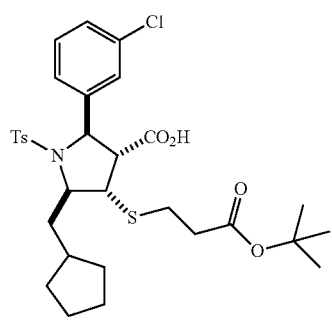
20.6/5.6

TABLE 3-continued
Exemplary Compounds Based on Scaffold 10
C20
R³ = 3,4-dimethoxyphenyl
P = 4-methylbenzene-sulfonyl
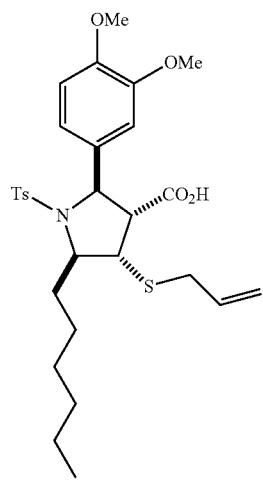
22.3/8.1
C11
R³ = 4-chlorophenyl
P = 4-methylbenzene-sulfonyl
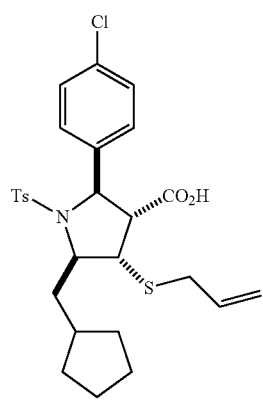
25.2/7.7
C24
R³ = 4-isopropylphenyl
P = 4-methylbenzene-sulfonyl
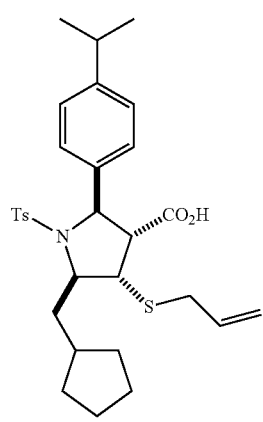
31.7/6.1

TABLE 3-continued
Exemplary Compounds Based on Scaffold 10
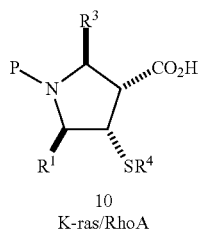
10
K-ras/RhoA
E04
R⁴ = 4-methoxyphenyl
E02
R⁴ = 4-methylphenyl
C26
R³ = 3-fluorophenyl
P = 4-methylbenzenesulfonyl
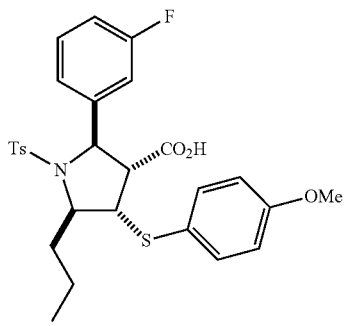
27.4/3.5
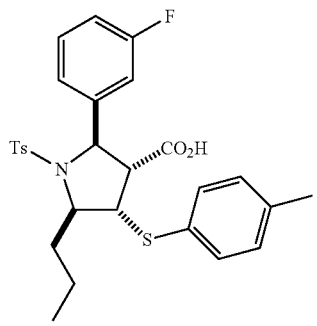
14.7/4.1
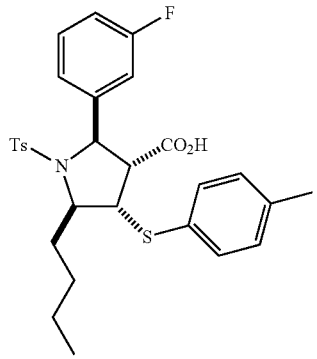
31.5/7.1
C13
R³ = 3,4-dichlorophenyl
P = 4-methylbenzene-sulfonyl
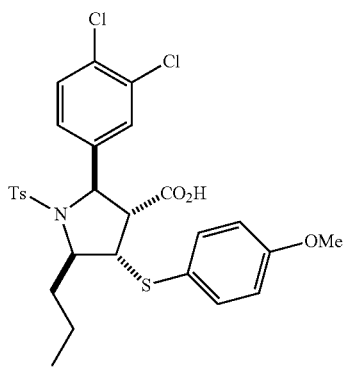
10.9/1.1
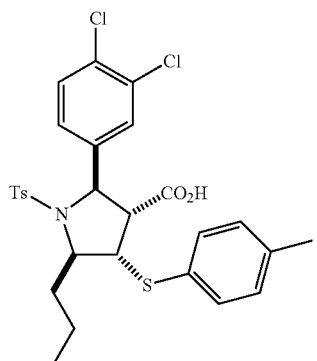
21.3/9.2

TABLE 3-continued
Exemplary Compounds Based on Scaffold 10
C27
R³ = 4-chlorophenyl
P = 4-chlorobenzene-sulfonyl
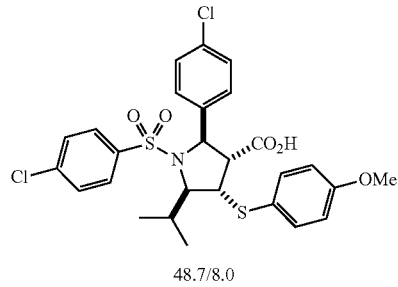 [SMILES: COc1ccc(S[C@H]2[C@@H](C(=O)O)[C@H](c3ccc(Cl)cc3)N(S(=O)(=O)c3ccc(Cl)cc3)[C@@H]2C(C)C)cc1]
48.7/8.0
C29
R³ = 4-chlorophenyl
P = benzene-sulfonyl
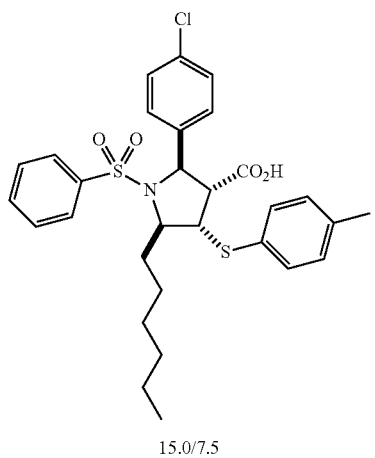 [SMILES: CCCCCC[C@@H]1[C@@H](Sc2ccc(C)cc2)[C@@H](C(=O)O)[C@H](c2ccc(Cl)cc2)N1S(=O)(=O)c1ccccc1]
15.0/7.5
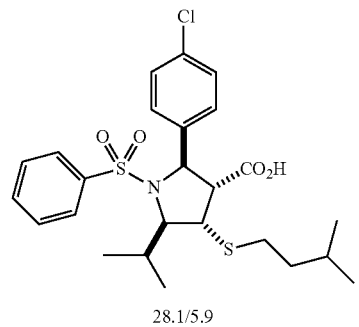 [SMILES: CC(C)CCS[C@H]1[C@@H](C(=O)O)[C@H](c2ccc(Cl)cc2)N(S(=O)(=O)c2ccccc2)[C@@H]1C(C)C]
28.1/5.9
C12
R³ = 2-chlorophenyl
P = 4-methylbenzene-sulfonyl
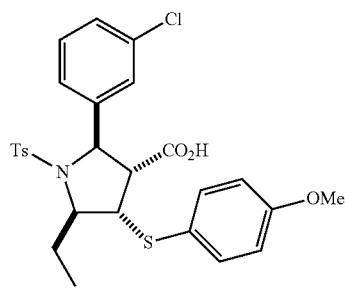
25.5/6.5

TABLE 3-continued

Exemplary Compounds Based on Scaffold 10

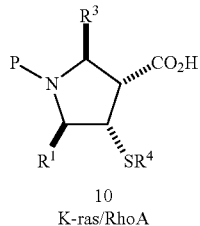

10
K-ras/RhoA

E23
R⁴ = 3-methyl-1-butyl or
E24
R⁴ = pentyl or
E28
R⁴ = cyclopentyl

C26
R³ = 3-fluorophenyl
P = 4-methylbenzenesulfonyl

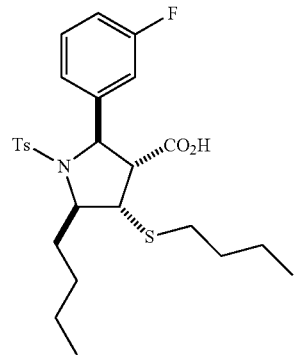

23.5/7.1

C09
R³ = 4-cyanophenyl
P = 4-methylbenzene-sulfonyl

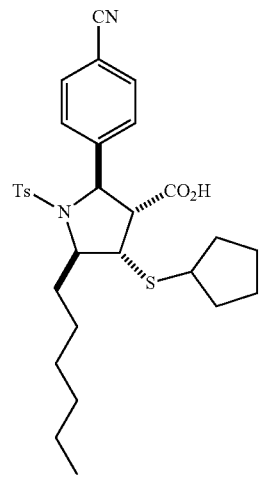

20.1/7.4

In some embodiments, GGTase I inhibiting compounds can be based on scaffold 7. The compounds based on scaffold 11 may include substituents at R3, P R2, and SR4. R3 is represented herein as W and any of the groups described in relation to W may be used at position R3.

In some embodiments, P is a protecting group as described above.

R2 can be, for example, an unsubstituted phenyl or a substituted phenyl ring. The substitution (also represented as J) can be at any position on the phenyl ring.

SR4 can be represented as thiols, with R4 being selected from the group consisting of hydrogen, alkyl of from 2 to 10 carbons. Compounds prepared using scaffold 11 are disclosed herein.

In some embodiments, the GGTI compound can be selected from the following additional examples of GGTIs that have been made by the methods described herein.

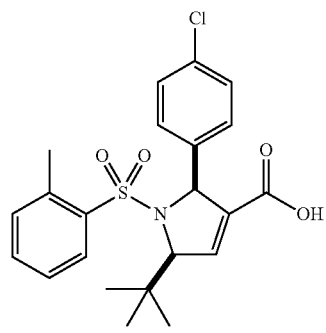

P5-H6

-continued
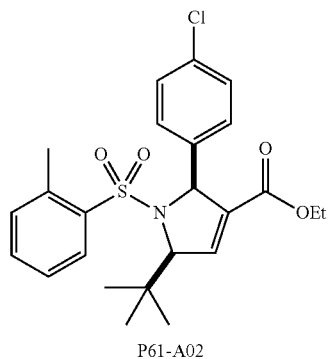
P61-A02
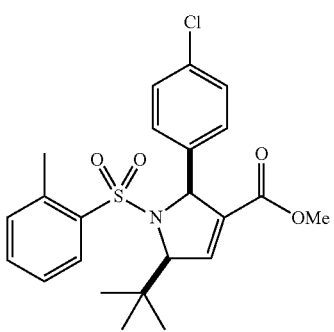
P09-C10
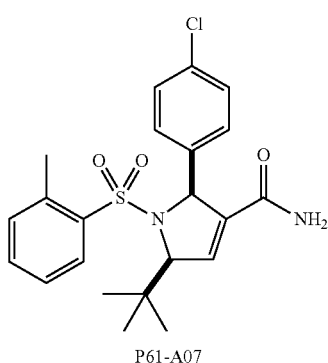
P61-A07
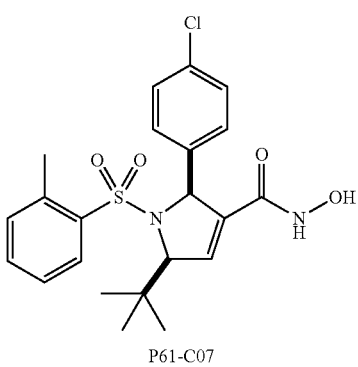
P61-C07
-continued
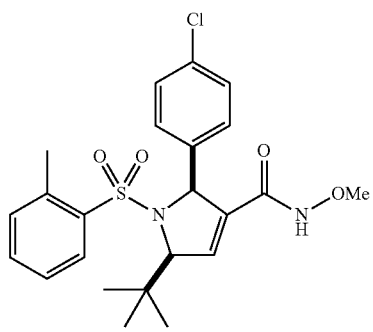
P61-E05
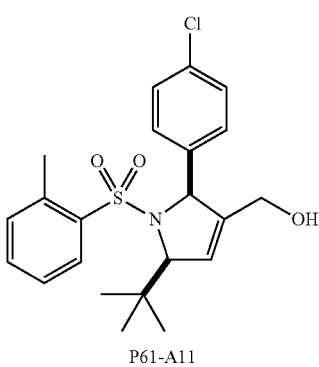
P61-A11
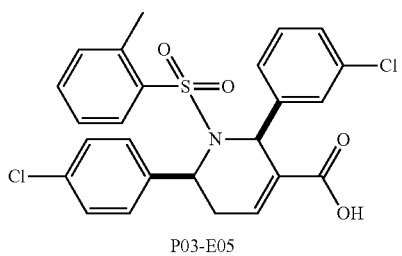
P03-E05
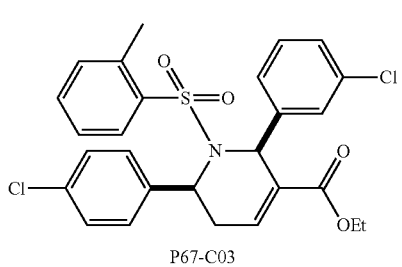
P67-C03
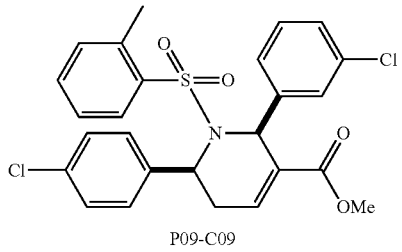
P09-C09

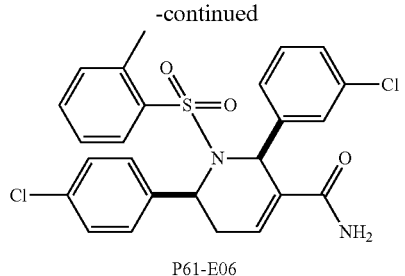
P61-E06
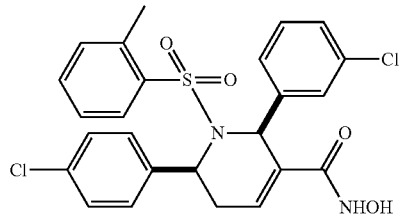
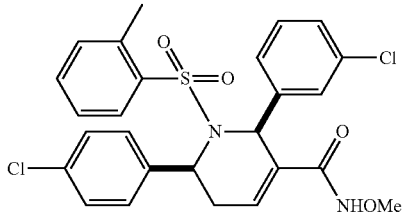
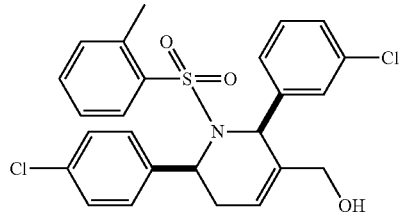
P61-B03
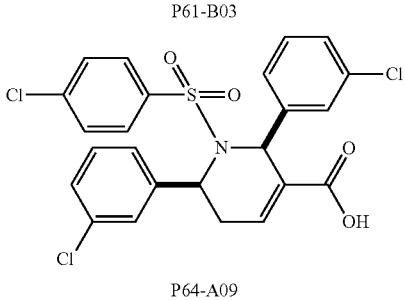
P64-A09
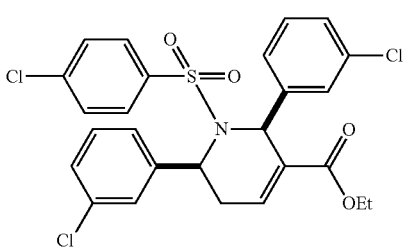
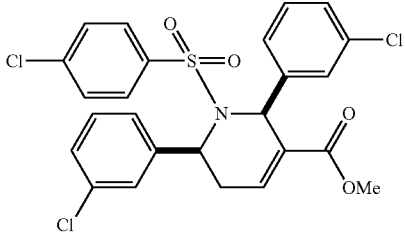
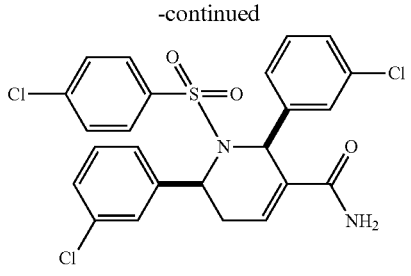
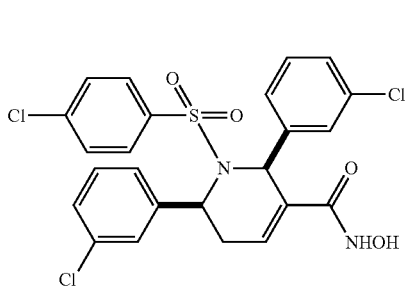
P67-A11
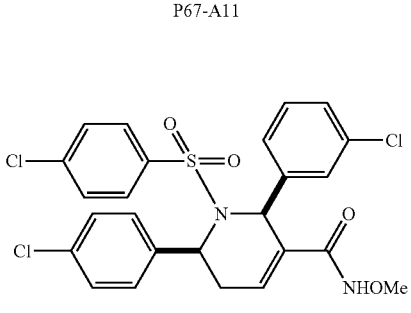
P67-B08
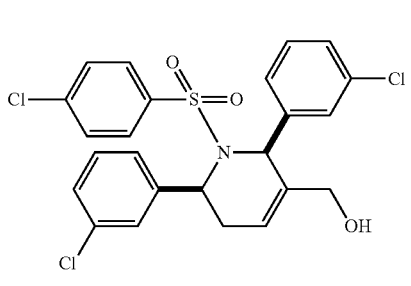
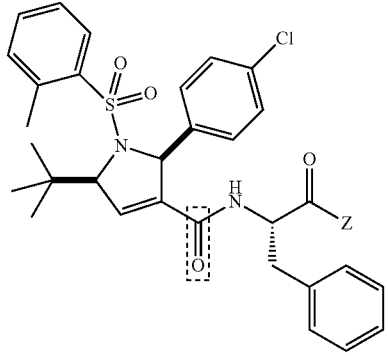
Z = OMe   P61A4 & P61A5
Z = OH    P61A8
Z = NH₂   P61A6 & P61B7

63
-continued
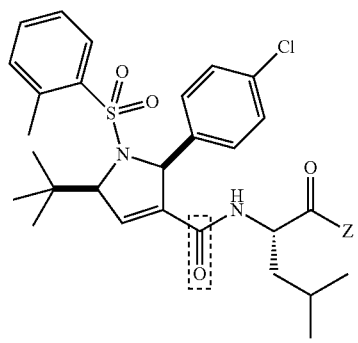
Z = OMe P67B9
Z = OH
Z = NH₂ P61B2
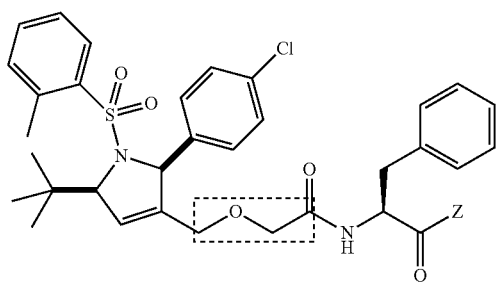
Z = OMe P61B4
Z = OH P61B5
Z = NH₂ P61B6
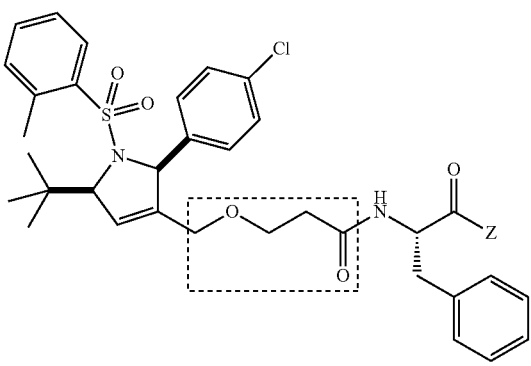
Z = OMe P61E4
Z = OH
Z = NH₂
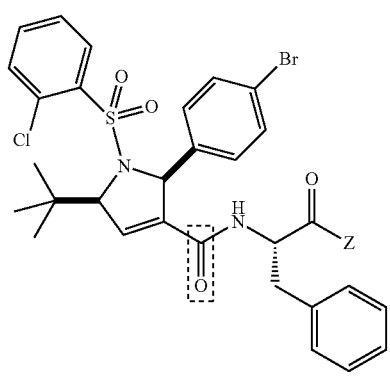
Z = OMe
Z = OH
Z = NH₂ P61B8 & P61B9
64
-continued
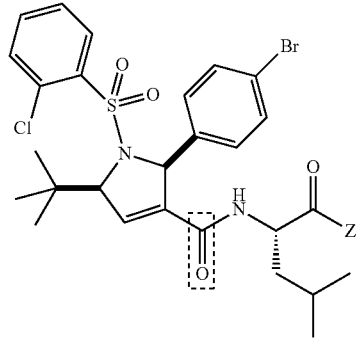
Z = OMe
Z = OH
Z = NH₂
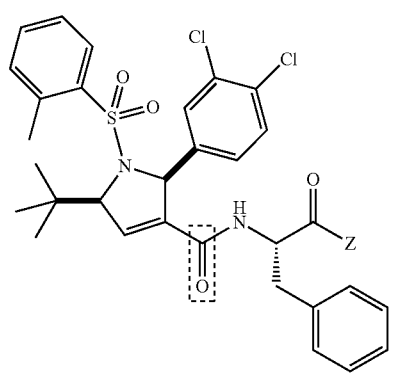
Z = OMe
Z = OH
Z = NH₂ P61B10 & P61B11
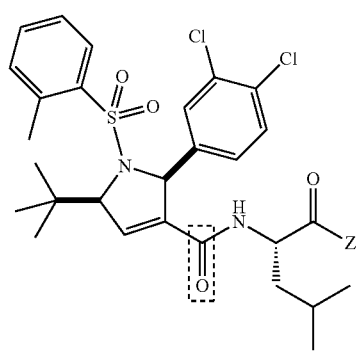
Z = OMe
Z = OH
Z = NH₂

65
-continued
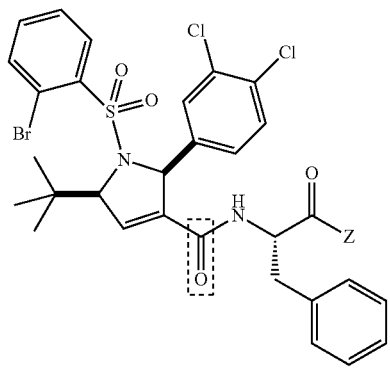
Z = OMe
Z = OH
Z = NH₂  P61E3
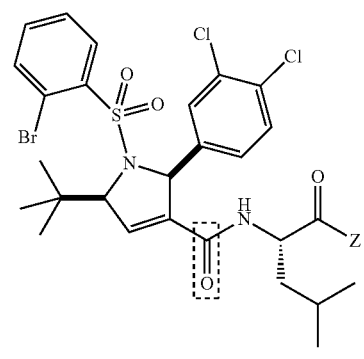
Z = OMe
Z = OH
Z = NH₂
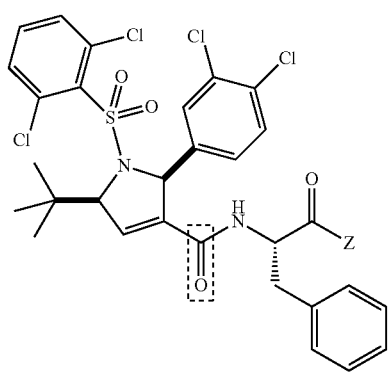
Z = OMe
Z = OH
Z = NH₂  P61D9 & P61D10
66
-continued
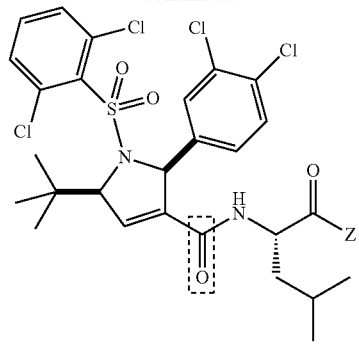
Z = OMe
Z = OH
Z = NH₂
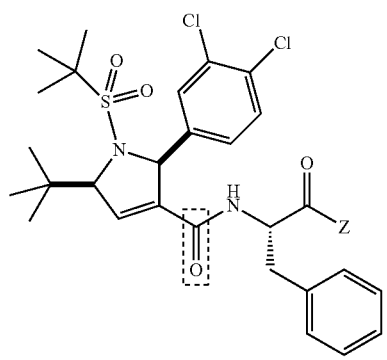
Z = OMe
Z = OH
Z = NH₂  P61D11 & P61E2
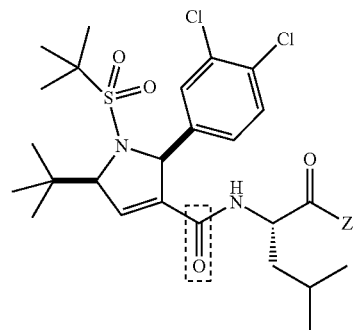
Z = OMe
Z = OH
Z = NH₂
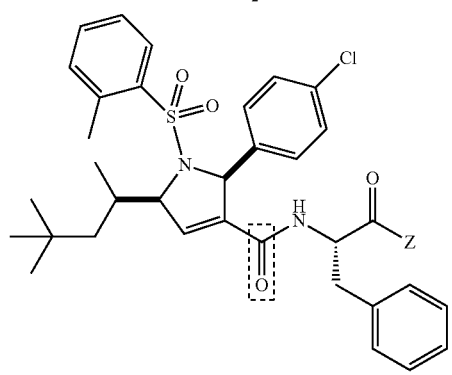
Z = OMe
Z = OH
Z = NH₂  P61C3 & P61C4

-continued
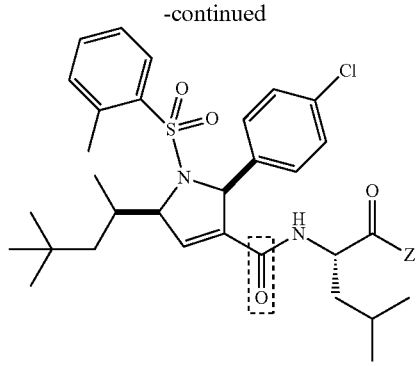
Z = OMe
Z = OH
Z = NH₂
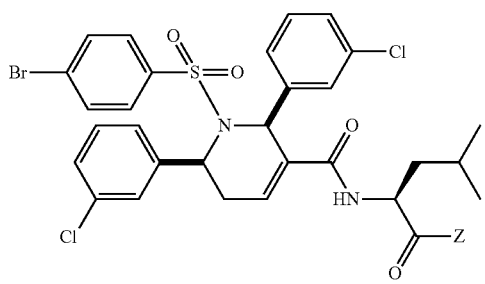
Z = OMe   P67-A04
Z = OH    P61-H03
Z = NH₂   P61-C09 & P61-C10
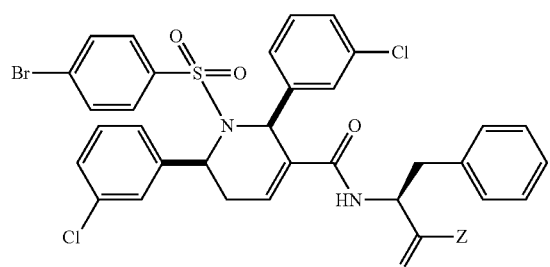
Z = OMe   P67-A08
Z = OH    P61-G05
Z = NH₂   P61-D04 & P61-D05
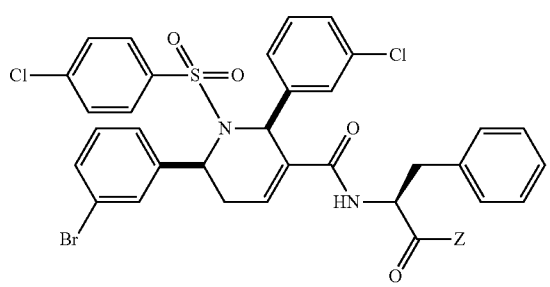
Z = OMe   P67-A10
Z = OH    P61-G07
Z = NH₂   P61-F11 & P61-G02
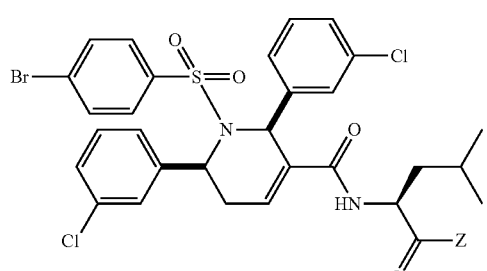
Z = OMe   P67-A09
Z = OH    P61-E11
Z = NH₂   P61-E08
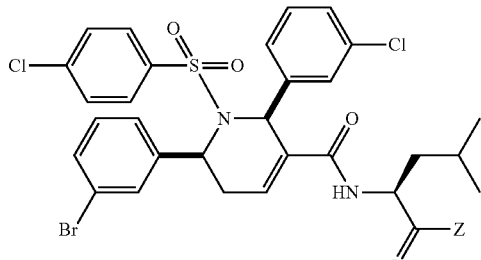
Z = OMe   P67-A07
Z = OH    P61-G08
Z = NH₂   P61-C06
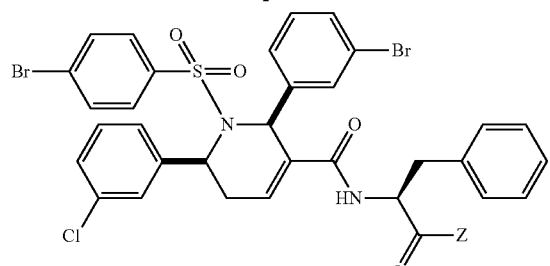
Z = OMe   P67-A03
Z = OH    P61-G06
Z = NH₂   P61-E09 & P61-E10
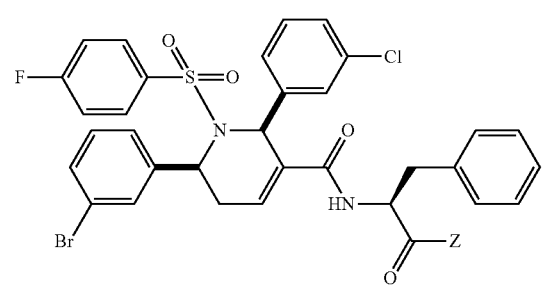
Z = OMe   P67-A06
Z = OH    P61-H07
Z = NH₂   P61-H04

-continued

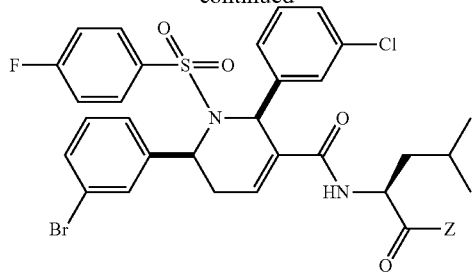

Z = OMe  P61-H11
Z = OH   P61-H06
Z = NH₂  P61-C11 & P61-D03

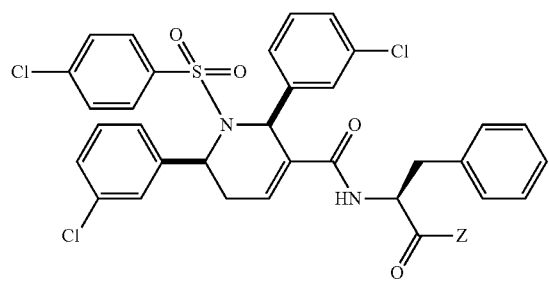

Z = OMe  P67-A02
Z = OH   P61-H09
Z = NH₂  P61-D02

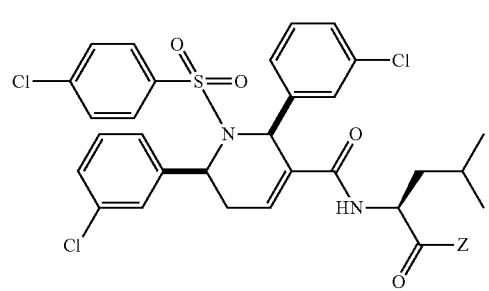

Z = OMe  P67-A05
Z = OH   P61-H08
Z = NH₂  P61H05

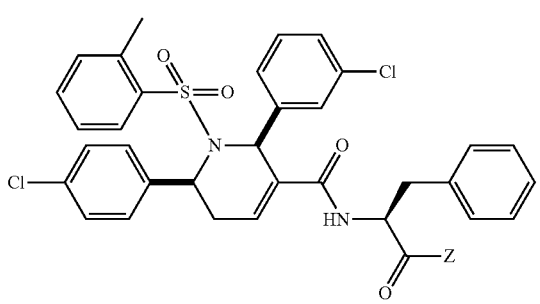

Z = OMe  P67-B02, P67-B03, P67-B04
Z = OH   P67-B06
Z = NH₂  P67-B05

-continued

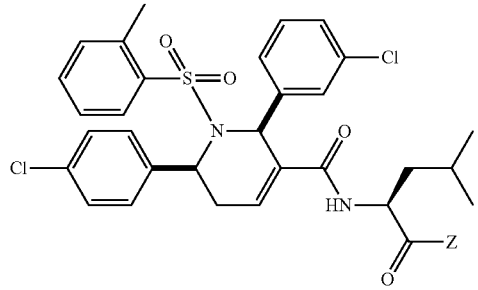

Z = OMe  P61-E07
Z = OH   P67-B07
Z = NH₂  P61-C05

One example embodiment of the compounds that may be built from Formula 1 and/or the scaffolds disclosed herein is compound P61-A6. This compound has the following chemical structure and has been found to inhibit GGTase I activity:

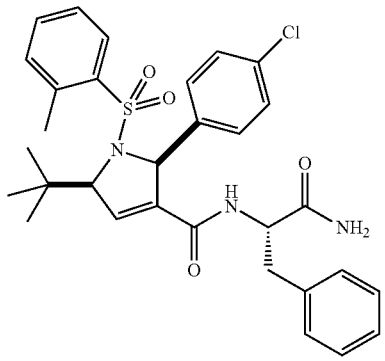 [SMILES: Cc1ccccc1S(=O)(=O)N1[C@@H](c2ccc(Cl)cc2)C(C(=O)N[C@@H](Cc2ccccc2)C(N)=O)=C[C@H]1C(C)(C)C]

Some exemplary compounds that inhibit GGTase I activity based on Formula 1 include those listed in Table 3 below. In Table 3 in vitro $IC_{50}$ values for the GGTase I activity are reported. In Table 3 the isolated yield of each synthetic step for the synthesis of corresponding compounds are also reported.

TABLE 3
In Vitro (Enzyme Assay) IC$_{50}$ of Dihydropyrroles with Linker 1
| Dihydropyrrole | PheOMe | PheOH | PheNH$_2$ | LeuOMe | LeuOH | LeuNH$_2$ |
|---|---|---|---|---|---|---|
| 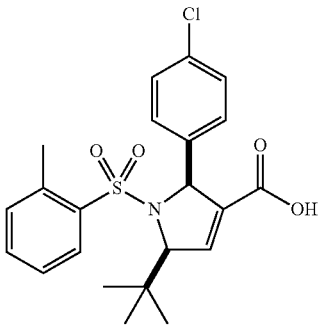<br>P5-H6<br>0.5 µM | P61-A04<br>>50 µM<br>P61-A05<br>>50 µM | P61-A08<br>1.4 µM | P61-A06<br>1.0 µM<br>P61-B07<br>7.7 µM | P67-B09 | | P61-B02<br>8.1 µM |
| Synthesis Yield | 98% | 97% | 80% | 95% | 91% | 60% |
| 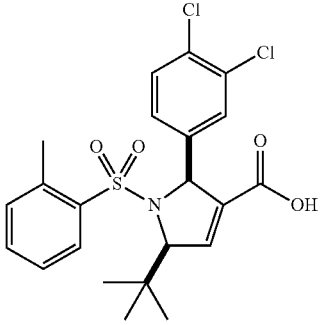<br>P62-A02<br>0.363 µM | | | P61-B10<br>5.4 µM<br>P61-B11<br>7.6 µM | P67-C02 | | |
| Synthesis Yield | 95% | 90% | 95% | 96% | 91% | 80% |
| 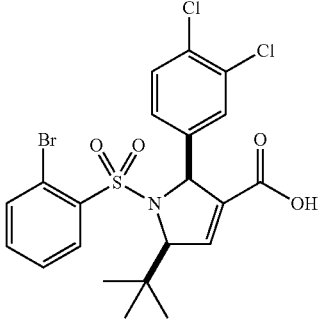<br>P62-A11<br>0.348 µM | | | P61-E03<br>>20 µM | P67-B10 | | |
| Synthesis Yield | 92% | 95% | 95% | >90% | 89% | >78% |

TABLE 3-continued
In Vitro (Enzyme Assay) IC$_{50}$ of Dihydropyrroles with Linker 1
| Dihydropyrrole | PheOMe | PheOH | PheNH$_2$ | LeuOMe | LeuOH | LeuNH$_2$ |
|---|---|---|---|---|---|---|
| 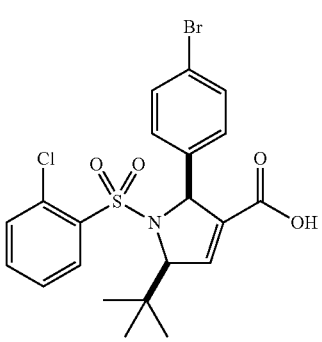<br>P62-D11<br>0.349 μM | | | P61-B08<br>16.0 μM<br>P61-B09<br>>10 μM | | | |
| Synthesis Yield | 91% | 91% | 99% | >91% | 90% | >65% |
| 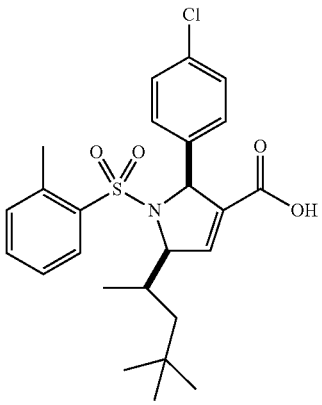<br>P61-C02<br>3.4 μM | | | P61-C03<br>>10 μM<br>P61-C04<br>>50 μM | | | |
| Synthesis Yield | — | — | 72% | — | — | — |
| 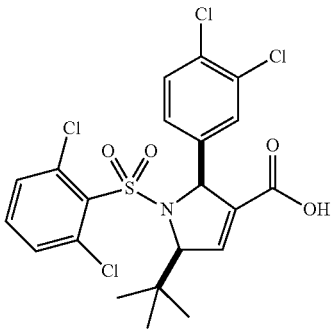<br>P61-C08<br>4.4 μM | | | P61-D09<br>>50 μM<br>P61-D10<br>>50 μM | | | |
| Synthesis Yield | — | — | 95% | — | — | — |

TABLE 3-continued

In Vitro (Enzyme Assay) IC$_{50}$ of Dihydropyrroles with Linker 1

| Dihydropyrrole | PheOMe | PheOH | PheNH$_2$ | LeuOMe | LeuOH | LeuNH$_2$ |
|---|---|---|---|---|---|---|
| P61-D08  4.4 µM | — | — | P61-D11 >50 µM  P61-E02 2.7 µM | | | |
| Synthesis Yield | — | — | 85% | — | — | — |

Some exemplary compounds that inhibit GGTase I activity based on Formula 1 include those listed in Table 4. In Table 4 in cell GI$_{50}$ values for the growth inhibition of Jurkat cells are reported. The GI$_{50}$ value is the concentration of a test compound needed to produce 50% growth inhibition in the cell type listed. In Table 4 the isolated yield of each synthetic step for the synthesis of corresponding compounds are also reported.

TABLE 4

Jurkat Cell GI$_{50}$ of Dihydropyrroles with Linker 1

| Dihydropyrrole | PheOMe | PheOH | PheNH$_2$ | LeuOMe | LeuOH | LeuNH$_2$ |
|---|---|---|---|---|---|---|
| P5-H6  20 µM | P61-A04 19.0 µM  P61-A05 10.50 µM | P61-A08 13.0 µM | P61-A06 4.89 µM  P61-B07 6.1 µM | P67-B09 | | P61-B02 6.58 µM |
| Synthesis Yield | 98% | 97% | 80% | 95% | 91% | 60% |
| P62-A02 | | P67-B11 | P61-B10 5.62 µM  P61-B11 6.90 µM | | P67-C02 | |
| Synthesis Yield | 95% | 90% | 95% | 96% | 91% | 80% |

TABLE 4-continued
Jurkat Cell GI$_{50}$ of Dihydropyrroles with Linker 1
| Dihydropyrrole | PheOMe | PheOH | PheNH$_2$ | LeuOMe | LeuOH | LeuNH$_2$ |
|---|---|---|---|---|---|---|
| 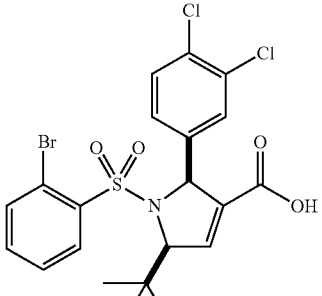  P62-A11 | | | P61-E03 | | P67-B10 | |
| Synthesis Yield | 92% | 95% | 95% | >90% | 89% | >78% |
| 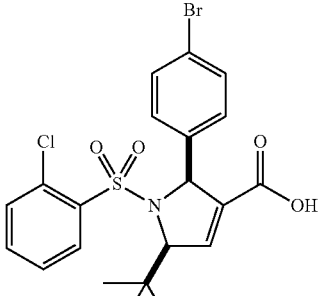  P62-D11 | | | P61-B08 4.74 μM P61-B09 8.75 μM | | | |
| Synthesis Yield | 91% | 91% | 99% | >91% | 90% | >65% |
| 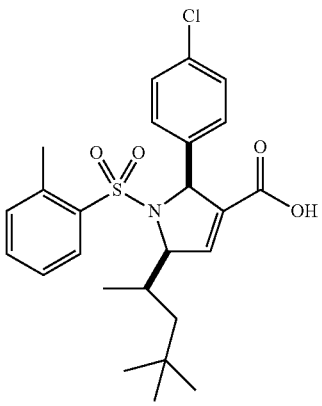  P61-C02 | | | P61-C03 9.76 μM P61-C04 6.40 μM | | | |
| Synthesis Yield | — | — | 72% | — | — | — |

TABLE 4-continued

Jurkat Cell GI$_{50}$ of Dihydropyrroles with Linker 1

| Dihydropyrrole | PheOMe | PheOH | PheNH$_2$ | LeuOMe | LeuOH | LeuNH$_2$ |
|---|---|---|---|---|---|---|
| [structure] P61-C08 2.76 µM | | | P61-D09 4.91 µM P61-D10 5.28 µM | | | |
| Synthesis Yield | — | — | 95% | — | — | — |
| [structure] P61-D06 5.36 µM | | | P61-D11 5.91 µM P61-E02 4.57 µM | | | |
| Synthesis Yield | — | — | 85% | — | — | — |

One embodiment of the compounds that may be built from Formula 1 is compound P61-H7. This compound has the following chemical structure:

Some exemplary compounds that inhibit GGTase I activity based on Formula 1 include those listed in Table 5. In Table 5 in vitro IC$_{50}$ values for the GGTase I activity are reported. In Table 5 the isolated yield of each synthetic step for the synthesis of corresponding compounds are also reported.

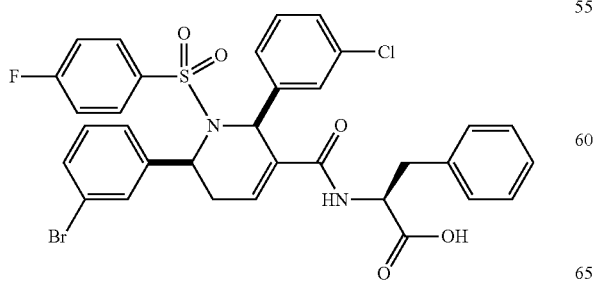

TABLE 5

In Vitro (Enzyme Assay) IC$_{50}$ of Tetrahydropyridines with Linker 1

| Tetrahydropyridine | PheOMe | PheOH | PheNH$_2$ | LeuOMe | LeuOH | LeuNH$_2$ |
|---|---|---|---|---|---|---|
| P64-B04<br>86 nM | P67-A08 | P61-G05<br>150 nM | P61-D04<br>1.3 μM<br>P61-D05<br>>20 μM | P67-A09<br>>20 μM | P61-E11<br>500 nM | P61-E08<br>>20 μM |
| Synthesis Yield | 95% | 94%, 95% | 85% | 91% | 95%, 94% | 82% |
| P64-H10<br>155 nM | P67-A03 | P61-G06<br>32 nM | P61-E09<br>>20 μM<br>P61-E10<br>>20 μM | P67-A04<br>>20 μM | P61-H03<br>40 nM | P61-C09<br>>50 μM<br>P61-C10<br>>50 μM |
| Synthesis Yield | 92% | 90%, 95% | 80% | 94% | 92%, 90% | 85% |
| P64-A10<br>154 nM | P67-A10 | P61-G07<br>70 nM | P61-F11<br>300 nM<br>P61-G02<br>450 nM | P67-A07<br>>20μM | P61-G08<br>60 nM | P61-C06<br>39.1 μM |
| Synthesis Yield | 90% | 91%, 97% | 92% | 93% | 90%, 95% | 91% |
| P64-B10<br>212 nM | P67-A06 | P61-H07<br>11 nM | P61-H04 | P67-H11<br>>20 μM | P61-H06<br>210 nM | P61-C11<br>32.9 μM<br>P61-D03<br>6.9 μM |
| Synthesis Yield | 71% | 90%, 92% | 75% | 70% | 90%, 91% | 79% |

TABLE 5-continued

In Vitro (Enzyme Assay) IC$_{50}$ of Tetrahydropyridines with Linker 1

| Tetrahydropyridine | PheOMe | PheOH | PheNH$_2$ | LeuOMe | LeuOH | LeuNH$_2$ |
|---|---|---|---|---|---|---|
| (structure) P64-A09 241 nM | P67-A02 | P61-H09 21 nM | P61-D02 600 nM | P67-A05 >20 μM | P61-H08 180 nM | P61-H05 |
| Synthesis Yield | 75% | 91%, 95% | 81% | 67% | 91%, 93% | 81% |
| (structure) P3-E05 313 nM | P67-B02 P67-B03 P67-B04 | P67-B06 | P67-B05 | P61-E07 >20 μM | P67-B07 | P61-C05 >50 μM |
| Synthesis Yield | 95% | 90%, 92% | 82% | 91% | 92%, 91% | 89% |

One embodiment of the compounds that may be built from Formula 1 is compound P61-D3. This compound has the following chemical structure:

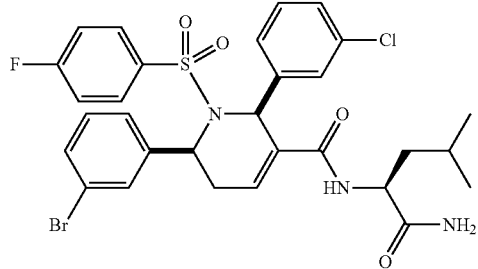 [SMILES: CC(C)C[C@H](NC(=O)C1=CC[C@@H](c2cccc(Br)c2)N(S(=O)(=O)c2ccc(F)cc2)[C@H]1c1cccc(Cl)c1)C(N)=O]

One embodiment of the compounds that may be built from Formula 1 is compound P61-E7. This compound has the following chemical structure:

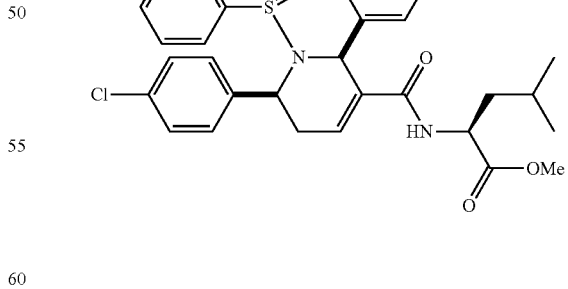

Some exemplary compounds that inhibit GGTase I activity based on Formula 1 include those listed in Table 6. In Table 6 in cell GI$_{50}$ values for the growth inhibition of Jurkat cells are reported. In Table 6 the isolated yield of each synthetic step for the synthesis of corresponding compounds are also reported.

TABLE 6
Jurkat Cell GI$_{50}$ Data of Tetrahydropyridines with Linker 1
| Tetrahydropyridine | PheOMe | PheOH | PheNH$_2$ | LeuOMe | LeuOH | LeuNH$_2$ |
|---|---|---|---|---|---|---|
| 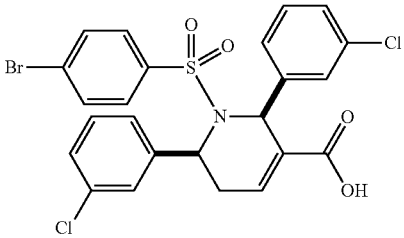 P64-B04 | P67-A08 | P61-G05 | P61-D04 4.86 μM P61-D05 3.57 μM | P67-A09 3.81 μM | P61-E11 | P61-E08 |
| Synthesis Yield | 95% | 94%, 95% | 85% | 91% | 95%, 94% | 82% |
| 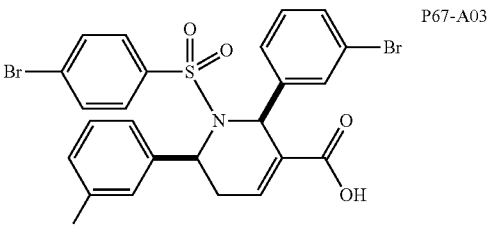 P64-H10 | P67-A03 | P61-G06 | P61-E09 P61-E10 | P67-A04 8.0 μM | P61-H03 | P61-C09 6.38 μM P61-C10 2.22 μM |
| Synthesis Yield | 92% | 90%, 95% | 80% | 94% | 92%, 90% | 85% |
| 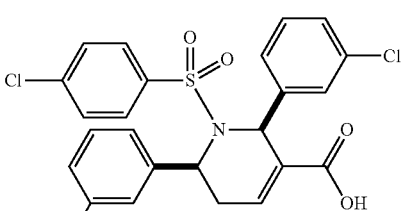 P64-A10 | P67-A10 | P61-G07 | P61-F11 P61-G02 | P67-A07 | P61-G08 | P61-C06 3.15 μM |
| Synthesis Yield | 90% | 91%, 97% | 92% | 93% | 90%, 95% | 91% |
| 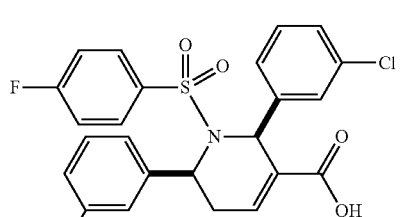 P64-B10 | P67-A06 | P61-H07 | P61-H04 | P61-H11 | P61-H06 210 nM | P61-C11 1.76 μM P61-D03 0.32 μM |
| Synthesis Yield | 71% | 90%, 92% | 75% | 70% | 90%, 91% | 79% |

TABLE 6-continued

Jurkat Cell GI$_{50}$ Data of Tetrahydropyridines with Linker 1

| Tetrahydropyridine | PheOMe | PheOH | PheNH$_2$ | LeuOMe | LeuOH | LeuNH$_2$ |
|---|---|---|---|---|---|---|
| 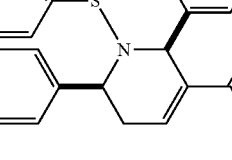 P64-A09 | P67-A02 | P61-H09 | P61-D02 1.96 µM | P67-A05 | P61-H08 | P61-H05 |
| Synthesis Yield | 75% | 91%, 95% | 81% | 67% | 91%, 93% | 81% |
| 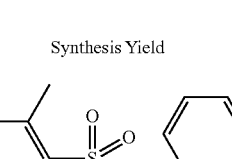 P3-E05 | P67-B02 P67-B03 P67-B04 | P67-B06 | P67-B05 | P61-E07 3.53 | P67-B07 | P61-C05 6.10 µM |
| Synthesis Yield | 95% | 90%, 92% | 82% | 91% | 92%, 91% | 89% |

Some exemplary compounds that inhibit GGTase I activity based on Formula 1 include those listed in Tables 7-15. In FIG. 9-24 in vitro IC$_{50}$ values for the GGTase I activity are reported. In Tables 7-15 in cell GI$_{50}$ values for the growth inhibition of a variety of cancer cell lines (e.g., Jurkat, K562, MDA-MB-231, BT474, MCF7, MiaPaCa2, Aspc-1, Panc-1, Capan-2, CFpac-1, and MCF10a) are reported.

TABLE 7

Dihydropyrroles with varying terminal groups (µM unless otherwise specified)

| | | Leukemic cells | | Breast Cancer Cells | | | | Pancreatic Cancer Cells | | | | |
|---|---|---|---|---|---|---|---|---|---|---|---|---|
| Structure | In vitro | Jurkat | K562 | MDA-MB-231 | BT474 | MCF7 | MCF10a | MiaPaCa2 | Aspc-1 | Panc-1 | Capan-2 | CFpac-1 |
| P5-H6 | 0.5 | 20.00 | | | | | | | | | | |

TABLE 7-continued

Dihydropyrroles with varying terminal groups (μM unless otherwise specified)

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P61-A02 | >50 | 18.50 | | | | | | | | | | |
| P09-C10 | | | | | | | | | | | | |
| P61-A07 | | 1.6 | 11.00 | 4.80 | | | | | | | | |
| P61-C07 | | 1.3 | 4.02 | 10.33 | | 2.52 | 11.37 | | | | | |

TABLE 7-continued

Dihydropyrroles with varying terminal groups (μM unless otherwise specified)

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P61-E05 | 3.8 | 12.57 | | | | | | | | | | |
| P61-A11 | 2.2 | 5.80 | 6.00 | | | | | | | | | |

TABLE 8

Different Dihydropyrroles

| Structure | In vitro | Leukemic cells | | Breast Cancer Cells | | | | Pancreactic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P5-H6 | 0.5 | 20.00 | | | | | | | | | | |

TABLE 8-continued
Different Dihydropyrroles
| Structure | In vitro | Leukemic cells | | Breast Cancer Cells | | | | Pancreactic Cancer Cells | | | |
|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
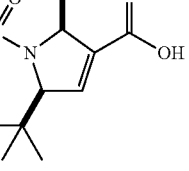
P62-A02 — 0.363
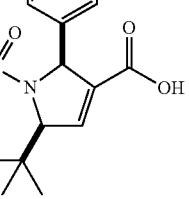
P62-A11 — 0.348
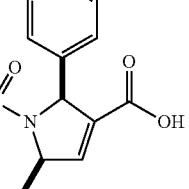
P62-D11 — 0.349
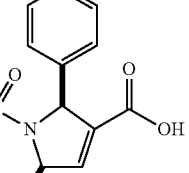
P61-C02 — 3.4

TABLE 8-continued

Different Dihydropyrroles

| Structure | In vitro | Leukemic cells | | Breast Cancer Cells | | | | Pancreactic Cancer Cells | | | |
|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P61-C08 | 4.4 | 2.76 | 8.26 | | | | | | | | |
| P61-D06 | 28.9 | 5.36 | >20 | | | | | | | | |

TABLE 9

P5-H06 with Different Linkers

| Structure | In vitro | Leukemic cells | | Breast Cancer Cells | | | |
|---|---|---|---|---|---|---|---|
| | | Jurkat | K562 | MDA-MB-231 | BT474 | MCF7 | MCF10a |
| P5-H6 | 0.5 | 20.00 | | | | | |

TABLE 9-continued
P5-H06 with Different Linkers
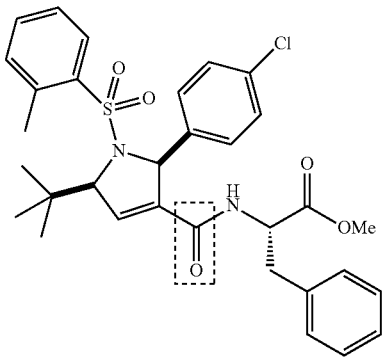
P61-A4
&
P61-A5
| P61A4 | P61A4 | P61A4 |
|---|---|---|
| >50 | 19.0 | 14.0 |
| P61A5 | P61A5 | P61A5 |
| >50 | 10.5 | 17.0 |
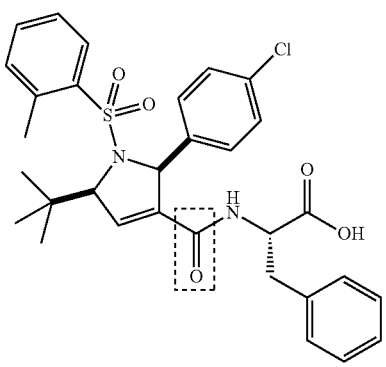
P61-A8
1.4   13.0   20.0
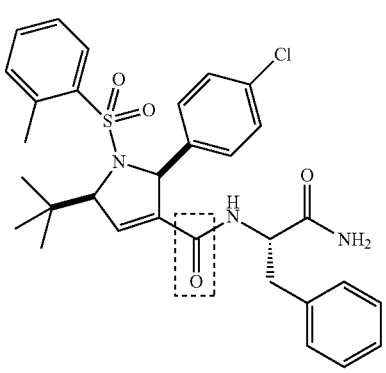
P61-A6
&
P61-B7
| P61A6 | P61A6 | P61A6 | P61A6 | P61A6 | P61A6 | P61A6 |
|---|---|---|---|---|---|---|
| 1.0 | 4.89 | 6.28 | 8.25 | 8.64 | 3.72 | 13.25 |
| P61B7 | | | | | | |
| 7.7 | | | | | | |

TABLE 9-continued
P5-H06 with Different Linkers
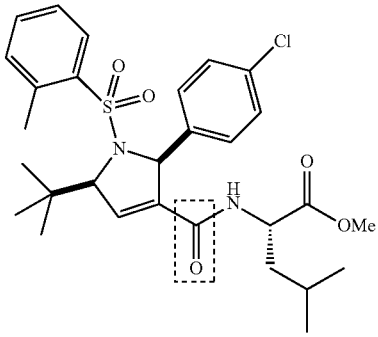
P67-B09
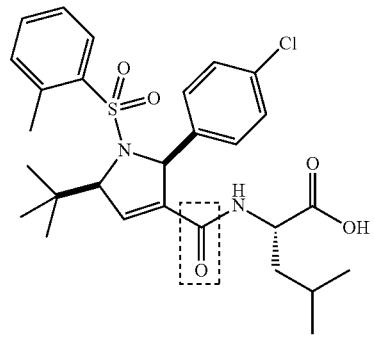 [SMILES: Cc1ccccc1S(=O)(=O)N1[C@@H](c2ccc(Cl)cc2)C(C(=O)N[C@@H](CC(C)C)C(=O)O)=C[C@H]1C(C)(C)C]
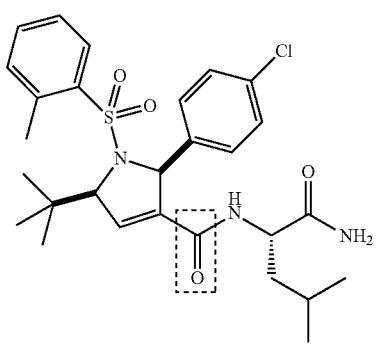
| 8.1 | 6.58 | 6.70 | 6.68 | 5.28 |
P61-B02
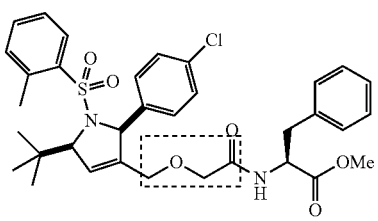
| 2.1 | 3.51 | 6.01 | | 6.78 | −20 |
P61-B4

TABLE 9-continued
P5-H06 with Different Linkers
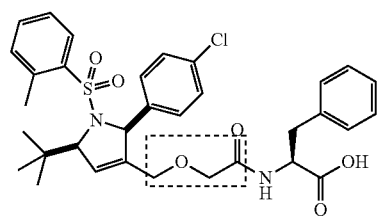
P61-B5
0.1  12.0  17.0
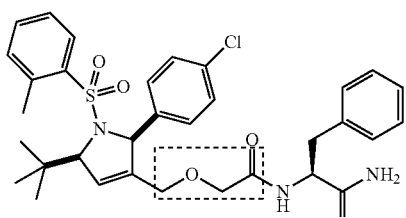
P61-B6
0.7  1.3  5.0
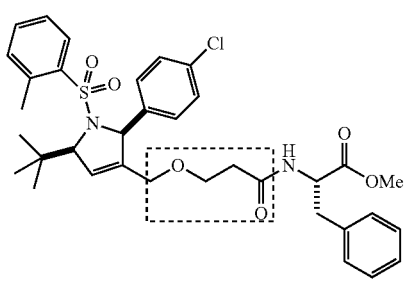
P61-B4
>20  5.1
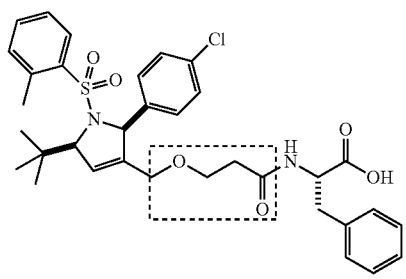 [SMILES: Cc1ccccc1S(=O)(=O)N1[C@@H](c2ccc(Cl)cc2)C(COCCC(=O)N[C@@H](Cc2ccccc2)C(=O)O)=C[C@H]1C(C)(C)C]
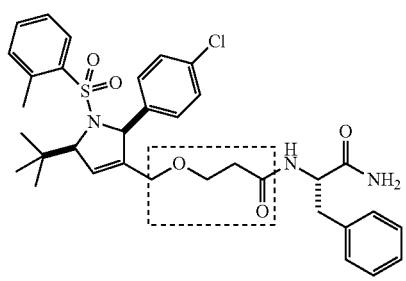 [SMILES: Cc1ccccc1S(=O)(=O)N1[C@@H](c2ccc(Cl)cc2)C(COCCC(=O)N[C@@H](Cc2ccccc2)C(N)=O)=C[C@H]1C(C)(C)C]

TABLE 9-continued

P5-H06 with Different Linkers

| Structure | Pancreatic Cancer Cells | | | | |
|---|---|---|---|---|---|
| | MiaPaCa2 | Aspc-1 | Panc-1 | Capan-2 | CFpac-2 |
| 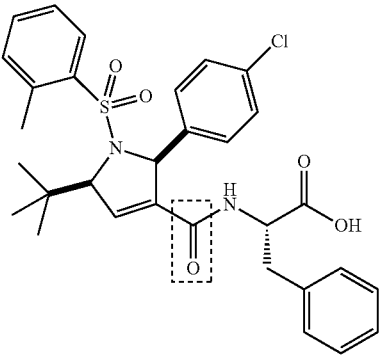<br>P61-A8 | P61A6<br>7.48 | P61A6<br>12.39 | P61A6<br>13.01 | P61A6<br>11.54 | P61A6<br>6.38 |
| 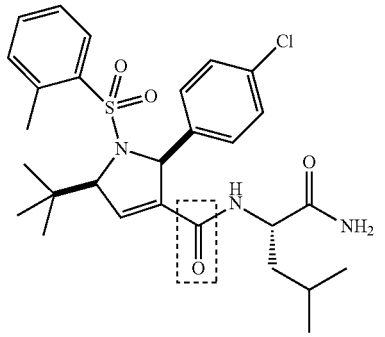 [SMILES: CC(C)C[C@H](NC(=O)C1=C[C@@H](C(C)(C)C)N(S(=O)(=O)c2ccccc2Cl)[C@H]1c1ccc(Br)cc1)C(N)=O]<br>P61-B02 | 7.24 | 11.44 | 6.45 | 6.69 | <1.25 |

TABLE 10

Different Dihydropyrroles Coupled with L-Phenylalaninamide

| Structure | In vitro | Leukemic cells | | Breast Cancer Cells | | | |
|---|---|---|---|---|---|---|---|
| | | Jurkat | K562 | MDA-MB-231 | BT474 | MCF7 | MCF10a |
| 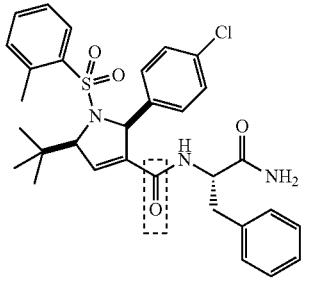<br>P61-A6<br>&<br>P61-B7 | P61A6<br>1.0<br>P61B7<br>7.7 | P61A6<br>4.89 | P61A6<br>6.28 | P61A6<br>8.25 | P61A6<br>8.64 | P61A6<br>3.72 | P61A6<br>13.25 |

TABLE 10-continued
Different Dihydropyrroles Coupled with L-Phenylalaninamide
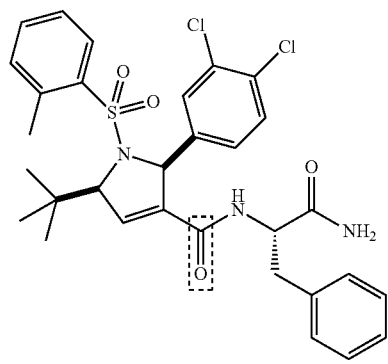
P61-B10
&
P61-B11
| P61B10 | P61B10 | P61B10 | P61B10 | P61B10 | P61B11 | P61B11 |
|--------|--------|--------|--------|--------|--------|--------|
| 5.4    | 5.62   | 6.74   | 12.63  | 10.81  | 4.74   | 9.38   |
| P61B11 | P61B11 | P61B11 | P61B11 | P61B11 |        |        |
| 7.6    | 6.90   | 6.90   | 5.54   | 10.55  |        |        |
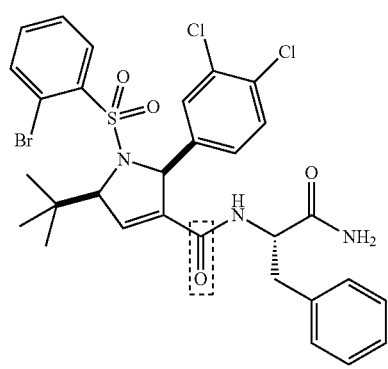
P61-E3
>20
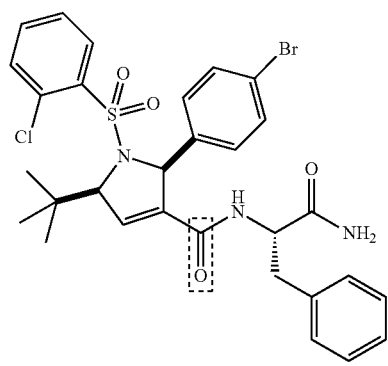
P61-B8
&
P61-B9
| P61B8 | P61B8 | P61B8 | P61B8 | P61B8 |
|-------|-------|-------|-------|-------|
| 6.0   | 4.74  | 5.21  | 4.43  | 9.08  |
| P61B9 | P61B9 | P61B9 | P61B9 | P61B9 |
| >10   | 8.75  | 9.18  | 11.28 | 9.90  |

TABLE 10-continued
Different Dihydropyrroles Coupled with L-Phenylalaninamide
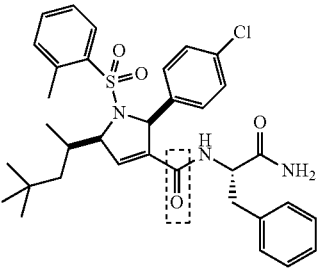
P61-C3
&
P61-C4
| | P61C3 >10 P61C4 >50 | P61C3 9.79 P61C4 6.40 | P61C3 6.30 P61C4 5.95 | | P61C3 10.81 P61C4 10.11 | P61C3 3.1 P61C4 4.71 | P61C3 9.16 P61C4 11.31 |
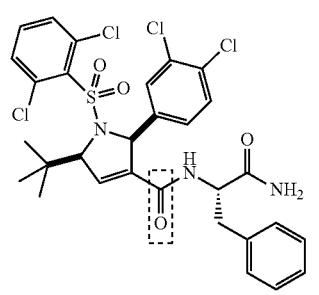
P61-D9
&
P61-D10
| | P61D9 >50 P61D10 >50 | P61D9 4.91 P61D10 5.28 | P61D9 3.63 P61D10 3.67 |
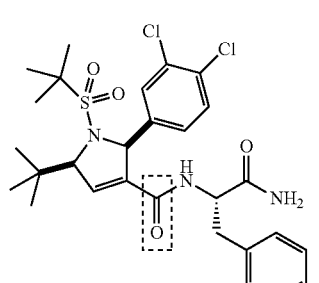
P61-D11
&
P61-E2
| | P61D11 >50 P61E2 2.7 | P61D11 5.91 P61E2 4.57 | P61D11 5.90 P61E2 4.22 |
| | Pancreatic Cancer Cells | | | | |
|---|---|---|---|---|---|
| | MiaPaCa2 | Aspc-1 | Panc-1 | Capan-2 | CFpac-1 |
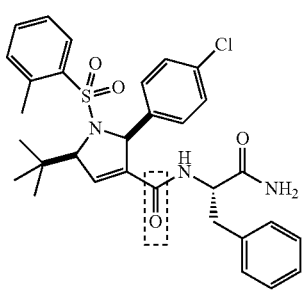
P61-A6
&
P61-B7
| | P61A6 7.48 | P61A6 12.39 | P61A6 13.01 | P61A6 11.54 | P61A6 6.38 |

TABLE 10-continued
Different Dihydropyrroles Coupled with L-Phenylalaninamide
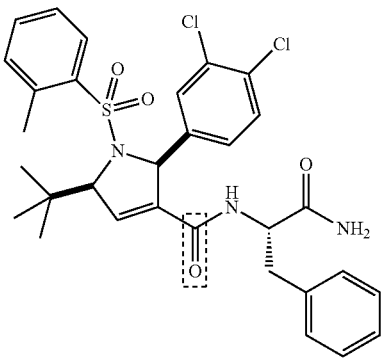
P61-B10
&
P61-B11
| P61B10 | P61B10 | P61B10 | P61B10 | P61B10 |
|---|---|---|---|---|
| 8.06 | 12.92 | 11.69 | 8.45 | 6.09 |
| P61B11 | P61B11 | P61B11 | P61B11 | P61B11 |
| 7.49 | 11.51 | 7.52 | 11.28 | 2.03 |
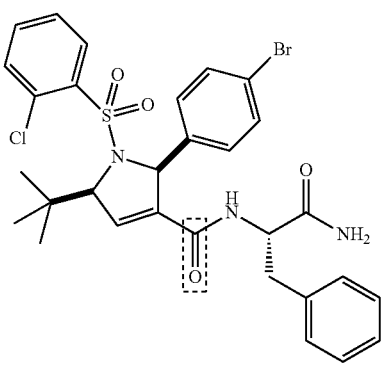
P61-B8
&
P61-B9
| P61B8 | P61B8 | P61B8 | P61B8 | P61B8 |
|---|---|---|---|---|
| 6.15 | 12.17 | 9.05 | 8.32 | 6.16 |
| P61B9 | P61B9 | P61B9 | P61B9 | P61B9 |
| 12.06 | 16.83 | 11.97 | 10.69 | 6.30 |
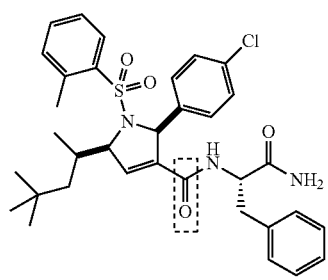
P61-C3
&
P61-C4
| P61C3 | P61C3 | P61C3 | P61C3 | P61C3 |
|---|---|---|---|---|
| 7.17 | 11.43 | 8.85 | 10.45 | −1.25 |
| P61C4 | P61C4 | P61C4 | P61C4 | P61C4 |
| 6.70 | 8.61 | 8.60 | 7.5 | −1.25 |

TABLE 11

Different Dihydropyrroles Coupled with L-Leucinamide

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P61-B02 | 8.1 | 6.58 | 6.70 | 6.68 | 5.28 | | | 7.24 | 11.44 | 6.45 | 6.69 | <1.25 |

TABLE 11-continued

Different Dihydropyrroles Coupled with L-Leucinamide

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |

TABLE 12

Tetrahydropyridines with varying terminal groups

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P03-E05 | 0.31 | 20 | | | | | | | | | | |

TABLE 12-continued

Tetrahydropyridines with varying terminal groups

| Structure | In vitro | Leukemic cells | | Breast Cancer Cells | | | Pancreatic Cancer Cells | | | | |
|---|---|---|---|---|---|---|---|---|---|---|---|
| | | Jurkat | K562 | MDA-MB-231 | BT474 | MCF7 | MCF10a | MiaPaCa2 | Aspc-1 | Panc-1 | Capan-2 | CFpac-1 |
| P09-C09 | | | | | | | | | | | | |
| P61-E06 | >20 | 5.36 | | | | | | | | | | |
| P67-A11 | | | | | | | | | | | | |
| P67-B08 | | | | | | | | | | | | |
| P67-B03 | >100 | 7.5 | 5.80 | | | | | | | | | |

TABLE 13

P3E5 with Different Linkers

| Structure | In vitro | Leukemic cells | | Breast Cancer Cells | | | |
|---|---|---|---|---|---|---|---|
| | | Jurkat | K562 | MDA-MB-231 | BT474 | MCF7 | MCF10a |
| P03-E05 | 0.31 | 20 | | | | | |
| P67B2 & P67B3 & B6764 | | | | | | | |
| P67B6 | | | | | | | |
| P67B5 | | | | | | | |
| P61E7 | >50 | 6.10 | | | | | |

TABLE 13-continued
P3E5 with Different Linkers
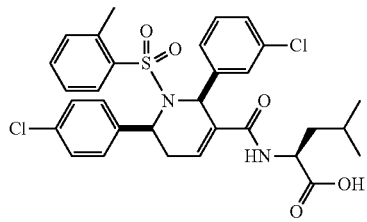
P67B7
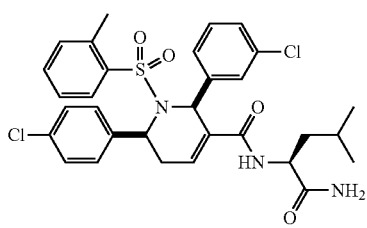
P61C5
| >50 | 6.10 | 6.15 | 10.86 | >20 |
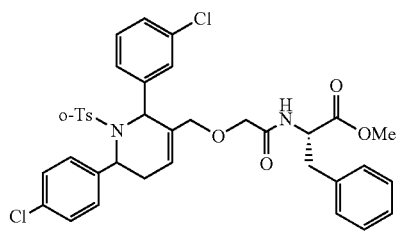
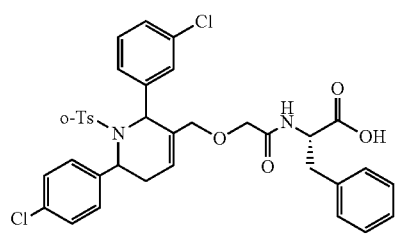
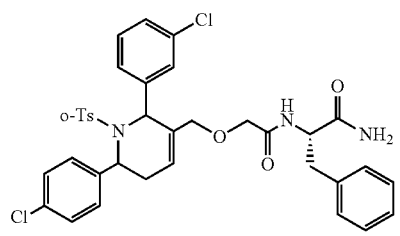
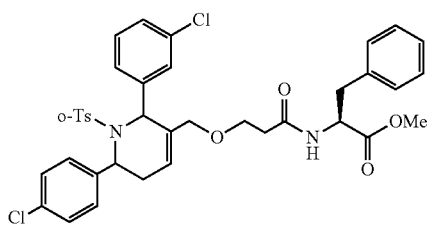

TABLE 13-continued
P3E5 with Different Linkers
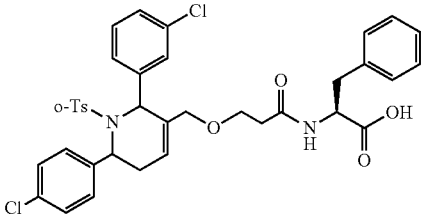
|  | Pancreatic Cancer Cells | | | |
|---|---|---|---|---|
| MiaPaCa2 | Aspc-1 | Panc-1 | Capan-2 | CFpac-1 |
| 11.99 |  |  | 13.96 | 13.69 |
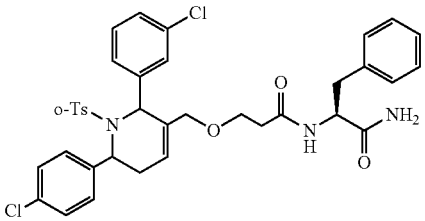
P61C5
TABLE 14
Tetrahydropyridines coupled with L-Phenylalaninamide
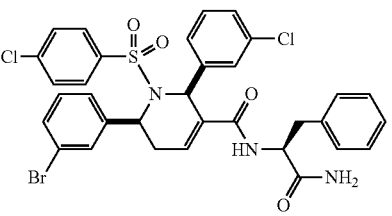
| Structure | In vitro | Leukemic cells | | Breast Cancer Cells | | | |
|---|---|---|---|---|---|---|---|
|  |  | Jurkat | K562 | MDA-MB-231 | BT474 | MCF7 | MCF10a |
|  | P61D4 1.3 P61D5 >20 | P61D4 4.86 P61D5 3.57 | P61D4 7.69 P61D5 10.30 |  |  |  |  |
P61-D04 & P61-D05

TABLE 14-continued
Tetrahydropyridines coupled with L-Phenylalaninamide
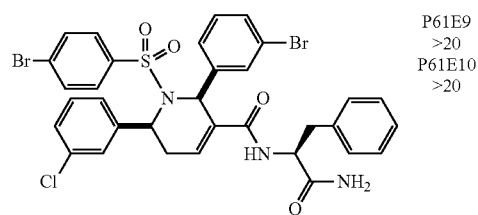
P61-E09
&
P61-E10
P61E9
>20
P61E10
>20
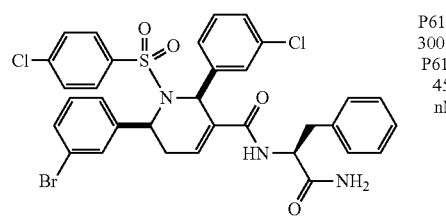
P61-F11
&
P61-G02
P61F11
300 nM
P61G2
450
nM
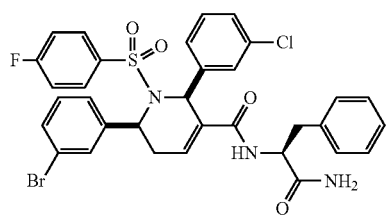
P61-H04
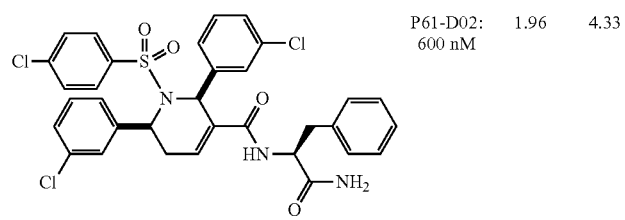
P61-D02
P61-D02:
600 nM
1.96   4.33
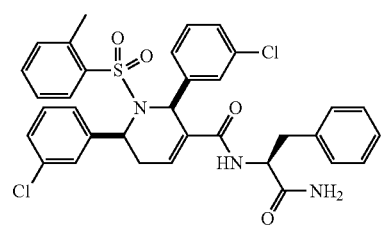
P67-B05
| | Pancreatic Cancer Cells | | | | |
|---|---|---|---|---|---|
| | Mia-PaCa2 | Aspc-1 | Panc-1 | Capan-2 | CFpac-1 |

TABLE 15

Tetrahydropyridines coupled with L-Leucinamide

| Structure | In vitro | Leukemic cells | | Breast Cancer Cells | | | |
| --- | --- | --- | --- | --- | --- | --- | --- |
| | | Jurkat | K562 | MDA-MB-231 | BT474 | MCF7 | MCF10a |
| P61-E08 | >20 | | | | | | |
| P61-C09 & P61-C10 | P61C9 >50 P61C10 >50 | P61C9 6.38 P61C10 2.22 | P61C9 12.86 P61C10 4.37 | | | | |
| P61-C06 | 39.1 | 3.15 | 7.06 | | | 3.43 | 14.18 |
| P61-C11 & P61-D03 | P61C11 32.9 P61D3 6.9 | P61C11 1.76 P61D3 0.32 | P61C11 10.22 P61D3 1.70 | | | | |
| P61-H05 | | | | | | | |

TABLE 15-continued

Tetrahydropyridines coupled with L-Leucinamide

| Structure | In vitro | Leukemic cells | | Breast Cancer Cells | | | |
|---|---|---|---|---|---|---|---|
| | | Jurkat | K562 | MDA-MB-231 | BT474 | MCF7 | MCF10a |
| 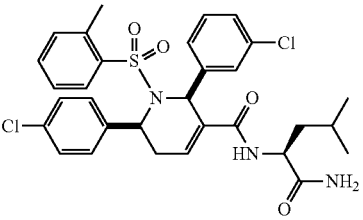 P61-C05 | >50 | 6.10 | 6.15 | | | 10.86 | >20 |

| Structure | Pancreatic Cancer Cells | | | | |
|---|---|---|---|---|---|
| | MiaPaCa2 | Aspc-1 | Panc-1 | Capan-2 | CFpac-1 |
| 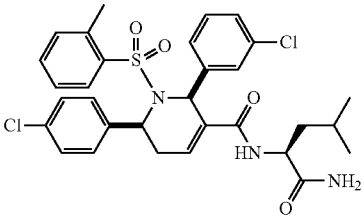 P61-C05 | 11.99 | | | 13.96 | 13.69 |

IV. RabGGTase Inhibiting Compounds

In addition to or alternatively to GGTase I inhibition, protein prenyltransferase inhibiting compounds described herein can be effective as inhibitors of RabGGTase. As shown in the examples below, some of these compounds can exhibit dual specificity and can inhibit both RabGGTase and GGTase I.

Prior to the present compounds, only a handful of RabGGTase inhibitors have been identified in the past (26). Commonly used inhibitors are bisphosphonate type compounds, however the inhibition of RabGGTase requires about mM concentration of the compounds. In contrast, in some embodiments, the compounds described herein suprisingly inhibit RabGGTase at a µM concentration. Accordingly, the RabGGTase inhibitors can be used at a concentration of about 1 µM up to about 50 µM, for example at concentrations between 1 µM and 25 µM.

In some embodiments, these RabGGTase inhibiting compounds use the scaffolds of the previously described GGTI compounds but possess an extra hydrophobic tail emanating from the core ring. Such hydrophic tails have been illustrated throughout the application. As one of skill in the art will appreciate, these compounds can also use the previously described substituent groups in addition to the hydrophic tail.

Embodiments of the present invention are also directed to RabGGTase compounds with a six-atom aliphatic tail attached to the penta-substituted pyrrolidine core via thioether linkage to the 5-member ring core. These compounds can have an unexpectedly potent effect in vivo and/or in vitro on cancer cell proliferation. In some embodiments, these compounds can have dual specificity for RabGGTase and GGTase I.

Recent studies suggest that RabGGTIs may be valuable as anticancer drugs. A study using siRNA showed that the inhibition of RabGGTase leads to apoptosis induction in human cancer cells (42). Elevated levels of RabGGTase are detected in a number of human cancers (42). Furthermore FTI compounds which inhibit RabGGTase induce mislocalization of Rab protein and apoptosis (42). Accordingly, these compounds can be useful as cancer therapeutics.

One of skill in the art will appreciate that the various substituent groups depicted and described as part of the library can be added to each scaffold to produce compounds that fall within the scope of the present invention. For example, the substituent groups illustrated in Tables 1, 2, and 3 or elsewhere in the specification may be placed on scaffold 6, 7, 10, 11 or within any formula described herein, regardless of whether the substituent group is depicted on that scaffold herein.

Furthermore, compounds described as GGTase I inhibitors or RabGGTase inhibitors are not limited to only that characterization. For example, as described herein, a compound can have dual specificity to inhibit both GGTase I and RabGGTase. Therefore, as one of skill in the art will appreciate, the compounds described herein are protein prenyltransferase inhibitors capable of inhibiting GGTase I, RabGGTase, other protein prenyltransferases, and combinations thereof.

V. Synthesis Methods

The compounds described herein can be made using any method known to one of skill in the art or as described herein. Suitable methods have previously been disclosed in relation to Formula I in section I above and additional methods are described to follow. Accordingly, the present invention is also directed to novel, improved methods of synthesizing protein prenyl transferase inhibitors.

Some embodiments of the invention include the following method of preparing a compound according to formula I

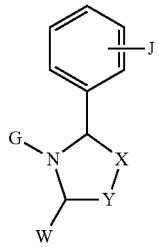

I wherein:
  wherein J is hydrogen or is 1-2 substituents independently selected from the group consisting of halogen, $C_1$-$C_3$ alkyl, OR', SR', and NR'$_2$, where R' is alkyl,
  wherein W is selected from the group consisting of hydrogen, cyclic, linear, or branched alkyl of from 2 to 8 carbons, unsubstituted phenyl, and phenyl substituted with $C_1$-$C_3$ alkyl, halogen, OR', SR', and NR'$_2$, where R' is alkyl,
  G is

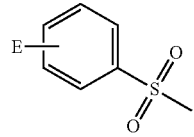

wherein E is hydrogen or is 1-2 substituents selected from the group consisting of halogen, $C_1$-$C_3$ alkyl, OR', SR', and NR'$_2$, where R' is alkyl,

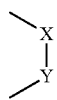

is selected from the group consisting of

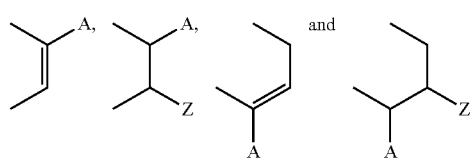

wherein A is

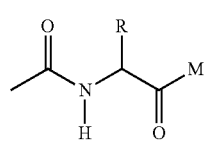

and M=OH, OR or NH$_2$; and R is, an alpha-substituent of a natural or non-natural amino acid;

comprising,
reacting a compound according to formula I'

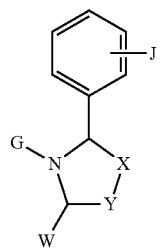

I' wherein
  J, G, and W are as defined above and

is selected from the group consisting of

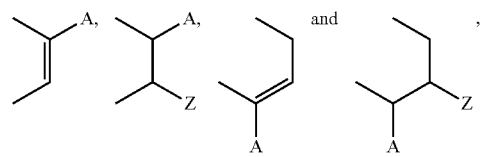

wherein A=CO$_2$H;
with a compound having the formula

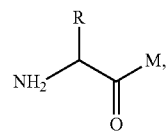

wherein R and M are as defined above

For example, the following example synthesis scheme can be used to produce protein prenyltransferase inhibiting compounds:

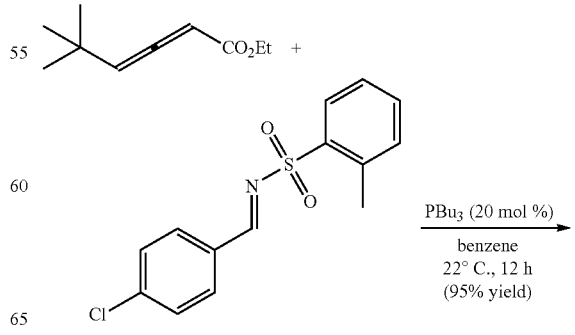

C40

PBu$_3$ (20 mol %)
benzene
22° C., 12 h
(95% yield)

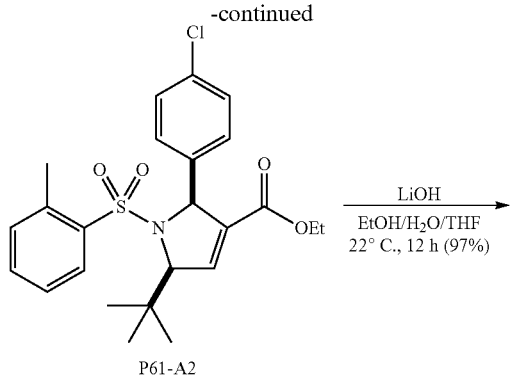
P61-A2
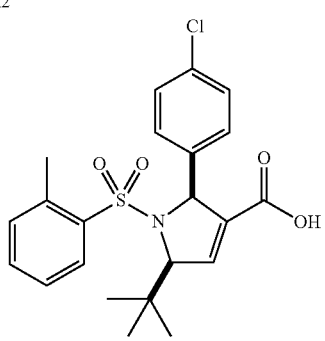
P5-H6 (racemic)
P61-A3 (80% ee)
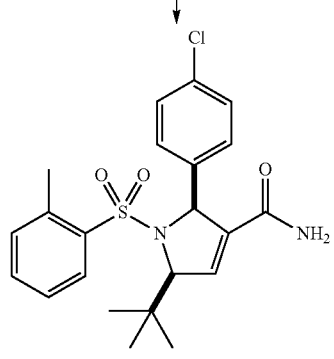
P61-A7
Compositions having linker 1 (as shown previously) can be prepared using the following example reaction scheme:
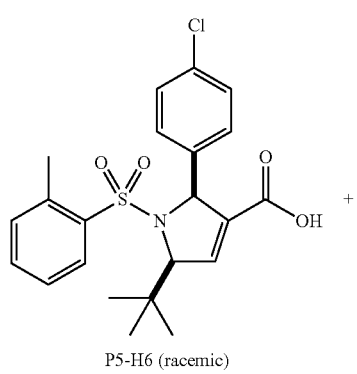
P5-H6 (racemic)
+
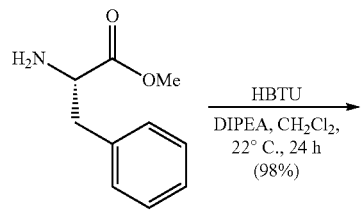
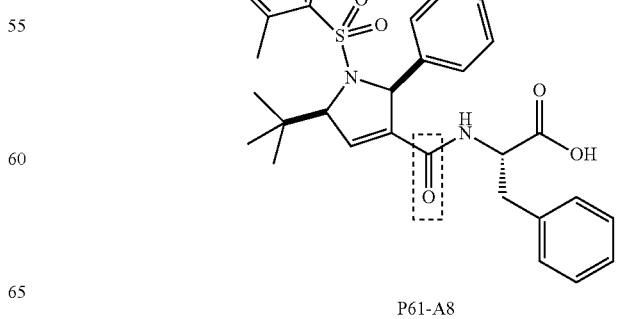
P61-A4
&
P61-A5
P61-A8

133
-continued
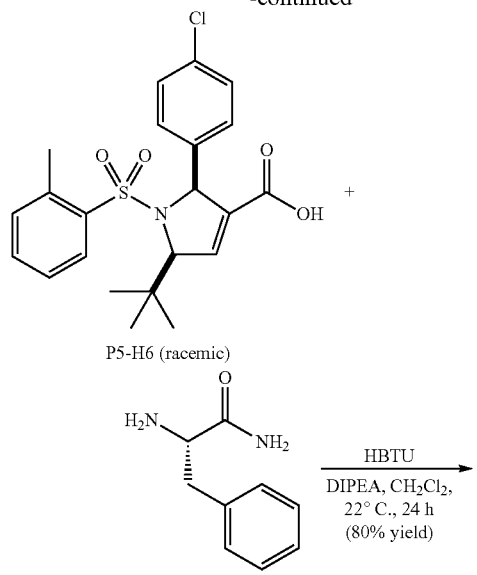
P5-H6 (racemic)
HBTU
DIPEA, CH₂Cl₂,
22° C., 24 h
(80% yield)
134
-continued
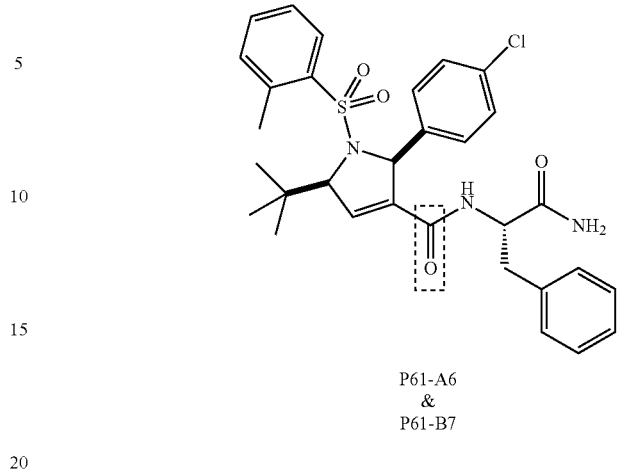
P61-A6
&
P61-B7
Compositions having linker 2 (as shown previously) can be prepared using the following example reaction scheme:
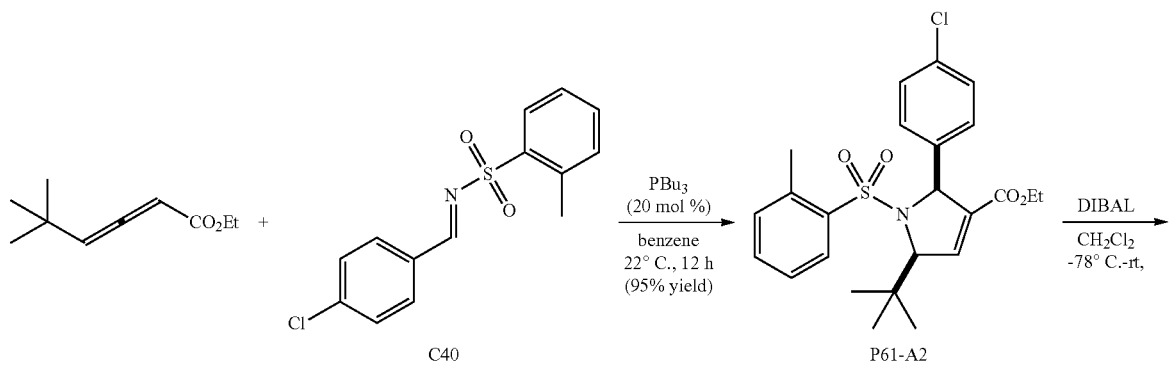
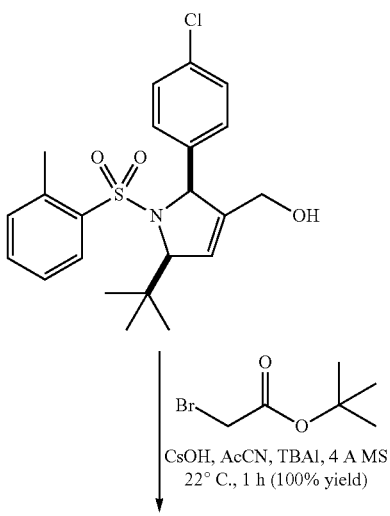
CsOH, AcCN, TBAI, 4 A MS
22° C., 1 h (100% yield)

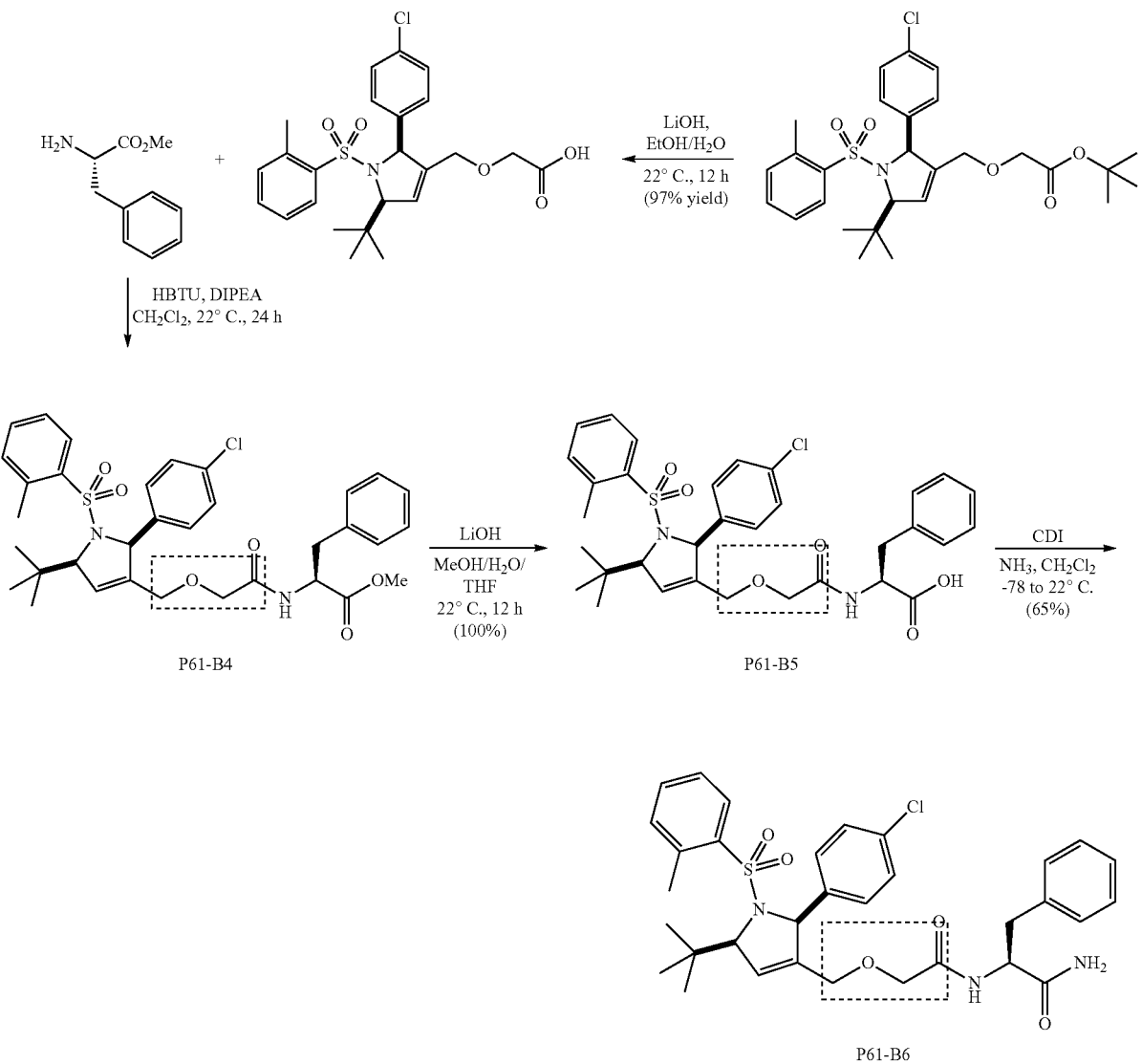
Compositions having linker 3 (as shown previously) can be prepared using the following example reaction scheme:
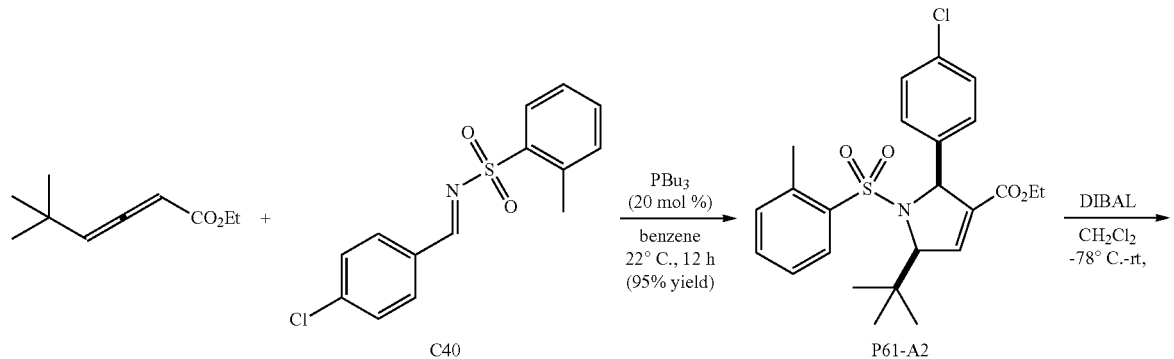

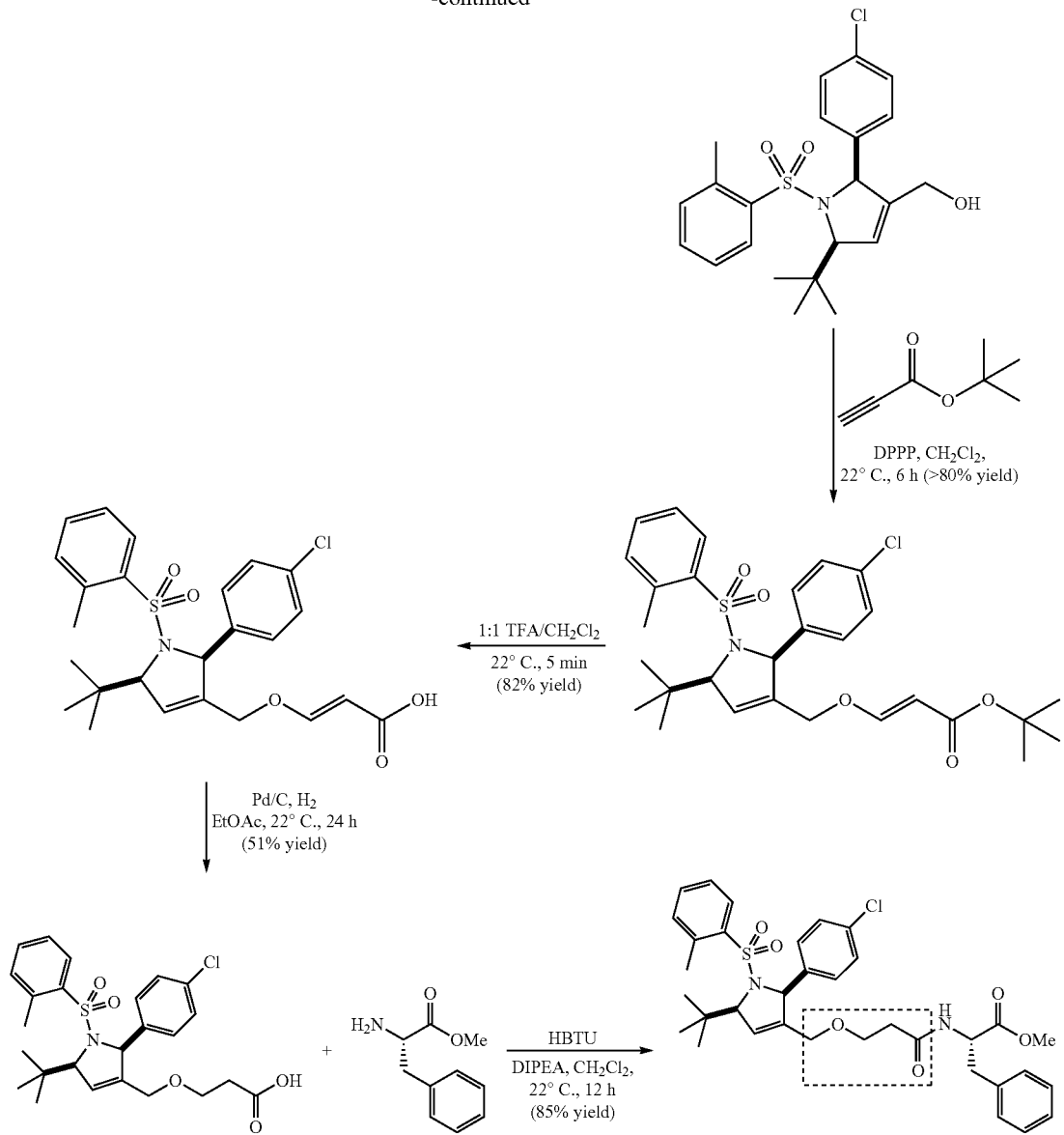

P61-E4

As one of skill in the art will appreciate, synthesis methods other than those disclosed may be used to produce the compounds of the present invention. Such methods are also encompassed by the present invention.

VI. Pharmaceutical Compositions

The compounds of the invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the compounds include, lozenges, troches, tablets, capsules, effervescent tablets, orally disintegrating tablets, floating tablets designed to increase gastric retention times, buccal patches, and sublingual tablets.

The compounds of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's), which is herein incorporated by reference in its entirety.

The compounds may be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form. The amount of compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the compounds may be incorporated into sustained-release preparations and devices. For example, the compounds may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an, effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

In some embodiments, the pharmaceutical compositions described herein contain a therapeutically effective dose of the compound. The term "effective amount" or "therapeutically effective amount," as used herein, refers to the amount of the active compound that is effective to achieve its intended purpose after a single dose, wherein a single dose comprises one or more dosage units, or after a course of doses, e.g., during or at the end of the treatment period. Thus, for example, the term "therapeutically effective amount" of the compounds disclosed herein, when used in a method of treating a cancer, refers to that dose of the compound that lessens or prevents the occurrence of cancer when administered to a mammal in need of such treatment. The therapeutically effective amount will vary depending on the needs of the subject, but this amount can readily be determined by one of skill in the art, for example, a physician.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 750 mg, or about 1000 mg of active ingredient.

The compounds can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

VII. Methods of Treating, Assays, and Kits

Some embodiments of the present invention are directed to methods of using the compounds described herein. These compounds, as illustrated in the examples below and throughout the specification, are useful in inhibiting the geranylgeranylation of signaling proteins by inhibiting the activity of at least GGTase I and/or RabGGTase. However, because GGTIs such as those described herein can inhibit geranylgeranylation of a number of signaling proteins the compounds described herein are effective for the treatment of a wide range of human cancers. For example, mP5-H6 inhibits proliferation of a leukemic cell line (Jurkat), breast cancer cell lines (BT474 and MDA-MB231) and pancreatic cancer cell lines (Panc-1 and MiaPaCa2).

Pancreatic cancer is of particular interest, as recent studies (Lim, K-H et al., Current Biology 16, 2385; Lim, K-H et al., Cancer Cell 7, 533) have established the importance of RalA and RalB proteins (both are geranylgeranylated) in pancreatic cancer. RalA is commonly activated in a panel of cell lines from pancreatic cancer. Studies using siRNA showed that inhibition of RalA reduced tumor growth. RalB is found to be important for metastasis. Interestingly, the RalA activation occurs downstream of K-ras activation that is seen in more than 80% of pancreatic cancer cases. Since K-ras prenylation can be inhibited by the combination of GGTI and FTI, GGTIs may be particularly important for pancreatic cancer.

Breast cancer is also of interest, as GGTIs have been shown to inhibit proliferation of breast cancer cells (Vogt, A. et al., J. Biol. Chem. 272, 27224). This is accompanied by the accumulation of G1 phase cells and the increase of p21. In addition, a geranylgeranylated protein Rac3 is reported to be overactivated in breast cancer cells (Mira J-P et al., PNAS 97, 185). Finally, inhibition of RhoA or RhoC by siRNA inhibited proliferation and invasiveness of breast cancer cells in vitro and in vivo (Pille, J-Y et al., Molecular Therapy 11, 267).

GGTIs and/or RabGGTase inhibitors may also be valuable in inhibiting cancer metastasis. This is based, in part, on findings that indicate geranylgeranylated proteins play important roles in metastasis. In addition to RalB discussed above, another geranylgeranylated protein RhoC plays essential roles in cancer metastasis (Hakem A. et al., Genes & Dev. 19, 1974; Clark, E. A. et al., Nature 406, 532).

Accordingly, the compounds described herein can be used in methods of treating cancer and/or in methods of reducing the size of a cancerous tumor. In some embodiments, the method of treating cancer involves inhibiting a protein prenyltransferase by administering the compound described herein to a subject in need of treatment. The methods of treating cancer can be applied to any cancer that is activated through a signaling pathway incorporating GGTase I and/or RabGGTase. For example, Rho protein activation, e.g., RhoA and Rac in cancer cells. In some embodiments, the cancer is selected from the group consisting of pancreatic, leukemia, breast, and prostate. In some embodiments, the cancer is selected from the group consisting of pancreatic, leukemia, breast, prostate, colon, ovarian, lung, and stomach cancer.

The compounds described herein are also useful in methods of inhibiting the activity of GGTase I and/or RabGGTase by administering the compounds described herein to a cell. These methods can be applied either in vivo or in vitro. For example, these compounds can be used for therapeutic purposes associated with inhibiting the activity of GGTase I and/or RabGGTase in a subject in need of treatment thereof. These compounds can also be used in research methods designed to develop such therapeutics, for example, as part of a library screening as described herein.

The compounds described herein are also useful in methods of cytostatically inhibiting the growth of a cancer cell. These methods can be used as a stand alone therapeutic or in conjunction with a cytotoxic treatment or a surgical procedure. The compounds described herein can be administered following surgery to remove a tumor or following chemotherapy designed to kill the tumor cells to control the growth of any cancer cells that these treatments may have missed. These compounds, when administered in these embodiments, may function as a preventative measure designed to reduce the likelihood of remission.

The compounds herein are also useful in assays for measuring the GGTase I and/or RabGGTase inhibiting activity of a compound. For example, the compounds disclosed herein can be used as controls to evaluate new compounds for potential GGTase I and/or RabGGTase inhibiting activity. The compounds disclosed herein can be used as part of assays to determine therapeutic compounds for use in the methods disclosed herein as well.

The invention also provides kits comprising a compound of the invention in the form of a pharmaceutically acceptable dosage form or as a compound. These kits can include one or more containers filled with one or more of the ingredients of the pharmaceutical dosage forms.

In some embodiments, the kit comprises a container for the dosage form or compound. Suitable containers include, for example, a bottle, a box, a blister card, a foil packet, or a combination thereof. Optionally, the kit also contains directions for properly administering the dosage form or for properly using the compound, for example, as part of an assay. The kits can also be designed in a manner such that they are tamper resistant or designed to indicate if tampering has occurred. Optionally, the kit can contain the dosage form or compound with another pharmaceutical composition or compound, for example, an FTI.

Optionally associated with the container(s) in the kits can be a notice or printed instructions. Such printed instructions can be in a form prescribed by a governmental agency regulating the manufacture, use, or sale of pharmaceuticals or biological products, which notice reflects approval by the agency of the manufacture, use, or sale for human administration to treat a condition that could be treated by the compounds and dosage forms described herein. In some embodiments, the kit further comprises printed matter, which, e.g., provides information on the use of the dosage form to treat a condition or disease or a pre-recorded media device which, e.g., provides information on the use of the dosage form to treat a condition or disease, or a planner, integrally linked to the particular methods of using the compositions.

"Printed matter" can be, for example, one of a book, booklet, brochure or leaflet. The printed matter can describe the use of the dosage forms described herein to treat a condition or disease, for example, to treat a cancer involving GGTase I modification of proteins. Possible formats include, but are not limited to, a bullet point list, a list of frequently asked questions (FAQ) or a chart. Additionally, the information to be imparted can be illustrated in non-textual terms using pictures, graphics, or other symbols.

"Pre-recorded media device" can be, for example, a visual media device, such as a videotape cassette, a DVD (digital video disk), filmstrip, 35 mm movie, or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette, or audio compact disk. The information contained on the pre-recorded media device can describe the use of the dosage forms and compounds described herein to treat a condition or disease, for example, to treat a cancer involving GGTase I modification of proteins.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered dosage form as described herein. Alternately, the planner can be a calendar which will provide a means to monitor when a dosage has been taken and when it has not been taken. This type of planner will be particularly useful for patients having unusual schedules for administering medication to themselves. Additionally, the planner can be useful for the elderly, children, or other patient group who may administer medication to themselves and may become forgetful. One skilled in the art will appreciate the variety of planning tools that would be appropriate for use with compounds and dosage forms described herein.

The kit can also include a container for storing the other components of the kit. The container can be, for example, a bag, box, envelope or any other container that would be suitable for use with the compounds and dosage forms described herein. Preferably, the container is large enough to accommodate each component and/or any administrative devices that may be accompany the dosage form of the present invention. However, in some cases, it may be desirable to have a smaller container which can be hidden in a patient's pocketbook, briefcase, or pocket.

In some embodiments, the present invention includes a kit comprising a pharmaceutical dosage form described herein. In some embodiments, the kit further comprises printed instructions for its use. In some embodiments, the kit further comprises a printed matter, a pre-recorded media device, or a planner describing the use of the pharmaceutical dosage form of the present invention to treat or prevent a condition which could be aided by taking the compositions disclosed herein.

In some aspects, the present invention provides a method of delivering a pharmaceutical dosage form described herein, to a patient in need thereof, the method comprising:

(a) registering in a computer readable storage medium the identity of a physician permitted to prescribe the pharmaceutical dosage form;

(b) providing the patient with counseling information concerning a risk attendant to the pharmaceutical dosage form;

(c) obtaining informed consent of the patient to receive the pharmaceutical dosage form despite the risk;

(d) registering the patient in the computer readable medium after obtaining the informed consent; and (e) permitting the patient access to the pharmaceutical dosage form.

In some embodiments of this method, the access to the pharmaceutical dosage form is a prescription.

Still other aspects of the present invention include a method of educating a consumer regarding the pharmaceutical dosage forms described herein, the method comprising distributing the oral pharmaceutical dosage form to a consumer with consumer information at a point of sale.

In some embodiments, the consumer information is presented in a format selected from the group consisting of: English language text, a foreign language text, a visual image, a chart, a telephone recording, a website, and access to a live customer service representative. In some embodiments, the consumer information is a direction for use, appropriate age use, indication, contraindication, appropriate dosing, warning, telephone number, or website address.

In some embodiments, the method of educating the consumer further comprises providing professional information to a relevant person in a position to answer a consumer question regarding the pharmaceutical dosage form. In some embodiments, the relevant person is a physician, physician assistant, nurse practitioner, pharmacist, or customer service representative.

In some embodiments, the distributing of the pharmaceutical dosage form is to a location with a pharmacist or a health care provider.

Example 1

This example demonstrates phosphine catalysis of polymer-bound allenoates and a combinatorial library approach to the development of potent inhibitors of protein geranylgeranyltransferase type I (GGTase-I). These methods are applicable to synthesizing the "left hand" (e.g., the A group in Formula I) of the compounds of the present invention having the particular scaffolds described herein.

A collection of 138 heterocycles was screened for their ability to inhibit the activity of human GGTase-I to geranylgeranylate K-Ras4B or RhoA. Purified GGTase-I was incubated with its substrate protein K-Ras4B or RhoA, [$^3$H] GGPP, and the 138 compounds. After 30 min, the degree of incorporation of tritiated geranylgeranyl groups was measured using a scintillation counter.

A number of compounds were identified as GGTIs including the following compounds numbered 1 and 2:

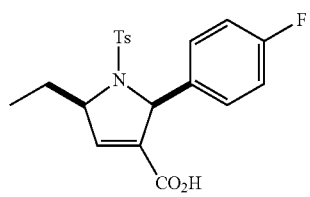

$IC_{50}$ 200 µM, RhoA
$IC_{50}$ 250 µM, KRas4B

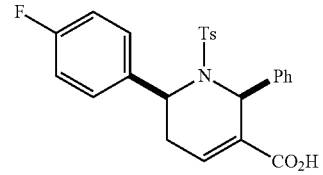

$IC_{50}$ 120 µM, RhoA
$IC_{50}$ 80 µM, KRas4B

This discovery of promising lead GGTI compounds and their moderate activity warranted the development of efficient and rapid syntheses and evaluations of analogous structures in the search for better inhibitors; we envisioned a short, modular synthetic route (Scheme 1), using SynPhase™ lanterns as the solid support. Validation of the synthetic route on the polymer support commenced with formation of resin-bound allenoates 5. The loading of allenoic acids onto solid supports has not been reported previously. The allenoic acids 4 were coupled to the benzyl alcohol units of the SynPhase-PS lanterns grafted with Wang resin 3 using Mukaiyama's reagent and Hünig's base for 4a/b or Et$_3$N for 4c/d. The direct use of an unmodified Wang resin minimizes the number of synthetic operations run on solid support. In addition, our strategy enabled simple trifluoroacetic acid (TFA)-mediated cleavage to release the carboxylic acid group, a key functional group in our GGTIs.

Scheme 1. Solid phase syntheses of dihydropyrroles 8 and tetrahydropyridines 9.

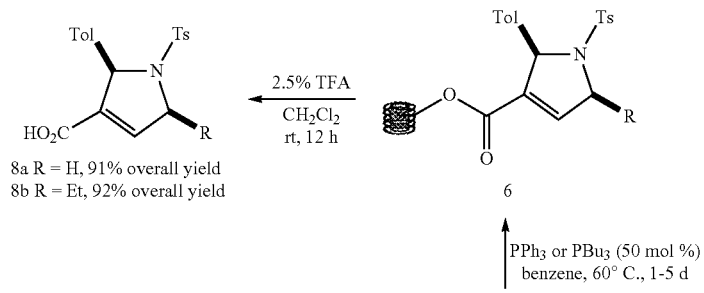

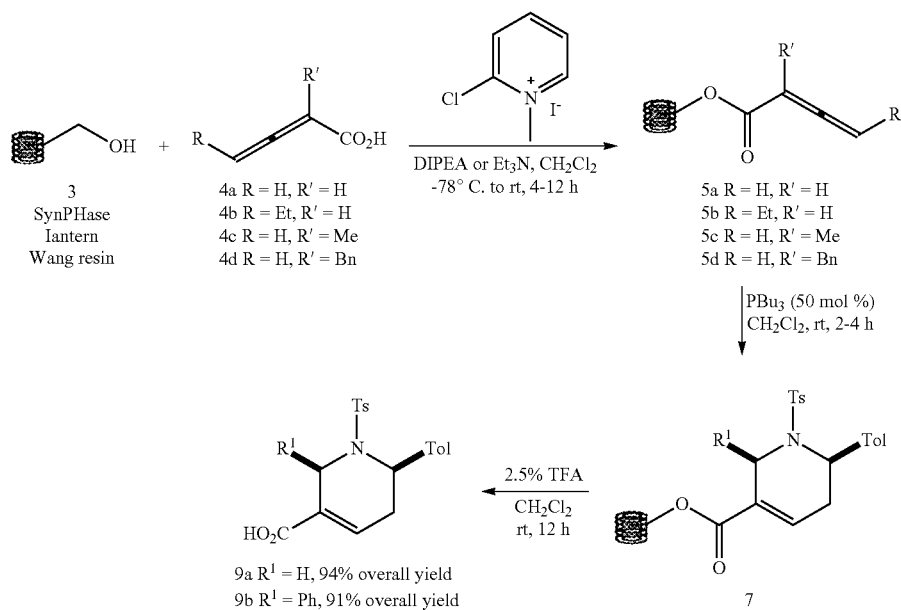

The phosphine-catalyzed annulation between solid-bound polymer-supported allenoates 5 and N-tosylimines proceeded smoothly. The allenoates 5a and 5b were treated with N-tosyltolualdimine and 50 mol % of $PPh_3$ (for 5a) or $PBu_3$ (for 5b) in benzene at 60° C. to provide the polymer-bound dihydropyrroles 6. Tetrahydropyridines 7 were formed from the reactions of 5c and 5d with N-tosyltolualdimine in the presence of 50 mol % of $PBu_3$ at room temperature for 2 and 4 days, respectively. Heterocycles 6 and 7 were cleaved from the resin using 2.5% TFA in DCM to provide the carboxylic acids 8 and 9 in 91-94% yield (based on a theoretical loading of 15 μmol/lantern) with high diastereoselectivities (dr=99:1 for 8b; 93:7 for 9b) after chromatographic purification.

The α,β-unsaturated enoate functionalities in 6 and 7 were utilized to further increase the modularity and number of analogs. For example, the Michael additions of thiols to 6 and 7 using n-butyllithium as base provided 10 and 11, respectively, which upon TFA-mediated cleavage yielded 12 and 13, respectively, in 77-95% yield (Scheme 2). These two-step sequences occurred with high diastereoselectivities, providing the pentasubstituted pyrrolidine 12 and the tetrasubstituted piperidine 13 as single diastereoisomeric products. Apparently, thiols added opposite to the preexisting substituents in both the dihydropyrrole 6 and the tetrahydropyridine 7. Interestingly, however, the protonation of the resulting α-carbanions occurred anti (for 10) and syn (for 11) to the added β-mercapto groups.

Scheme 2. Solid phase diastereoselective Michael additions.

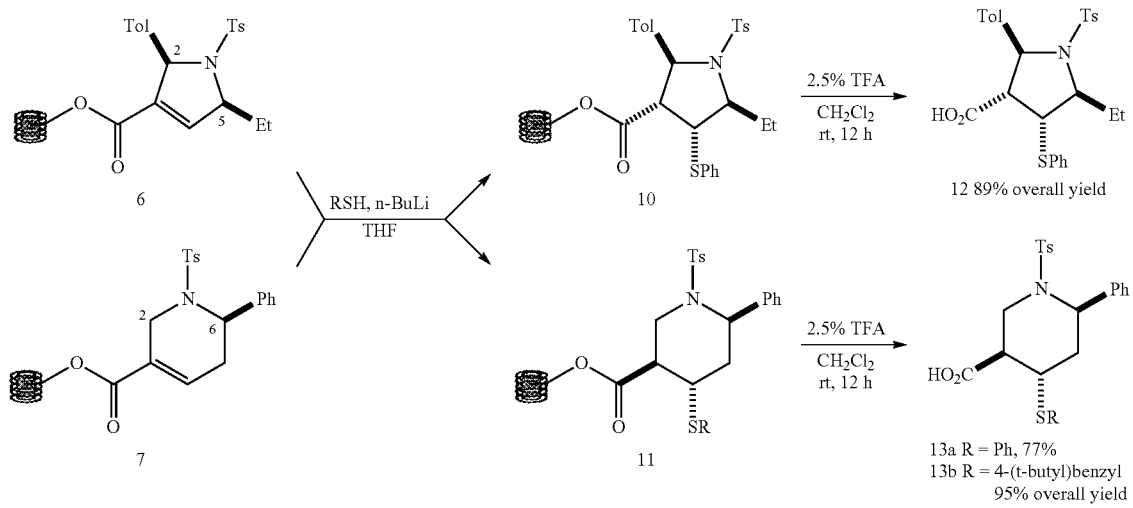

Having successfully established the solid phase reaction conditions, we next prepared the α- and γ-substituted allenoic acids building blocks (Scheme 3). The reactions between the phosphorane 14 and the acid chlorides 15 (1 equiv) in the presence of Et$_3$N (1 equiv) provided the allenoates 16, which were hydrolyzed into γ-substituted allenoic acids A. Phosphorane 14 was treated with the alkyl halides 17 to give the phosphonium salts 18, which we converted to the α-substituted allenoates 19 upon treatment with Et$_3$N (2 equiv) and acetyl chloride (1 equiv). α-Substituted allenoic acids B were prepared through saponification of the esters 19. The N-sulfonylimines C were formed simply through azeotropic removal of water from a mixture of the appropriate sulfonamide 20, aldehyde 21, and BF$_3$·OEt$_2$ under reflux in toluene. Chart 1 presents the building blocks synthesized as illustrated in Scheme 3 and the commercially available thiol building blocks D.

CHART 1

Eleven γ-substituted allenoic acids A, 12 α-substituted allenoic acids B, 46 N-sulfonimines C, and 32 thiols D.

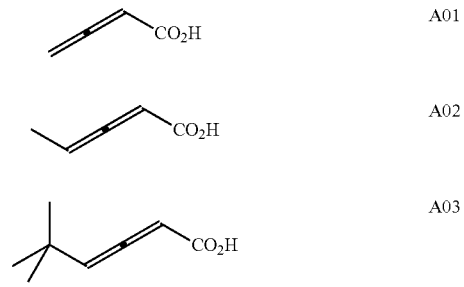

Scheme 3. Building block preparation.

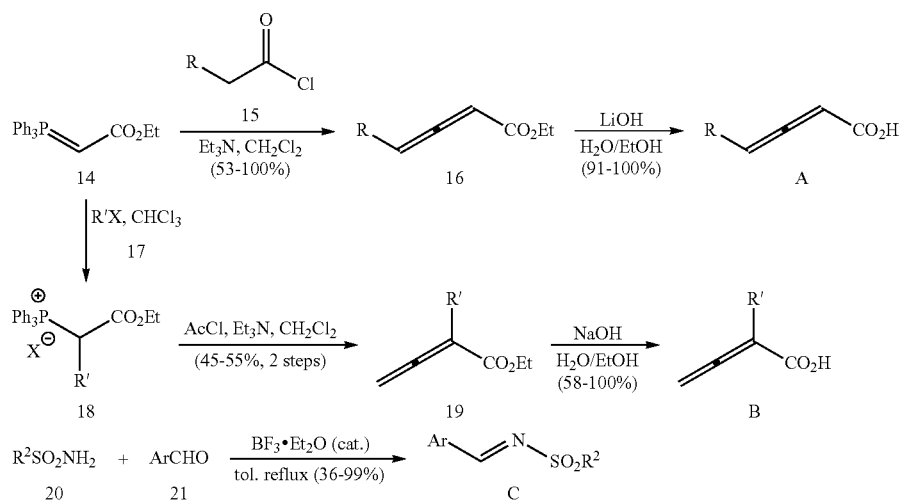

The building blocks were tested so that only the ones that provided high purity and stereoselectivity (as judged from $^1$H NMR spectra and LCMS analyses) for their crude cleavage products would be used in the synthesis of the GGTI analog library. Eleven γ-substituted allenoic acids A and 12 α-substituted allenoic acids B were loaded and reacted with imine C02 in the presence of a catalytic amount of phosphine, as indicated in Scheme 1. After cleavage with TFA and analysis ($^1$H NMR and LCMS spectra) of the purity and diastereoselectivity of the 23 annulation products 6 and 7, we found that each of the allenoic acids, except for A10, yielded a single identifiable compound (dr≥12:1; $^1$H NMR) in high purity (72-100%; LCMS/UV210). The resin-bound allenoates derived from allenoic acids A01, A05, B01, and B05 were selected to assess the reactivity and stereoselectivity of 46 imines in phosphine-catalyzed annulations (because A01, A02-A11, B01, and B02-B12 required different annulation reaction conditions). Using the criteria of >70% purity and >9:1 dr, we selected 30 (of 46) imine building blocks for allenoate A01, 21 for A05, 25 for B01, and 31 for B05.

CHART 1-continued

Eleven γ-substituted allenoic acids A, 12 α-substituted allenoic acids B, 46 N-sulfonimines C, and 32 thiols D.

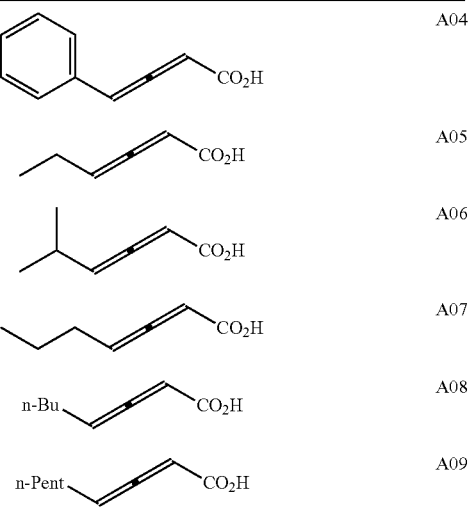

CHART 1-continued
Eleven γ-substituted allenoic acids A, 12 α-substituted allenoic acids B, 46 N-sulfonimines C, and 32 thiols D.
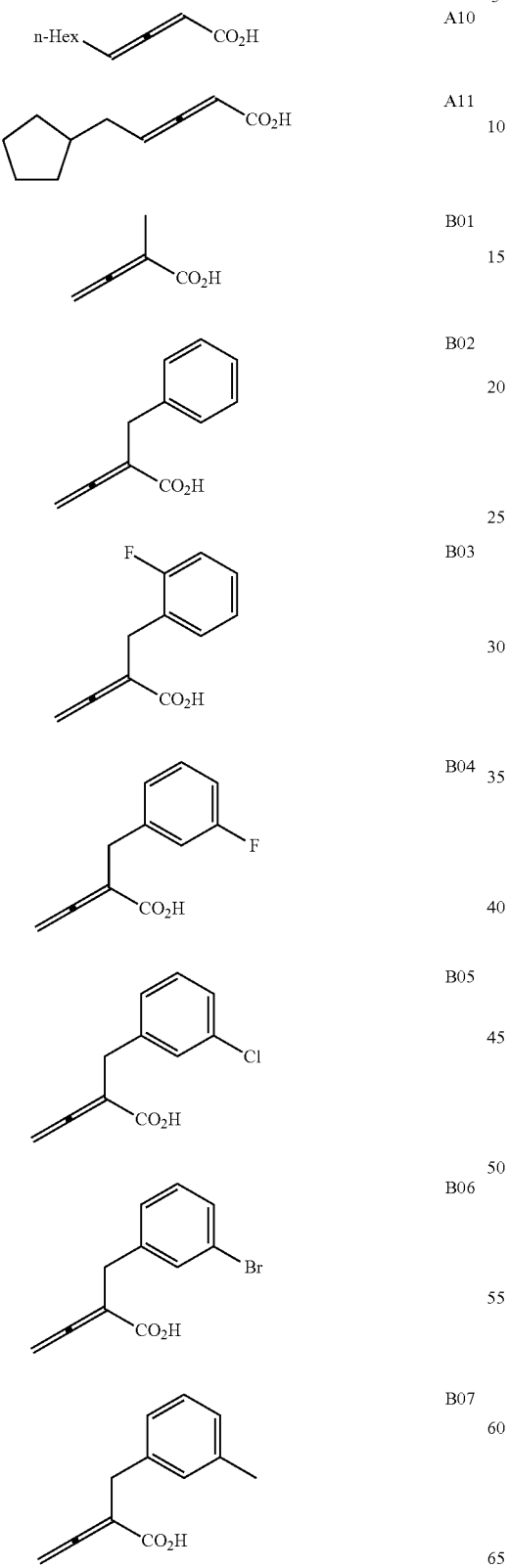
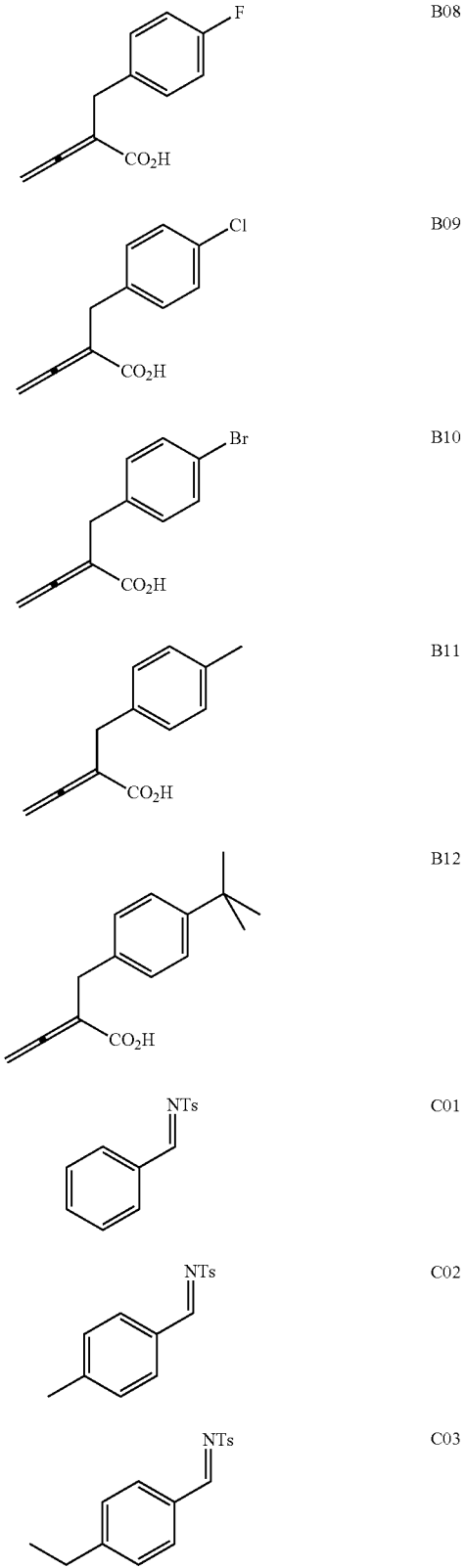

CHART 1-continued
Eleven γ-substituted allenoic acids A, 12 α-substituted allenoic acids B, 46 N-sulfonimines C, and 32 thiols D.
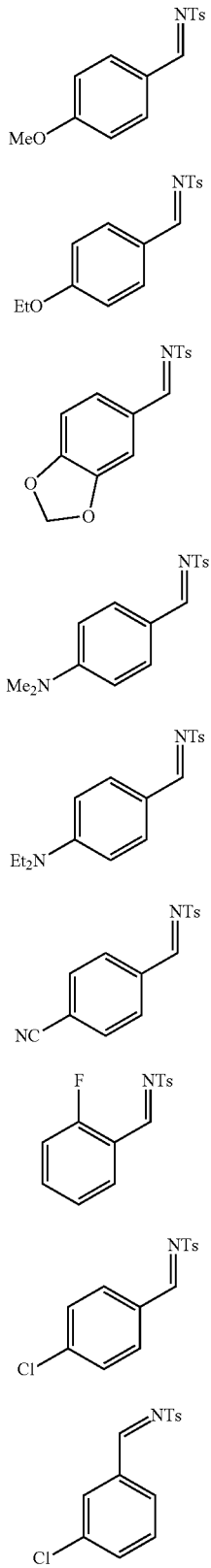
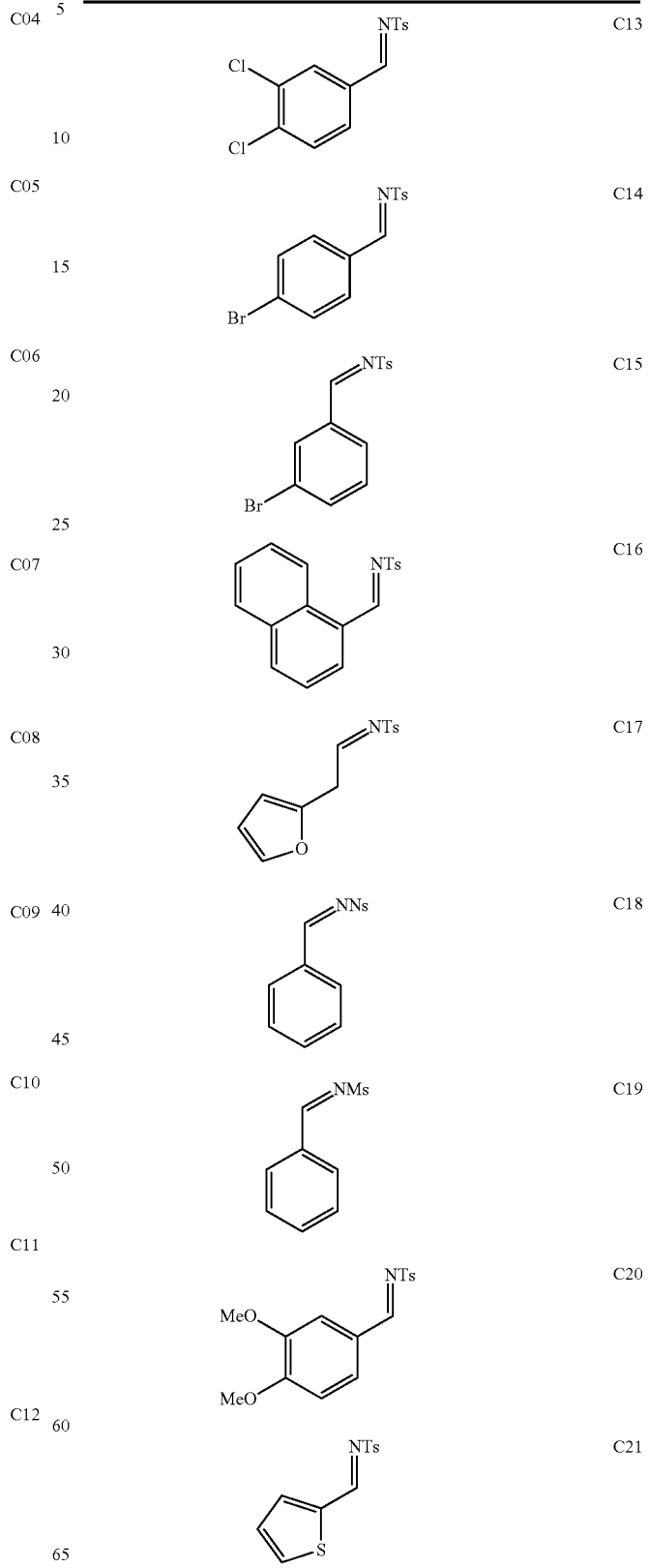

CHART 1-continued
Eleven γ-substituted allenoic acids A, 12 α-substituted allenoic acids B, 46 N-sulfonimines C, and 32 thiols D.
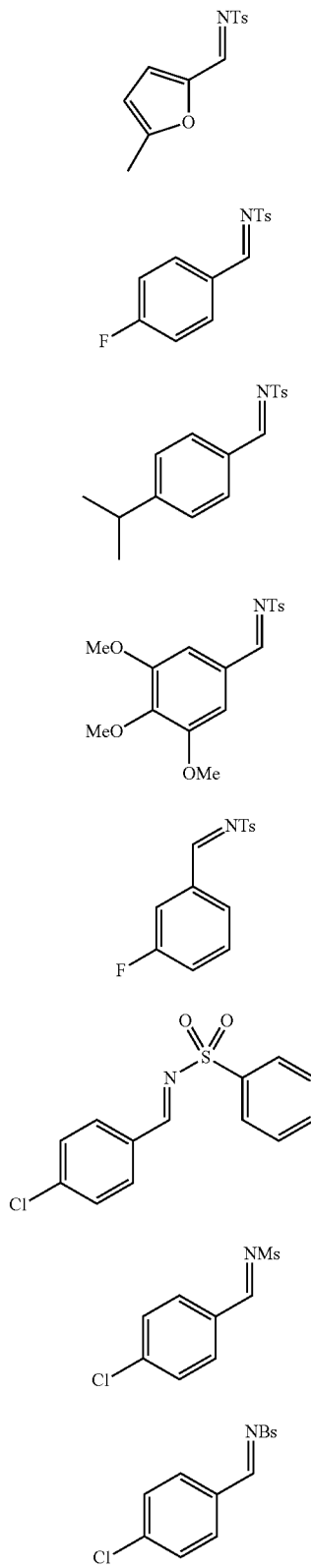
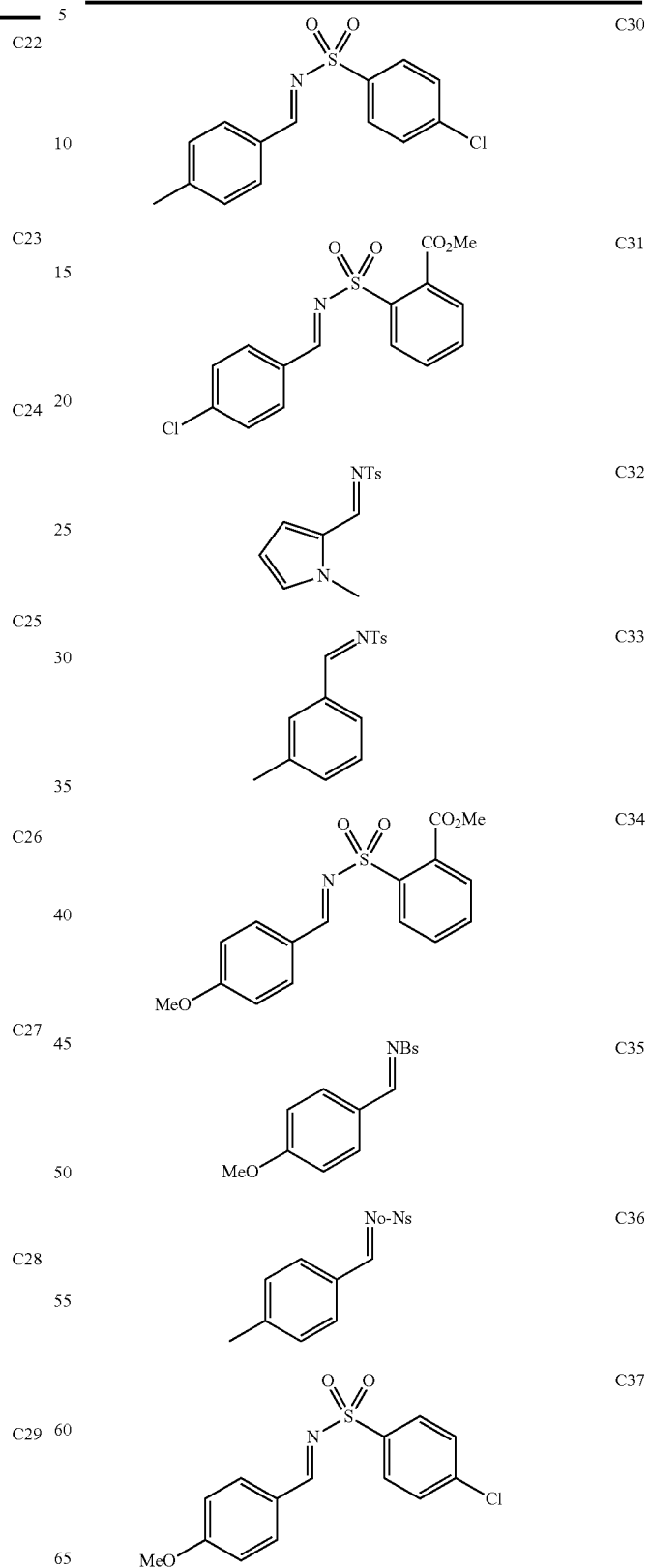

CHART 1-continued
Eleven γ-substituted allenoic acids A, 12 α-substituted allenoic acids B, 46 N-sulfonimines C, and 32 thiols D.
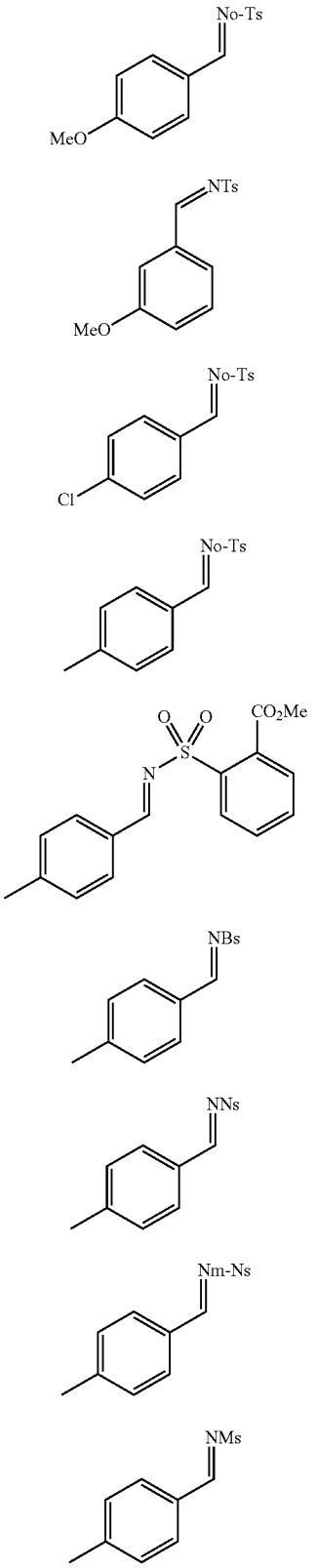
C38
C39
C40
C41
C42
C43
C44
C45
C46
CHART 1-continued
Eleven γ-substituted allenoic acids A, 12 α-substituted allenoic acids B, 46 N-sulfonimines C, and 32 thiols D.
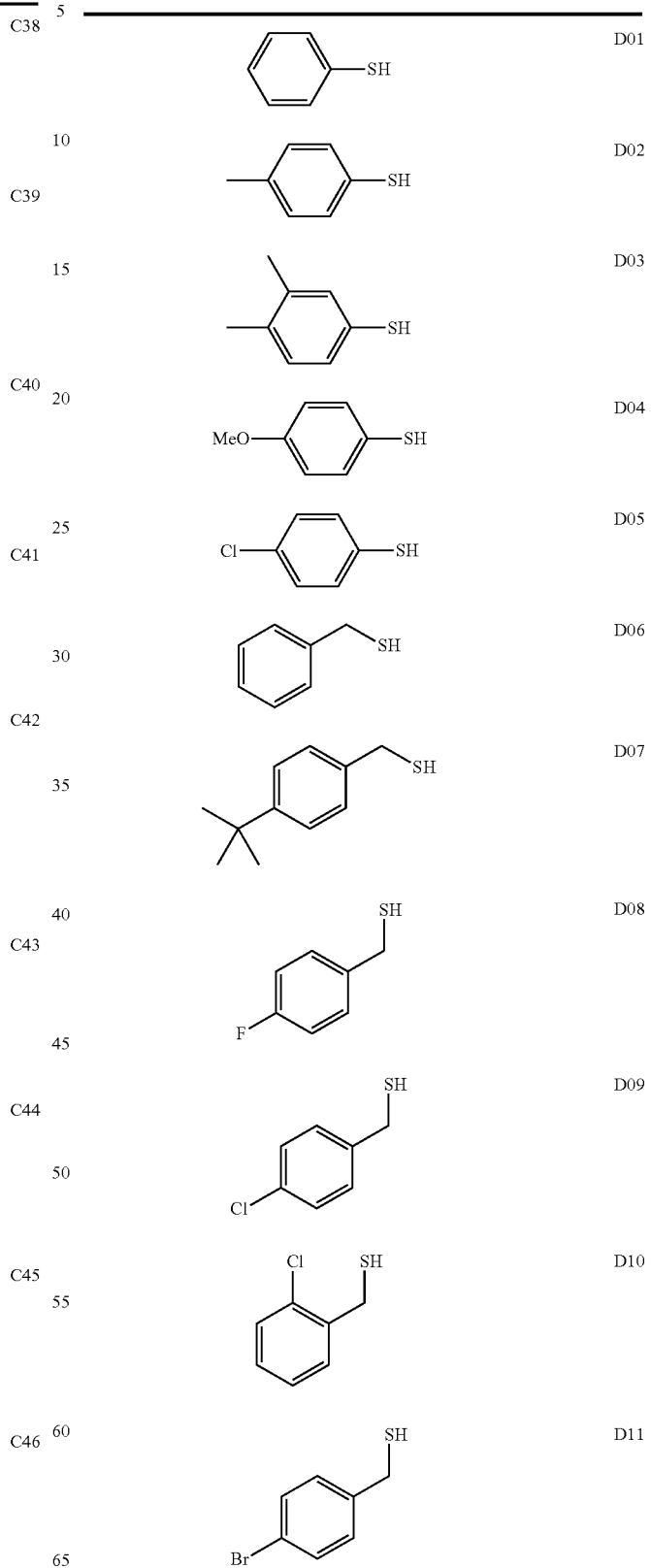
D01
D02
D03
D04
D05
D06
D07
D08
D09
D10
D11

CHART 1-continued

Eleven γ-substituted allenoic acids A, 12 α-substituted allenoic acids B, 46 N-sulfonimines C, and 32 thiols D.

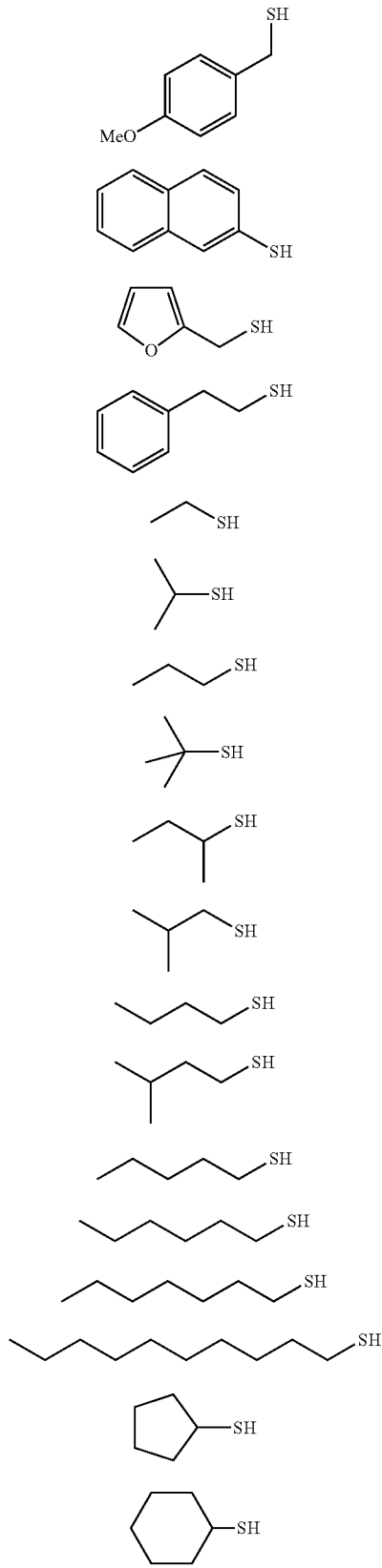

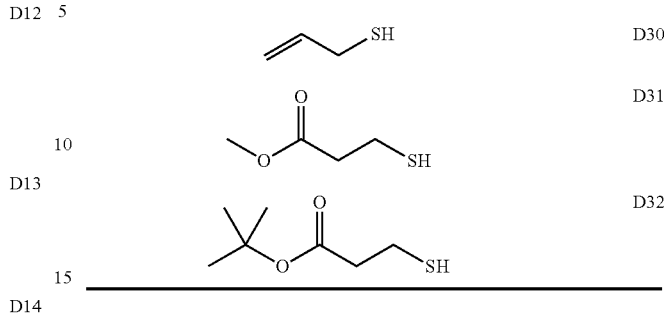

For Michael addition of the thiols, all three building blocks were tested as follows: To select suitable allenoic acids, the 23 annulation products synthesized above were subjected to Michael addition using benzenethiol, toluenethiol, or benzyl thiol. Analysis of the cleaved products indicated that eight (of 23) allenoic acids were suitable candidates. For imine selection, the annulation products of 46 imines with A05 and B01 were tested because the allenoic acids A01-04 and B02-B12 were excluded from the Michael addition sequence. The number of imines selected was 25 (of 46) for A05 and 21 for B01. The annulation products 6 and 7 (Scheme 2) were used to select the thiols; the various thiols required different reaction times and temperatures. Upon extensive optimization, 19 (of 32) thiols for dihydropyrrole 6 and 17 for tetrahydropyridine 7 were selected. The combination of these selected building blocks resulted in the preparation of 4288 compounds.

Using the chosen building blocks, we commenced the split-pool syntheses of the 4288 GGTI analogs on the SynPhase lanterns. Tagging was performed by inserting colored spindles and cogs into the lanterns prior to synthesis of the library.[14] Twenty-three allenoic acids A and B were loaded onto the Wang resin 3 using Mukaiyama's reagent (Scheme 1). The resulting allenoate-loaded lanterns 5 were pooled and split into a number of flasks corresponding to the number of imines for each group of allenoic acids (A01, A02-A11, B01, and B02-B12). Sets of 240 dihydropyrrole-loaded lanterns 6 and 366 tetrahydropyridine-loaded lanterns 7 were placed aside for cleavage. Sets of 3325 dihydropyrrole-bound lanterns 6 and 357 tetrahydropyridine-bound lanterns 7 were further divided into 19 and 17 flasks, respectively, and subjected to the thiol Michael reactions (Scheme 2).

The 4288 lanterns were inserted into 4288 vials and treated with 2.5% TFA in $CH_2Cl_2$ for 12 h; the lanterns were then removed and rinsed with $CH_2Cl_2$. The resulting solution was concentrated and further co-evaporated with $CHCl_3$ to effectively remove TFA. The cleaved compounds were weighed and redissolved in $CHCl_3$; a portion (2 mop of each compound was transferred into 54 96-well plates (80 compounds per well; two columns of wells in each plate were left empty to accommodate controls in subsequent assays) and the solvents were left to evaporate. The products were redissolved in DMSO and analyzed in the same assay for activity against GGTase-I.

In the in vitro assay, active compounds were sought for their ability to inhibit the geranylgeranylation of both RhoA and K-Ras4B. The two compounds (22 and 23) that exhibited some of the highest activities obtained so far are shown in (a) below. These compounds exhibit specific inhibition of GGTase-I; i.e., they did not inhibit FTase at concentrations at which they inhibited GGTase-I by more than 90%.

(a)

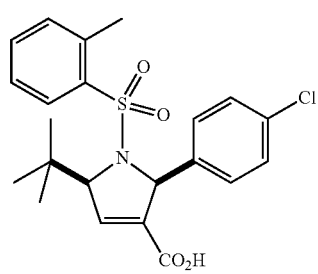

22

IC$_{50}$ 0.5 μM, RhoA
IC$_{50}$ 0.9 μM, KRas4B

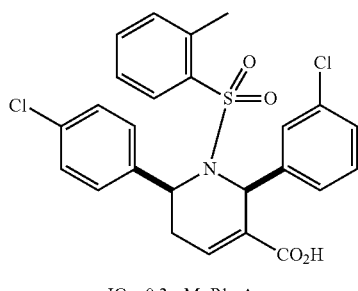

23

IC$_{50}$ 0.3 μM, RhoA
IC$_{50}$ 2 μM, KRas4B

Figure 33:
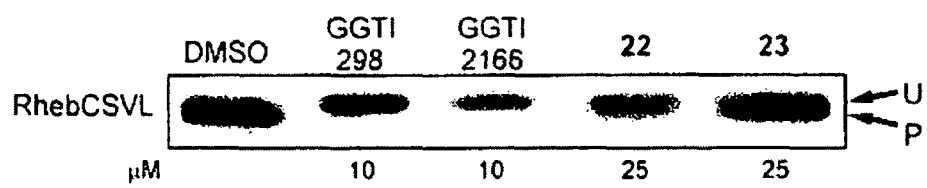
FIG. 33 shows Western blots of cell lysates with geranylgeranylated Rheb, using compounds 22 and 23.

FIG. 33 shows Western blot of the cell lysate qualitatively detecting the amount of gernanylgeranylated Rheb. The descriptors P and U designate processed and unprocessed Rheb, respectively.

Finally, we investigated in vivo effects of compounds 22 (also known as UC-22) and 23 (also known as UC-23). Human embryonic kidney (HEK) 293 cells were transfected with the Rheb-CSVL construct that expresses the geranylgeranylated form of the Rheb protein. Inhibition of the geranylgeranylation of this protein can be detected from a shift in its mobility on SDS polyacrylamide gel; the unprocessed form appears as a slowly migrating band. FIG. 33 indicates that treatment of the cells with compound 22 or 23 resulted in the appearance of a slowly migrating band (cf. the DMSO lane with lanes compounds 22 and 23); known GGTIs (GGTI298, GGTI2166) were used as controls. These results suggest that compounds 22 and 23 inhibit geranylgeranylation within the cell.

Example 2

Examples 2-8 illustrate assays of bioactivity. These methods are applicable to the compounds of the present invention having the particular linkers and scaffolds described herein, to determine their activity. As illustrated in FIGS. 20A-20C, compounds P3-E5 and P5-H6 specifically inhibit GGTase I. The graph illustrates the effect of P3-E5 and P5-H6 on the enzymatic activity of GGTase-I (A), FTase (B) GGTase-II (C). Varying concentrations of the two compounds were added to each enzyme reaction. The FTase (protein farnesyl-transferase) assay was carried out using K-Ras4B as a substrate protein, FTase (JENA Bioscience, San Diego, Calif.) and [3H]farnesyl pyrophosphate. Incubation was for 30 min at 37° C.

The GGTase-I assay was carried out using RhoA as a substrate protein, GGTase-I (JENA Bioscience) and [3H] geranylgeranyl pyrophosphate. Incubation was for 30 min at 37° C. GGTase-II (or RabGGTase) assay was carried out using YPTI as a substrate protein, GGTase-II (Calbiochem, San Diego, Calif.) plus REP1 (Calbiochem) and [3H]geranylgeranyl pyrophosphate. Incubation was for 30 min at 37° C. FIGS. 20D-20F show the three dimensional structure of GGTase I (D), FTsse (E) and GGTase II (F) which can be obtained from X-ray diffraction studies of protein crystals.

Example 3

As illustrated in FIGS. 21A-21D, P3-E5 and P5-H6 compete with a substrate protein but do not compete with GGPP. The graphs in FIG. 21 show double reciprocal plots obtained from substrate velocity curves for the inhibition of GGTase-I by P3-E5 (left) and P5-H6 (right). The upper figures show varying GGPP concentrations with a fixed RhoA protein concentration were used. The lower figures show varying RhoA protein concentrations with a fixed GGPP concentration was used. The following scale was used to prepare the graphs: Y-axis: 1/v, fmol/min. X-axis: 1/s, mM.

Example 4

Figure 22:
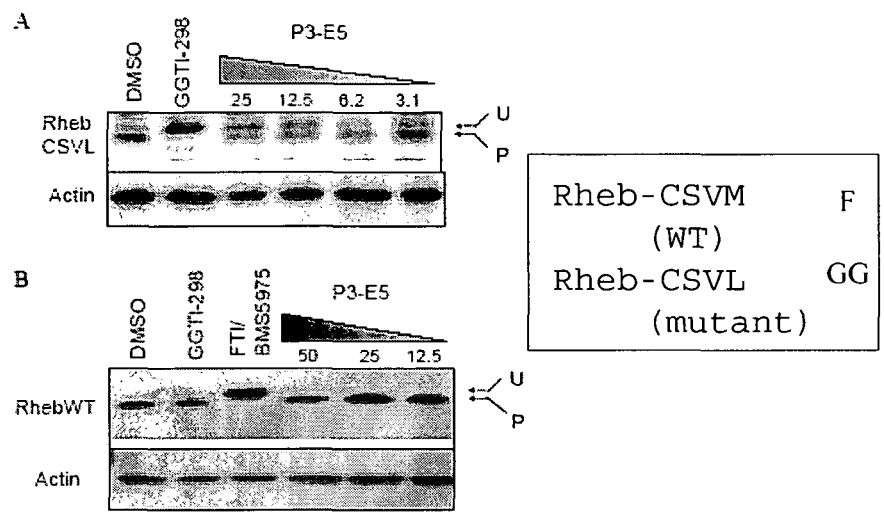

As illustrated in FIGS. 22A and 22B, P3-E5 inhibits geranylgeranylation in cells. Human embryonic kidney (HEK) 293 cells expressing Myc-HA tagged-Rheb-CVSL (upper) or Myc-HA tagged-Rheb-WT (lower) were treated with P3-E5 for 48 hours and then lysed. The cell lysates were run on a SDS polyacrylamide gel and immunoblotted using anti-Myc or anti-Actin antibody. The descriptors P and U indicate processed and unprocessed Rheb, respectively. Similar results have been obtained with P5-H6 but are not depicted in FIG. 22.

Example 5

Figure 23:
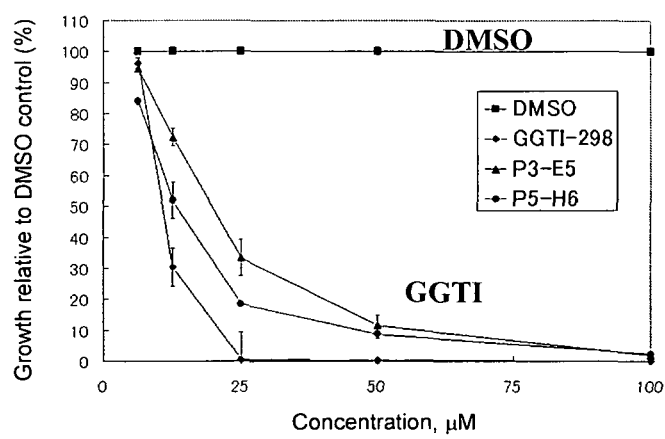
Figure 24:
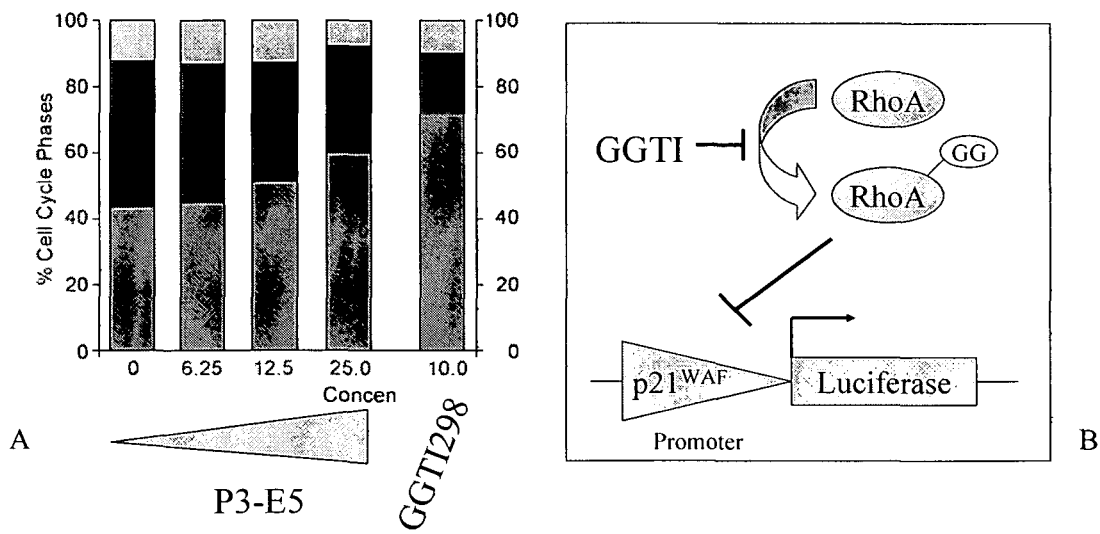

As illustrated in FIG. 23, P3-E5 and P5-H6 inhibit proliferation of K562 cells. K562 cells are a cell line of human erythroleukemia cells. The K562 cells were treated with P3-E5, P5-H6 or GGTI-298 (a known GGTI compound illustrated in FIG. 27) for 72 hours and then cell number was counted using cell counting kit-8 (Dojindo, Gaithersburg, Md.). Cell viability relative to the DMSO control and the known GGTI compound is plotted in FIG. 23. It can be seen that both P3-E5 and P5-H6 inhibit the growth of the K562 cells.

Example 6

As illustrated in FIG. 24A, P3-E5 induces G1 arrest in K562 cells. K562 cells were treated with indicated concentrations (mM) of P3-E5 (ranging from 0 to 10 mM) or GGTI-298 (ranging from 0 to 10 mM) for 48 hours. Cell cycle profiles were monitored by flow cytometry. Percentages of cells in each phase of the cell cycle are indicated by different colors. Red: G0/G1 phase. Black: S phase. Gray: G2/M phase. Similar results were obtained with P5-H6.

While not wishing to be bound to a single theory, FIG. 24B illustrates an exemplary mechanism to explain the cell cycle effect of GGTIs. RhoA is known to inhibit expression of p21WAF. GGTI may function by inhibiting geranylgeranylation of RhoA leading to the increase in p21WAF expression. This could result in G1 arrest.

Example 7

Figure 25:
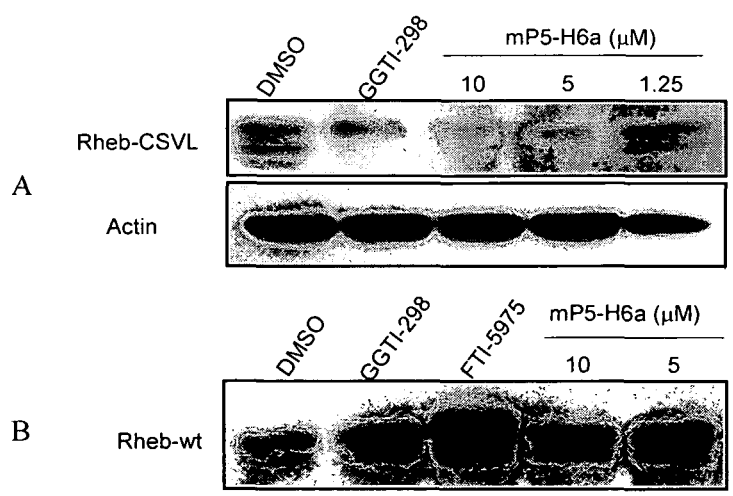

As illustrated in FIG. 25, mP5-H6 inhibits geranylgeranylation in vivo. Human embryonic kidney (HEK) 293 cells expressing Myc-HA tagged-Rheb-CVSL (upper) or Myc-HA tagged-Rheb-WT (lower) were treated with mP5-H6a (also referred to as mP5-H6), or GGTI-298 for 48 hours and then lysed. Lysates were run on a SDS polyacrylamide gel and immunoblotted with anti-Myc or anti-Actin antibody. Processed and unprocessed Rheb may be used in the method described in this example as shown in FIG. 22.

Example 8

Figure 26:
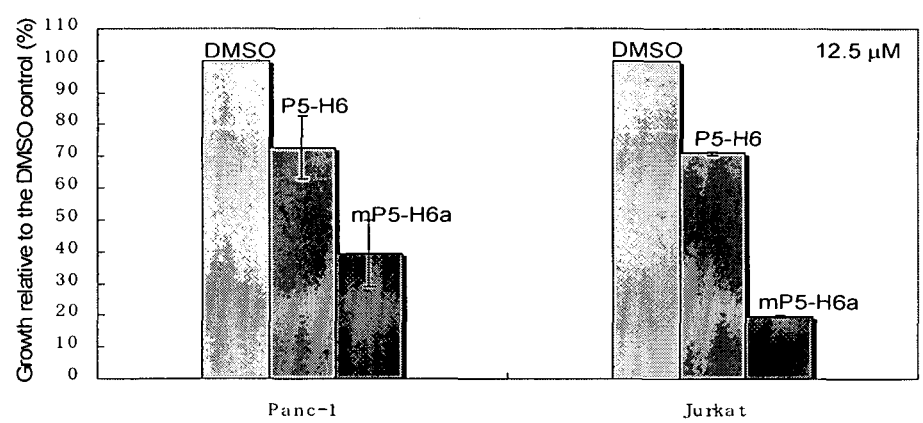
Figure 27:
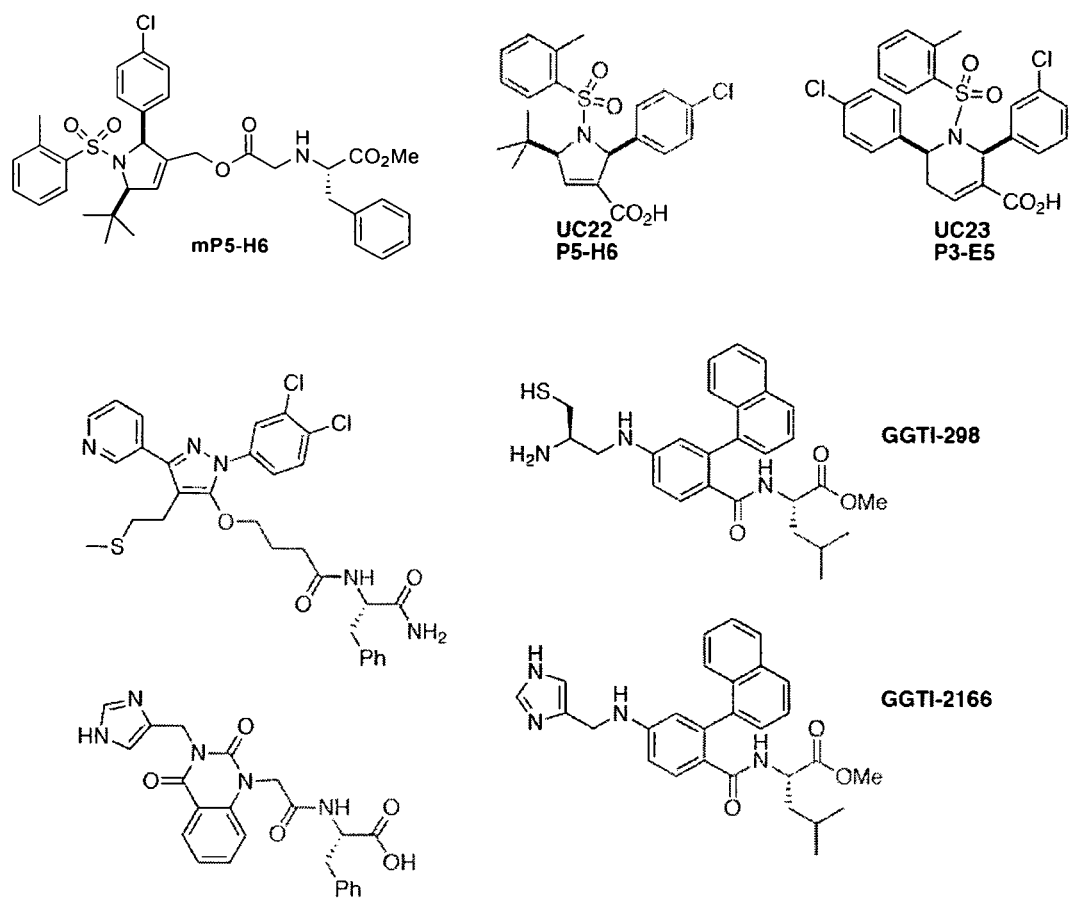
Figure 29A:
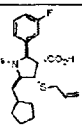
Figure 29B:
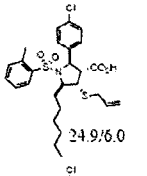
Figure 30A:
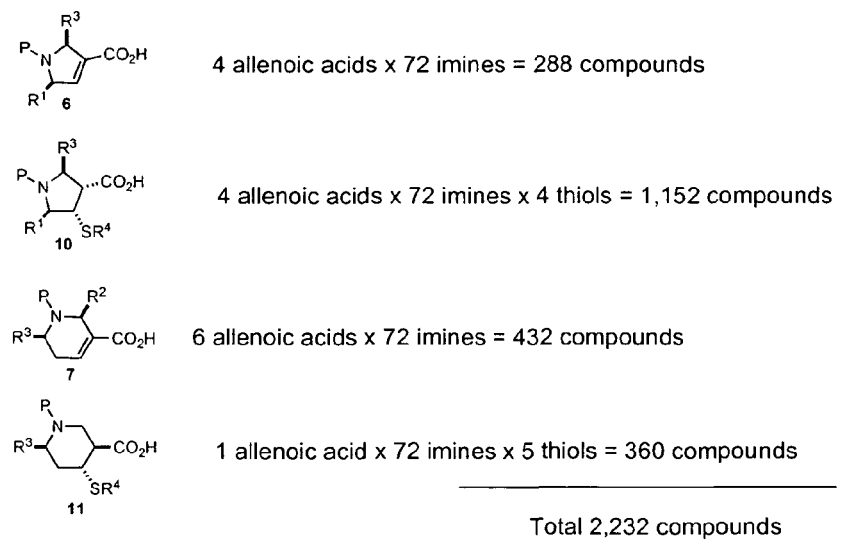
FIGS. 30A to 30E illustrate structures and members of a library of compounds.
Figure 30B:
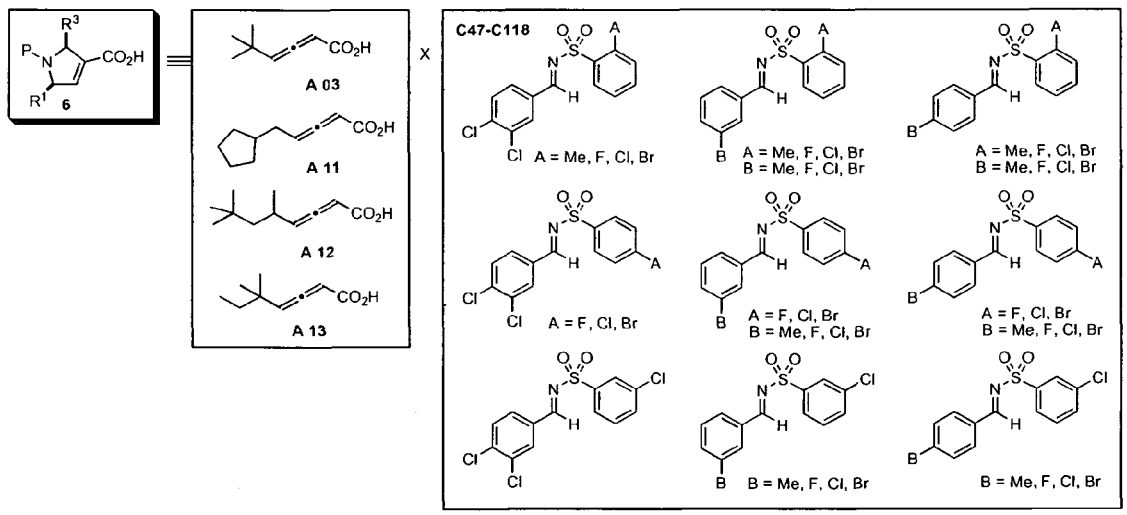
Figure 30C:
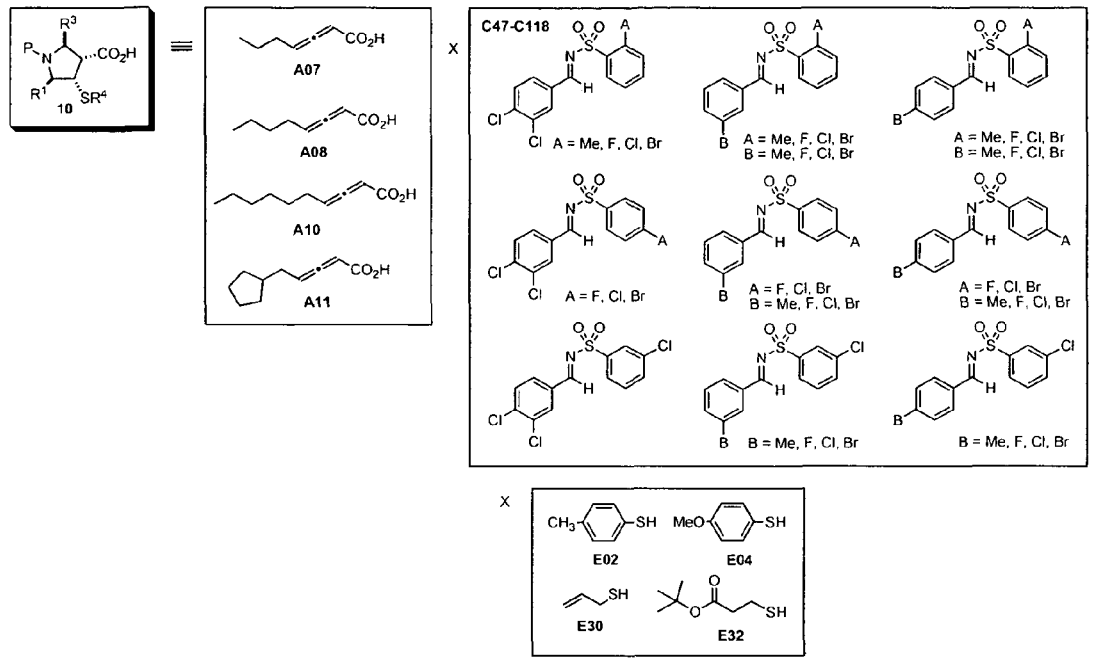
Figure 30D:
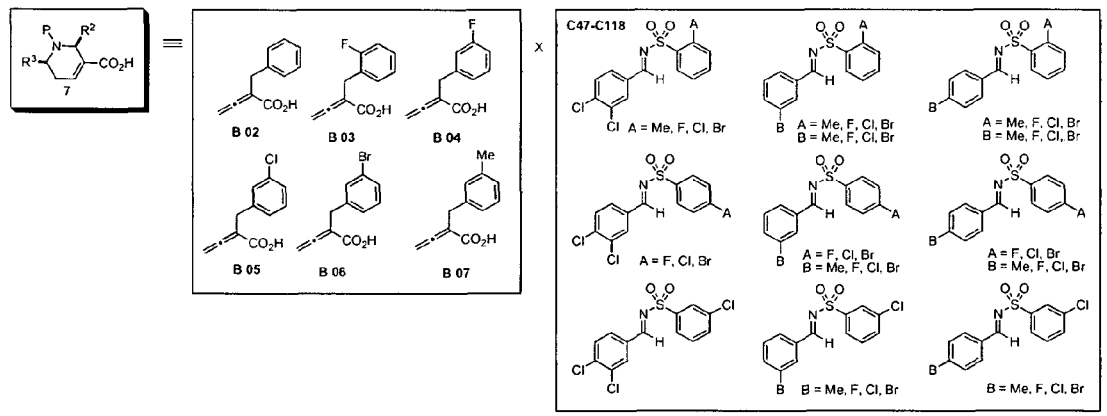
Figure 30E:
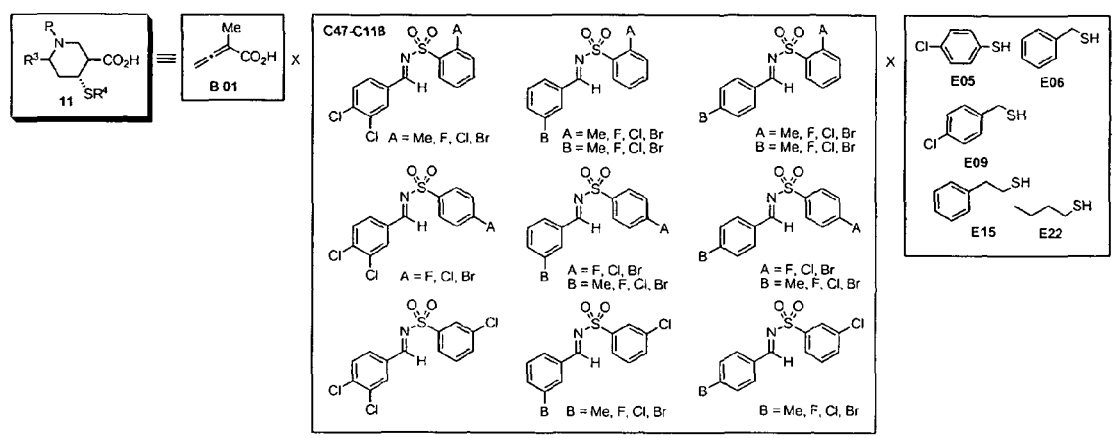

As shown in FIG. 26, mP5-H6 exhibits increased potency to inhibit proliferation relative to P5-H6. Panc-1 cells (Pancreatic cancer cell line) and Jurkat cells (T-cell leukemia) were treated with 12.5 μM of P5-H6 or 12.5 μM of mP5-H6a for 72 hours. The cell number was counted as described in Example 5. The graph shows that mP5-H6a inhibits the growth of Panc-1 cells and Jurkat cells better than P5-H6.

Example 9

Further screening of the libraries described herein has yielded additional GGTI compounds and the identification and characterization of novel RabGGTase inhibiting compounds. The experimental procedures and results of this research is described below.

EXPERIMENTAL PROCEDURES

The following experimental procedures were used:
A. Cell Lines and Cell Culture

NIH3T3 cells were maintained in Dulbecco's modified Eagle's medium (DMEM; Cellgro, Herndon, Va.) supplemented with 10% (v/v) fetal bovine serum (FBS; Hyclone, Logan, Utah), 2% L-glutamine, 1% penicillin, and 1% streptomycin stock solutions (Life Technologies, Gaithersburg, Md.). K562 cells were maintained in RPMI-1640 medium (Cellgro) supplemented with 10% (v/v) FBS and penicillin/streptomycin. PANC-1 cells were maintained in DMEM/F12 medium (Invitrogen, Grand Island, N.Y.) supplemented with 10% (v/v) FBS and penicillin/streptomycin. MCF-7 cells were maintained in Eagle's Minimum Essential Medium (EMEM; Cellgro) supplemented with 10% (v/v) FBS and penicillin/streptomycin.
B. Materials

[$^3$H]-farnesyl diphosphate (FPP) (21.5 Ci/mmol) and [$^3$H]-geranylgeranyl diphosphate (GGPP) (23.0 Ci/mmol) were purchased from PerkinElmer Life Sciences. BMS-225975 was kindly provided by Dr. Veeraswamy Manne (Bristol-Myers Squibb). GGTI-298 was purchased from Calbiochem (La Jolla, Calif.). Prenyltransferases used are recombinant enzymes. GGTase-I, FTase, RabGGTase, REP-1 and Rab7 were purchased from JENA BIOSCIENCE (Jena, Germany). Other chemicals were obtained from Sigma. The allenoate derived compounds library including P3-E5 and P5-H6 were synthesized as described in (28). Examples of suitable methods for the synthesis of P63-F10, P63-C7, P63-E11, P62-A5, P62-C11, P62-E4 and modified P5-H6 compounds (P61-A2, P61-A5, P61-A6, P61-A7 and P61-B4) have been described above.
C. In Vitro Enzyme Assays GGTase-I and FTase activities were determined by following the incorporation of radiolabeled isoprenoid [$^3$H]-geranylgeranyl or [$^3$H]-farnesyl into substrate proteins. FTase or GGTase-I (50 nM) were used to initiate reactions containing 0.4 μM of [$^3$H]-FPP or 0.5 μM of [$^3$H]-GGPP and 2 μM of MBP-tagged substrates (K-Ras4B for FTase; RhoA for GGTase-I) in 20 μl of buffer {50 mM Tris-HCl (pH 7.5), 10 mM MgCl$_2$, 50 mM ZnCl$_2$ and 5 mM DTT}. Inhibitors were added at the indicated concentrations. The final DMSO concentration was 2.5% for all samples.

Reactions were carried out for 10 min at 30° C. The reaction mixture was spotted onto a filter paper, treated with 10% trichloroacetic acid (TCA) followed by ethanol and acetone washing. The filter was counted using a scintillation counter. Kinetic assays in which the GGPP concentration was varied employed fixed concentrations of GGTase-I and RhoA, and reactions were carried out for 5 min. Similarly, fixed concentrations of GGTase-I and GGPP were used when the amount of RhoA was varied.

For RabGGTase assays, the reaction contained the following components in 20 μl; 0.625 μl of [$^3$H]-GGPP (0.7 μM), 25 nM RabGGTase, 0.6 μM REP-1, 0.6 μM purified Rab7 or Ypt1 protein, 40 mM HEPES (pH 7.5), 150 mM NaCl, 5 mM DTT, 3 mM MgCl$_2$ and 0.3% CHAPS. Reactions were carried out for 20 min at 37° C. and the products were analyzed as described above for the GGTase-I reaction. Graphing and Michaelis-Menten analysis were performed using Prism version5 (GraphPad, San Diego Calif.).
D. Inhibition of Geranylgeranylation in Cells The inhibition of GGTase-I catalyzed protein geranylgeranylation was assessed by examining the accumulation of unprenylated Rap1. To measure the level of unprenylated Rap1, cells were cultured in DMEM plus 10% (v/v) FBS overnight, and then DMSO or appropriate inhibitors were added. Incubation was continued for 48 hours. The cells were harvested and lysed in lysis buffer (20 mM Tris-HCl, pH 7.5, 150 mM NaCl, 1 mM EDTA, 1% NP-40 and 1× Protease Inhibitor Cocktail). Whole cell lysates of NIH3T3 cells were electrophoresed on a 12% SDS-PAGE, transferred to nitrocellulose membranes and immunoblotted with the antibody against unprenylated form of Rap1 (Santa Cruz Biotechnology catalog number sc-1482, goat), total-Rap1 (Santa Cruz: sc-65) or actin (Sigma: A4700). Actin was used as a loading control.

The inhibition of Rab geranylgeranylation in cells (FIG. 43) was examined according to (29). Briefly, whole cell lysates were subjected to 15% SDS-PAGE containing 4M urea followed by immunoblotting with the antibody against Rab5b (Santa Cruz: sc-598) or actin. Subcellular fractionations (FIG. 44) were performed as described by Gomes et al. (30). Briefly, cells were treated with P49-F6 for 48 hours. After osmotic lysis, cell debris were removed by centrifugation at 500×g for 10 min, and the supernatant was subjected to ultracentrifugation at 100,000×g for 60 min. The supernatant of ultracentrifugation was collected as a soluble fraction. The pellet was collected as a membrane fraction. These fractions were subjected to electrophoresis on 10% SDS-PAGE gels followed by immunoblotting with the antibody against Rab5b. RhoGDI (Santa Cruz: sc-360) and Na$^+$/K$^+$ ATPase (Sigma: A276) were used as markers for soluble and membrane fractions, respectively.
E. Cell Viability, Cell Cycle Analysis Cell viability was determined by Cell Counting Kit-8 (CCK-8, Dojindo, Kumamoto, Japan) as described previously (31). Briefly, cells (5×10$^3$) were plated onto 96-well plates and treated with the appropriate inhibitor as indicated in figure legends. Cell viability was calculated relative to the DMSO control. Cell cycle profile was analyzed by flow cytometry as described previously (32).
F. Transcriptional Reporter Assays For the p21$^{WAF1/CIP1}$ promoter luciferase assay, NIH3T3 cells were transfected with p21$^{WAF1/CIP1}$ promoter-Luc or vector plasmids (33) (both plasmids are provided by Dr. Genhong Cheng). Cells were treated with GGTI compounds. Promega luciferase assay kit was used according to the manufacturer's protocol.

G. Statistical Analysis

Statistical significance of difference was determined using the unpaired Student's t-test. P value<0.05 was considered statistically significant.

Results

Allenoic Acid Based Chemical Compound Library and Identification of GGTase-I Inhibitors.

As described above, we have reported construction of a library of allenoate derived compounds and identification of novel GGTI compounds (28). The library construction involved the use of allenoates as multireactive core molecules. Using the second set of building blocks (imines, aldehydes and maleimides) that react with allenoates under similar reaction conditions (phosphine catalysis), we have produced diverse compounds including dihydropyrroles (34), tetrahydropyridines (35), bicyclic succinimides (unpublished results), dioxanylidenes (36) and alpha-pyrones (37).

The identification of GGTI compounds from within this library was carried out by screening a 171-compound pilot library using an in vitro assay with RhoA protein as a substrate. Scaffolds that initially showed activity were optimized by solid-phase split-and-pool combinatorial synthesis. This enabled us to identify at least two types of novel compounds; one group containing a tetrahydropyridine ring as its core scaffold and the other group having a dihydropyrrole ring as its core scaffold.

Figure 34:
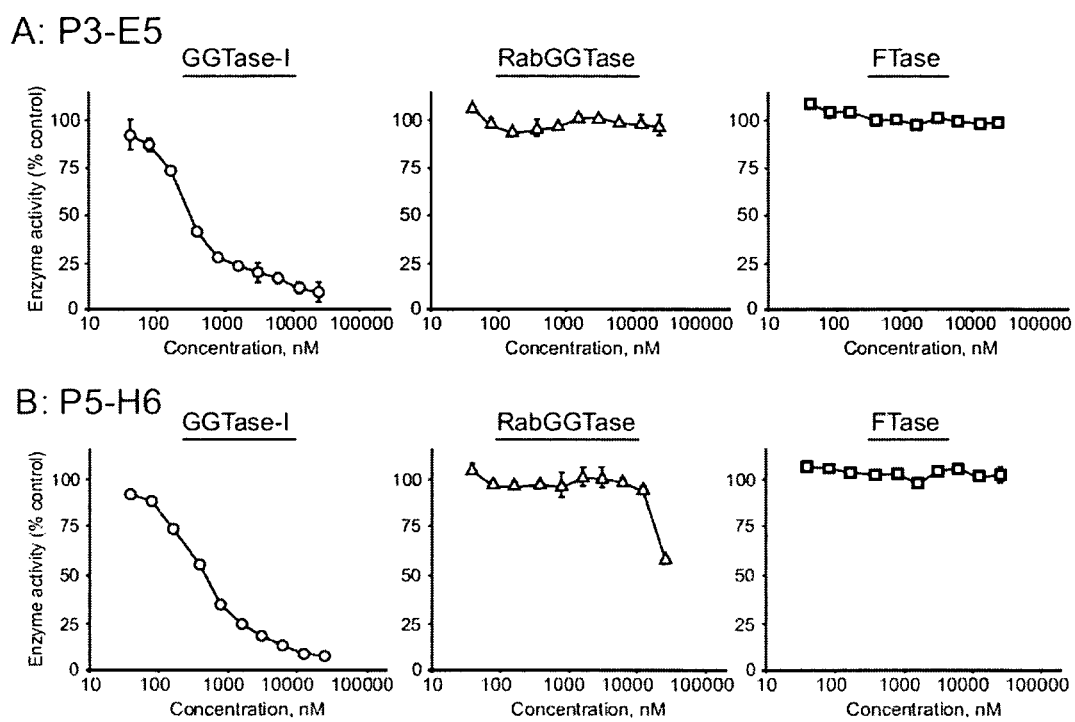
FIG. 34 shows the effect of P3-E5 (A) and P5-H6 (B) on the enzymatic activity of GGTase-I (left), RabGGTase (middle) and FTase (right). Varying concentrations of compounds were added to each enzyme reaction. Data represent the mean+/−S.D. of two measurements from two independent experiments.

After identification, two compounds with high potencies in each group, P3-E5 and P5-H6, were further characterized. As described herein, P3-E5 and P5-H6 inhibit GGTase-I with $IC_{50}$ values of 313 and 466 nM, respectively. The specificity of GGTase-I inhibition by P3-E5 and P5-H6 was examined by assaying their ability to inhibit two closely related enzymes, FTase and RabGGTase. As can be seen, no significant inhibition of FTase activity was observed by these compounds even when the concentration was increased to 50,000 nM (FIG. 34). Similarly, P3-E5 showed little inhibition against RabGGTase even at 50,000 nM. P5-H6 showed little inhibition against RabGGTase up to 10,000 nM.

GGTIs Compete with Substrate Protein.

Michaelis-Menten analysis of the inhibition of GGTase-I is shown in FIG. 35. The upper panels show the data derived from the results obtained using varying concentrations of geranylgeranyl pyrophosphate (GGPP), while the lower panels show data derived from the results obtained using varying concentrations of the substrate protein, RhoA. These results demonstrated that P3-E5 and P5-H6 are competitive inhibitors with respect to the protein substrate and uncompetitive inhibitors with respect to GGPP. P3-E5 and P5-H6 compete for binding of the protein substrate but not the isoprenoid substrate of GGTase-I. Ki values of 187±13 nM and 408±32 nM, respectively, were calculated for P3-E5 and P5H6.

Improvement of Cellular Activity of GGTI by the Modification of P5-H6.

It was found that replacing a carboxyl group of the dihydropyrrole ring of P5-H6 can significantly improve its cellular activity. This is shown in FIG. 36A where we synthesized a series of compounds with different moieties replacing the carboxyl group. Potency of these compounds to inhibit proliferation of K562 leukemic cells was examined and their IC50 values are shown. The original P5-H6 compound containing a carboxylic acid moiety exhibited inhibition of proliferation of K562 cells with IC50 of 20 µM. Converting the free acid to an ethyl ester did not improve its cellular potency. However, amidation of this moiety led to improvement in its potency. Moreover, coupling of P5-H6 with an L-phenylalanine group resulted in an improvement of cellular potency. Two compounds, P61-A6 and P61-B6, showed good potency with IC50 of 2.2 µM and 5.0 µM to inhibit proliferation of K562 cells, respectively. Comparison of inhibitory activity of P5-H6 and P61-A6 on a pancreatic cancer cell line PANC-1 and Jurkat cells is shown in FIG. 36B.

The improved potency of these compounds to inhibit cell proliferation correlates with their increased ability to inhibit protein geranylgeranylation inside the cell. Results illustrating this correlation using P5-H6 and P61-A6 are shown in FIG. 36C. In this experiment, the inhibition of protein geranylgeranylation can be evaluated using an antibody that specifically detects unprenylated Rap1. Treatment with P5-H6 or P61-A6 led to the appearance of the unprocessed Rap1 band in a dose dependent manner. The appearance of the Rap1 band is observed at 2.5 µM concentration with P61-A6, while this is not seen with P5-H6, reflecting improvement in the potency of P61-A6 to inhibit protein geranylgeranylation.

In contrast to its effects on GGTase-I, P61-A6 did not inhibit protein farnesylation. This was examined by using a farnesylated protein H-Ras. While farnesyltransferase inhibitor (FTI) (BMS-225975) slowed the mobility of H-Ras protein on a SDS polyacrylamide gel, no such mobility shift was observed with P61-A6 or another GGTI compound, GGTI-298. Similarly, P61-A6 did not inhibit geranylgeranylation of Rab5b, as a slow migrating band representing that of unmodified Rab5b was detected only after the treatment with RabGGTase inhibitors (P49-F6) and not with P61-A6 (FIG. 36E).

Although P61-A6 exhibits improved ability to inhibit geranylgeranylation in cells, its ability to inhibit GGTase-I enzyme was less than that of P5-H6, as the $IC_{50}$ value for the enzyme inhibition was 1 µM. No significant inhibition of FTase or RabGGTase activity was observed by P61-A6 compound even when the concentration was increased to 100,000 nM (data not shown).

GGTI Compounds Inhibit Proliferation of Various Human Cancer Cell Lines and Cause $G_1$ Cell Cycle Arrest.

As shown in Table S1, inhibition of cellular proliferation was observed in a variety of human cancer cell lines. These results indicate that a broad range of human cancer cell lines can be inhibited using the GGTI compounds described herein.

TABLE S1

Table S1. Potencies of GGTIs toward human cancer cell lines

|  |  | P61-A6 | P61-B6 |
| --- | --- | --- | --- |
| Jurkat | Blood | 2.9 | 1.3 |
| SE-Mk2 | Blood | 6.4 | 14.1 |
| PANC-1 | Pancreas | 5.2 | 12.6 |
| MiaPaCa2 | Pancreas | 4.7 | 13.9 |
| AsPc-1 | Pancreas | 11.7 | >20.0 |
| Capan-2 | Pancreas | 11.5 | 11.1 |
| CFpac-1 | Pancreas | 6.3 | 8.1 |
| HPAC | Pancreas | 3.9 | 11.7 |
| MDA-MB-231 | Breast | 8.7 | 12.5 |
| BT474 | Breast | 8.5 | 11.6 |
| MCF-7 | Breast | 4.5 | 6.4 |

Cancer cells were treated with the indicated GGTIs for 3 days (Jurkat, PANC-1, MiaPaCa2, Capan-2, CFpac-1, HPAC, MDA-MB-231 and BT474) or 6 days (SE-MK2, AsPc-1 and MCF-7), and cell number was counted using CCK-8 and compared with vehicle (DMSO) treated cells. Values are the $IC_{50}$ (µM) for at least two separate experiments.

While not wishing to be bound to a single theory, the inhibition of cellular proliferation by GGTI can be due to the inhibition of cell cycle progression. As shown in FIG. 5A, treatment of a breast cancer cell line (MCF-7) with P61-A6 or P61-B6 caused dose-dependent inhibition of proliferation.

Figure 37:
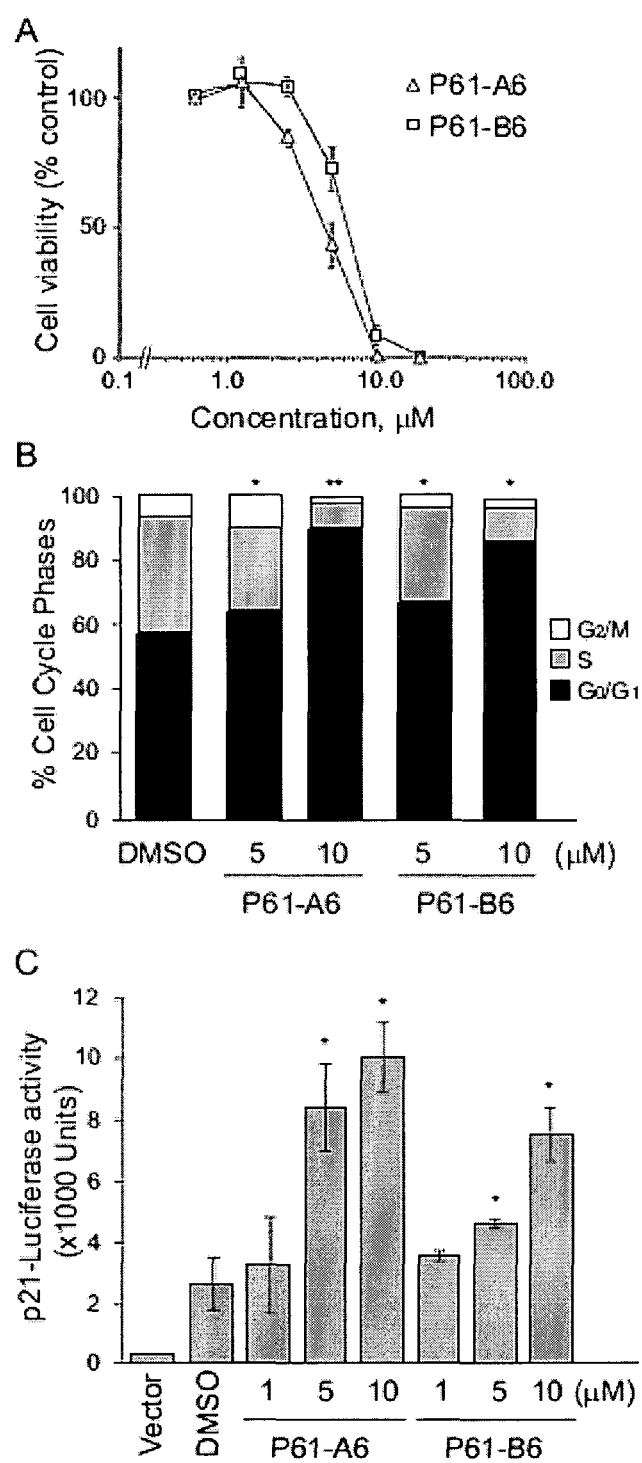
FIG. 37 shows the effects of P61-A6 or P61-B6 on cell proliferation and cell cycle in MCF-7 cells. (A) shows the inhibition of proliferation of MCF-7 by P61-A6 and P61-B6. MCF-7 cells were treated with P61-A6, P61-B6 or DMSO for 72 hours. Cell viability relative to the DMSO control (100% value) is plotted. (B) MCF-7 cells were treated with indicated concentrations (μM) of P61-A6, P61-B6 or DMSO for 48 hours. Cell cycle profiles were monitored by flow cytometry. Percentages of cells in each phase of the cell cycle are indicated by different shades. (C) NIH3T3 cells were transfected with $p21^{CIP1/WAF1}$-luciferase or empty vector. Cells were treated with P61-A6 or P61-B6 compound at indicated concentrations or with DMSO for 48 hours and luciferase assay was performed. Data represent the mean+/−S.D. of two measurements from two independent experiments. *, P<0.05; **, P<0.005 compared with the value for DMSO.
Figure 41:
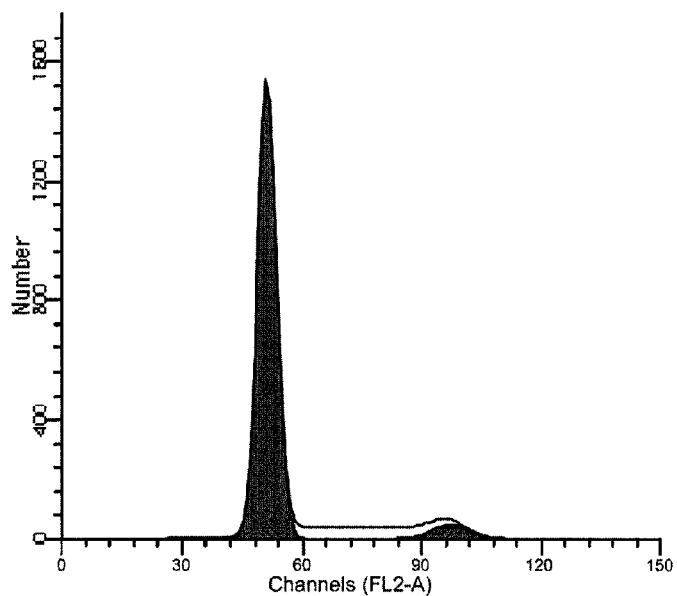
FIG. 41 Primary FACS data. MCF-7 cells were treated with 10 μM of P61-A6, P61-B6 or DMSO for 48 hours. Data shown here are representative of two independent experiments for each treatment.

This is associated with a significant dose-dependent enrichment of $G_1$ phase cells, while the percentage of S-phase cells decreased (FIG. 37B, FIG. 41). Similar $G_1$ enrichment was observed with leukemic cell line, Jurkat, two pancreatic cancer cell lines, PANC-1 and MiaPaCa2, as well as with another breast cancer cell line MDA-MB-231 (Table S2).

TABLE S2

Table S2. Effects of GGTIs on cell cycle phase distribution in cancer cells

| Cell line | Tissue | Percent $G_0/G_1$ | | P value | Percent $G_2/M$ | |
| --- | --- | --- | --- | --- | --- | --- |
| | | DMSO | P61-A6 | | DMSO | P61-A6 |
| Jurkat | Blood | 46.92 | 57.87 | <0.05 | 11.80 | 11.60 |
| PANC-1 | Pancreas | 42.08 | 54.13 | <0.005 | 24.21 | 19.81 |
| MiaPaCa2 | Pancreas | 77.85 | 87.98 | <0.05 | 14.12 | 10.81 |
| MDA-MB-231 | Breast | 73.78 | 85.16 | <0.05 | 7.74 | 5.15 |

NOTE:
Cancer cells were treated with the P61-A6 (10 μM) for 48 hours, and cell cycle distribution was determined by flow cytometry as described under "Experimental Procedures". Data are representative of at least two independent experiments.

Another mechanism through which GGTI can effect cell cycle progression is to inhibit RhoA which negatively regulates expression of a Cdk inhibitor $p21^{CIP1/WAF1}$. To investigate whether the GGTI compounds described herein can induce $p21^{CIP1/WAF1}$ expression, luciferase transcriptional activation from the $p21^{CIP1/WAF1}$ promoter (33) was measured. Transient expression systems with NIH3T3 cells were used to examine the ability of P61-A6 to induce $p21^{CIP1/WAF1}$-luciferase expression. P61-A6 induced significant (4-fold) inductions of luciferase activity versus DMSO in a dose dependence manner (FIG. 37C).

Identification of Dual Specificity Inhibitors of GGTase-I and RabGGTase.

Characterization of the library of allenoate derived compounds described herein yielded novel compounds that inhibit RabGGTase. To find RabGGTase inhibitors, we examined our library of 3601 compounds related to P5-H6 and listed all the compounds that exhibited GGTase-I inhibition. These compounds were further screened to see whether they also inhibited RabGGTase. The assay was carried out using RabGGTase as described in the "Experimental Procedures" section of this example.

Out of 428 compounds that exhibited GGTase-I inhibition (more than 50% inhibition at 50 μM concentration), we found that 60 compounds also exhibited the ability to inhibit RabGGTase (more than 50% inhibition at 25 μM concentration). FIG. 38 shows four examples of compounds (P8-G7, P8-H6, P8-H7 and P49-F5) that exhibit inhibition of both GGTase-I and RabGGTase at a single μM range. On the other hand, these compounds do not inhibit FTase even with more than 100 μM concentration (FIGS. 39B and C).

As shown in FIG. 38, these compounds share a common structural feature. These dual specificity compounds all have a characteristic six-atom aliphatic tail attached to the pentasubstituted pyrrolidine core via thioether linkage (putative RabGGTI feature) to the 5-member ring core.

Identification of RabGGTase Inhibitors.

The putative RabGGTI feature was used to predict RabGGTI activity. We first examined our 3601 compound library and identified 524 compounds that have this feature. We then screened these compounds by carrying out RabGGTase assay. 23 compounds were identified that exhibited preferential inhibition of RabGGTase (less than 50% inhibition of GGTase-I at 50 μM and more than 50% inhibition of RabG-GTase at 25 μM concentration). FIG. 39 shows the structure and $IC_{50}$ values for five example RabGGTase preferential inhibitors, P23-D6, P47-D11, P49-A6, P49-F6 and P50-E11. Three of these compounds contain n-hexylmercapto substituent at C4 of the pyrrolidine ring. Additionally, we find n-pentyl thioether (P47-D11) and para-methoxyphenyl thioether (P23-D6) appendages in the group of RabGGTase preferential inhibitors.

As shown in FIGS. 39B and 39C, these compounds inhibit RabGGTase with an $IC_{50}$ value of about 2-5 μM, while the inhibition of GGTase-I required more than 50 μM No significant inhibition of FTase was observed using 100 μM of these compounds.

Figure 42:
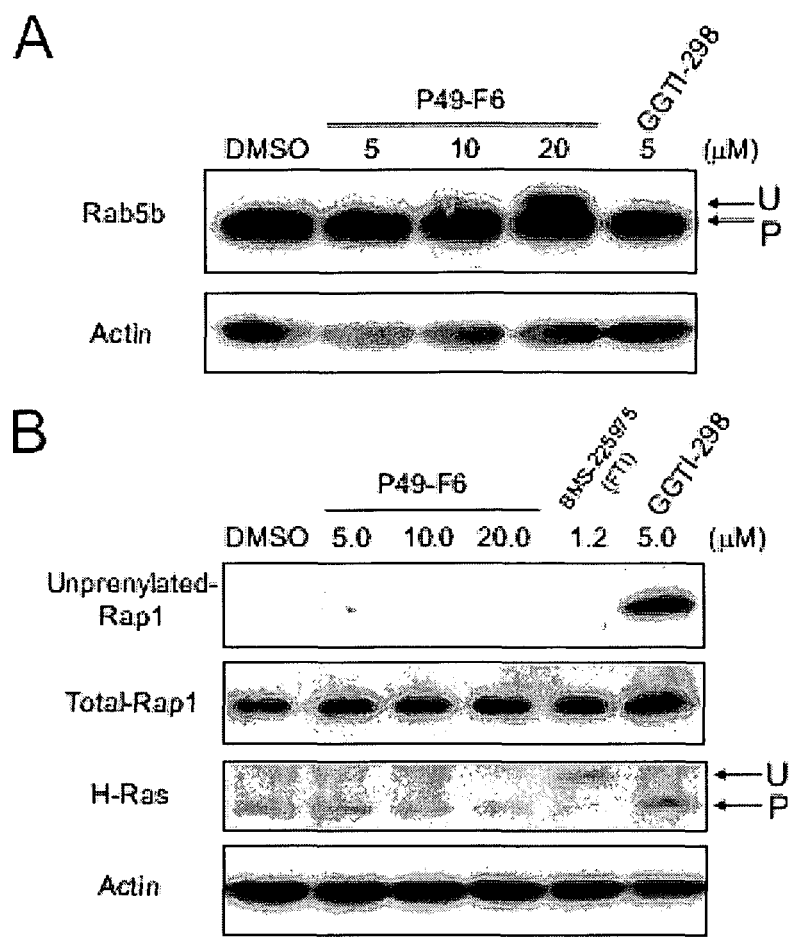
FIG. 42 shows the inhibition of RabGGTase activity in cells. (A) shows that P49-F6 treatment inhibits Rab5b geranylgeranylation in NIH3T3 cells. Whole cell lysates from cells treated with DMSO or P49-F6 for 48 hours were prepared and processed for immunoblot analysis using antibody against Rab5b (upper panel) or actin (lower panel). (B) shows whole cell lysates from NIH3T3 cells treated with DMSO or P49-F6 for 48 hours were prepared and processed for immunoblot analysis using antibody against unprenylated form of Rap1 (upper panel), total-Rap1 (upper middle panel), H-Ras (lower middle panel) or actin (lower panel).
Figure 43:
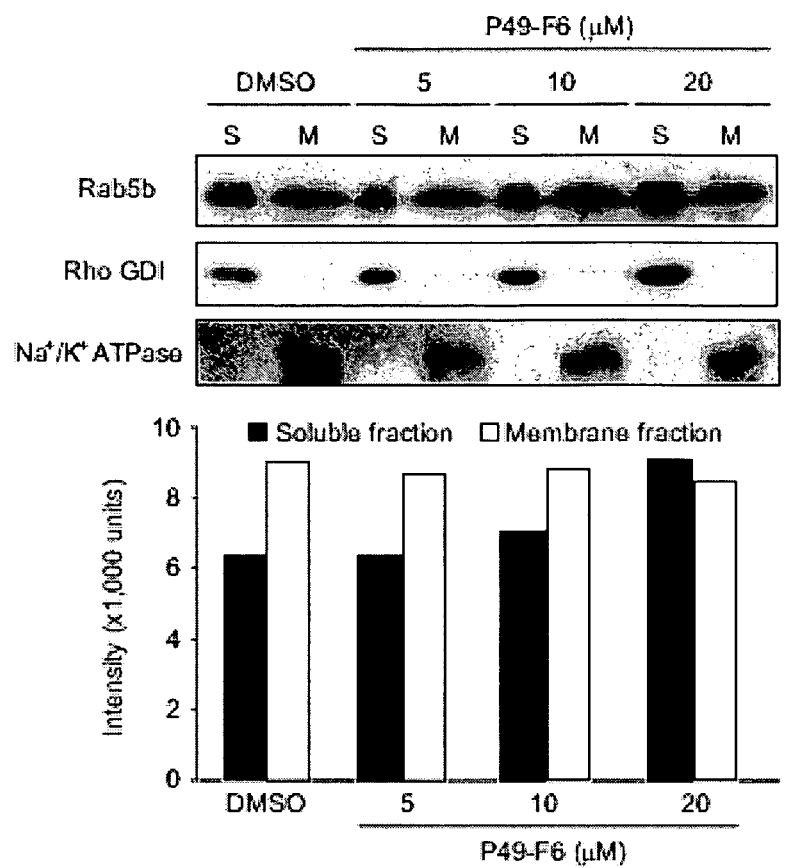
FIG. 43 shows the effects of RabGGTI on membrane association of Rab5b protein. Western blots of Rab5b in the soluble fractions or membrane fractions prepared from NIH3T3 cells treated for 48 hours. Rho GDI and $Na^+/K^+$ ATPase were used as marker proteins for the soluble and membrane fractions, respectively. Bars indicate intensity of protein bands after normalization using loading control.

Inhibition of Rab geranylgeranylation in cells was examined using Rab5b protein. In this experiment, we examined the mobility of Rab5b proteins (FIG. 42A). P49-F6, one of the RabGGTase preferential inhibitors caused the appearance of a slow migrating Rab5b protein which represents an unprenylated form (29). On the other hand, P49-F6 did not cause mobility shift of H-Ras and did not induce appearance of unprenylated Rap1, indicating that it does not appear to inhibit FTase or GGTase-I (FIG. 42B). We also examined intracellular localization of Rab5b proteins (FIG. 43). Treatment with P49-F6 resulted in the increase of Rab5b protein in the soluble fraction.

RabGGTI Competes with the Substrate Protein.

Figure 40:
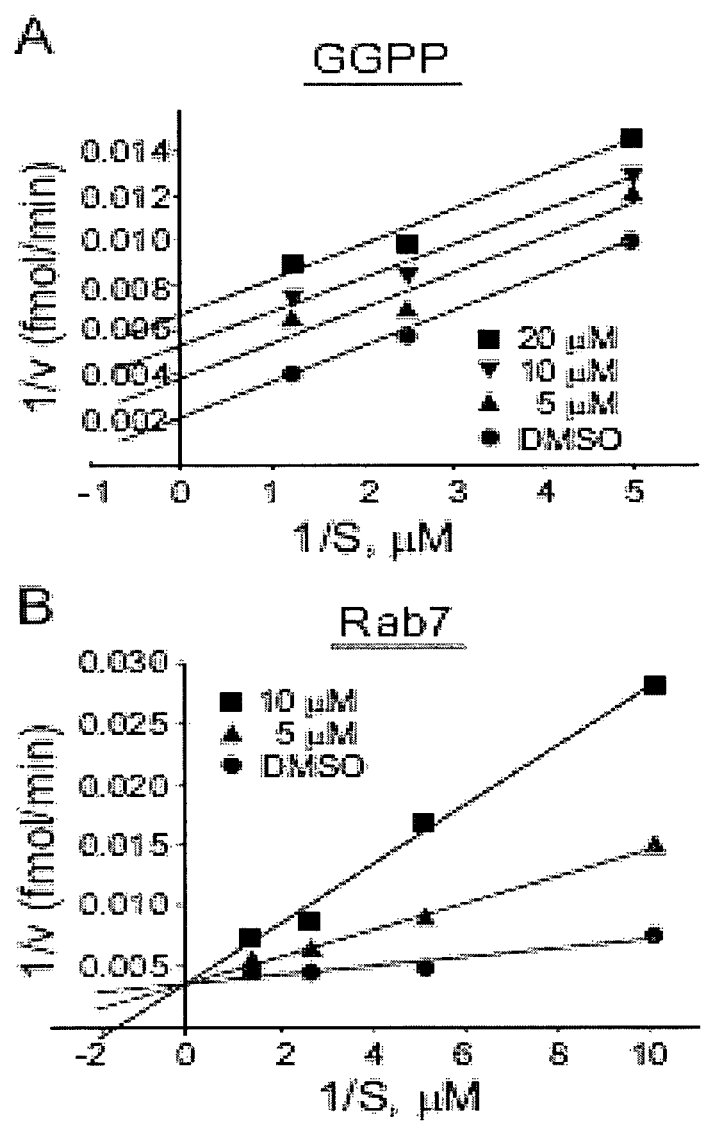
FIG. 40 shows a characterization of P49-F6 inhibition of RabGGTase. in vitro RabGGTase assay was carried out with varying concentration of GGPP (A) or Rab7 (B). Each reaction mixture contained recombinant RabGGTase and recombinant REP-1 protein. They were mixed with a low concentration of GGPP (0.125 μM) to form an active enzyme first. Duplicate reactions were carried out. The amount of RabGGTI used is indicated.

Kinetic analysis was carried out to examine whether our RabGGTI compounds compete with substrate protein. Rab geranylgeranyltransferase consists of a tightly bound core complex, the alpha and beta subunits, and the third subunit REP protein. These subunits were first mixed together in the presence of a low concentration of GGPP and then the concentration of each substrate was altered and the effect of inhibition by RabGGTI was examined. As can be seen in FIG. 40, a RabGGTI compound P49-F6 inhibits RabGGTase activity with respect to the substrate protein Rab7 (FIG. 40B). On the other hand, increasing concentration of GGPP did not influence the inhibition by RabGGTI (FIG. 8A), showing that they are uncompetitive inhibitors with respect to GGPP. A Ki value of 1.36±0.38 μM was calculated from these experiments.

DISCUSSION

The above experiments illustrate the identification of novel small molecule inhibitors of GGTase-I from the diversity library of allenoate-derived compounds. Two novel scaffolds were identified. Our compounds are non-peptidomimetic inhibitors that compete with the substrate protein. Specific inhibition of protein geranylgeranylation but not protein farnesylation was established with the purified enzymes as well as with treated cells. Other non-peptidomimetic GGTI compounds have been reported (25). However, a surprising low concentration of 2-20 μM of the compounds described herein can be used to exert cellular activity with tissue culture cells (25).

We found that derivatizing the carboxyl group of the dihydropyrrole ring of compound P5-H6 results in an increase in their cellular potency. In particular, changing the carboxyl group to the corresponding amide by coupling it with L-phenylalanine is effective. On the other hand, converting the free carboxylic acid into the ethyl ester did not lead to any improvement. Similarly, converting to a methyl ester did not result in improvement either (unpublished results). These results indicate that the improvement is not simply due to the removal of the charge but that the phenylalanine moiety exerted additional effect.

The improvement of the cellular activity of our GGTI compound can be correlated with the increase in the ability to inhibit protein geranylgeranylation, as detected by the appearance of unprenylated Rap1 protein. On the other hand, the modification did not improve potency of these compounds to inhibit GGTase-I enzyme. Therefore, the improvement of cellular activity may reflect increased cellular uptake or stability of the compound.

The GGTI compounds described herein exhibit inhibition of proliferation of human cancer cell lines including leukemic, pancreatic cancer and breast cancer cell lines. One of the hallmarks of GGTI is that this class of inhibitors causes cell cycle arrest at the $G_1$ phase (38,39). These inhibitors exhibit significant $G_1$ arrest with the human cancer cell lines examined (FIG. 37B, Table S2). In particular, dramatic $G_1$ arrest is observed with a breast cancer cell line MCF-7. In addition, our GGTI compounds induce $p21^{CIP1/WAF1}$ expression, as observed by using a luciferase reporter assay. These results indicate that our GGTI inhibits RhoA which acts as a negative regulator of $p21^{CIP1/WAF1}$ expression (39,40,41).

The experiments above also illustrate that the compounds described herein can be a novel type of RabGGTase inhibitor. We have shown that the RabGGTI compounds described herein inhibit the enzyme by competing with the substrate protein. Because our RabGGTI compounds are derived from GGTI compounds, RabGGTI and GGTI share the same scaffold.

While not wishing to be bound to a single theory, this may indicate that both the GGTI and RabGGTI compounds work by competing with the protein substrate. Further, GGTase-I and RabGGTase share similar active site structures (16,26); both enzymes have a core structure that consists of alpha and beta subunits. In addition, the corresponding subunits in these enzymes share significant homology. Therefore, in some embodiments, these inhibitors bind to similar pockets in these enzymes.

Further, we found that RabGGTI compounds possess a structural feature that is unique to this group of inhibitors. They contain a characteristic long aliphatic tail attached to the penta-substituted pyrrolidine core. While not wishing to be bound to a single theory, it is believed that the aliphatic tail fits into a pocket or interferes with an enzymatic process that is specific to RabGGTase, but not to GGTase-I. For example, the significance of lipid binding pockets of REP for RabGGTase reaction has been suggested (18,43).

REFERENCES

1. Tamanoi, F., and Sigman D. S. *The Enzymes*. (2001), Vol. 21, 2001 Academic Press, San Diego,
2. Zhang, F. L., and Casey, P. J. (1996) *Annu. Rev. Biochem.* 65, 241-270
3. Glomset, J. A., Gelb, M. H. and Farnsworth, C. C. (1990) *Trends Biochem. Sci.* 15, 139-142
4. Gelb, M. H., Brunsveld, L., Hrycyna, C. A., Michaelis, S., Tamanoi, F., Van Voorhis, W. C., and Waldmann, H., Waldmann H. (2006) *Nat. Chem. Biol.* 10, 518-528
5. Cox, A. D. and Der, C. J. (1992) *Curr. Opin. Cell Biol.* 4, 1008-1016
6. Sjogren, A. K., Andersson, K. M., Liu, M., Cutts, B. A., Karlsson, C., Wahlstrom, A. M., Dalin, M., Weinbaum, C., Casey, P. J., Tarkowski, A., Swolin, B., Young, S. G., and Bergo, M. O. (2007) *J. Clin. Invest.* 117, 1294-1304
7. Lim, K. H., Baines, A. T., Fiordalisi, J. J., Shipitsin, M., Feig, L. A., Cox, A. D., Der, C. J., and Counter, C. M., Der C J, Counter C M. (2005) *Cancer Cell* 6, 533-545
8. Chien, Y., and White, M. A. (2003) *EMBO Rep.* 4, 800-806
9. Clark, E. A., Golub, T. R., Lander, E. S., and Hynes, R. O. (2000) *Nature* 406, 532-535
10. Hakem, A., Sanchez-Sweatman, O., You-Ten, A., Duncan, G., Wakeham, A., Khokha, R., Mak, T. W., Mak T W. (2005) *Genes and Develop.* 19, 1974-1979
11. Cheng, K. W., Lahad, J. P., Kuo, W. L., Lapuk, A., Yamada, K., Auersperg, N., Liu, J., Smith-McCune, K., Lu, K. H., Fishman, D., Gray, J. W., and Mills, G. B. (2004) *Nat. Med.* 10, 1251-1256
12. Cheng, K. W. Lahad, J. P., Gray, J. W. and Mills, G. B. (2005) *Cancer Res.* 65, 2516-2519
13. Croizet-Berger, K., Daumerie, C., Couvreur, M., Courtoy, P. J., and van den Hove, M. F. (2002) *Proc. Nat. Acad. Sci. USA* 99, 8277-8282
14. He, H., Dai F., Yu, L., She, X., Zhao, Y., Jiang, J., Chen, X., and Zhao, S. (2002) *Gene Expr.* 10, 231-242
15. Taylor, J. S., Reid, T. S., Terry, K. L., Casey, P. J., and Beese, L. S. (2003) *EMBO J.* 22, 5963-5974
16. Leung, K. F., Baron, R., and Seabra, M. C. (2006) *J. Lipid Res.* 47, 467-475
17. Zhang, H., Seabra, M. C., and Deisenhofer, J. (2000) *Structure* 8, 241-251
18. Pylypenko, 0., Rak, A., Reents, R., Niculae, A., Sidorovitch, V., Cioaca, M. D., Bessolitsyna, E., Thoma, N. H., Waldmann, H., Schlichting, I., Goody, R. S., and Alexandrov, K. (2003) *Mol. Cell* 11, 483-494
19. Rak, A., Pylypenko, 0., Niculae, A., Pyatkov, K., Goody, R. S, and Alexandrov, K. (2004) *Cell* 117, 749-760
20. Sebti, S. M., and Adjei, A. A. (2004) *Semin. Oncol.* 31, 28-39
21. Lerner, E. C., Qian, Y., Hamilton, A. D., and Sebti, S. M. (1995) *J. Biol. Chem.* 270, 26770-26773
22. Vasudevan, A., Qian, Y., Vogt, A., Blaskovich, M. A., Ohkanda, J., Sebti, S. M., and Hamilton, A. D. (1999), and
23. Hamilton, A. D. *J. Med. Chem.* 42, 1333-1340
24. Sun, J., Qian, Y., Hamilton, A. D., and Sebti, S. M. (1998) *Oncogene* 16, 1467-1473
25. Sun, J., Ohkanda, J., Coppola, D., Yin, H., Kothare, M., Busciglio, B., Hamilton, A. D., and Sebti, S. M. (2003) *Cancer Res.* 63, 8922-8929
26. Peterson, Y. K. Kelly, P. Weinbaum, C. A. and Casey, P. J. (2006) *J. Biol. Chem.* 281, 12445-12450
27. El Oualid, F., Cohen, L. H., van der Marel, G. A., and Overhand, M. (2006) *Curr. Med. Chem.* 13, 2385-2427
28. Coxon, F. P., Helfrich, M. H., Larijani, B., Muzylak, M., Dunford, J. E., Marshall, D., McKinnon, A. D., Nesbitt, S. A., Horton, M. A., Seabra, M. C., Ebetino, F. H., and Rogers, M. J., McKinnon A D, Nesbitt S A, Horton M A, Seabra M C, Ebetino F H, Rogers M J. (2001) *J. Biol. Chem.* 276, 48213-4822
29. Castellano, S., Fiji, H. D., Kinderman, S. S., Watanabe, M., Leon, P., Tamanoi, F., and Kwon, O., Kwon O. (2007) *J. Am. Chem. Soc.* 129, 5843-5845
30. Sanford, J. C., Foster, L., Kapadia, Z., and Wessling-Resnick M. (1995) *Anal Biochem.* 224, 547-556
31. Gomes, A. Q., Ali, B. R., Ramalho, J. S., Godfrey, R. F., Banal, D. C., Hume, A. N., and Seabra, M. C. (2003) *Mol. Biol. Cell* 14, 1882-1899
32. Lu, J., Liong, M., Zink, J. I., and Tamanoi, F. (2007) *Small* 3, 1341-1346
33. Kato-Stankiewicz, J., Hakimi, I., Zhi, G., Zhang, J., Serebriiskii, I., Guo, L., Edamatsu, H., Koide, H., Menon, S., Eckl, R., Sakamuri, S., Lu, Y., Chen, Q. Z., Agarwal, S., Baumbach, W. R., Golemis, E. A., Tamanoi, F., and Khazak, V. (2002) *Proc. Natl. Acad. Sci. USA* 99, 14398-14403

34. Guo, W., Baluda, M. A., and Park, N. H. (1997) *Oncogene* 15, 1143-1149
35. Zhu, X., Henry, C. E., and Kwon, O. (2005) *Tetrahedron* 61, 6276-6282
36. Zhu, X., Lan, J., and Kwon, 0. (2003) *J. Am. Chem. Soc.* 125, 4716-4717
37. Zhu, X., Henry, C. E., Wang, J., Dudding, T., and Kwon, 0. (2005) *Org. Lett.* 7, 1387-1390
38. Zhu, X., Schaffner, A., Li, R. C., and Kwon, 0. (2005) *Org. Lett.* 7, 2977-2980
39. Vogt, A. Sun, J. Qian, Y. Hamilton, A. D., and Sebti, S. M. (1997) *J. Biol. Chem.* 272, 27224-27229
40. Sun, J. Qian, Y., Chen, Z., Marfurt, J. Hamilton, A. D., and Sebti, S. M. (1999) *J. Biol. Chem.* 274, 6930-6934
41. Adnane, J., Bizouarn, F. A., Qian, Y., Hamilton, A. D., and Sebti, S. M. (1998) *Mol. Cell. Biol.* 18, 6962-6970
42. Olson, M. F., Paterson, H. F., and Marshall, C. J. (1998) *Nature* 394, 295-299
43. Lackner, M. R., Kindt, R. M., Carroll, P. M., Brown, K., Cancilla, M. R., Chen, C., de Silva, H., Franke, Y., Guan, B., Heuer, T., Hung, T., Keegan, K., Lee, J. M., Manne, V., O'Brien, C., Parry, D., Perez-Villar, J. J., Reddy, R. K., Xiao, H., Zhan, H., Cockett, M., Plowman, G., Fitzgerald, K., Costa, M., and Ross-Macdonald, P. (2005) *Cancer Cell* 7, 325-336
44. Pylypenko, O., Rak, A., Durek, T., Kushnir, S., Dursina, B. E., Thomae, N. H., Constantinescu, A. T., Brunsveld, L., Watzke, A., Waldmann, H., Goody, R. S., Alexandrov, K. (2006) *EMBO J.* 25, 13-23

Example 10

Xenograft tumor experiments have shown that GGTI's can inhibit PANC-1 tumor growth in mice. Seven SCID mice (six weeks old) received a subcutaneous implantation of 5 million PANC-1 cells. The mice were supplied with food and water for 14 days before treatment was started. The treatment group received 160 uM GGTI (p61A6) in 0.25 ml 0.9% NaCl while the control group received 0.25 ml 0.9% NaCl. Each dosage was injected 3 times per week. These dosage were designed to administer p61A6 at approximately 1.16 mg/kg of body weight. Also, since the mouse has about 2 ml blood, the final concentration of p61A6 in vivo was approximately 20 uM. The final DMSO concentration in the control group was approximately 0.8%.

Figure 44:
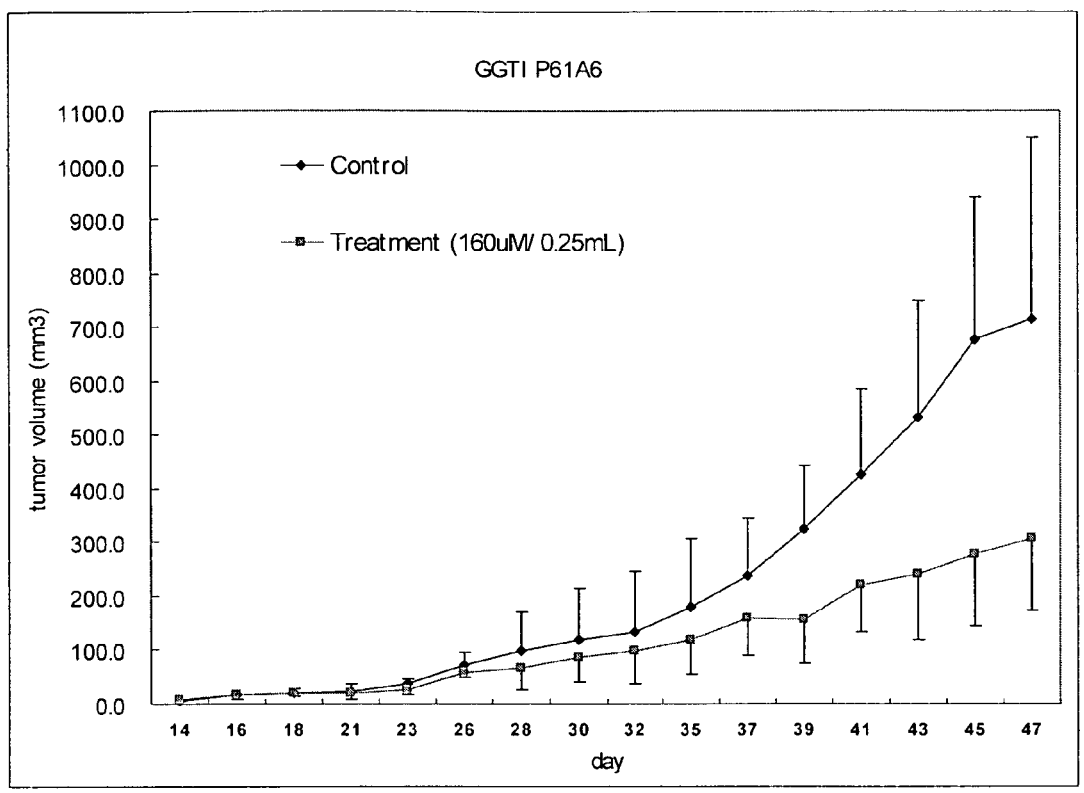
FIG. 44 shows that P61A6 inhibits PANC-1 xenograft tumor growth in SCID mice.
Figure 45:
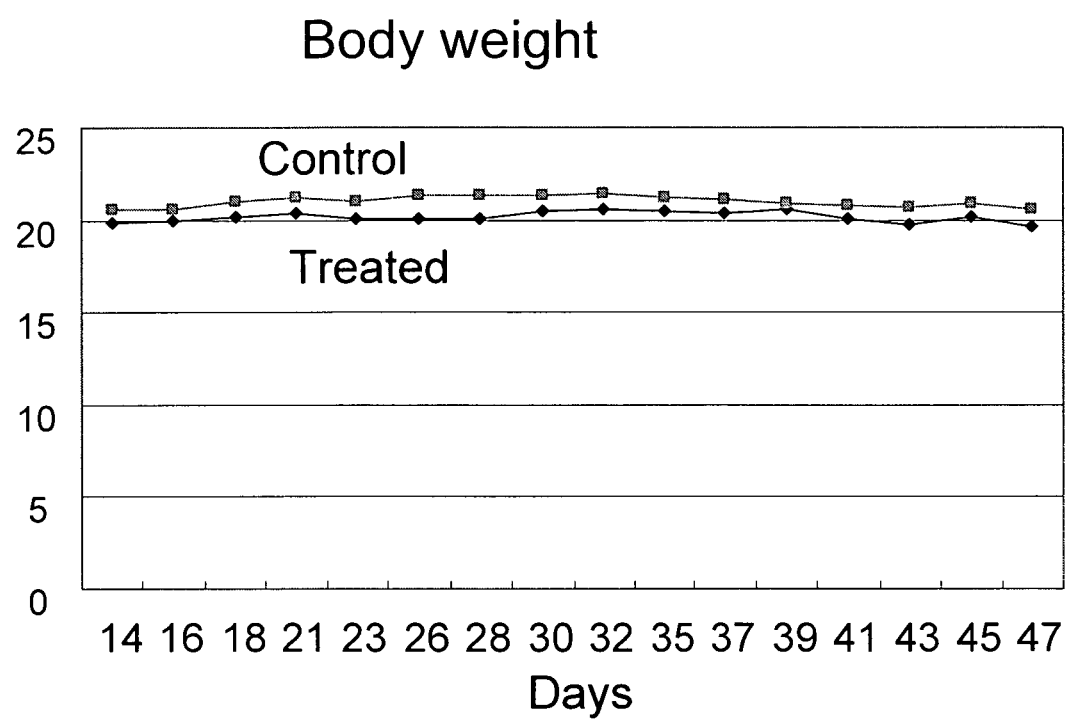
FIG. 45 shows an examination of mouse body weight indicating that the GGTI treatment did not cause adverse effects.

Results from the test are shown in FIGS. 44 and 45 and table S3 below. These results indicate that GGTI P61A6 inhibits PANC-1 xenograft tumor growth in SCID mice. FIG. 45 and table S3 show examinations of body weight as well as hematological and biochemical examinations indicating that the GGTI treatment did not cause adverse effects.

TABLE S3

|   | GGTI treated 4 | control 1 |
|---|---|---|
| ALB | N | N |
| ALT (7-227) | N | N |
| AST (37-329) | N | N |
| BUN | N | N |
| CREAT | N | N |
| CHOL | N | N |
| CK | N | N |
| ALP | N | N |
| GLU | N | N |
| CA | N | N |

TABLE S3-continued

|   | GGTI treated 4 | control 1 |
|---|---|---|
| RBC | N | N |
| WBC | N | N |
| NE | N | N |
| LY | N | N |
| PLT | N | N |

Example 11

Additional xenograft tumor experiments have shown that GGTI's can inhibit PANC-1 tumor growth in mice and reduce the size of the tumor. Six SCID mice (six weeks old) received a subcutaneous implantation of 3 million PANC-1 cells. The mice were supplied with food and water for 14 days before treatment began. The mice were divided into the following treatment groups (all non-control groups administer P61-A6 at the dose listed): (1) control: 0.25 ml 0.9% Nacl; (2) treatment group 1: 1.16 mg/kg of body weight in 0.25 ml 0.9% Nacl, 1/week, i.p. (20 uM); (3) treatment group 2: 1.16 mg/kg of body weight in 0.25 ml 0.9% Nacl, 6/week, i.p. (20 uM); (4) treatment group 3: 0.58 mg/kg of body weight in 0.25 ml 0.9% Nacl, 3/week, i.p. (10 uM); and (5) treatment group 5: 0.29 mg/kg of body weight in 0.25 ml 0.9% Nacl, 3/week, i.p. (5 uM). Every two weeks each mouse's body weight and tumor volume was measured.

Figure 46:
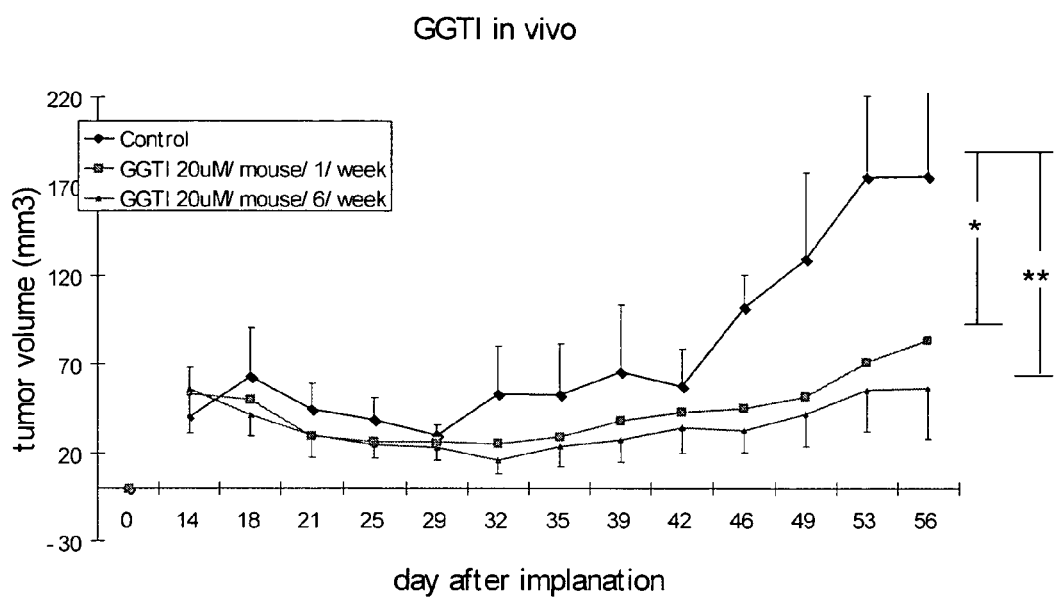
FIG. 46 shows that P61A6 inhibits PANC-1 xenograft tumor growth in SCID mice.
Figure 47:
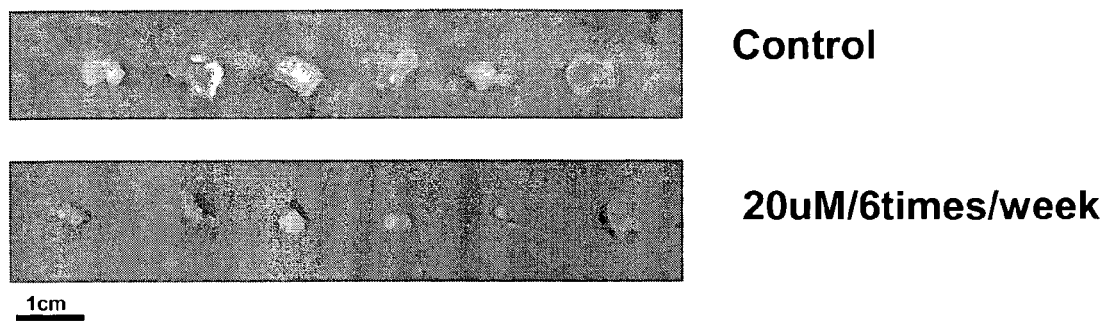
FIG. 47 shows that the PANC-1 cell tumor size was reduced by administering P61A6 six times per week.
Figure 48:
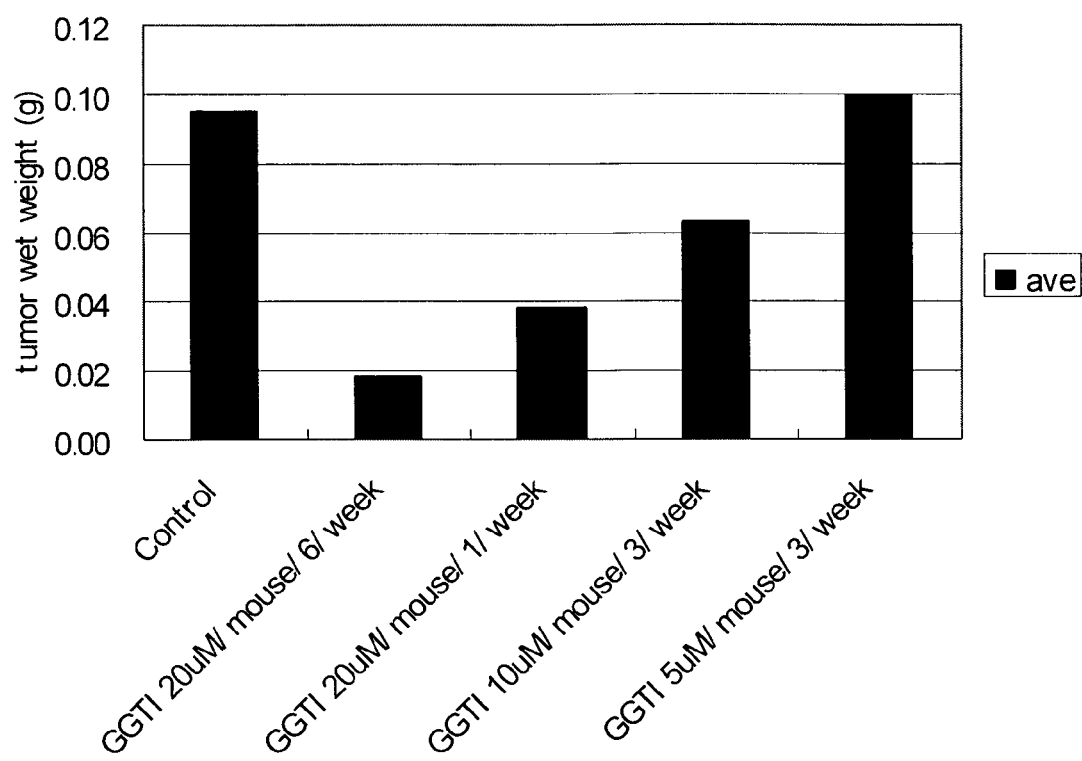
FIG. 48 shows dose dependent inhibition of a xenograft tumor by P61A6.
Figure 49:
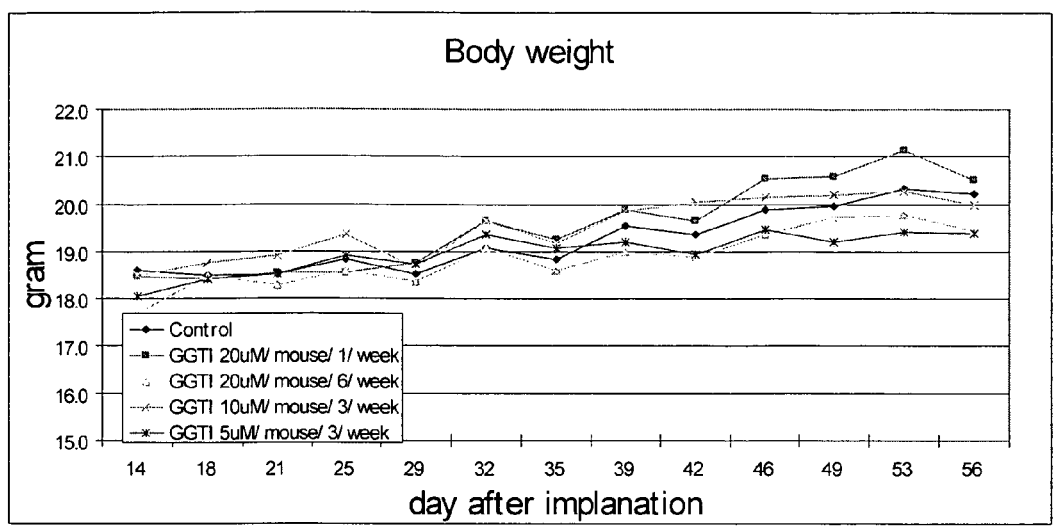
FIG. 49 shows that the administration of P61A6 did not significantly effect mouse body weight.
Figure 50:
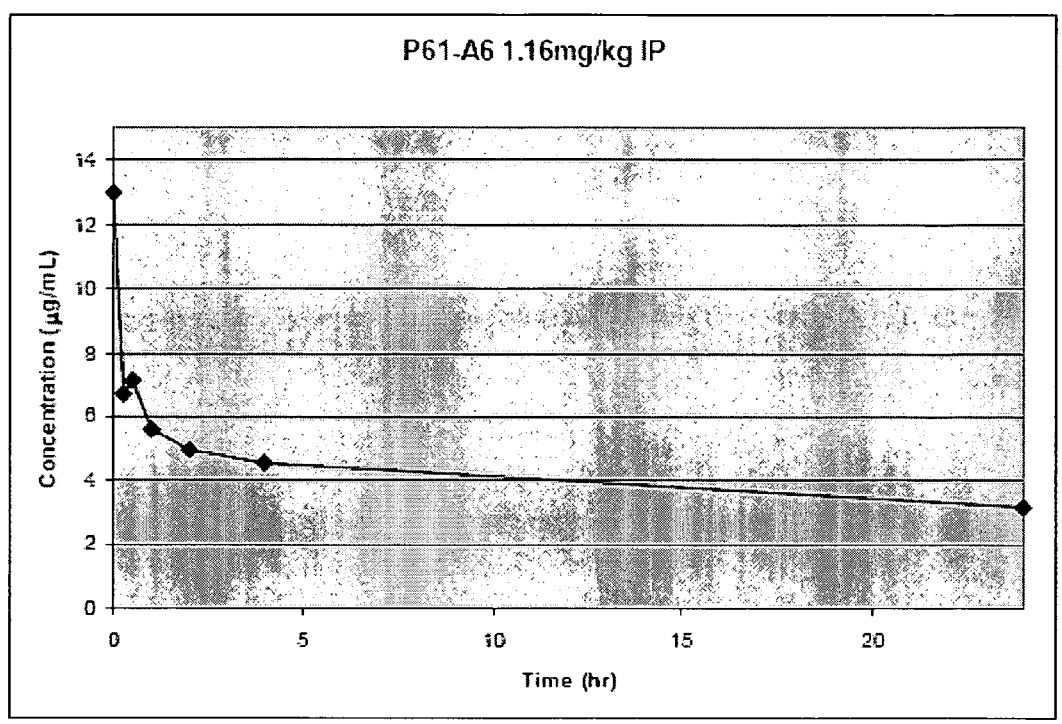
FIG. 50 shows the serum levels of P61A6 over time.
Figure 51:
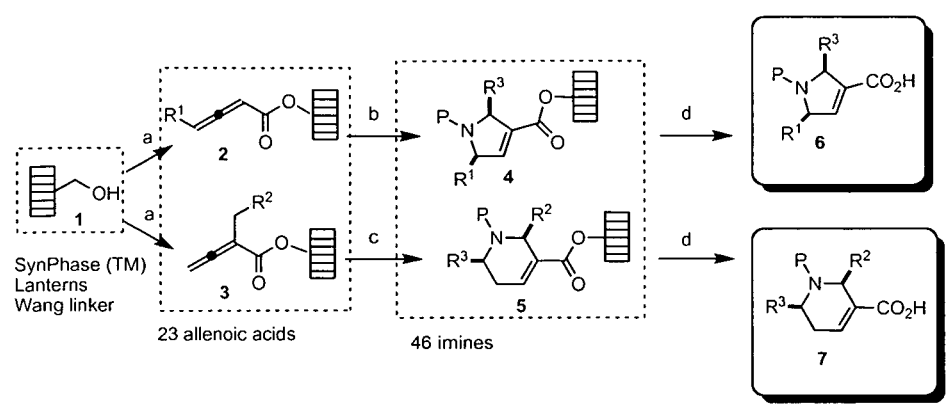
FIG. 51 shows an example synthesis method for preparing the second-generation library. The following reaction conditions can be used: (a) allenoic acid, Mukaiyama's reagent, DIPEA or $Et_3N$, DCM, rt, 12 h; (b) $PBu_3$, imine, benzene, 60° C. (c) $PBu_3$, imine, DCM, rt (d) 2.5% TFA/DCM, 12 h.
Figure 52:
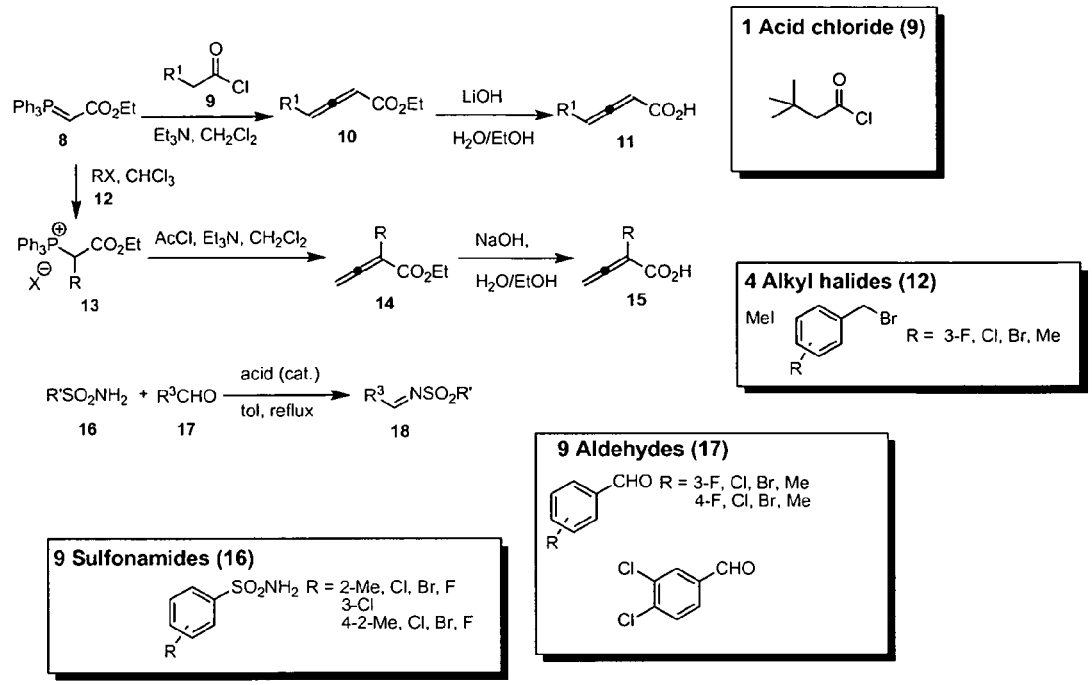
FIG. 52 shows the synthesis of the building blocks for the focused second-generation library.
Figure 53:
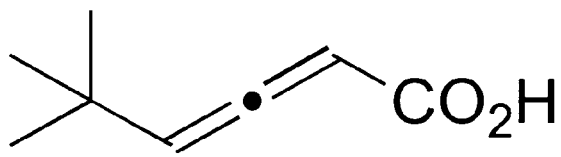
FIG. 53 shows the structure of an example gamma-substituted allenoic acid used in the synthesis of the focused second-generation library.
Figure 54:
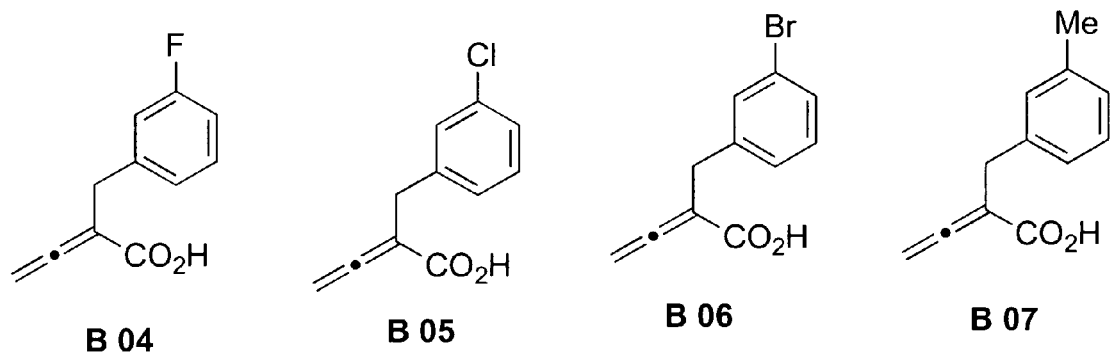
FIG. 54 shows the structures of example alpha-substituted allenoic acids used in the synthesis of the focused second-generation library.
Figure 55:
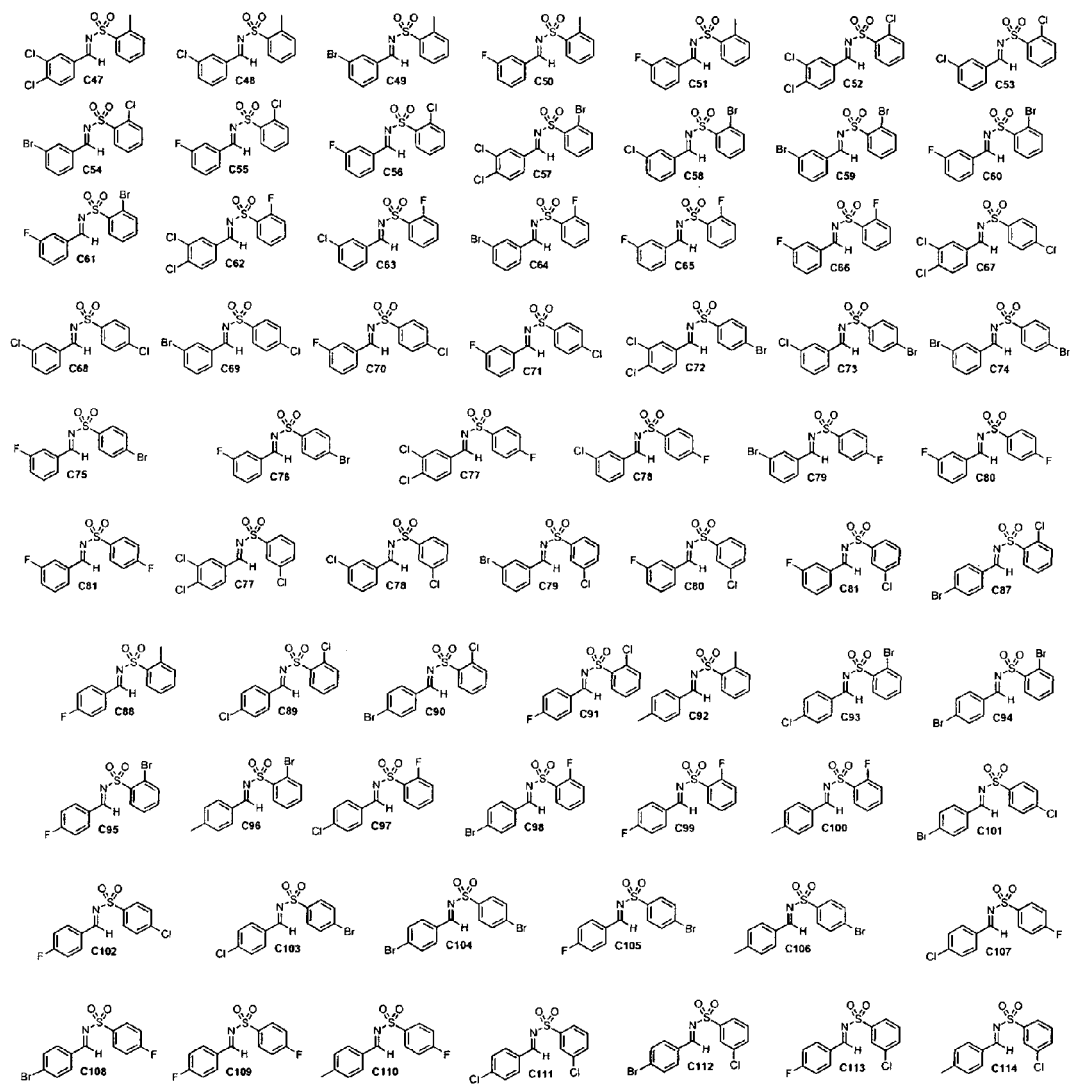
FIG. 55 shows the structures of example imines used in the synthesis of the focused second-generation library.
Figure 57:
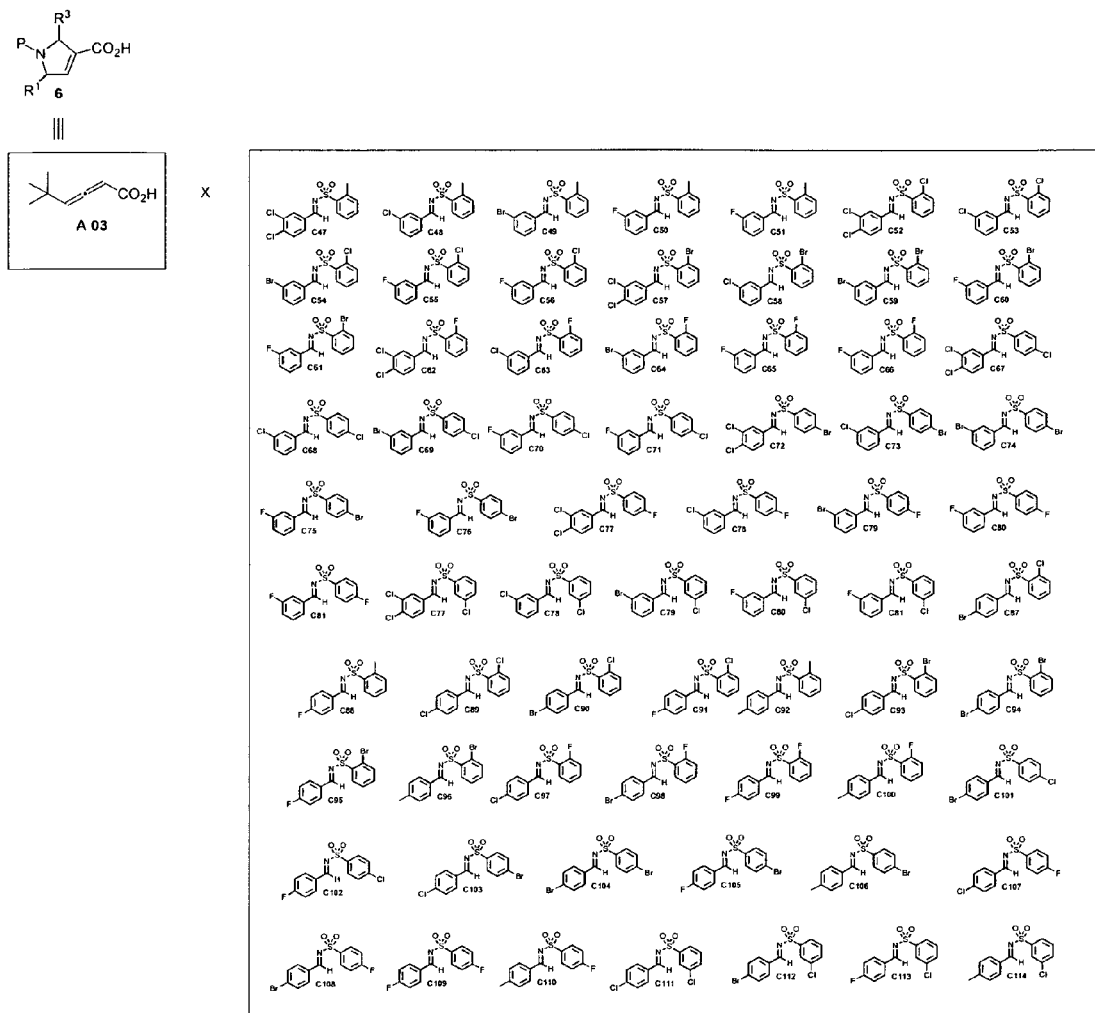
FIG. 57 shows the structures of the building blocks used in the synthesis of the focused second-generation library compounds with scaffold 6.
Figure 58:
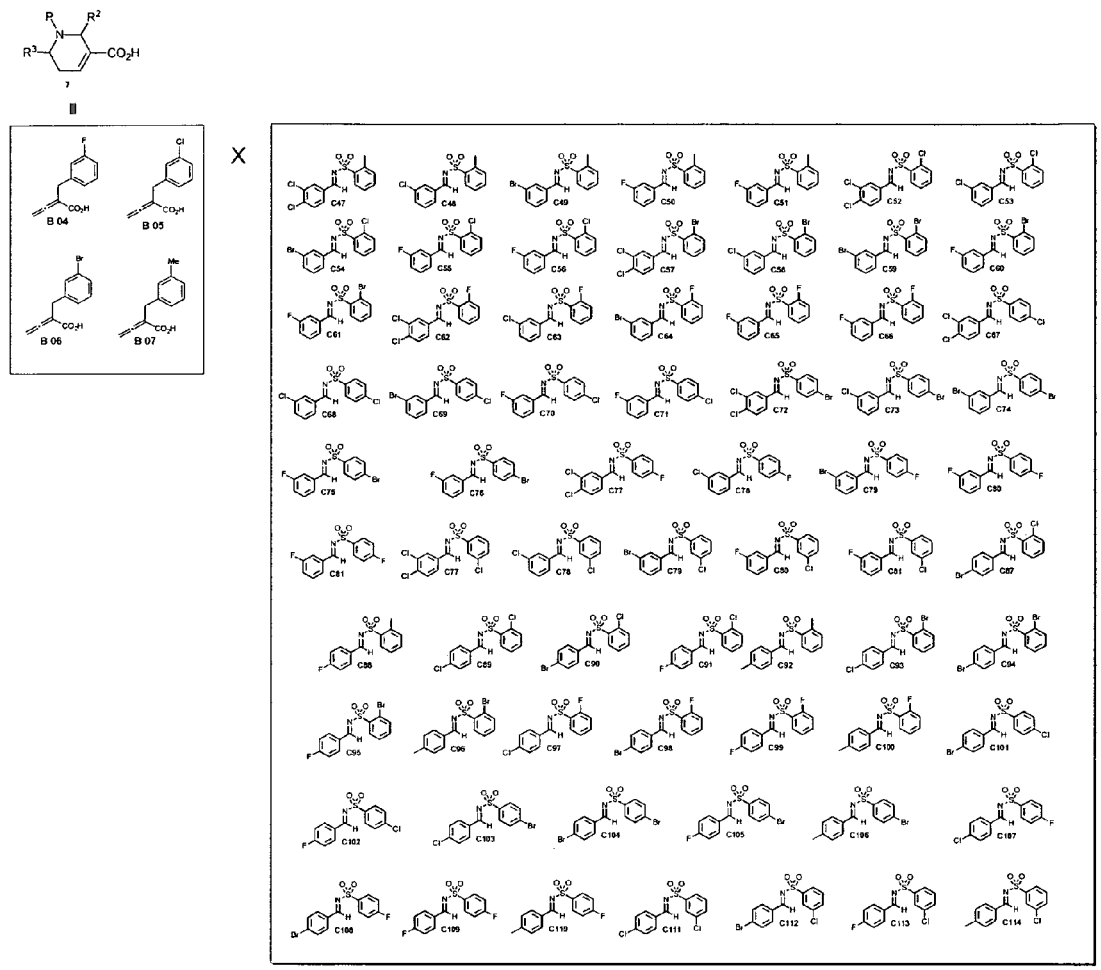
FIG. 58 shows the structures of the building blocks used in the synthesis of the focused second-generation library compounds with scaffold 7.

As shown in FIG. 46, almost complete inhibition of PANC-1 tumor growth was obtained by administering GGTI P61-A6 six times per week. Surprisingly, similar inhibition was administering GGTI P61-A6 once a week. This may be due to slow metabolism of the compound. Table S4 illustrates that GGTI P61-A6 was found to have a half life of 16.9 hours. Thus, in some embodiments, the compositions of the invention can be administered is a dosage regimen that is highly convenient, e.g., once weekly instead of daily. The compositions of the present invention can be administered every 1, 2, 3, 4, 5, 6, or 7 days, or may be administered otherwise.

TABLE S4

| Parameter | IP |
|---|---|
| Dose | 1.16 mg/kg |
| $C_{max}$ | 13 µg/ml (22.4 µM) |
| $AUC_{0-4\,h}$ | 22.2 µg*hr/ml |
| Clearance | 1.04 ml/hr |
| Half-life | 16.9 hr |

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A compound having the formula

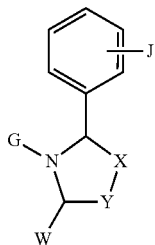

wherein J is hydrogen or is 1-2 substituents independently selected from the group consisting of halogen, C1-C3 alkyl, OR', SR', and NR'2, where R' is alkyl,
wherein G is

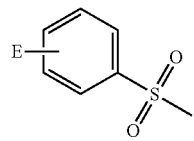

wherein E is hydrogen or is 1-2 substituents selected from the group consisting of halogen, C1-C3 alkyl, OR', SR', and NR'2, where R' is alkyl,
wherein W is selected from the group consisting of hydrogen, cyclic, linear, or branched alkyl of from 2 to 8 carbons, unsubstituted phenyl, and phenyl substituted with C1-C3 alkyl, halogen, OR', SR', and NR'2, where R' is alkyl,
wherein

is selected from the group consisting of

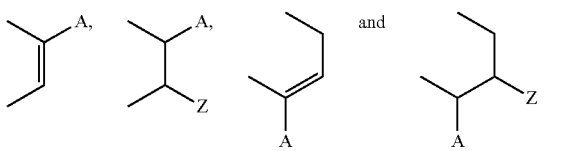

wherein A is selected from the group consisting of:

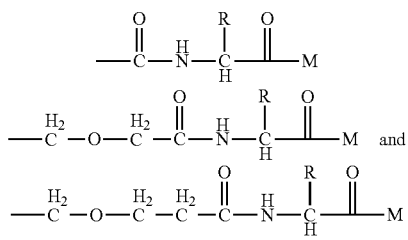

wherein M is selected from the group consisting of OH, OR", NH2, NHOH, NHOR", wherein R" is methyl or ethyl, or any other group that has a polar metal binder wherein R corresponds to an alpha-substituent of natural or non-natural alpha-amino acid;

wherein Z is S—U; and wherein U is selected from the group consisting of alkyl having 10 or fewer carbons, phenyl, optionally substituted with halogen or OR", wherein R" is methyl or ethyl, and (CH2)n-COOR4, wherein n=1-4 and R4 is a linear or branched alkyl having four or fewer carbons; or the compound P61-A7

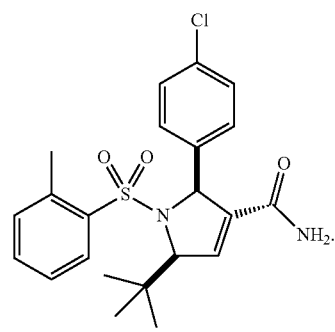

2. A compound of claim 1, wherein A is

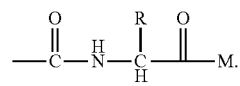

3. A compound of claim 1, wherein A is

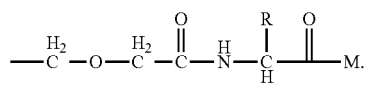

4. A compound of claim 1, wherein A is

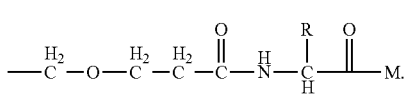

5. The compound of claim 1, wherein M is OEt, OMe, Ot-Bu, OH, NH2, NHOH, NHOMe, or any other groups that have a polar metal binder.

6. The compound of claim 1, wherein the compound is selected from the group consisting of

P61-A6

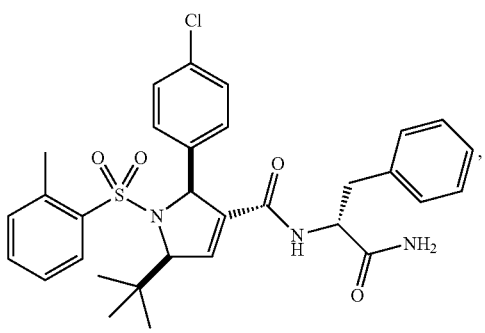

P61-A5

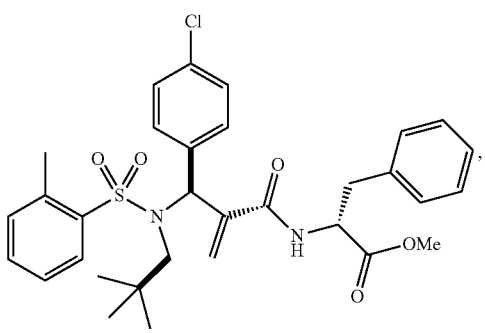

P61-B4

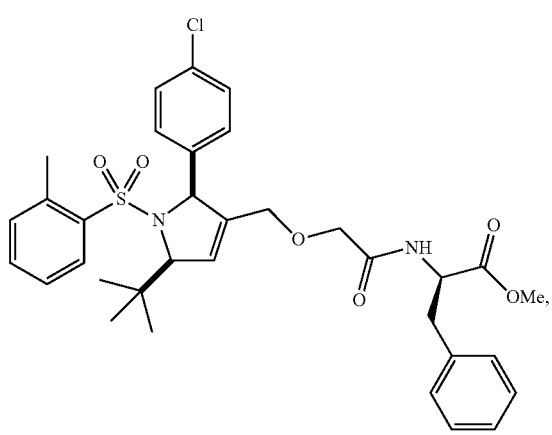

and

P61-B6

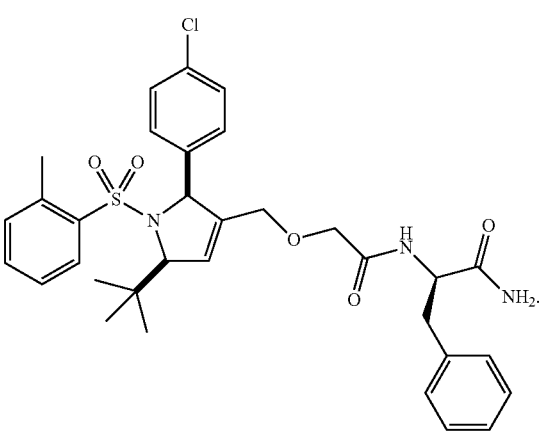

7. The compound of claim 1, wherein G is

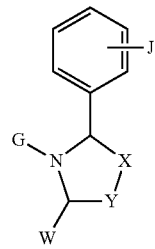

8. The compound of claim 1, wherein the compound inhibits the activity of a protein prenyltransferase.

9. The compound of claim 1, wherein the compound inhibits the activity of a RabGGTase.

10. The compound of claim 1, wherein the compound inhibits the activity of GGTase I.

11. The compound of claim 1, wherein the compound inhibits the activity of GGTase I and RabGGTase.

12. A pharmaceutical composition comprising the compound of claim 1 and a pharmaceutically acceptable carrier or diluent.

13. A method comprising administering the compound of claim 1 to a cell in an amount sufficient to inhibit the activity of GGTase I and/or RabGGTase.

14. The method of claim 13, wherein the compound is administered at a micromolar concentration.

15. A method comprising administering a compound of claim 1 in an amount sufficient to inhibit the growth of a cancer cell or to reduce the size of a tumor of cancer cells.

16. The method of claim 15, wherein the cancer cell comprises GGTase I and/or RabGGTase modified proteins.

17. A method comprising administering to a subject in need of treatment for a cancer the pharmaceutical composition of claim 12 in an amount sufficient to inhibit the activity of a protein prenyltransferase.

18. The method of claim 17, wherein the protein prenyltransferase is GGTase I, RabGGTase, or both.

19. The method of claim 17, wherein the cancer cell comprises GGTase I and/or RabGGTase modified proteins.

20. A method comprising measuring the GGTase I and/or RabGGTase inhibiting activity of a compound of claim 1.

21. A method of preparing a compound according to formula I

I

[structure]

wherein:
wherein J is hydrogen or is 1-2 substituents independently selected from the group consisting of halogen, C1-C3 alkyl, OR', SR', and NR'2, where R' is alkyl,
wherein W is selected from the group consisting of hydrogen, cyclic, linear, or branched alkyl of from 2 to 8 carbons, unsubstituted phenyl, and phenyl substituted with C1-C3 alkyl, halogen, OR', SR', and NR12, where R' is alkyl, G is

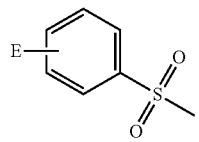

wherein E is hydrogen or is 1-2 substituents selected from the group consisting of halogen, C1-C3 alkyl, OR', SR', and NR'2, where R' is alkyl,

is selected from the group consisting of

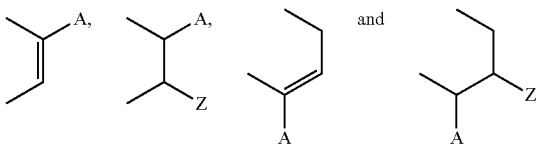

wherein A is

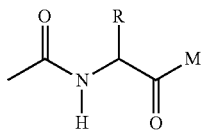

and M=OH, OR, or NH2; and R is, an alpha-substituent of a natural or non-natural amino acid;
comprising,
reacting a compound according to formula I'

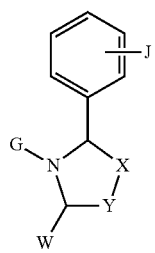

wherein
J, G, and W are as defined above and

is selected from the group consisting of

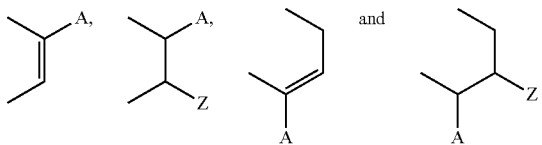

wherein A=CO2H;
with a compound having the formula

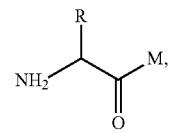

wherein R and M are as defined above.

22. The pharmaceutical composition of claim 12, wherein the pharmaceutically acceptable carrier or diluent comprises a liposome.

23. A pharmaceutical composition comprising the compound of claim 2 and a pharmaceutically acceptable carrier or diluent.

24. The pharmaceutical composition of claim 23, wherein the pharmaceutically acceptable carrier or diluent comprises a liposome.

25. A pharmaceutical composition comprising the compound of claim 3 and a pharmaceutically acceptable carrier or diluent.

26. The pharmaceutical composition of claim 25, wherein the pharmaceutically acceptable carrier or diluent comprises a liposome.

27. A pharmaceutical composition comprising the compound of claim 4 and a pharmaceutically acceptable carrier or diluent.

28. The pharmaceutical composition of claim 27, wherein the pharmaceutically acceptable carrier or diluent comprises a liposome.

29. A pharmaceutical composition comprising the compound of claim 6 and a pharmaceutically acceptable carrier or diluent.

30. The pharmaceutical composition of claim 29, wherein the pharmaceutically acceptable carrier or diluent comprises a liposome.

* * * * *